United States Patent
Mukumoto et al.

(10) Patent No.: US 9,894,901 B2
(45) Date of Patent: *Feb. 20, 2018

(54) METHOD FOR PROMOTING PLANT GROWTH

(71) Applicant: SUMITOMO CHEMICAL COMPANY, LIMITED, Tokyo (JP)

(72) Inventors: Fujio Mukumoto, Takarazuka (JP); Hiroaki Tamaki, Takarazuka (JP); Shintaro Kusaka, Takarazuka (JP); Mitsuhiko Iwakoshi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 52 days.

This patent is subject to a terminal disclaimer.

(21) Appl. No.: 14/441,760

(22) PCT Filed: Oct. 31, 2013

(86) PCT No.: PCT/JP2013/080167
§ 371 (c)(1),
(2) Date: May 8, 2015

(87) PCT Pub. No.: WO2014/073622
PCT Pub. Date: May 15, 2014

(65) Prior Publication Data
US 2015/0282482 A1  Oct. 8, 2015

(30) Foreign Application Priority Data

Nov. 9, 2012  (JP) ................................. 2012-247318

(51) Int. Cl.
| | | |
|---|---|---|
| C07D 409/04 | (2006.01) |
| A01G 1/00 | (2006.01) |
| C07D 333/70 | (2006.01) |
| A01N 47/06 | (2006.01) |
| A01N 47/32 | (2006.01) |
| A01N 43/36 | (2006.01) |
| A01N 43/40 | (2006.01) |
| A01N 47/04 | (2006.01) |
| A01N 43/54 | (2006.01) |

(Continued)

(52) U.S. Cl.
CPC ............ *A01N 43/12* (2013.01); *A01G 1/001* (2013.01); *A01N 43/36* (2013.01); *A01N 43/40* (2013.01); *A01N 43/54* (2013.01); *A01N 43/56* (2013.01); *A01N 43/80* (2013.01); *A01N 47/02* (2013.01); *A01N 47/04* (2013.01); *A01N 47/06* (2013.01); *A01N 47/32* (2013.01); *C07D 333/70* (2013.01); *C07D 409/04* (2013.01)

(58) Field of Classification Search
None
See application file for complete search history.

(56) References Cited

U.S. PATENT DOCUMENTS 2,533,086 A   12/1950  Blicke
3,592,907 A * 7/1971  Chandler ............... A01N 25/02
                                              514/443

(Continued)

FOREIGN PATENT DOCUMENTS

| CN | 101137641 A | 3/2008 |
| GB | 2253847 A | 9/1992 |
| JP | 4-342507 A | 11/1992 |
| WO | WO 2006/071047 A1 | 7/2006 |
| WO | WO 2007/009661 A2 | 1/2007 |
| WO | WO2007009661 A2 * | 1/2007 |
| WO | WO 2009/030467 A2 | 3/2009 |
| WO | WO 2012/153860 A1 | 11/2012 |
| WO | WO 2012/153861 A1 | 11/2012 |

OTHER PUBLICATIONS

Tachibana et al., "Synthesis and Physiological Activity of Thiophenes and Furans with 3- and 4-Methoxyacetophenone Derivatives" J Oleo Sci 57: 107-113 (2008).*

(Continued)

*Primary Examiner* — Robert A Wax
*Assistant Examiner* — Thor Nielsen
(74) *Attorney, Agent, or Firm* — Birch, Stewart, Kolasch & Birch, LLP

(57) ABSTRACT

The present invention provides a method for promoting plant growth, which comprises treating a plant with a compound represented by the following Formula (1):

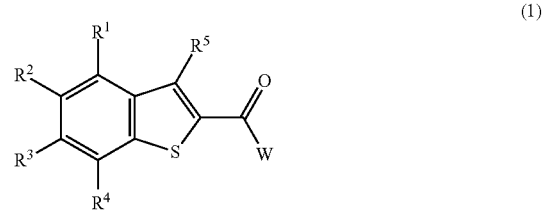

(1)

provided that a method for promoting plant growth which comprises treating plants with a compound corresponding to any one of the following (1) to (8) is excluded: (1) Methyl 4-(trifluoromethyl)benzo[b]thiophene-2-carboxylate, (2) Methyl 5-(trifluoromethyl)benzo[b]thiophene-2-carboxylate, (3) Methyl 6-(trifluoromethyl)benzo[b]thiophene-2-carboxylate, (4) Methyl 7-(trifluoromethyl)benzo[b]thiophene-2-carboxylate, (5) Ethyl 4-(trifluoromethyl)benzo[b]thiophene-2-carboxylate, (6) Ethyl 5-(trifluoromethyl)benzo[b]thiophene-2-carboxylate, (7) Ethyl 6-(trifluoromethyl)benzo[b]thiophene-2-carboxylate, and (8) Ethyl 7-(trifluoromethyl)benzo[b]thiophene-2-carboxylate.

12 Claims, No Drawings

(51) Int. Cl.
  *A01N 43/56* (2006.01)
  *A01N 43/80* (2006.01)
  *A01N 47/02* (2006.01)
  *A01N 43/12* (2006.01)

(56) References Cited

U.S. PATENT DOCUMENTS 5,118,680 A    6/1992  Muller et al.
2010/0298356 A1* 11/2010 Murphy ............... A01N 39/04
                                                514/266.1

OTHER PUBLICATIONS

Old Farmer's Almanac, 2012.*
U.S. Appl. No. 14/441,552, filed May 8, 2015.
U.S. Appl. No. 14/441,626, filed May 8, 2015.
U.S. Appl. No. 14/441,574, filed May 8, 2015.
European Patent Office Communication pursuant to Rule 164(1) EPC and partial supplemental search report issued in the corresponding European Patent Application No. 13853426.8 dated Apr. 29, 2016.
Badger et al., "Thionaphthencarboxylic Acids," Journal of the Chemical Society, 1957, pp. 2624-2630.
Burström et al., "Root Growth Effects of Indan, Indene, and Thionaphthene Derivatives," Physiologia Plantarum, vol. 9, No. 3, 1956, pp. 502-514.
International Preliminary Report on Patentability and Written Opinion of the International Searching Authority (Forms PCT/IB/373 and PCT/ISA/237) for International Application No. PCT/JP2013/080167, dated May 12, 2015.
International Search Report (Form PCT/ISA/210) for International Application No. PCT/JP2013/080167, dated Feb. 10, 2014.
Kasemura et al., "Synthesis and Physiological Activities of Furan and Thiophenes with Methylacetophenone Residues," Bokin Bobai, Journal of Antibacterial and Antifungal Agents, vol. 30, No. 12, 2002, pp. 777-784, with an English abstract.
Sasaki et al., "Biosynthesis, biotechnological production and applications of 5-aminolevulinic acid," Applied Microbiology and Biotechnology, vol. 58, 2002 (Published online Nov. 17, 2001), pp. 23-29.
Tachibana et al., "Synthesis and Physiological Activity of Thiophenes and Furans with 3- and 4-Methoxyacetophenone Derivatives," Journal of Oleo Science, vol. 57, No. 2, 2008, pp. 107-113.
First Office Action (including an English translation thereof) issued in the corresponding Chinese Patent Application No. 201380069593.0 dated Mar. 29, 2016.
Extended European Search Report, dated Sep. 12, 2016, for European Application No. 13853426.8.

* cited by examiner

METHOD FOR PROMOTING PLANT GROWTH

TECHNICAL FIELD

The present invention relates to a method for promoting plant growth.

BACKGROUND ART

Some chemical substances are known to exert an effect of promoting plant growth by being applied to plants. For example, when aminolevulinic acid is applied to plants, this substance exerts an effect of promoting growth of the plants.

RELATED ART DOCUMENT

Non-Patent Document

Non-Patent Document-1: <Biosynthesis, biotechnological production and applications of 5-aminolevulinic acid> K. Sasaki et al., (2002) Applied Microbiology and Biotechnology 58: pp 23-29

DISCLOSURE OF THE INVENTION

Objects of the present invention are to provide a method or the like that excellently promotes plant growth.

As a result of intensive studies, the present inventors found out that the application of a certain compound to plants promotes growth of the plants and have therefore completed the present invention.

That is, the present invention is as follows.

[1] A method for promoting plant growth, which comprises treating a plant with a compound represented by the following Formula (1):

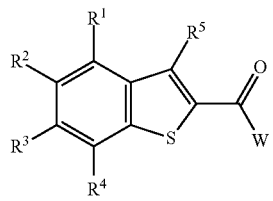

(1)

wherein

W represents —$OR^6$, —ON=$CR^7R^8$, —$SR^9$, or —$NR^7R^{10}$, $R^1$ represents a hydrogen atom, a halogen atom, a nitro group, a C1-C6 alkyl group optionally having one or more groups selected from a group X, a C2-C6 alkenyl group optionally having one or more groups selected from the group X, a C2-C6 alkynyl group optionally having one or more groups selected from the group X, a phenyl group optionally having one or more groups selected from a group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^{11}R^{12}$, —$S(O)_2NR^7R^{11}$, —$OR^{11}$, —$S(O)_mR^{11}$, or —$SF_5$, $R^2$ represents a hydrogen atom, a halogen atom, a cyano group, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^{12}R^{13}$, —$S(O)_2NR^7R^{11}$, —$OR^{13}$, —$S(O)_mR^{13}$, or —$SF_5$, $R^3$ and $R^4$ are the same or different and each represents a hydrogen atom, a halogen atom, a cyano group, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^{11}R^{12}$, —$S(O)_2NR^7R^{11}$, —$OR^{11}$, —$S(O)_mR^{11}$, or —$SF_5$, $R^5$ represents a hydrogen atom, a halogen atom, a cyano group, a nitro group, a C1-C6 alkyl group optionally having one or more groups selected from the group X, a carboxy group, a C2-C6 alkoxycarbonyl group, —$NR^{11}R^{12}$, —$S(O)_2NR^7R^{11}$, —$OR^{14}$, a phenyl group optionally having one or more groups selected from the group Y, a 6-membered aromatic heterocyclic group optionally having one or more groups selected from the group Y, or a 5-membered aromatic heterocyclic group optionally having one or more groups selected from the group Y, $R^6$ represents a C1-C6 alkyl group optionally having one or more groups selected from a group Z, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a phenyl group optionally having one or more groups selected from the group Y, or a C7-C9 phenylalkyl group wherein a benzene ring portion may have optionally one or more groups selected from the group Y, $R^7$ and $R^8$ are the same or different and each represents a C1-C6 alkyl group optionally having one or more halogen atoms, a phenyl group optionally having one or more groups selected from the group Y, or a hydrogen atom, $R^9$ represents a hydrogen atom, a C1-C6 alkyl group optionally having one or more groups selected from the group Z, a C3-C6 alkenyl group optionally having one or more groups selected from the group X, a C3-C6 alkynyl group optionally having one or more groups selected from the group X, a phenyl group optionally having one or more groups selected from the group Y, or a C7-C9 phenylalkyl group wherein a benzene ring portion may have optionally one or more groups selected from the group Y, $R^{10}$ represents a hydrogen atom, a cyano group, a C1-C6 alkyl group optionally having one or more groups selected from the group Z, a phenyl group optionally having one or more groups selected from the group Y, a benzyl group wherein a benzene ring portion may have optionally one or more groups selected from the group Y, —$OR^7$, or —$NR^7R^8$, $R^{11}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C7-C9 phenylalkyl group wherein a benzene ring portion may have optionally one or more groups selected from the group Y, a 6-membered aromatic heterocyclic-C1-C3 alkyl group wherein a 6-membered aromatic heterocyclic portion may have optionally one or more groups selected from the group Y, a phenyl group optionally having one or more groups selected from the group Y, a C3-C6 cycloalkyl group optionally having one or more halogen atoms, or a hydrogen atom (provided that when m in —$S(O)_mR^{11}$ is 1 or 2, $R^{11}$ is not a hydrogen atom), $R^{12}$ represents a hydrogen atom, a C1-C4 alkyl group optionally having one or more halogen atoms, a C1-C4 alkylsulfonyl group optionally having one or more halogen atoms, a phenylsulfonyl group optionally having one or more groups selected from the group Y, a C7-C9 phenylalkylsulfonyl group wherein a benzene ring portion may have optionally one or more groups selected from the group Y, a C2-C6 alkoxycarbonyl group, —$C(O)R^{15}$, or —$C(O)NR^7R^8$, $R^{13}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a C7-C9 phenylalkyl group wherein a benzene ring portion may have optionally one or more groups selected from the group Y, or a hydrogen atom (provided that when m in —$S(O)_mR^{13}$ is 1 or 2, $R^{13}$ is not a hydrogen atom), $R^{14}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a C7-C9 phenylalkyl group wherein a benzene ring portion may have optionally one or more groups selected from the group Y, a phenyl group optionally having one or more groups selected from the group Y, a C2-C6 alkylcarbonyl group optionally having one or more halogen atoms, a benzoyl group optionally having one or more groups selected from the group Y, a C1-C6 alkylsulfonyl group optionally having one or more halogen atoms, a phenylsulfonyl group optionally having one or more groups selected from the group Y, or a hydrogen atom, $R^{15}$ represents a hydrogen atom, a C1-C6 alkyl group optionally having one or more halogen atoms, a phenyl group optionally having one or more groups selected from the group Y, a 5-membered aromatic heterocyclic group optionally having one or more groups selected from the group Y, or a 6-membered aromatic heterocyclic group optionally having one or more groups selected from the group Y, and m represents 0, 1, or 2, the group X represents a group consisting of a halogen atom, a cyano group, and a C1-C6 alkoxy group optionally having one or more halogen atoms, the group Y represents a group consisting of a halogen atom, a cyano group, a nitro group, a C1-C6 alkyl group optionally having one or more halogen atoms, and a C1-C6 alkoxy group optionally having one or more halogen atoms, and the group Z represents a group consisting of a halogen atom, a hydroxy group, a C1-C6 alkoxy group optionally having one or more halogen atoms, and a C2-C6 alkoxycarbonyl group, (hereinafter, described as a "compound of the present invention"), provided that a method for promoting plant growth which comprises treating plants with a compound corresponding to any one of the following (1) to (8) is excluded, (1) Methyl 4-(trifluoromethyl)benzo[b]thiophene-2-carboxylate,
(2) Methyl 5-(trifluoromethyl)benzo[b]thiophene-2-carboxylate,
(3) Methyl 6-(trifluoromethyl)benzo[b]thiophene-2-carboxylate,
(4) Methyl 7-(trifluoromethyl)benzo[b]thiophene-2-carboxylate,
(5) Ethyl 4-(trifluoromethyl)benzo[b]thiophene-2-carboxylate,
(6) Ethyl 5-(trifluoromethyl)benzo[b]thiophene-2-carboxylate,
(7) Ethyl 6-(trifluoromethyl)benzo[b]thiophene-2-carboxylate,
(8) Ethyl 7-(trifluoromethyl)benzo[b]thiophene-2-carboxylate.

[2] The method according to [1], in which the compound represented by Formula (1) is a compound wherein $R^1$ represents a hydrogen atom, a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl croup, —$NR^{11}R^{12}$, —$S(O)_2NR^7R^{11}$, —$OR^{11}$, —$S(O)_mR^{11}$, or —$SF_5$, $R^4$ represents a hydrogen atom, a halogen atom, a cyano group, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, $-NR^{11}R^{12}$, $-S(O)_2NR^7R^{11}$, $-OR^{11}$, $-S(O)_m R^{11}$, or $-SF_5$.

[3] The method according to [1], in which the compound represented by Formula (1) is a compound wherein $R^1$ represents a hydrogen atom, a halogen atom, a nitro group, a C1-C4 alkyl group which may have optionally one or more halogen atoms, a C2-C4 alkenyl group optionally having one or more halogen atoms, a C2-C4 alkynyl group optionally having one or more halogen atoms, a phenyl group optionally having one or more groups selected from the group Y, a pyridyl group optionally having one or more groups selected from the group Y, a pyrimidinyl group optionally having one or more groups selected from the group Y, a thienyl group optionally having one or more groups selected from the group Y, a pyrrolyl group optionally having one or more groups selected from the group Y, a C2-C5 alkylcarbonyl group optionally having one or more halogen atoms, a benzoyl group optionally having one or more groups selected from the group Y, a C2-C4 alkoxycarbonyl group, an aminocarbonyl group, $-NR^{11}R^{12}$, $-OR^{11}$, $-S(O)_m R^{11}$, or $-SF_5$, $R^2$ represents a hydrogen atom, a halogen atom, a cyano group, a nitro group, a C1-C4 alkyl group optionally having one or more halogen atoms, a C2-C4 alkenyl group optionally having one or more halogen atoms, a C2-C4 alkynyl group optionally having one or more halogen atoms, a phenyl group optionally having one or more groups selected from the group Y, a pyridyl group optionally having one or more groups selected from the group Y, a pyrimidinyl group which may have optionally one or more groups selected from the group Y, a thienyl group optionally having one or more groups selected from the group Y, a pyrrolyl group optionally having one or more groups selected from the group Y, a C2-C5 alkylcarbonyl group optionally having one or more halogen atoms, a benzoyl group optionally having one or more groups selected from the group Y, a C2-C4 alkoxycarbonyl group, an aminocarbonyl group, $-NR^{12}R^{13}$, $-OR^{13}$, $-S(O)_m R^{13}$, or $-SF_5$, $R^3$ and $R^4$ are the same or different and each represents a hydrogen atom, a halogen atom, a cyano group, a nitro group, a C1-C4 alkyl group optionally having one or more halogen atoms, a C2-C4 alkenyl group optionally having one or more halogen atoms, a C2-C4 alkynyl group optionally having one or more halogen atoms, a phenyl group optionally having one or more groups selected from the group Y, a pyridyl group optionally having one or more groups selected from the group Y, a pyrimidinyl group optionally having one or more groups selected from the group Y, a thienyl group optionally having one or more groups selected from the group Y, a pyrrolyl group optionally having one or more groups selected from the group Y, a C2-C5 alkylcarbonyl group optionally having one or more halogen atoms, a benzoyl group optionally having one or more groups selected from the group Y, a C2-C4 alkoxycarbonyl group, an aminocarbonyl group, $-NR^{11}R^{12}$, $-OR^{11}$, $-S(O)_m R^{11}$, or $-SF_5$, $R^5$ represents a hydrogen atom, a halogen atom, a cyano group, a nitro group, a C1-C4 alkyl group optionally having one or more halogen atoms, a C2-C5 alkoxycarbonyl group, $-NR^{11}R^{12}$, $-S(O)_2NR^7R^{11}$, $-OR^{14}$, or a phenyl group optionally having one or more groups selected from the group Y, $R^6$ represents a C1-C6 alkyl group optionally having one or more groups selected from the group Z, a C3-C6 alkenyl group optionally having one or more halogen atoms, a C3-C6 alkynyl group optionally having one or more halogen atoms, a phenyl group optionally having one or more groups selected from the group Y, or a C7-C9 phenylalkyl group wherein a benzene ring portion may have optionally one or more groups selected from the group Y, $R^7$ and $R^8$ are the same or different and each represents a C1-C4 alkyl group optionally having one or more halogen atoms, a phenyl group optionally having one or more groups selected from the group Y, or a hydrogen atom, $R^9$ represents a hydrogen atom, a C1-C6 alkyl group optionally having one or more groups selected from the group Z, a C3-C6 alkenyl group optionally having one or more halogen atoms, a C3-C6 alkynyl group optionally having one or more halogen atoms, a phenyl group optionally having one or more groups selected from the group Y, or a C7-C9 phenylalkyl group wherein a benzene ring portion may have optionally one or more groups selected from the group Y, $R^{10}$ represents a hydrogen atom, a cyano group, a C1-C6 alkyl group optionally having one or more groups selected from the group Z, a phenyl group optionally having one or more groups selected from the group Y, $-OR^7$, or $-NR^7R^8$, $R^{11}$ represents a C1-C3 alkyl group optionally having one or more halogen atoms, a C3-C4 alkynyl group optionally having one or more groups selected from the group X, a C7-C9 phenylalkyl group wherein a benzene ring portion may have optionally one or more groups selected from the group Y, a pyridyl-C1-C3 alkyl group wherein a pyridine ring portion may have optionally one or more groups selected from the group Y, a phenyl group optionally having one or more groups selected from the group Y, or a hydrogen atom (provided that when m in $-S(O)_m R^{11}$ is 1 or 2, $R^{11}$ is not a hydrogen atom), $R^{12}$ represents a hydrogen atom, a C1-C4 alkyl group optionally having one or more halogen atoms, a C1-C4 alkylsulfonyl group optionally having one or more halogen atoms, a phenylsulfonyl group optionally having one or more groups selected from the group Y, a benzylsulfonyl group wherein a benzene ring portion may have optionally one or more groups selected from the group Y, $-C(O)R^{15}$, or $-C(O)NR^7R^8$, $R^{13}$ represents a C1-C3 alkyl group optionally having one or more halogen atoms or a hydrogen atom (provided that when m in $-S(O)_m R^{13}$ is 1 or 2, $R^{13}$ is not a hydrogen atom), $R^{14}$ represents a C1-C4 alkyl group optionally having one or more groups selected from the group X, a C3-C6 alkenyl group optionally having one or more halogen atoms, a benzyl group wherein a benzene ring portion may have optionally one or more groups selected from the group Y, a phenyl group optionally having one or more groups selected from the group Y, a C2-C5 alkylcarbonyl group optionally having one or more halogen atoms, a benzoyl group optionally having one or more groups selected from the group Y, a phenylsulfonyl group optionally having one or more groups selected from the group Y, or a hydrogen atom, $R^{15}$ represents a hydrogen atom, a C1-C4 alkyl group optionally having one or more halogen atoms, a phenyl group optionally having one or more groups selected from the group Y, a thienyl group optionally having one or more groups selected from the group Y, a pyrazolyl group optionally having one or more groups selected from the group Y, or an isoxazolyl group optionally having one or more groups selected from the group Y.

[4] The method for promoting plant growth according to any one of [1] to [3], in which the plant is a plant that has been or will be exposed to abiotic stress.

[5] The method according to any one of [1] to [4], in which the application to the plant includes a spraying treatment, a soil treatment, a seed treatment, or a hydroponic treatment.
[6] The method according to any one of [1] to [4], in which the application to the plant is the seed treatment.
[7] The method according to any one of [1] to [6], in which the plant is rice, corn, or wheat.
[8] The method according to any one of [1] to [7], [15] or [16], in which the plant is a transgenic plant.
[9] The method according to any one of [4] to [8], [15] or [16], in which the abiotic stress is high-temperature stress.
[10] The method according to any one of [4] to [8], [15] or [16], in which the abiotic stress is low-temperature stress.
[11] The method according to any one of [4] to [8], [15] or [16], in which the abiotic stress is drought stress.
[12] Use of the compound represented the Formula (1) described in above [1] for promoting plant growth

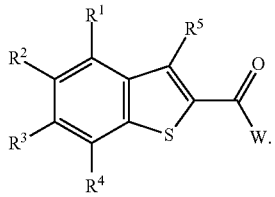

(1)

[13] A plant seed which is obtained by being treated with the compound represented by the Formula (1) described in above [1] in an effective dose,

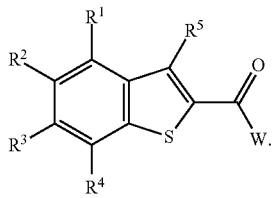

(1)

[14] A composition for promoting plant growth comprising the compound represented by the Formula (1) described in above [1] and inactive ingredients

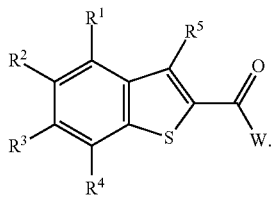

(1)

[15] The method according to any one of [1] to [6], in which the plant is soybean.
[16] The method according to any one of [1] to [6], in which the plant is cotton.

MODE FOR CARRYING OUT THE INVENTION

Herein, the "promotion of the growth of a plant (hereinafter, sometimes described as "growth promotion")" may mean the increase in the rate of seedling establishment, increase in the number of healthy leaves, increase in the height of the plant, increase in the weight of the plant, increase in the leaf area, increase in the number or weight of seeds or fruits, increase in the number of occasion of flower setting or fruit setting, and promoted growth of a root.

The growth promotion may be quantified by the following parameters.

(1) Rate of Seedling Establishment

Seeds of a plant are seeded in, for example, soil, filter paper, an agar medium, or sand and cultured for a certain period of time. Thereafter, the proportion of the surviving seedlings is examined.

(2) Number of Healthy Leaves or Proportion of Healthy Leaves

For each plant, the number of healthy leaves is counted, and the total number of healthy leaves is examined. Alternatively, a ratio of the number of healthy leaves to the total number of the leaves of the plant is examined.

(3) Plant Height

For each plant, a length from the base to the terminal branch or leave of the aerial part is measured.

(4) Plant Weight

The aerial part of each plant is cut and collected, and the weight thereof is measured to determine a fresh weight of the plant. Alternatively, the cut and collected sample is dried, and then a weight thereof is measured to determine a dry weight of the plant.

(5) Leaf Area

A plant is imaged with a digital camera, and the area of the green portion in the picture is quantified by image analysis software, for example, Win ROOF (manufactured by MITANI CORPORATION), or visually evaluated to determine a leaf area of the plant.

(6) Leaf Color

A leaf of a plant is sampled, and an amount of chlorophyll is measured using a chlorophyll meter (for example, SPAD-502, manufactured by Konica Minolta Sensing Europe B.V.) to determine the leaf color. In addition, the plant is imaged with a digital camera, and the area of the green portion in the picture is quantified by performing color extraction by using image analysis software, for example, Win ROOF (manufactured by MITANI CORPORATION), whereby the area of the green portion of the leaf of the plant is determined.

(7) Number or Weight of Seeds or Fruits

A plant is cultured until it produces seeds or fruits or until the seeds or fruits ripen, and then the number of fruits per plant or the total weight of fruits per plant is measured. Moreover, the plant is cultured until the seeds ripen, and then constituents of the yield, for example, the number of ears, ripening rate, and thousand kennel weight, are examined.

(8) Flower Setting Rate, Fruit Setting Rate, Fruition Rate, or Grain Filling Rare A plant is cultured until it fruits, and the number of set flowers and fruits are counted to determine a fruit setting rate (number of set fruit/number of set flower×100). After the seeds ripen, the number of produced fruits and the number of filled grains are counted to determine a fruition rate (number of produced fruit/number of set flower×100) and a grain filling rate (number of filled grain/number of produced fruit×100) respectively.

(9) Promoted Growth of Root

A plant is cultured in soil or cultured hydroponically, and a length of the root is measured. Alternatively, the root is cut and collected, and a fresh weight thereof or the like is measured.

When a plant is treated with the compound of the present invention by the method of the present invention, the whole plant may be treated, or a portion thereof (foliage, a sprout, a flower, a fruit, an ear, a seed, a bulb, a tuber, a root, and the like) may be treated. Moreover, the plant may be treated at various growth stages thereof (a germination period including a pre-seeding stage, a seeding stage, a post-seeding stage, pre- and post-budding stages, and the like, a period of vegetative growth including a seedling stage, a seedling transplant stage, and a pre-cuttage stage or a seedling insertion stage, a growth stage after planting, a reproductive period including a pre-flowering stage, a flowering stage, a post-flowering stage, a stage immediately before emergence of ear, an ear emergence stage, and the like, a harvesting period including a stage prospect of harvest, a stage before prospect of ripening, the period during which fruits start to be colored, and the like). Herein, a bulb refers to a discoid stem, a corm, a rhizome, a tuberous root, a rhizophore, and the like. In addition, a seedling includes a nursery plant raised from a seed, a cuttage, and the like.

Examples of substituents to be used herein are described below with referring to specific examples.

Examples of the "halogen atom" in the compound of the present invention include a fluorine atom, a chlorine atom, a bromine atom, an iodine atom, and the like.

Examples of the "C1-C6 alkyl group" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, a 3,3-dimethylbutyl group, a hexyl group, and the like.

Examples of the "C1-C6 alkyl group optionally having one or more groups selected from the group X" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, a 3,3-dimethylbutyl group, a hexyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, a cyanomethyl group, a 2-cyanoethyl group, a methoxymethyl group, a 2-methoxyethyl group, an ethoxymethyl group, a 2-ethoxyethyl group, a trifluoromethoxymethyl group, a 2,2,2-trifluoroethoxymethyl group, and the like.

Examples of the "C1-C6 alkyl group optionally having one or more groups selected from the group Z" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, 3,3-dimethylbutyl group, a hexyl group, a trichloromethyl group, a difluoromethyl group, a trifluoromethyl group, a 2,2,2-trifluoroethyl group, a pentafluoroethyl group, a pentafluoropropyl group, a heptafluoroisopropyl group, a 2-hydroxyethyl group, a methoxymethyl group, a 2-methoxyethyl group, an ethoxymethyl group, a 2-ethoxyethyl group, a trifluoromethoxymethyl group, a 2,2,2-trifluoroethoxyethyl group, a methoxycarbonylmethyl group, and the like.

Examples of the "C1-C6 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a pentyl group, a 2,2-dimethylpropyl group, a 3-methylbutyl group, a 2,3-dimethylbutyl group, a 3,3-dimethylbutyl group, a hexyl group, a chloromethyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, and the like.

Example of the "C1-C4 alkyl group" in the compound of the present invention include a methyl group, an ethyl group, a propyl group, an isopropyl group, a butyl group, an isobutyl group, a sec-butyl group, and a tert-butyl group.

Examples of the "C1-C4 alkyl group optionally having one or more groups selected from the group X" in the compound of the present invention include a methyl group, an ethyl group, a propyl group, an isopropyl group, a butyl group, an isobutyl group, a sec-butyl group, a tert-butyl group, a chloromethyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, a cyanomethyl group, a 2-cyanomethyl group, a methoxymethyl group, a 2-methoxyethyl group, an ethoxymethyl group, a 2-ethoxyethyl group, a trifluoromethoxymethyl group, a 2,2,2-trifluoroethoxymethyl group, and the like.

Examples of the "C1-C4 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a trichloromethyl group, a difluoromethyl group, a trifluoromethyl group, a 2,2,2-trifluoroethyl group, a pentafluoroethyl group, a heptafluoropropyl group, a heptafluoroisopropyl group, and the like.

Examples of the "C1-C3 alkyl group" in the compound of the present invention include a methyl group, an ethyl group, a propyl group, and an isopropyl group.

Examples of the "C1-C3 alkyl group optionally having one or more halogen atoms" in the compound of the present invention include a methyl group, an ethyl group, a propyl group, an isopropyl group, a difluoromethyl group, a trifluoromethyl group, a 2,2,2-trifluoroethyl group, a pentafluoroethyl group, a heptafluoropropyl group, a heptafluoroisopropyl group, and the like.

Examples of the "C4-C7 cycloalkylalkyl group" in the compound of the present invention include a cyclopropyl methyl group, a 1-cyclopropyl ethyl group, a 2-cyclopropyl ethyl group, a cyclobutyl methyl group, a 1-cyclobutyl ethyl group, a cyclopentyl methyl group, a cyclohexyl methyl group, and the like.

Examples of the "C4-C7 cycloalkyl alkyl group optionally having one or more halogen atoms" in the compound of the present invention include a cyclopropylmethyl group, a 1-cyclopropylethyl group, a 2-cyclopropylethyl group, a cyclobutylmethyl group, a 1-cyclobutylethyl group, a cyclopentylmethyl group, a cyclohexylmethyl group, a 2,2-difluorocyclopropylmethyl group, a 1-(2,2-dichlorocyclopropyl)ethyl group, a 2,2-dibromocyclobutylmethyl group, a 2-chlorocyclopentylmethyl group, and the like.

Examples of the "C3-C6 cycloalkyl group" in the compound of the present invention include a cyclopropyl group, a cyclobutyl group, a cyclopentyl group, a cyclohexyl group, and the like.

Examples of the "C3-C6 cycloalkyl group optionally having one or more halogen atoms" in the compound of the present invention include a cyclopropyl group, a cyclobutyl group, a cyclopentyl group, a cyclohexyl group, a 2,2- difluorocyclopropyl group, a 2,2-dichlorocyclopropyl group, a 2-chlorocyclopentyl group, a 4-iodocyclohexyl group, and the like.

Examples of the "C2-C6 alkenyl group" in the compound of the present invention include a vinyl group, a 1-propenyl group, an allyl group, an isopropenyl group, a 2-methyl-1-propenyl group, a 1-butenyl group, a 2-butenyl group, a 3-butenyl group, a 1-pentenyl group, a 1-hexenyl group, and the like.

Examples of the "C2-C6 alkenyl group optionally having one or more groups selected from the group X" in the compound of the present invention include a vinyl group, a 1-propenyl group, an allyl group, an isopropenyl group, a 2-methyl-1-propenyl group, a 1-butenyl group, a 2-butenyl group, a 3-butenyl group, a 1-pentenyl group, a 1-hexenyl group, a 2,2-difluoroethenyl group, a 2,2-dichloroethenyl group, a 2-cyano-1-ethenyl group, a 2-methoxy-1-ethenyl group, a 2-ethoxy-1-ethenyl group, a 3,3-difluoro-2-propenyl group, a 3,3-dichloro-2-propenyl group, a 4-methoxy-2-methyl-2-butenyl group, a 3-cyano-2-butenyl group, and the like.

Examples of the "C3-C6 alkenyl group" in the compound of the present invention include an allyl group, a 1-methyl-2-propenyl group, a 2-methyl-2-propenyl group, a 2-butenyl group, a 3-butenyl group, a 2-pentenyl group, a 4-pentenyl group, a 2-hexenyl group, a 5-hexenyl group, and the like.

Examples of the "C3-C6 alkenyl group optionally having one or more groups selected from the group X" in the compound of the present invention include an allyl group, a 1-methyl-2-propenyl group, a 2-methyl-2-propenyl group, a 2-butenyl group, a 3-butenyl group, a 2-pentenyl group, a 4-pentenyl group, a 2-hexenyl group, a 5-hexenyl group, a 3,3-difluoro-2-propenyl group, a 3,3-dichloro-2-propenyl group, a 4-methoxy-2-methyl-2-butenyl group, a 3-cyano-2-butenyl group, and the like.

Examples of the "C3-C6 alkenyl group optionally having one or more halogen atoms" in the compound of the present invention include a 2-propenyl group, a 1-methyl-2-propenyl group, a 2-methyl-2-propenyl group, a 2-butenyl group, a 3-butenyl group, a 2-pentenyl group, a 4-pentenyl group, a 2-hexenyl group, a 5-hexenyl group, a 3,3-difluoro-2-propenyl group, a 3,3-dichloro-2-propenyl group, and the like.

Examples of the "C2-C4 alkenyl group" in the compound of the present invention include a vinyl group, a 1-propenyl group, an allyl group, an isopropenyl group, a 2-methyl-1-propenyl group, a 1-butenyl group, a 2-butenyl group, a 3-butenyl group, and the like.

Examples of the "C2-C4 alkenyl group optionally having one or more halogen atoms" in the compound of the present invention include a vinyl group, a 1-propenyl group, an allyl group, an isopropenyl group, a 2-methyl-1-propenyl group, a 1-butenyl group, a 2-butenyl group, a 3-butenyl group, a 2,2-difluoroethenyl group, a 2,2-dichloroethenyl group, a 3,3-difluoro-2-propenyl group, a 3,3-dichloro-2-propenyl group, and the like.

Examples of the "C2-C6 alkynyl group" in the compound of the present invention include an ethynyl group, a 1-propynyl group, a propargyl group, a 1-butynyl group, a 2-butynyl group, a 3-butynyl group, a 3,3-dimethyl-1-butynyl group, a 1-pentynyl group, a 2-pentynyl group, a 1-hexynyl group, and the like.

Examples of the "C2-C6 alkynyl group optionally having one or more groups selected from the group X" in the compound of the present invention include an ethynyl group, a propargyl group, a 1-propynyl group, a 1-butynyl group, a 2-butynyl group, a 3-butynyl group, a 3,3-dimethyl-1-butynyl group, a 1-pentynyl group, a 1-hexynyl group, a 4-chloro-2-butynyl group, a 4-cyano-2-butynyl group, a 5-cyano-2-pentynyl group, a 4-methoxy-2-butynyl group, a 4-(2-chloroethoxy)-2-butynyl group, and the like.

Examples of the "C3-C6 alkynyl group" in the compound of the present invention include a propargyl group, a 2-butynyl group, a 3-butynyl group, a 2-pentynyl group, a 4-pentynyl group, a 2-hexynyl group, a 5-hexynyl group, and the like.

Examples of the "C3-C6 alkynyl group optionally having one or more groups selected from the group X" in the compound of the present invention include a propargyl group, a 2-butynyl group, a 3-butynyl group, a 2-pentynyl group, a 2-hexynyl group, a 4-chloro-2-butynyl group, a 4-cyano-2-butynyl group, a 5-cyano-2-pentynyl group, a 4-methoxy-2-butynyl group, a 4-(2-chloroethoxy)-2-butynyl group, and the like.

Examples of the "C3-C6 alkynyl group optionally having one or more halogen atoms" in the compound of the present invention include a propargyl group, a 2-butynyl group, a 3-butynyl group, a 3,3-dimethyl-1-butynyl group, a 2-pentynyl group, a 4-pentynyl group, a 2-hexynyl group, a 5-hexynyl group, a 4-chloro-2-butynyl group, and the like.

Examples of the "C2-C4 alkynyl group" in the compound of the present invention include an ethynyl group, a propargyl group, a 1-propynyl group, a 1-butynyl group, a 2-butynyl group, a 3-butynyl group, and the like.

Examples of the "C2-C4 alkynyl group optionally having one or more halogen atoms" in the compound of the present invention include an ethynyl group, a propargyl group, a 1-propynyl group, a 1-butynyl group, a 2-butynyl group, a 3-butynyl group, a 4-chloro-2-butynyl group, and the like.

Examples of the "C3-C4 alkynyl group" in the compound of the present invention include a propargyl group, a 2-butynyl group, a 3-butynyl group, and the like.

Examples of the "C3-C4 alkynyl group optionally having one or more groups selected from the group X" in the compound of the present invention include a propargyl group, a 2-butynyl group, a 3-butynyl group, a 4-chloro-2-butynyl group, a 4-methoxy-2-butynyl group, and the like.

Examples of the "phenyl group optionally having one or more groups selected from the group Y" in the compound of the present invention include a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-isopropylphenyl group, a 3-isopropylphenyl group, a 4-isopropylphenyl group, a 2-butylphenyl group, a 3-butylphenyl group, a 4-butylphenyl group, a 2-isobutylphenyl group, a 3-isobutylphenyl group, a 4-isobutylphenyl group, a 3-tert-butylphenyl group, a 4-tert-butylphenyl group, a 2-difluoromethylphenyl group, a 3-difluoromethylphenyl group, a 4-difluoromethylphenyl group, a 2-trifluoromethylphenyl group, a 3-trifluoromethylphenyl group, a 4-trifluoromethylphenyl group, a 2-(2,2,2-trifluoroethyl)phenyl group, a 3-(2,2,2-trifluoroethyl)phenyl group, a 4-(2,2,2-trifluoroethyl)phenyl group, a 2-pentafluoroethylphenol group, a 3-pentafluoroethylphenol group, a 4-pentafluoroethylphenyl group, a 2-heptafluoropropylphenyl group, a 3-heptafluoropropylphenyl group, a 4-heptafluoropropylphenyl group, a 2-heptafluoroisopropylphenyl group, a 3-heptafluoroisopropylphenyl group, a 4-heptafluoroisopropylphenyl group, a 2-methoxyphenyl group, a 3-methoxyphenyl group, a 4-methoxyphenyl group, a 2-tert-butoxyphenyl group, a 3-tert-butoxyphenyl group, a 4-tert-butoxyphenyl group, a 2-pentyloxyphenyl group, a 3-pentyloxyphenyl group, a 4-pentyloxyphenyl group, a 2-(2,2-dimethoxypropoxy)phenyl group, a 3-(2,2-dimethoxypropoxy)phenyl group, a 4-(2,2-dimethoxypropoxy)phenyl group, a 2-(3-methylbutoxy)phenyl group, a 3-(3-methylbutoxy)phenyl group, a 4-(3-methylbutoxy)phenyl group, a 2-difluoromethoxyphenyl group, a 3-difluoromethoxyphenyl group, a 4-difluoromethoxyphenyl group, a 2-trifluoromethoxyphenyl group, a 3-trifluoromethoxyphenyl group, a 4-trifluoromethoxyphenyl group, a 4-(2,2,2-trifluoroethoxy)phenyl group, a 2,4-dimethoxyphenyl group, a 3-chloro-4-methylphenyl group, and the like.

Examples of the "C7-C9 phenylalkyl group" in the compound of the present invention include a benzyl group, a 1-phenylethyl group, a 2-phenylethyl group, a 1-phenylpropyl group, a 2-phenylpropyl group, a 3-phenylpropyl group, a 1-methyl-1-phenylethyl group, and the like.

Examples of the "C7-C9 phenylalkyl group wherein a benzene ring portion may have optionally one or more groups selected from the group Y" in the compound of the present invention include a benzyl group, a 2-fluorobenzyl group, a 3-chlorobenzyl group, a 3-methoxybenzyl group, a 4-chlorobenzyl group, a 4-methylbenzyl group, a 4-trifluoromethyl group, a 1-(3-chlorophenyl)ethyl group, a 2-(4-bromophenyl)ethyl group, a 1-(2-cyanophenyl)propyl group, a 2-(3-nitrophenyl)propyl group, a 3-(3-methoxyphenyl)propyl group, a 1-methyl-1-(4-trifluoromethoxyphenyl)ethyl group, and the like.

Examples of the "benzyl group wherein a benzene ring portion may have optionally one or more groups selected from the group Y" in the compound of the present invention include a 2-fluorobenzyl group, a 3-chlorobenzyl group, a 4-bromobenzyl group, a 2-cyanobenzyl group, a 3-nitrobenzyl group, a 3-methoxybenzyl group, a 4-trifluoromethoxybenzyl group, a 4-chlorobenzyl group, a 4-methylbenzyl group, a 4-trifluoromethylbenzyl group, and the like.

Examples of the "6-membered aromatic heterocyclic group" in the compound of the present invention include a 2-pyridyl group, a 3-pyridyl group, a 4-pyridyl group, a 3-pyridazinyl group, a 4-pyridazinyl group, a 2-pyrimidinyl group, a 4-pyrimidinyl group, a 5-pyrimidinyl group, a 2-pyrazinyl group, a 4-(1,2,3-triazinyl) group, a 5-(1,2,3-triazinyl) group, a 3-(1,2,4-triazinyl) group, a 5-(1,2,4-triazinyl) group, a 6-(1,2,4-triazinyl) group, and a 2-(1,3,5-triazinyl) group, and the like.

Examples of the "6-membered aromatic heterocyclic group optionally having one or more groups selected from the group Y" in the compound of the present invention include a 2-pyridyl group, a 3-fluoro-2-pyridyl group, a 4-fluoro-2-pyridyl group, a 5-fluoro-2-pyridyl group, a 6-fluoro-2-pyridyl group, a 3-chloro-2-pyridyl group, a 4-chloro-2-pyridyl group, a 5-chloro-2-pyridyl group, a 6-chloro-2-pyridyl group, a 3-bromo-2-pyridyl group, a 4-bromo-2-pyridyl group, a 5-bromo-2-pyridyl group, a 6-bromo-2-pyridyl group, a 3-iodo-2-pyridyl group, a 4-iodo-2-pyridyl group, a 5-iodo-2-pyridyl group, a 6-iodo-2-pyridyl group, a 3-cyano-2-pyridyl group, a 4-cyano-2-pyridyl group, a 5-cyano-2-pyridyl group, a 6-cyano-2-pyridyl group, a 3-nitro-2-pyridyl group, a 4-nitro-2-pyridyl group, a 5-nitro-2-pyridyl group, a 6-nitro-2-pyridyl group, a 3-methyl-2-pyridyl group, a 4-methyl-2-pyridyl group, a 5-methyl-2-pyridyl group, a 6-methyl-2-pyridyl group, a 3-ethyl-2-pyridyl group, a 4-ethyl-2-pyridyl group, a 5-ethyl-2-pyridyl group, a 6-ethyl-2-pyridyl group, a 3-propyl-2-pyridyl group, a 4-propyl-2-pyridyl group, a 5-propyl-2-pyridyl group, a 6-propyl-2-pyridyl group, a 3-isopropyl-2-pyridyl group, a 4-isopropyl-2-pyridyl group, a 5-isopropyl-2-pyridyl group, a 6-isopropyl-2-pyridyl group, a 3-butyl-2-pyridyl group, a 4-butyl-2-pyridyl group, a 5-butyl-2-pyridyl group, a 6-butyl-2-pyridyl group, a 3-isobutyl-2-pyridyl group, a 4-isobutyl-2-pyridyl group, a 5-isobutyl-2-pyridyl group, a 6-isobutyl-2-pyridyl group, a 3-sec-butyl-2-pyridyl group, a 4-sec-butyl-2-pyridyl group, a 5-sec-butyl-2-pyridyl group, a 6-sec-butyl-2-pyridyl group, a 3-tert-butyl-2-pyridyl group, a 4-tert-butyl-2-pyridyl group, a 5-tert-butyl-2-pyridyl group, a 6-tert-butyl-2-pyridyl group, a 3-difluoromethyl-2-pyridyl group, a 4-difluoromethyl-2-pyridyl group, a 5-difluoromethyl-2-pyridyl group, a 6-difluoromethyl-2-pyridyl group, a 3-trifluoromethyl-2-pyridyl group, a 4-trifluoromethyl-2-pyridyl group, a 5-trifluoromethyl-2-pyridyl group, a 6-trifluoromethyl-2-pyridyl group, a 3-(2,2,2-trifluoroethyl)-2-pyridyl group, a 4-(2,2,2-trifluoroethyl)-2-pyridyl group, a 5-(2,2,2-trifluoroethyl)-2-pyridyl group, a 6-(2,2,2-trifluoroethyl)-2-pyridyl group, a 3-pentafluoroethyl-2-pyridyl group, a 4-pentafluoroethyl-2-pyridyl group, a 5-pentafluoroethyl-2-pyridyl group, a 6-pentafluoroethyl-2-pyridyl group, a 3-heptafluoropropyl-2-pyridyl group, a 4-heptafluoropropyl-2-pyridyl group, a 5-heptafluoropropyl-2-pyridyl group, a 6-heptafluoropropyl-2-pyridyl group, a 3-heptafluoroisopropyl-2-pyridyl group, a 4-heptafluoroisopropyl-2-pyridyl group, a 5-heptafluoroisopropyl-2-pyridyl group, a 6-heptafluoroisopropyl-2-pyridyl group, a 3-pyridyl group, a 2-methyl-3-pyridyl group, a 4-methyl-3-pyridyl group, a 5-methyl-3-pyridyl group, a 6-methyl-3-pyridyl group, a 2-ethyl-3-pyridyl group, a 4-ethyl-3-pyridyl group, a 5-ethyl-3-pyridyl group, a 6-ethyl-3-pyridyl group, a 2-propyl-3-pyridyl group, a 4-propyl-3-pyridyl group, a 5-propyl-3-pyridyl group, a 6-propyl-3-pyridyl group, a 2-isopropyl-3-pyridyl group, a 4-isopropyl-3-pyridyl group, a 5-isopropyl-3-pyridyl group, a 6-isopropyl-3-pyridyl group, a 2-butyl-3-pyridyl group, a 4-butyl-3-pyridyl group, a 5-butyl-3-pyridyl group, a 6-butyl-3-pyridyl group, a 2-isobutyl-3-pyridyl group, a 4-isobutyl-3-pyridyl group, a 5-isobutyl-3-pyridyl group, a 6-isobutyl-3-pyridyl group, a 2-sec-butyl-3-pyridyl group, a 4-sec-butyl-3-pyridyl group, a 5-sec-butyl-3-pyridyl group, a 6-sec-butyl-3-pyridyl group, a 2-tert-butyl-3-pyridyl group, a 4-tert-butyl-3-pyridyl group, a 5-tert-butyl-3-pyridyl group, a 6-tert-butyl-3-pyridyl group, a 2-difluoromethyl-3-pyridyl group, a 4-difluoromethyl-3-pyridyl group, a 5-difluoromethyl-3-pyridyl group, a 6-difluoromethyl-3-pyridyl group, a 2-trifluoromethyl-3-pyridyl group, a 4-trifluoromethyl-3-pyridyl group, a 5-trifluoromethyl-3-pyridyl group, a 6-trifluoromethyl-3-pyridyl group, a 2-(2,2,2-trifluoroethyl)-3-pyridyl group, a 4-(2,2,2-trifluoroethyl)-3-pyridyl group, a 5-(2,2,2-trifluoroethyl)-3-pyridyl group, a 6-(2,2,2-trifluoroethyl)-3-pyridyl group, a 2-pentafluoroethyl-3-pyridyl group, a 4-pentafluoroethyl-3-pyridyl group, a 5-pentafluoroethyl-3-pyridyl group, a 6-pentafluoroethyl-3-pyridyl group, a 2-heptafluoropropyl-3-pyridyl group, a 4-heptafluoropropyl-3-pyridyl group, a 5-heptafluoropropyl-3-pyridyl group, a 6-heptafluoropropyl-3-pyridyl group, a 2-heptafluoroisopropyl-3-pyridyl group, a 4-heptafluoroisopropyl-3-pyridyl group, a 5-heptafluoroisopropyl-3-pyridyl group, a 6-heptafluoroisopropyl-3-pyridyl group, a 4-pyridyl group, a 2-methyl-4-pyridyl group, a 3-methyl-4-pyridyl group, a 2-ethyl-4-pyridyl group, a 3-ethyl-4-pyridyl group, a 2-propyl-4-pyridyl group, a 3-propyl-4-pyridyl group, a 2-isopropyl-4-pyridyl group, a 3-isopropyl-4-pyridyl group, a 2-butyl-4-pyridyl group, a 3-butyl-4- pyridyl group, a 2-isobutyl-4-pyridyl group, a 3-isobutyl-4-pyridyl group, a 2-sec-butyl-4-pyridyl group, a 3-sec-butyl-4-pyridyl group, a 2-tert-butyl-4-pyridyl group, a 3-tert-butyl-4-pyridyl group, a 2-difluoromethyl-4-pyridyl group, a 3-difluoromethyl-4-pyridyl group, a 2-trifluoromethyl-4-pyridyl group, a 3-trifluoromethyl-4-pyridyl group, a 2-(2,2,2-trifluoroethyl)-4-pyridyl group, a 3-(2,2,2-trifluoroethyl)-4-pyridyl group, a 2-pentafluoroethyl-4-pyridyl group, a 3-pentafluoroethyl-4-pyridyl group, a 2-heptafluoropropyl-4-pyridyl group, a 3-heptafluoropropyl-4-pyridyl group, a 2-heptafluoroisopropyl-4-pyridyl group, a 3-heptafluoroisopropyl-4-pyridyl group, a 3-pyridazinyl group, a 4-methyl-3-pyridazinyl group, a 5-methyl-3-pyridazinyl group, a 6-methyl-3-pyridazinyl group, a 4-ethyl-3-pyridazinyl group, a 5-ethyl-3-pyridazinyl group, a 6-ethyl-3-pyridazinyl group, a 4-propyl-3-pyridazinyl group, a 5-propyl-3-pyridazinyl group, a 6-propyl-3-pyridazinyl group, a 4-isopropyl-3-pyridazinyl group, a 5-isopropyl-3-pyridazinyl group, a 6-isopropyl-3-pyridazinyl group, a 4-butyl-3-pyridazinyl group, a 5-butyl-3-pyridazinyl group, a 6-butyl-3-pyridazinyl group, a 4-isobutyl-3-pyridazinyl group, a 5-isobutyl-3-pyridazinyl group, a 6-isobutyl-3-pyridazinyl group, a 4-sec-butyl-3-pyridazinyl group, a 5-sec-butyl-3-pyridazinyl group, a 6-sec-butyl-3-pyridazinyl group, a 4-tert-butyl-3-pyridazinyl group, a 5-tert-butyl-3-pyridazinyl group, a 6-tert-butyl-3-pyridazinyl group, a 4-difluoromethyl-3-pyridazinyl group, a 5-difluoromethyl-3-pyridazinyl group, a 6-difluoromethyl-3-pyridazinyl group, a 4-trifluoromethyl-3-pyridazinyl group, a 5-trifluoromethyl-3-pyridazinyl group, a 6-trifluoromethyl-3-pyridazinyl group, a 4-(2,2,2-trifluoroethyl)-3-pyridazinyl group, a 5-(2,2,2-trifluoroethyl)-3-pyridazinyl group, a 6-(2,2,2-trifluoroethyl)-3-pyridazinyl group, a 4-pentafluoroethyl-3-pyridazinyl group, a 5-pentafluoroethyl-3-pyridazinyl group, a 6-pentafluoroethyl-3-pyridazinyl group, a 4-heptafluoropropyl-3-pyridazinyl group, a 5-heptafluoropropyl-3-pyridazinyl group, a 6-heptafluoropropyl-3-pyridazinyl group, a 4-heptafluoroisopropyl-3-pyridazinyl group, a 5-heptafluoroisopropyl-3-pyridazinyl group, a 6-heptafluoroisopropyl-3-pyridazinyl group, a 6-chloro-3-pyridazinyl group, a 6-methoxy-3-pyridazinyl group, a 6-cyano-3-pyridazinyl group, a 4-pyridazinyl group, a 3-methyl-4-pyridazinyl group, a 5-methyl-4-pyridazinyl group, a 6-methyl-4-pyridazinyl group, a 3-ethyl-4-pyridazinyl group, a 5-ethyl-4-pyridazinyl group, a 6-ethyl-4-pyridazinyl group, a 3-propyl-4-pyridazinyl group, a 5-propyl-4-pyridazinyl group, a 6-propyl-4-pyridazinyl group, a 3-isopropyl-4-pyridazinyl group, a 5-isopropyl-4-pyridazinyl group, a 6-isopropyl-4-pyridazinyl group, a 3-butyl-4-pyridazinyl group, a 5-butyl-4-pyridazinyl group, a 6-butyl-4-pyridazinyl group, a 3-isobutyl-4-pyridazinyl group, a 5-isobutyl-4-pyridazinyl group, a 6-isobutyl-4-pyridazinyl group, a 3-sec-butyl-4-pyridazinyl group, a 5-sec-butyl-4-pyridazinyl group, a 6-sec-butyl-4-pyridazinyl group, a 3-tert-butyl-4-pyridazinyl group, a 5-tert-butyl-4-pyridazinyl group, a 6-tert-butyl-4-pyridazinyl group, a 3-difluoromethyl-4-pyridazinyl group, a 5-difluoromethyl-4-pyridazinyl group, a 6-difluoromethyl-4-pyridazinyl group, a 3-trifluoromethyl-4-pyridazinyl group, a 5-trifluoromethyl-4-pyridazinyl group, a 6-trifluoromethyl-4-pyridazinyl group, a 3-(2,2,2-trifluoroethyl)-4-pyridazinyl group, a 5-(2,2,2-trifluoroethyl)-4-pyridazinyl group, a 6-(2,2,2-trifluoroethyl)-4-pyridazinyl group, a 3-pentafluoroethyl-4-pyridazinyl group, a 5-pentafluoroethyl-4-pyridazinyl group, a 6-pentafluoroethyl-4-pyridazinyl group, a 3-heptafluoropropyl-4-pyridazinyl group, a 5-heptafluoropropyl-4-pyridazinyl group, a 6-heptafluoropropyl-4-pyridazinyl group, a 3-heptafluoroisopropyl-4-pyridazinyl group, a 5-heptafluoroisopropyl-4-pyridazinyl group, a 6-heptafluoroisopropyl-4-pyridazinyl group, a 2-pyrimidinyl group, a 4-methyl-2-pyrimidinyl group, a 5-methyl-2-pyrimidinyl group, a 4-ethyl-2-pyrimidinyl group, a 5-ethyl-2-pyrimidinyl group, a 4-propyl-2-pyrimidinyl group, a 5-propyl-2-pyrimidinyl group, a 4-isopropyl-2-pyrimidinyl group, a 5-isopropyl-2-pyrimidinyl group, a 4-butyl-2-pyrimidinyl group, a 5-butyl-2-pyrimidinyl group, a 4-isobutyl-2-pyrimidinyl group, a 5-isobutyl-2-pyrimidinyl group, a 4-sec-butyl-2-pyrimidinyl group, a 5-sec-butyl-2-pyrimidinyl group, a 4-tert-butyl-2-pyrimidinyl group, a 5-tert-butyl-2-pyrimidinyl group, a 4-difluoromethyl-2-pyrimidinyl group, a 5-difluoromethyl-2-pyrimidinyl group, a 4-trifluoromethyl-2-pyrimidinyl group, a 5-trifluoromethyl-2-pyrimidinyl group, a 4-(2,2,2-trifluoroethyl)-2-pyrimidinyl group, a 5-(2,2,2-trifluoroethyl)-2-pyrimidinyl group, a 4-pentafluoroethyl-2-pyrimidinyl group, a 5-pentafluoroethyl-2-pyrimidinyl group, a 4-heptafluoropropyl-2-pyrimidinyl group, a 5-heptafluoropropyl-2-pyrimidinyl group, a 4-heptafluoroisopropyl-2-pyrimidinyl group, a 5-heptafluoroisopropyl-2-pyrimidinyl group, a 4-chloro-2-pyrimidinyl group, a 5-chloro-2-pyrimidinyl group, a 4-cyano-2-pyrimidinyl group, a 5-cyano-2-pyrimidinyl group, a 5-nitro-2-pyrimidinyl group, a 4-pyrimidinyl group, a 2-methyl-4-pyrimidinyl group, a 5-methyl-4-pyrimidinyl group, a 6-methyl-4-pyrimidinyl group, a 2-ethyl-4-pyrimidinyl group, a 5-ethyl-4-pyrimidinyl group, a 6-ethyl-4-pyrimidinyl group, a 2-propyl-4-pyrimidinyl group, a 5-propyl-4-pyrimidinyl group, a 6-propyl-4-pyrimidinyl group, a 2-isopropyl-4-pyrimidinyl group, a 5-isopropyl-4-pyrimidinyl group, a 6-isopropyl-4-pyrimidinyl group, a 2-butyl-4-pyrimidinyl group, a 5-butyl-4-pyrimidinyl group, a 6-butyl-4-pyrimidinyl group, a 2-isobutyl-4-pyrimidinyl group, a 5-isobutyl-4-pyrimidinyl group, a 6-isobutyl-4-pyrimidinyl group, a 2-sec-butyl-4-pyrimidinyl group, a 5-sec-butyl-4-pyrimidinyl group, a 6-sec-butyl-4-pyrimidinyl group, a 2-tert-butyl-4-pyrimidinyl group, a 5-tert-butyl-4-pyrimidinyl group, a 6-tert-butyl-4-pyrimidinyl group, a 2-difluoromethyl-4-pyrimidinyl group, a 5-difluoromethyl-4-pyrimidinyl group, a 6-difluoromethyl-4-pyrimidinyl group, a 2-trifluoromethyl-4-pyrimidinyl group, a 5-trifluoromethyl-4-pyrimidinyl group, a 6-trifluoromethyl-4-pyrimidinyl group, a 2-(2,2,2-trifluoroethyl)-4-pyrimidinyl group, a 5-(2,2,2-trifluoroethyl)-4-pyrimidinyl group, a 6-(2,2,2-trifluoroethyl)-4-pyrimidinyl group, a 2-heptafluoroethyl-4-pyrimidinyl group, a 5-heptafluoroethyl-4-pyrimidinyl group, a 6-heptafluoroethyl-4-pyrimidinyl group, a 2-heptafluoropropyl-4-pyrimidinyl group, a 5-heptafluoropropyl-4-pyrimidinyl group, a 6-heptafluoropropyl-4-pyrimidinyl group, a 2-heptafluoroisopropyl-4-pyrimidinyl group, a 5-heptafluoroisopropyl-4-pyrimidinyl group, a 6-heptafluoroisopropyl-4-pyrimidinyl group, a 2-chloro-4-pyrimidinyl group, a 2-cyano-4-pyrimidinyl group, a 5-chloro-4-pyrimidinyl group, a 5-cyano-4-pyrimidinyl group, a 5-nitro-4-pyrimidinyl group, a 5-pyrimidinyl group, a 2-methyl-5-pyrimidinyl group, a 4-methyl-5-pyrimidinyl group, a 2-ethyl-5-pyrimidinyl group, a 4-ethyl-5-pyrimidinyl group, a 2-propyl-5-pyrimidinyl group, a 4-propyl-5-pyrimidinyl group, a 2-isopropyl-5-pyrimidinyl group, a 4-isopropyl-5-pyrimidinyl group, a 2-butyl-5-pyrimidinyl group, a 4-butyl-5-pyrimidinyl group, a 2-isobutyl-5-pyrimidinyl group, a 4-isobutyl-5-pyrimidinyl group, a 2-sec-butyl-5-pyrimidinyl group, a 4-sec-butyl-5-pyrimidinyl group, a 2-tert-butyl-5-pyrimidinyl group, a 4-tert-butyl-5-pyrimidinyl group, a 2-difluoromethyl-5-pyrimidinyl group, a 4-difluoromethyl-5-pyrimidinyl group, a 2-trifluromethyl-5-pyrimidinyl group, a 4-trifluromethyl-5-pyrimidinyl group, a 2-(2,2,2-trifluoroethyl)-5-pyrimidinyl group, a 4-(2,2,2-trifluoroethyl)-5-pyrimidinyl group, a 2-pentafluoroethyl-5-pyrimidinyl group, a 4-pentafluoroethyl-5-pyrimidinyl group, a 2-heptafluoropropyl-5-pyrimidinyl group, a 4-heptafluoropropyl-5-pyrimidinyl group, a 2-heptafluoroisopropyl-5-pyrimidinyl group, a 4-heptafluoroisopropyl-5-pyrimidinyl group, a 2-pyrazinyl group, a 3-methyl-2-pyrazinyl group, a 5-methyl-2-pyrazinyl group, a 6-methyl-2-pyrazinyl group, a 3-ethyl-2-pyrazinyl group, a 5-ethyl-2-pyrazinyl group, a 6-ethyl-2-pyrazinyl group, a 3-propyl-2-pyrazinyl group, a 5-propyl-2-pyrazinyl group, a 6-propyl-2-pyrazinyl group, a 3-isopropyl-2-pyrazinyl group, a 5-isopropyl-2-pyrazinyl group, a 6-isopropyl-2-pyrazinyl group, a 3-butyl-2-pyrazinyl group, a 5-butyl-2-pyrazinyl group, a 6-butyl-2-pyrazinyl group, a 3-isobutyl-2-pyrazinyl group, a 5-isobutyl-2-pyrazinyl group, a 6-isobutyl-2-pyrazinyl group, a 3-sec-butyl-2-pyrazinyl group, a 5-sec-butyl-2-pyrazinyl group, a 6-sec-butyl-2-pyrazinyl group, a 3-tert-butyl-2-pyrazinyl group, a 5-tert-butyl-2-pyrazinyl group, a 6-tert-butyl-2-pyrazinyl group, a 3-difluoromethyl-2-pyrazinyl group, a 5-difluoromethyl-2-pyrazinyl group, a 6-difluoromethyl-2-pyrazinyl group, a 3-trifluoromethyl-2-pyrazinyl group, a 5-trifluoromethyl-2-pyrazinyl group, a 6-trifluoromethyl-2-pyrazinyl group, a 3-(2,2,2-trifluoroethyl)-2-pyrazinyl group, a 5-(2,2,2-trifluoroethyl)-2-pyrazinyl group, a 6-(2,2,2-trifluoroethyl)-2-pyrazinyl group, a 3-pentafluoroethyl-2-pyrazinyl group, a 5-pentafluoroethyl-2-pyrazinyl group, a 6-pentafluoroethyl-2-pyrazinyl group, a 3-heptafluoropropyl-2-pyrazinyl group, a 5-heptafluoropropyl-2-pyrazinyl group, a 6-heptafluoropropyl-2-pyrazinyl group, a 3-heptafluoroisopropyl-2-pyrazinyl group, a 5-heptafluoroisopropyl-2-pyrazinyl group, a 6-heptafluoroisopropyl-2-pyrazinyl group, a 3-chloro-2-pyrazinyl group, a 3-cyano-2-pyrazinyl group, a 3-nitro-2-pyrazinyl group, a 5-chloro-2-pyrazinyl group, a 5-cyano-2-pyrazinyl group, a 5-nitro-2-pyrazinyl group, a 6-chloro-2-pyrazinyl group, a 4-(1,2,3-triazinyl) group, a 5-methyl-4-(1,2,3-triazinyl) group, a 6-methyl-4-(1,2,3-triazinyl) group, a 5-ethyl-4-(1,2,3-triazinyl) group, a 6-ethyl-4-(1,2,3-triazinyl) group, a 5-propyl-4-(1,2,3-triazinyl) group, a 6-propyl-4-(1,2,3-triazinyl) group, a 5-isopropyl-4-(1,2,3-triazinyl) group, a 6-isopropyl-4-(1,2,3-triazinyl) group, a 5-butyl-4-(1,2,3-triazinyl) group, a 6-butyl-4-(1,2,3-triazinyl) group, a 5-isobutyl-4-(1,2,3-triazinyl) group, a 6-isobutyl-4-(1,2,3-triazinyl) group, a 5-sec-butyl-4-(1,2,3-triazinyl) group, a 6-sec-butyl-4-(1,2,3-triazinyl) group, a 5-tert-butyl-4-(1,2,3-triazinyl) group, a 6-tert-butyl-4-(1,2,3-triazinyl) group, a 5-difluoromethyl-4-C1,2,3-triazinyl) group, a 6-difluoromethyl-4-(1,2,3-triazinyl) group, a 5-trifluoromethyl-4-(1,2,3-triazinyl) group, a 6-trifluoromethyl-4-(1,2,3-triazinyl) group, a 5-(2,2,2-trifluoroethyl)-4-(1,2,3-triazinyl) group, a 6-(2,2,2-trifluoroethyl)-4-(1,2,3-triazinyl) group, a 5-pentafluoroethyl-4-(1,2,3-triazinyl) group, a 6-pentafluoroethyl-4-(1,2,3-triazinyl) group, a 5-heptafluoropropyl-4-(1,2,3-triazinyl) group, a 6-heptafluoropropyl-4-(1,2,3-triazinyl) group, a 5-heptafluoroisopropyl-4-(1,2,3-triazinyl) group, a 6-heptafluoroisopropyl-4-(1,2,3-triazinyl) group, a 5-(1,2,3-triazinyl) group, a 4-methyl-5-(1,2,3-triazinyl)group, a 4-ethyl-5-(1,2,3-triazinyl)group, a 4-propyl-5-(1,2,3-triazinyl)group, a 4-isopropyl-5-(1,2,3-triazinyl) group, a 4-butyl-5-(1,2,3-triazinyl)group, a 4-isobutyl-5-(1,2,3-triazinyl) group, a 4-sec-butyl-5-(1,2,3-triazinyl)group, a 4-tert-butyl-5-(1,2,3-triazinyl)group, a 4-difluoromethyl-5-(1,2,3-triazinyl)group, a 4-trifluoromethyl-5-(1,2,3-triazinyl)group, a 4-(2,2,2-trifluoroethyl)-5-(1,2,3-triazinyl)group, a 4-pentafluoroethyl-5-(1,2,3-triazinyl) group, a 4-heptafluoropropyl-5-(1,2,3-triazinyl)group, a 4-heptaflu- oroisopropyl-5-(1,2,3-triazinyl) group, a 3-(1,2,4-triazinyl) group, a 5-methyl-3-(1,2,4-triazinyl)group, a 6-methyl-3-(1,2,4-triazinyl)group, a 5-ethyl-3-(1,2,4-triazinyl)group, a 6-ethyl-3-(1,2,4-triazinyl) group, a 5-propyl-3-(1,2,4-triazinyl) group, a 6-propyl-3-(1,2,4-triazinyl)group, a 5-isopropyl-3-(1,2,4-triazinyl)group, a 6-isopropyl-3-(1,2,4-triazinyl)group, a 5-butyl-3-(1,2,4-triazinyl)group, a 6-butyl-3-(1,2,4-triazinyl) group, a 5-isobutyl-3-(1,2,4-triazinyl)group, a 6-isobutyl-3-(1,2,4-triazinyl)group, a 5-sec-butyl-3-(1,2,4-triazinyl)group, a 6-sec-butyl-3-(1,2,4-triazinyl)group, a 5-tert-butyl-3-(1,2,4-triazinyl)group, a 6-tert-butyl-3-(1,2,4-triazinyl)group, a 5-difluoromethyl-3-(1,2,4-triazinyl)group, a 6-difluoromethyl-3-(1,2,4-triazinyl)group, a 5-trifluoromethyl-3-(1,2,4-triazinyl)group, a 6-trifluoromethyl-3-(1,2,4-triazinyl)group, a 5-(2,2,2-trifluoroethyl)-3-(1,2,4-triazinyl) group, a 6-(2,2,2-trifluoroethyl)-3-(1,2,4-triazinyl)group, a 5-pentafluoroethyl-3-(1,2,4-triazinyl)group, a 6-pentafluoroethyl-3-(1,2,4-triazinyl)group, a 5-heptafluoropropyl-3-(1,2,4-triazinyl)group, a 6-heptafluoropropyl-3-(1,2,4-triazinyl)group, a 5-heptafluoroisopropyl-3-(1,2,4-triazinyl) group, a 6-heptafluoroisopropyl-3-(1,2,4-triazinyl)group, a 5-(1,2,4-triazinyl)group, a 3-methyl-5-(1,2,4-triazinyl) group, a 6-methyl-5-(1,2,4-triazinyl)group, a 3-ethyl-5-(1,2,4-triazinyl)group, a 6-ethyl-5-(1,2,4-triazinyl)group, a 3-propyl-5-(1,2,4-triazinyl)group, a 6-propyl-5-(1,2,4-triazinyl)group, a 3-isopropyl-5-(1,2,4-triazinyl)group, a 6-isopropyl-5-(1,2,4-triazinyl)group, a 3-butyl-5-(1,2,4-triazinyl)group, a 6-butyl-5-(1,2,4-triazinyl)group, a 3-isobutyl-5-(1,2,4-triazinyl)group, a 6-isobutyl-5-(1,2,4-triazinyl) group, a 3-sec-butyl-5-(1,2,4-triazinyl)group, a 6-sec-butyl-5-(1,2,4-triazinyl)group, a 3-tert-butyl-5-(1,2,4-triazinyl) group, a 6-tert-butyl-5-(1,2,4-triazinyl)group, a 3-difluoromethyl-5-(1,2,4-triazinyl)group, a 6-difluoromethyl-5-(1,2,4-triazinyl) group, a 3-trifluoromethyl-5-(1,2,4-triazinyl)group, a 6-trifluoromethyl-5-(1,2,4-triazinyl) group, a 3-(2,2,2-trifluoroethyl)-5-(1,2,4-triazinyl)group, a 6-(2,2,2-trifluoroethyl)-5-(1,2,4-triazinyl)group, a 3-pentafluoroethyl-5-(1,2,4-triazinyl)group, a 6-pentafluoroethyl-5-(1,2,4-triazinyl) group, a 3-heptafluoropropyl-5-(1,2,4-triazinyl) group, a 6-heptafluoropropyl-5-(1,2,4-triazinyl) group, a 3-heptafluoroisopropyl-5-(1,2,4-triazinyl)group, a 6-heptafluoroisopropyl-5-(1,2,4-triazinyl)group, a 6-(1,2,4-triazinyl)group, a 3-methyl-6-(1,2,4-triazinyl)group, a 5-methyl-6-(1,2,4-triazinyl)group, a 3-ethyl-6-(1,2,4-triazinyl)group, a 5-ethyl-6-(1,2,4-triazinyl)group, a 3-propyl-6-(1,2,4-triazinyl)group, a 5-propyl-6-(1,2,4-triazinyl)group, a 3-isopropyl-6-(1,2,4-triazinyl)group, a 5-isopropyl-6-(1,2,4-triazinyl)group, a 3-butyl-6-(1,2,4-triazinyl)group, a 5-butyl-6-(1,2,4-triazinyl)group, a 3-isobutyl-6-(1,2,4-triazinyl) group, a 5-isobutyl-6-(1,2,4-triazinyl)group, a 3-sec-butyl-6-(1,2,4-triazinyl)group, a 5-sec-butyl-6-(1,2,4-triazinyl)group, a 3-tert-butyl-6-(1,2,4-triazinyl)group, a 5-tert-butyl-6-(1,2,4-triazinyl)group, a 3-difluoromethyl-6-(1,2,4-triazinyl)group, a 5-difluoromethyl-6-(1,2,4-triazinyl)group, 3-trifluoromethyl-6-(1,2,4-triazinyl)group, 5-trifluoromethyl-6-(1,2,4-triazinyl)group, a 3-(2,2,2-trifluoroethyl)-6-(1,2,4-triazinyl)group, a 5-(2,2,2-trifluoroethyl)-6-(1,2,4-triazinyl)group, a 3-pentafluoroethyl-6-(1,2,4-triazinyl)group, a 5-pentafluoroethyl-6-(1,2,4-triazinyl)group, a 3-heptafluoropropyl-6-(1,2,4-triazinyl)group, a 5-heptafluoropropyl-6-(1,2,4-triazinyl)group, 3-heptafluoroisopropyl-6-(1,2,4-triazinyl)group, a 5-heptafluoroisopropyl-6-(1,2,4-triazinyl) group, a 2-(1,3,5-triazinyl)group, a 4-chloro-2-(1,3,5-triazinyl)group, a 4,6-dichloro-2-(1,3,5-triazinyl)group, a 4-methyl-2-(1,3,5-triazinyl)group, a 4-ethyl-2-(1,3,5-triazinyl)group, a 4-propyl-2-(1,3,5-triazinyl)group, a 4-isopropyl-2-(1,3,5-triazinyl)group, a 4-butyl-2-(1,3,5-triazinyl)

group, a 4-isobutyl-2-(1,3,5-triazinyl)group, a 4-sec-butyl-2-(1,3,5-triazinyl)group, a 4-tert-butyl-2-(1,3,5-triazinyl) group, a 4-difluoromethyl-2-(1,3,5-triazinyl)group, a 4-trifluoromethyl-2-(1,3,5-triazinyl)group, a 4-(2,2,2-trifluoroethyl)-2-(1,3,5-triazinyl)group, 4-pentafluoroethyl-2-(1,3,5-triazinyl)group, 4-heptafluoropropyl-2-(1,3,5-triazinyl)group, 4-heptafluoroisopropyl-2-(1,3,5-triazinyl)group, and the like.

Examples of the "6-membered aromatic heterocyclic —C1-C3 alkyl group" in the compound of the present invention include a 2-pyridylmethyl group, a 2-(2-pyridyl)ethyl group, a 1-(2-pyridyl)propyl group, a 3-pyridylmethyl group, a 4-pyridylmethyl group, a 3-pyridazinylmethyl group, a 2-pyrimidinylmethyl group, a 2-pyrazinylmethyl group, a 1-[4-(1,2,3-triazinyl)]ethyl group, and the like.

Examples of the 6-membered aromatic heterocyclic C1-C3 alkyl group wherein a 6-membered aromatic heterocyclic portion may have optionally one or more groups selected from the group Y" in the compound of the present invention include a 2-pyridylmethyl group, a 3-fluoro-2-pyridylmethyl group, a 5-chloro-2-pyridylmethyl group, a 5-trifluoromethyl-2-pyridylmethyl group, a 2-(4-chloro-2-pyridyl)ethyl group, a 1-(5-bromo-2-pyridyl)propyl group, a 6-bromo-2-pyridylmethyl group, a 3-iodo-2-pyridylmethyl group, a 4-cyano-2-pyridylmethyl group, a 5-nitro-2-pyridylmethyl group, a 6-methyl-2-pyridylmethyl group, a 3-difluoromethyl-2-pyridylmethyl group, a 4-trifluoromethyl-2-pyridylmethyl group, a 3-pyridylmethyl group, a 6-chloro-3-pyridylmethyl group, a 4-pyridylmethyl group, a 2-chloro-4-pyridylmethyl group, a 4-methyl-3-pyridazinylmethyl group, a 6-difluoromethyl-3-pyridazinylmethyl group, a 4-trifluoromethyl-3-pyridazinylmethyl group, a 4-methyl-2-pyrimidinylmethyl group, a 5-difluoromethyl-2-pyrimidinylmethyl group, a 5-trifluoromethyl-2-pyrimidinylmethyl group, a 5-isopropyl-2-pyrazinylmethyl group, a 5-difluoromethyl-2-pyrazinylmethyl group, a 6-trifluoromethyl-2-pyrazinylmethyl group, a 3-(2,2,2-trifluoroethyl)-2-pyrazinylmethyl group, a 1-[5-tert-butyl-4-(1,2,3-triazinyl)]ethyl group, and the like.

Examples of the "pyridyl group optionally having one or more groups selected from the group Y" in the compound of the present invention include a 2-pyridyl group, a 3-fluoro-2-pyridyl group, a 4-fluoro-2-pyridyl group, a 5-fluoro-2-pyridyl group, a 6-fluoro-2-pyridyl group, a 3-chloro-2-pyridyl group, a 4-chloro-2-pyridyl group, a 5-chloro-2-pyridyl group, a 6-chloro-2-pyridyl group, a 3-bromo-2-pyridyl group, a 4-bromo-2-pyridyl group, a 5-bromo-2-pyridyl group, a 6-bromo-2-pyridyl group, a 3-iodo-2-pyridyl group, a 4-iodo-2-pyridyl group, a 5-iodo-2-pyridyl group, a 6-iodo-2-pyridyl group, a 3-cyano-2-pyridyl group, a 4-cyano-2-pyridyl group, a 5-cyano-2-pyridyl group, a 6-cyano-2-pyridyl group, a 3-nitro-2-pyridyl group, a 4-nitro-2-pyridyl group, a 5-nitro-2-pyridyl group, a 6-nitro-2-pyridyl group, a 3-methyl-2-pyridyl group, a 4-methyl-2-pyridyl group, a 5-methyl-2-pyridyl group, a 6-methyl-2-pyridyl group, a 3-ethyl-2-pyridyl group, a 4-ethyl-2-pyridyl group, a 5-ethyl-2-pyridyl group, a 6-ethyl-2-pyridyl group, a 3-propyl-2-pyridyl group, a 4-propyl-2-pyridyl group, a 5-propyl-2-pyridyl group, a 6-propyl-2-pyridyl group, a 3-isopropyl-2-pyridyl group, a 4-isopropyl-2-pyridyl group, a 5-isopropyl-2-pyridyl group, a 6-isopropyl-2-pyridyl group, a 3-butyl-2-pyridyl group, a 4-butyl-2-pyridyl group, a 5-butyl-2-pyridyl group, a 6-butyl-2-pyridyl group, a 3-isobutyl-2-pyridyl group, a 4-isobutyl-2-pyridyl group, a 5-isobutyl-2-pyridyl group, a 6-isobutyl-2-pyridyl group, a 3-sec-butyl-2-pyridyl group, a 4-sec-butyl-2-pyridyl group, a 5-sec-butyl-2-pyridyl group, a 6-sec-butyl-2-pyridyl group, a 3-tert-butyl-2-pyridyl group, a 4-tert-butyl-2-pyridyl group, a 5-tert-butyl-2-pyridyl group, a 6-tert-butyl-2-pyridyl group, a 3-difluoromethyl-2-pyridyl group, a 4-difluoromethyl-2-pyridyl group, a 5-difluoromethyl-2-pyridyl group, a 6-difluoromethyl-2-pyridyl group, a 3-trifluoromethyl-2-pyridyl group, a 4-trifluoromethyl-2-pyridyl group, a 5-trifluoromethyl-2-pyridyl group, a 6-trifluoromethyl-2-pyridyl group, a 3-(2,2,2-trifluoroethyl)-2-pyridyl group, a 4-(2,2,2-trifluoroethyl)-2-pyridyl group, a 5-(2,2,2-trifluoroethyl)-2-pyridyl group, a 6-(2,2,2-trifluoroethyl)-2-pyridyl group, a 3-pentafluoroethyl-2-pyridyl group, a 4-pentafluoroethyl-2-pyridyl group, a 5-pentafluoroethyl-2-pyridyl group, a 6-pentafluoroethyl-2-pyridyl group, a 3-heptafluoropropyl-2-pyridyl group, a 4-heptafluoropropyl-2-pyridyl group, a 5-heptafluoropropyl-2-pyridyl group, a 6-heptafluoropropyl-2-pyridyl group, a 3-heptafluoroisopropyl-2-pyridyl group, a 4-heptafluoroisopropyl-2-pyridyl group, a 5-heptafluoroisopropyl-2-pyridyl group, a 6-heptafluoroisopropyl-2-pyridyl group, a 3-pyridyl group, a 2-methyl-3-pyridyl group, a 4-methyl-3-pyridyl group, a 5-methyl-3-pyridyl group, a 6-methyl-3-pyridyl group, a 2-ethyl-3-pyridyl group, a 4-ethyl-3-pyridyl group, a 5-ethyl-3-pyridyl group, a 6-ethyl-3-pyridyl group, a 2-propyl-3-pyridyl group, a 4-propyl-3-pyridyl group, a 5-propyl-3-pyridyl group, a 6-propyl-3-pyridyl group, a 2-isopropyl-3-pyridyl group, a 4-isopropyl-3-pyridyl group, a 5-isopropyl-3-pyridyl group, a 6-isopropyl-3-pyridyl group, a 2-butyl-3-pyridyl group, a 4-butyl-3-pyridyl group, a 5-butyl-3-pyridyl group, a 6-butyl-3-pyridyl group, a 2-isobutyl-3-pyridyl group, a 4-isobutyl-3-pyridyl group, a 5-isobutyl-3-pyridyl group, a 6-isobutyl-3-pyridyl group, a 2-sec-butyl-3-pyridyl group, a 4-sec-butyl-3-pyridyl group, a 5-sec-butyl-3-pyridyl group, a 6-sec-butyl-3-pyridyl group, a 2-tert-butyl-3-pyridyl group, a 4-tert-butyl-3-pyridyl group, a 5-tert-butyl-3-pyridyl group, a 6-tert-butyl-3-pyridyl group, a 2-difluoromethyl-3-pyridyl group, a 4-difluoromethyl-3-pyridyl group, a 5-difluoromethyl-3-pyridyl group, a 6-difluoromethyl-3-pyridyl group, a 2-trifluoromethyl-3-pyridyl group, a 4-trifluoromethyl-3-pyridyl group, a 5-trifluoromethyl-3-pyridyl group, a 6-trifluoromethyl-3-pyridyl group, a 2-(2,2,2-trifluoroethyl)-3-pyridyl group, a 4-(2,2,2-trifluoroethyl)-3-pyridyl group, a 5-(2,2,2-trifluoroethyl)-3-pyridyl group, a 6-(2,2,2-trifluoroethyl)-3-pyridyl group, a 2-pentafluoroethyl-3-pyridyl group, a 4-pentafluoroethyl-3-pyridyl group, a 5-pentafluoroethyl-3-pyridyl group, a 6-pentafluoroethyl-3-pyridyl group, a 2-heptafluoropropyl-3-pyridyl group, a 4-heptafluoropropyl-3-pyridyl group, a 5-heptafluoropropyl-3-pyridyl group, a 6-heptafluoropropyl-3-pyridyl group, a 2-heptafluoroisopropyl-3-pyridyl group, a 4-heptafluoroisopropyl-3-pyridyl group, a 5-heptafluoroisopropyl-3-pyridyl group, a 6-heptafluoroisopropyl-3-pyridyl group, a 4-pyridyl group, a 2-methyl-4-pyridyl group, a 3-methyl-4-pyridyl group, a 2-ethyl-4-pyridyl group, a 3-ethyl-4-pyridyl group, a 2-propyl-4-pyridyl group, a 3-propyl-4-pyridyl group, a 2-isopropyl-4-pyridyl group, a 3-isopropyl-4-pyridyl group, a 2-butyl-4-pyridyl group, a 3-butyl-4-pyridyl group, a 2-isobutyl-4-pyridyl group, a 3-isobutyl-4-pyridyl group, a 2-sec-butyl-4-pyridyl group, a 3-sec-butyl-4-pyridyl group, a 2-tert-butyl-4-pyridyl group, a 3-tert-butyl-4-pyridyl group, a 2-difluoromethyl-4-pyridyl group, a 3-difluoromethyl-4-pyridyl group, a 2-trifluoromethyl-4-pyridyl group, a 3-trifluoromethyl-4-pyridyl group, a 2-(2,2,2-trifluoroethyl)-4-pyridyl group, a 3-(2,2,2-trifluoroethyl)-4-pyridyl group, a 2-heptafluoropropyl-4-pyridyl group, a 3-heptafluoropropyl-4-pyridyl group, a 2-heptafluoroisopropyl-4-pyridyl group, a 3-heptafluoroisopropyl-4-pyridyl group, and the like.

Examples of the "pyridyl C1-C3 alkyl group" in the compound of the present invention include a 2-pyridylmethyl group, a 3-pyridylmethyl group, a 4-pyridylmethyl group, a 2-(2-pyridyl)ethyl group, a 1-(2-pyridyl)propyl group, and the like.

Examples of the "pyridyl-C1-C3 alkyl group wherein a pyridine ring portion may have optionally one or more groups selected from the group Y" in the compound of the present invention include a 2-pyridylmethyl group, a 3-pyridylmethyl group, a 4-pyridylmethyl group, a (3-fluoro-2-pyridyl)methyl group, a (5-chloro-2-pyridyl)methyl group, a 2-(4-chloro-2-pyridyl)ethyl group, a 1-(5-bromo-2-pyridyl)propyl group, a (6-bromo-2-pyridyl)methyl group, a (3-iodo-2-pyridyl)methyl group, a (4-cyano-2-pyridyl)methyl group, a (5-nitro-2-pyridyl)methyl group, a (6-methyl-2-pyridyl)methyl group, a (3-difluoromethyl-2-pyridyl)methyl group, a (4-trifluoromethyl-2-pyridyl)methyl group, a (5-trifluoromethyl-2-pyridyl)methyl group, a (6-chloro-3-pyridyl)methyl group, a (2-chloro-4-pyridyl)methyl group, and the like.

Examples of the "pyrimidinyl group optionally having one or more groups selected from the group Y" in the compound of the present invention include a 2-pyrimidinyl group, a 4-methyl-2-pyrimidinyl group, a 5-methyl-2-pyrimidinyl group, a 4-ethyl-2-pyrimidinyl group, a 5-ethyl-2-pyrimidinyl group, a 4-propyl-2-pyrimidinyl group, a 5-propyl-2-pyrimidinyl group, a 4-isopropyl-2-pyrimidinyl group, a 5-isopropyl-2-pyrimidinyl group, a 4-butyl-2-pyrimidinyl group, a 5-butyl-2-pyrimidinyl group, a 4-isobutyl-2-pyrimidinyl group, a 5-isobutyl-2-pyrimidinyl group, a 4-sec-butyl-2-pyrimidinyl group, a 5-sec-butyl-2-pyrimidinyl group, a 4-tert-butyl-2-pyrimidinyl group, a 5-tert-butyl-2-pyrimidinyl group, a 4-difluoromethyl-2-pyrimidinyl group, a 5-difluoromethyl-2-pyrimidinyl group, a 4-trifluoromethyl-2-pyrimidinyl group, a 5-trifluoromethyl-2-pyrimidinyl group, a 4-(2,2,2-trifluoroethyl)-2-pyrimidinyl group, a 5-(2,2,2-trifluoroethyl)-2-pyrimidinyl group, a 4-pentafluoroethyl-2-pyrimidinyl group, a 5-pentafluoroethyl-2-pyrimidinyl group, a 4-heptafluoropropyl-2-pyrimidinyl group, a 5-heptafluoropropyl-2-pyrimidinyl group, a 4-heptafluoroisopropyl-2-pyrimidinyl group, a 5-heptafluoroisopropyl-2-pyrimidinyl group, a 4-pyrimidinyl group, a 2-methyl-4-pyrimidinyl group, a 5-methyl-4-pyrimidinyl group, a 6-methyl-4-pyrimidinyl group, a 2-ethyl-4-pyrimidinyl group, a 5-ethyl-4-pyrimidinyl group, a 6-ethyl-4-pyrimidinyl group, a 2-propyl-4-pyrimidinyl group, a 5-propyl-4-pyrimidinyl group, a 6-propyl-4-pyrimidinyl group, a 2-isopropyl-4-pyrimidinyl group, a 5-isopropyl-4-pyrimidinyl group, a 6-isopropyl-4-pyrimidinyl group, a 2-butyl-4-pyrimidinyl group, a 5-butyl-4-pyrimidinyl group, a 6-butyl-4-pyrimidinyl group, a 2-isobutyl-4-pyrimidinyl group, a 5-isobutyl-4-pyrimidinyl group, a 6-isobutyl-4-pyrimidinyl group, a 2-sec-butyl-4-pyrimidinyl group, a 5-sec-butyl-4-pyrimidinyl group, a 6-sec-butyl-4-pyrimidinyl group, a 2-tert-butyl-4-pyrimidinyl group, a 5-tert-butyl-4-pyrimidinyl group, a 6-tert-butyl-4-pyrimidinyl group, a 2-difluoromethyl-4-pyrimidinyl group, a 5-difluoromethyl-4-pyrimidinyl group, a 6-difluoromethyl-4-pyrimidinyl group, a 2-trifluoromethyl-4-pyrimidinyl group, a 5-trifluoromethyl-4-pyrimidinyl group, a 6-trifluoromethyl-4-pyrimidinyl group, a 2-(2,2,2-trifluoroethyl-4-pyrimidinyl group, a 5-(2,2,2-trifluoroethyl)-4-pyrimidinyl group, a 6-(2,2,2-trifluoroethyl)-4-pyrimidinyl group, a 2-pentafluoroethyl-4-pyrimidinyl group, a 5-pentafluoroethyl-4-pyrimidinyl group, a 6-pentafluoroethyl-4-pyrimidinyl group, a 2-heptafluoropropyl-4-pyrimidinyl group, a 5-heptafluoropropyl-4-pyrimidinyl group, a 6-heptafluoropropyl-4-pyrimidinyl group, a 2-heptafluoroisopropyl-4-pyrimidinyl group, a 5-heptafluoroisopropyl-4-pyrimidinyl group, a 6-heptafluoroisopropyl-4-pyrimidinyl group, a 5-pyrimidinyl group, a 2-methyl-5-pyrimidinyl group, a 4-methyl-5-pyrimidinyl group, a 2-ethyl-5-pyrimidinyl group, a 4-ethyl-5-pyrimidinyl group, a 2-propyl-5-pyrimidinyl group, a 4-propyl-5-pyrimidinyl group, a 2-isopropyl-5-pyrimidinyl group, a 4-isopropyl-5-pyrimidinyl group, a 2-butyl-5-pyrimidinyl group, a 4-butyl-5-pyrimidinyl group, a 2-isobutyl-5-pyrimidinyl group, a 4-isobutyl-5-pyrimidinyl group, a 2-sec-butyl-5-pyrimidinyl group, a 4-sec-butyl-5-pyrimidinyl group, a 2-tert-butyl-5-pyrimidinyl group, a 4-tert-butyl-5-pyrimidinyl group, a 2-difluoromethyl-5-pyrimidinyl group, a 4-difluoromethyl-5-pyrimidinyl group, a 2-trifluoromethyl-5-pyrimidinyl group, a 4-trifluoromethyl-5-pyrimidinyl group, a 2-(2,2,2-trifluoroethyl)-5-pyrimidinyl group, a 4-(2,2,2-trifluoroethyl)-5-pyrimidinyl group, a 2-pentafluoroethyl-5-pyrimidinyl group, a 4-pentafluoroethyl-5-pyrimidinyl group, a 2-heptafluoropropyl-5-pyrimidinyl group, a 4-heptafluoropropyl-5-pyrimidinyl group, a 2-heptafluoroisopropyl-5-pyrimidinyl group, a 4-heptafluoroisopropyl-5-pyrimidinyl group, and the like.

Examples of the "5-membered aromatic heterocyclic group" in the compound of the present invention include a 1-pyrazolyl group, a 3-pyrazolyl group, a 4-pyrazolyl group, a 5-pyrazolyl group, a 1-imidazolyl group, a 2-imidazolyl group, a 1-pyrrolyl group, a 2-pyrrolyl group, a 3-pyrrolyl group, a 1-(1,2,4-triazolyl)group, a 1-(1,2,3,4-tetrazolyl) group, a 1-(1,2,3,5-tetrazolyl)group, a 2-furyl group, a 3-furyl group, a 2-thienyl group, a 3-thienyl group, a 3-isoxazolyl group, a 4-isoxazolyl group, a 5-isoxazolyl group, and the like.

Examples of the "5-membered aromatic heterocyclic group optionally having one or more groups selected from the group Y" in the compound of the present invention include a 1-pyrazolyl group, a 3-chloro-1-pyrazolyl group, a 3-bromo-1-pyrazolyl group, a 3-nitro-1-pyrazolyl group, a 3-methyl-1-pyrazolyl group, a 3-trifluoromethyl-1-pyrazolyl group, a 4-methyl-1-pyrazolyl group, a 4-chloro-1-pyrazolyl group, a 4-bromo-1-pyrazolyl group, a 4-cyano-1-pyrazolyl group, a 1-methyl-3-pyrazolyl group, a 1-difluoromethyl-3-pyrazolyl group, a 1,5-dimethyl-3-pyrazolyl group, a 1,4-dimethyl-5-pyrazolyl group, a 3,5-dimethyl-1-pyrazolyl group, an 1-imidazolyl group, a 4-trifluoromethyl-1-imidazolyl group, a 1-pyrrolyl group, a 2-fluoro-1-pyrrolyl group, a 3-cyano-1-pyrrolyl group, a 2-methyl-1-pyrrolyl group, a 3-trifluoromethyl-1-pyrrolyl group, a 3-nitro-1-pyrrolyl group, a 2-pyrrolyl group, a 3-fluoro-2-pyrrolyl group, a 4-fluoro-2-pyrrolyl group, a 5-fluoro-2-pyrrolyl group, a 3-chloro-2-pyrrolyl group, a 4-chloro-2-pyrrolyl group, a 5-chloro-2-pyrrolyl group, a 3-bromo-2-pyrrolyl group, a 4-bromo-2-pyrrolyl group, a 5-bromo-2-pyrrolyl group, a 3-iodo-2-pyrrolyl group, a 4-iodo-2-pyrrolyl group, a 5-iodo-2-pyrrolyl group, a 3-cyano-2-pyrrolyl group, a 4-cyano-2-pyrrolyl group, a 5-cyano-2-pyrrolyl group, a 3-nitro-2-pyrrolyl group, a 4-nitro-2-pyrrolyl group, a 5-nitro-2-pyrrolyl group, a 3-methyl-2-pyrrolyl group, a 4-methyl-2-pyrrolyl group, a 5-methyl-2-pyrrolyl group, a 3-ethyl-2-pyrrolyl group, a 4-ethyl-2-pyrrolyl group, a 5-ethyl-2-pyrrolyl group, a 3-propyl-2-pyrrolyl group, a 4-propyl-2-pyrrolyl group, a 5-propyl-2-pyrrolyl group, a 3-isopropyl-2-pyrrolyl group, a 4-isopropyl-2-pyrrolyl group, a 5-isopropyl-2-pyrrolyl group, a 3-tert-butyl-2-pyrrolyl group, a 4-tert-butyl-2-pyrrolyl group, a 5-tert-butyl-2-pyrrolyl group, a 3-difluoromethyl-2-pyrrolyl group, a 4-difluoromethyl-2-pyrrolyl group, a 5-difluoromethyl-2-pyrrolyl group, a 3-trifluoromethyl-2- pyrrolyl group, a 4-trifluoromethyl-2-pyrrolyl group, a 5-trifluoromethyl-2-pyrrolyl group, a 3-pyrrolyl group, a 2-fluoro-3-pyrrolyl group, a 4-fluoro-3-pyrrolyl group, a 5-fluoro-3-pyrrolyl group, a 2-chloro-3-pyrrolyl group, a 4-chloro-3-pyrrolyl group, a 5-chloro-3-pyrrolyl group, a 2-bromo-3-pyrrolyl group, a 4-bromo-3-pyrrolyl group, a 5-bromo-3-pyrrolyl group, a 2-iodo-3-pyrrolyl group, a 4-iodo-3-pyrrolyl group, a 5-iodo-3-pyrrolyl group, a 2-cyano-3-pyrrolyl group, a 4-cyano-3-pyrrolyl group, a 5-cyano-3-pyrrolyl group, a 2-nitro-3-pyrrolyl group, a 4-nitro-3-pyrrolyl group, a 5-nitro-3-pyrrolyl group, a 2-methyl-3-pyrrolyl group, a 4-methyl-3-pyrrolyl group, a 5-methyl-3-pyrrolyl group, a 2-ethyl-3-pyrrolyl group, a 4-ethyl-3-pyrrolyl group, a 5-ethyl-3-pyrrolyl group, a 2-propyl-3-pyrrolyl group, a 4-propyl-3-pyrrolyl group, a 5-propyl-3-pyrrolyl group, a 2-isopropyl-3-pyrrolyl group, a 4-isopropyl-3-pyrrolyl group, a 5-isopropyl-3-pyrrolyl group, a 2-tert-butyl-3-pyrrolyl group, a 4-tert-butyl-3-pyrrolyl group, a 5-tert-butyl-3-pyrrolyl group, a 2-difluoromethyl-3-pyrrolyl group, a 4-difluoromethyl-3-pyrrolyl group, a 5-difluoromethyl-3-pyrrolyl group, a 2-trifluoromethyl-3-pyrrolyl group, a 4-trifluoromethyl-3-pyrrolyl group, a 5-trifluoromethyl-3-pyrrolyl group, a 1-(1,2,4-triazolyl)group, a 3-chloro-1-(1,2,4-triazolyl)group, a 1-(1,2,3,4-tetrazolyl)group, a 1-(1,2,3,5-tetrazolyl)group, a 2-furyl group, a 3-chloro-2-furyl group, a 5-bromo-2-furyl group, a 3-iodo-2-furyl group, a 4-cyano-2-furyl group, a 5-nitro-2-furyl group, a 3-methyl-2-furyl group, a 4-tert-butyl-2-furyl group, a 5-methyl-2-furyl group, a 5-trifluoromethyl-2-furyl group, a 3-furyl group, a 2-fluoro-3-furyl group, a 4-chloro-3-furyl group, a 2-bromo-3-furyl group, a 5-bromo-3-furyl group, a 2-iodo-3-furyl group, a 4-cyano-3-furyl group, a 4-nitro-3-furyl group, a 2-methyl-3-furyl group, a 2-tert-butyl-3-furyl group, a 4-difluoromethyl-3-furyl group, a 5-difluoromethyl-3-furyl group, a 2-trifluoromethyl-3-furyl group, a 4-trifluoromethyl-3-furyl group, a 5-trifluoromethyl-3-furyl group, a 2-thienyl group, a 3-fluoro-2-thienyl group, a 4-fluoro-2-thienyl group, a 5-fluoro-2-thienyl group, a 3-chloro-2-thienyl group, a 4-chloro-2-thienyl group, a 5-chloro-2-thienyl group, a 3-bromo-2-thienyl group, a 4-bromo-2-thienyl group, a 5-bromo-2-thienyl group, a 3-iodo-2-thienyl group, a 4-iodo-2-thienyl group, a 5-iodo-2-thienyl group, a 3-cyano-2-thienyl group, a 4-cyano-2-thienyl group, a 5-cyano-2-thienyl group, a 3-nitro-2-thienyl group, a 4-nitro-2-thienyl group, a 5-nitro-2-thienyl group, a 3-methyl-2-thienyl group, a 4-methyl-2-thienyl group, a 5-methyl-2-thienyl group, a 3-ethyl-2-thienyl group, a 4-ethyl-2-thienyl group, a 5-ethyl-2-thienyl group, a 3-propyl-2-thienyl group, a 4-propyl-2-thienyl group, a 5-propyl-2-thienyl group, a 3-isopropyl-2-thienyl group, a 4-isopropyl-2-thienyl group, a 5-isopropyl-2-thienyl group, a 3-tert-butyl-2-thienyl group, a 4-tert-butyl-2-thienyl group, a 5-tert-butyl-2-thienyl group, a 3-difluoromethyl-2-thienyl group, a 4-difluoromethyl-2-thienyl group, a 5-difluoromethyl-2-thienyl group, a 3-trifluoromethyl-2-thienyl group, a 4-trifluoromethyl-2-thienyl group, a 5-trifluoromethyl-2-thienyl group, a 3-thienyl group, a 2-fluoro-3-thienyl group, a 4-fluoro-3-thienyl group, a 5-fluoro-3-thienyl group, a 2-chloro-3-thienyl group, a 4-chloro-3-thienyl group, a 5-chloro-3-thienyl group, a 2-bromo-3-thienyl group, a 4-bromo-3-thienyl group, a 5-bromo-3-thienyl group, a 2-iodo-3-thienyl group, a 4-iodo-3-thienyl group, a 5-iodo-3-thienyl group, a 2-cyano-3-thienyl group, a 4-cyano-3-thienyl group, a 5-cyano-3-thienyl group, a 2-nitro-3-thienyl group, a 4-nitro-3-thienyl group, a 5-nitro-3-thienyl group, a 2-methyl-3-thienyl group, a 4-methyl-3-thienyl group, a 5-methyl-3-thienyl group, a 2-ethyl-3-thienyl group, a 4-ethyl-3-thienyl group, a 5-ethyl-3-thienyl group, a 2-propyl-3-thienyl group, a 4-propyl-3-thienyl group, a 5-propyl-3-thienyl group, a 2-isopropyl-3-thienyl group, a 4-isopropyl-3-thienyl group, a 5-isopropyl-3-thienyl group, a 2-tert-butyl-3-thienyl group, a 4-tert-butyl-3-thienyl group, a 5-tert-butyl-3-thienyl group, a 2-difluoromethyl-3-thienyl group, a 4-difluoromethyl-3-thienyl group, a 5-difluoromethyl-3-thienyl group, a 2-trifluoromethyl-3-thienyl group, a 4-trifluoromethyl-3-thienyl group, a 5-trifluoromethyl-3-thienyl group, a 2,5-dichloro-3-thienyl group, a 3-isoxazolyl group, a 4-chloro-3-isoxazolyl group, a 5-chloro-3-isoxazolyl group, a 3-bromo-4-isoxazolyl group, a 5-bromo-4-isoxazolyl group, a 3-nitro-5-isoxazolyl group, a 4-nitro-5-isoxazolyl group, a 4-methyl-3-isoxazolyl group, a 5-methyl-3-isoxazolyl group, a 3-trifluoromethyl-4-isoxazolyl group, a 5-trifluoromethyl-4-isoxazolyl group, a m-methyl-5-isoxazolyl group, a 4-methyl-5-isoxazolyl group, and the like.

Examples of the "thienyl group optionally having one or more groups selected from the group Y" in the compound of the present invention include a 2-thienyl group, a 3-fluoro-2-thienyl group, a 4-fluoro-2-thienyl group, a 5-fluoro-2-thienyl group, a 3-chloro-2-thienyl group, a 4-chloro-2-thienyl group, a 5-chloro-2-thienyl group, a 3-bromo-2-thienyl group, a 4-bromo-2-thienyl group, a 5-bromo-2-thienyl group, a 3-iodo-2-thienyl group, a 4-iodo-2-thienyl group, a 5-iodo-2-thienyl group, a 3-cyano-2-thienyl group, a 4-cyano-2-thienyl group, a 5-cyano-2-thienyl group, a 3-nitro-2-thienyl group, a 4-nitro-2-thienyl group, a 5-nitro-2-thienyl group, a 3-methyl-2-thienyl group, a 4-methyl-2-thienyl group, a 5-methyl-2-thienyl group, a 3-ethyl-2-thienyl group, a 4-ethyl-2-thienyl group, a 3-ethyl-2-thienyl group, a 3-propyl-2-thienyl group, a 4-propyl-2-thienyl group, a 5-propyl-2-thienyl group, a 3-isopropyl-2-thienyl group, a 4-isopropyl-2-thienyl group, a 5-isopropyl-2-thienyl group, a 3-tert-butyl-2-thienyl group, a 4-tert-butyl-2-thienyl group, a 5-tert-butyl-2-thienyl group, a 3-difluoromethyl-2-thienyl group, a 4-difluoromethyl-2-thienyl group, a 5-difluoromethyl-2-thienyl group, a 3-trifluoromethyl-2-thienyl group, a 4-trifluoromethyl-2-thienyl group, a 5-trifluoromethyl-2-thienyl group, a 3-thienyl group, a 2-fluoro-3-thienyl group, a 4-fluoro-3-thienyl group, a 5-fluoro-3-thienyl group, a 2-chloro-3-thienyl group, a 4-chloro-3-thienyl group, a 5-chloro-3-thienyl group, a 2-bromo-3-thienyl group, a 4-bromo-3-thienyl group, a 5-bromo-3-thienyl group, a 2-iodo-3-thienyl group, a 4-iodo-3-thienyl group, a 5-iodo-3-thienyl group, a 2-cyano-3-thienyl group, a 4-cyano-3-thienyl group, a 5-cyano-3-thienyl group, a 2-nitro-3-thienyl group, a 4-nitro-3-thienyl group, a 5-nitro-3-thienyl group, a 2-methyl-3-thienyl group, a 4-methyl-3-thienyl group, a 5-methyl-3-thienyl group, a 2-ethyl-3-thienyl group, a 4-ethyl-3-thienyl group, a 5-ethyl-3-thienyl group, a 2-propyl-3-thienyl group, a 4-propyl-3-thienyl group, a 5-propyl-3-thienyl group, a 2-isopropyl-3-thienyl group, a 4-isopropyl-3-thienyl group, a 5-isopropyl-3-thienyl group, a 2-tert-butyl-3-thienyl group, a 4-tert-butyl-3-thienyl group, a 5-tert-butyl-3-thienyl group, a 2-difluoromethyl-3-thienyl group, a 4-difluoromethyl-3-thienyl group, a 5-difluoromethyl-3-thienyl group, a 2-trifluoromethyl-3-thienyl group, a 4-trifluoromethyl-3-thienyl group, a 5-trifluoromethyl-3-thienyl group, a 2,5-dichloro-3-thienyl group, and the like.

Examples of the "pyrrolyl group optionally having one or more groups selected from the group Y" in the compound of the present invention include a 1-pyrrolyl group, a 2-fluoro-1-pyrrolyl group, a 3-cyano-1-pyrrolyl group, a 2-methyl-1-pyrrolyl group, a 3-trifluoromethyl-1-pyrrolyl group, a 3-nitro-1-pyrrolyl group, a 2-pyrrolyl group, a 3-fluoro-2-pyrrolyl group, a 4-fluoro-2-pyrrolyl group, a 5-fluoro-2-pyrrolyl group, a 3-chloro-2-pyrrolyl group, a 4-chloro-2-pyrrolyl group, a 5-chloro-2-pyrrolyl group, a 3-bromo-2-pyrrolyl group, a 4-bromo-2-pyrrolyl group, a 5-bromo-2-pyrrolyl group, a 3-iodo-2-pyrrolyl group, a 4-iodo-2-pyrrolyl group, a 5-iodo-2-pyrrolyl group, a 3-cyano-2-pyrrolyl group, a 4-cyano-2-pyrroyl group, a 5-cyano-2-pyrrolyl group, a 3-nitro-2-pyrrolyl group, a 4-nitro-2-pyrrolyl group, a 5-nitro-2-pyrrolyl group, a 3-methyl-2-pyrrolyl group, a 4-methyl-2-pyrrolyl group, a 5-methyl-2-pyrrolyl group, a 3-ethyl-2-pyrrolyl group, a 4-ethyl-2-pyrrolyl group, a 5-ethyl-2-pyrrolyl group, a 3-propyl-2-pyrrolyl group, a 4-propyl-2-pyrrolyl group, a 5-propyl-2-pyrrolyl group, a 3-isopropyl-2-pyrrolyl group, a 4-isopropyl-2-pyrrolyl group, a 5-isopropyl-2-pyrrolyl group, a 3-tert-butyl-2-pyrrolyl group, a 4-tert-butyl-2-pyrrolyl group, a 5-tert-butyl-2-pyrrolyl group, a 3-difluoromethyl-2-pyrrolyl group, a 4-difluoromethyl-2-pyrrolyl group, a 5-difluoromethyl-2-pyrrolyl group, a 3-trifluoromethyl-2-pyrrolyl group, a 4-trifluoromethyl-2-pyrrolyl group, a 5-trifluoromethyl-2-pyrrolyl group, a 3-pyrrolyl group, a 2-fluoro-3-pyrrolyl group, a 4-fluoro-3-pyrrolyl group, a 5-fluoro-3-pyrrolyl group, a 2-chloro-3-pyrrolyl group, a 4-chloro-3-pyrrolyl group, a 5-chloro-3-pyrrolyl group, a 2-bromo-3-pyrrolyl group, a 4-bromo-3-pyrrolyl group, a 5-bromo-3-pyrrolyl group, a 2-iodo-3-pyrrolyl group, a 4-iodo-3-pyrrolyl group, a 5-iodo-3-pyrrolyl group, a 2-cyano-3-pyrrolyl group, a 4-cyano-3-pyrrolyl group, a 5-cyano-3-pyrrolyl group, a 2-nitro-3-pyrrolyl group, a 4-nitro-3-pyrrolyl group, a 5-nitro-3-pyrrolyl group, a 2-methyl-3-pyrrolyl croup, a 4-methyl-3-pyrrolyl group, a 5-methyl-3-pyrrolyl group, a 2-ethyl-3-pyrrolyl group, a 4-ethyl-3-pyrrolyl group, a 5-ethyl-3-pyrrolyl group, a 2-propyl-3-pyrrolyl group, a 4-propyl-3-pyrrolyl group, a 5-propyl-3-pyrrolyl group, a 2-isopropyl-3-pyrrolyl group, a 4-isopropyl-3-pyrrolyl group, a 5-isopropyl-3-pyrrolyl group, a 2-tert-butyl-3-pyrrolyl group, a 4-tert-butyl-3-pyrrolyl group, a 5-tert-butyl-3-pyrrolyl group, a 2-difluoromethyl-3-pyrrolyl group, a 4-difluoromethyl-3-pyrrolyl group, a 5-difluoromethyl-3-pyrrolyl group, a 2-trifluoromethyl-3-pyrrolyl group, a 4-trifluoromethyl-3-pyrrolyl group, a 5-trifluoromethyl-3-pyrrolyl group, and the like.

Examples of the "pyrazolyl group optionally having one or more groups selected from the group Y" in the compound of the present invention include a 1-pyrazolyl group, a 3-chloro-1-pyrazolyl group, a 3-bromo-1-pyrazoyl group, a 3-nitro-1-pyrazolyl group, a 3-methyl-1-pyrazolyl group, a 3-trifluoromethyl-1-pyrazolyl group, a 4-methyl-1-pyrazolyl group, a 4-chloro-1-pyrazolyl group, a 4-bromo-1-pyrazolyl group, a 4-cyano-1-pyrazolyl group, a 1-methyl-3-pyrazolyl group, a 1-difluoromethyl-3-pyrazolyl group, a 1,5-dimethyl-3-pyrazolyl group, a 1,4-dimethyl-5-pyrazolyl group, a 3,5-dimethyl-1-pyrazolyl group, and the like.

Examples of the "isoxazolyl group optionally having one or more groups selected from the group Y" in the compound of the present invention include a 3-isoxazolyl group, a 4-chloro-3-isoxazolyl group, a 5-chloro-3-isoxazolyl group, a 3-bromo-4-isoxazoyl group, a 5-bromo-4-isoxazolyl group, a 3-nitro-5-isoxazolyl group, a 4-nitro-5-isoxazolyl group, a 4-methyl-3-isoxazolyl group, a 5-methyl-3-isoxazolyl group, a 3-trifluoromethyl-4-isoxazolyl group, a 5-trifluoromethyl-4-isoxazolyl group, a 3-methyl-5-isoxazolyl group, a 4-methyl-5-isoxazolyl group, and the like.

Examples of the "C2-C6 alkylcarbonyl group" in the compound of the present invention include an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a 2,2-dimethylpropylcarbonyl group, a 3-methylbutylcarbonyl group, a pentylcarbonyl group, and the like.

Examples of the "C2-C6 alkylcarbonyl group optionally having one or more halogen atoms" in the compound of the present invention include an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a pentylcarbonyl group, a 2,2-dimethylpropylcarbonyl group, a 3-methylbutylcarbonyl group, a trichloroacetyl group, a difluoroacetyl group, a trifluoroacetyl group, a (2,2,2-trifluoroethyl)carbonyl group, a pentafluoroethylcarbonyl group, a heptafluoropropylcarbonyl group, a heptafluoroisopropylcarbonyl group, and the like.

Examples of the "C2-C5 alkylcarbonyl group" in the compound of the present invention include an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, and the like.

Examples of the "C2-C5 alkylcarbonyl group optionally having one or more halogen atoms" in the compound of the present invention include an acetyl group, an ethylcarbonyl group, a propylcarbonyl group, an isopropylcarbonyl group, a butylcarbonyl group, an isobutylcarbonyl group, a sec-butylcarbonyl group, a tert-butylcarbonyl group, a trichloroacetyl group, a difluoroacetyl group, a trifluoroacetyl group, a (2,2,2-trifluoroethyl)carbonyl group, a pentafluoroethylcarbonyl group, a heptafluoropropylcarbonyl group, a heptafluoroisopropylcarbonyl group, and the like.

Examples of the "benzoyl group optionally having one or more groups selected from the group Y" in the compound of the present invention include a benzoyl group, a 2-fluorobenzoyl group, a 3-fluorobenzoyl group, a 4-fluorobenzoyl group, a 2-chlorobenzoyl group, a 3-chlorobenzoyl group, a 4-chlorobenzoyl group, a 2-bromobenzoyl group, a 3-bromobenzoyl group, a 4-bromobenzoyl group, a 2-iodobenzoyl group, a 3-iodobenzoyl group, a 4-iodobenzoyl group, a 2-cyanobenzoyl group, a 3-cyanobenzoyl group, a 4-cyanobenzoyl group, a 2-nitrobenzoyl group, a 3-nitrobenzoyl group, a 4-nitrobenzoyl group, a 2-methylbenzoyl group, a 3-methylbenzoyl group, a 4-methylbenzoyl group, a 2-ethylbenzoyl group, a 3-ethylbenzoyl group, a 4-ethylbenzoyl group, a 2-propylbenzoyl group, a 3-propylbenzoyl group, a 4-propylbenzoyl group, a 2-isopropylbenzoyl group, a 3-isopropylbenzoyl group, a 4-isopropylbenzoyl group, a 2-butylbenzoyl group, a 3-butylbenzoyl group, a 4-butylbenzoyl group, a 2-isobutylbenzoyl group, a 3-isobutylbenzoyl group, a 4-isobutylbenzoyl group, a 2-sec-butylbenzoyl group, a 3-sec-butylbenzoyl group, a 4-sec-butylbenzoyl group, a 2-tert-butylbenzoyl group, a 3-tert-butylbenzoyl group, a 4-tert-butylbenzoyl group, a 2-pentylbenzoyl group, a 3-pentylbenzoyl group, a 4-pentylbenzoyl group, a 2-(2,2-dimethylpropyl)benzoyl group, a 3-(2,2-dimethylpropyl)benzoyl group, a 4-(2,2-dimethylpropyl)benzoyl group, a 2-(3-methylbutyl)benzoyl group, a 3-(3-methylbutyl)benzoyl group, a 4-(3-methylbutyl)benzoyl group, a 2-(2,3-dimethylbutyl)benzoyl group, a 3-(2,3-dimethylbutyl)benzoyl group, a 4-(2,3-dimethylbutyl)benzoyl group, a 2-(3,3-dimethylbutyl)benzoyl group, a 3-(3,3-dimethylbutyl)benzoyl group, a 4-(3,3-dimethylbutyl)benzoyl group, a 2-hexylbenzoyl group, a 3-hexylbenzoyl group, a 4-hexylbenzoyl group, a 2-trichloromethylbenzoyl group, a 3-trichloromethylbenzoyl group, a 4-trichloromethylbenzoyl group, a 2-difluoromethylbenzoyl group, a 3-difluoromethylbenzoyl group, a 4-difluoromethylbenzoyl group, a 2-trifluoromethylbenzoyl group, a 3-trifluoromethylbenzoyl group, a 4-trifluoromethylbenzoyl group, a 2-(2,2,2-trifluoroethyl)benzoyl group, a 3-(2,2,2-trifluoromethyl) benzoyl group, a 4-(2,2,2-trifluoroethyl)benzoyl group, a 2-pentafluoroethylbenzoyl group, a 3-pentafluoroethylbenzoyl group, a 4-pentafluoroethylbenzoyl group, a 2-heptafluoropropylbenzoyl group, a 3-heptafluoropropylbenzoyl group, a 4-heptafluoropropylbenzoyl group, a 2-heptafluoroisopropylbenzoyl group, a 3-heptafluoroisopropylbenzoyl group, a 4-heptafluoroisopropylbenzoyl group, a 2-methoxybenzoyl group, a 3-methoxybenzoyl group, a 4-methoxybenzoyl group, a 2-ethoxybenzoyl group, a 3-ethoxybenzoyl group, a 4-ethoxybenzoyl group, a 2-propoxybenzoyl group, a 3-propoxybenzoyl group, a 4-propoxybenzoyl group, a 2-isopropoxybenzoyl group, a 3-isopropoxybenzoyl group, a 4-isopropoxybenzoyl group, a 2-butoxybenzoyl group, a 3-butoxybenzoyl group, a 4-butoxybenzoyl group, a 2-isobutoxybenzoyl group, a 3-isobutoxybenzoyl group, a 4-isobutoxybenzoyl group, a 2-sec-butoxybenzoyl group, a 3-sec-butoxybenzoyl group, a 4-sec-butoxybenzoyl group, a 2-tert-butoxybenzoyl group, a 3-tert-butoxybenzoyl group, a 4-tert-butoxybenzoyl group, a 2-pentyloxybenzoyl group, a 3-pentyloxybenzoyl group, a 4-pentyloxybenzoyl group, a 2-(2,2-dimethylpropoxyl)benzoyl group, a 3-(2,2-dimethylpropoxyl)benzoyl group, a 4-(2,2-dimethylpropoxyl)benzoyl group, a 2-pentafluoroethoxybenzoyl group, a 3-pentafluoroethoxybenzoyl group, a 4-pentafluoroethoxybenzoyl group, a 2-heptafluoropropoxybenzoyl group, a 3-heptafluoropropoxybenzoyl group, a 4-heptafluoropropoxybenzoyl group, a 2-heptafluoroisopropoxybenzoyl group, a 3-heptafluoroisopropoxybenzoyl group, a 4-heptafluoroisopropoxybenzoyl group, a 2-trifluoromethoxybenzoyl group, a 3-trifluoromethoxybenzoyl group, a 4-trifluoromethoxybenzoyl group, and the like.

Examples of the "C2-C6 alkoxycarbonyl group" in the compound of the present invention include an methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a 2,2-dimethylpropoxycarbonyl group, a 3-methylbutoxycarbonyl group, and the like.

Examples of the "C2-C5 alkoxycarbonyl group" in the compound of the present invention include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, and a tert-butoxycarbonyl group.

Examples of the "C2-C4 alkoxycarbonyl group" in the compound of the present invention include a methoxycarbonyl group, an ethoxycarbonyl group, a propoxycarbonyl group, and an isopropoxycarbonyl group.

Examples of the "C1-C4 alkylsulfonyl group" in the compound of the present invention include a methylsulfonyl group, an ethylsulfonyl group, a propylsulfonyl group, an isopropylsulfonyl group, a butylsulfonyl group, an isobutylsulfonyl group, a sec-butylsulfonyl group, and a tert-butylsulfonyl group.

Examples of the "C1-C4 alkylsulfonyl group optionally having one or more halogen atoms" in the compound of the present invention include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a trichloromethylsulfonyl group, a difluoromethylsulfonyl group, a trifluoromethylsulfonyl group, a 2,2,2-trifluoroethylsulfonyl group, and the like.

Examples of the "C1-C6 alkylsulfonyl group" in the compound of the present invention include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, a 2,2-dimethylpropylsulfonyl group, a 3-methylbutylsulfonyl group, a 2,3-dimethylbutylsulfonyl Group, a 3,3-dimethylbutylsulfonyl group, a hexylsulfonyl group, and the like.

Examples of the "C1-C6 alkylsulfonyl group optionally having one or more halogen atoms" in the compound of the present invention include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, a 2,2-dimethylpropylsulfonyl group, a 3-methylbutylsulfonyl group, a 2,3-dimethylbutylsulfonyl group, a 3,3-dimethylbutylsulfonyl group, a hexylsulfonyl group, a trichloromethylsulfonyl group, a difluoromethylsulfonyl group, a trifluoromethylsulfonyl group, a 2,2,2-trifluoroethylsulfonyl group, a pentafluoroethylsulfonyl group, a heptafluoropropylsulfonyl group, a heptafluoroisopropylsulfonyl group, and the like.

Examples of the "phenylsulfonyl group optionally having one or more groups selected from the group Y" in the compound of the present invention include a 2-fluorophenylsulfonyl group, a 3-chlorophenylsulfonyl group, a 4-chlorophenylsulfonyl group, a 2-iodophenylsulfonyl group, a 3-cyanophenylsulfonyl group, a 4-nitrophenylsulfonyl group, a 2-methylphenylsulfonyl group, a 4-methylphenylsulfonyl group, a 4-tert-butylphenylsulfonyl group, a 4-difluoromethylphenylsulfonyl group, a 2-trifluoromethylphenylsulfonyl group, a 2-(2,2,2-trifluoroethyl)phenylsulfonyl group, a 4-pentafluoroethylphenylsulfonyl group, a 4-heptafluoroisopropylphenylsulfonyl group, a 2-methoxyphenylsulfonyl group, a 3-difluoromethoxyphenylsulfonyl group, a 4-difluoromethoxyphenylsulfonyl group, a 2-trifluoromethoxyphenylsulfonyl group, a 4-(2,2,2-trifluoroethoxy)phenylsulfonyl group, and the like.

Examples of the "C7-C9 phenylalkylsulfonyl group" in the compound of the present invention include a benzylsulfonyl group, a 1-phenylethylsulfonyl group, a 2-phenylethylsulfonyl group, a 1-phenylpropylsulfonyl group, a 2-phenylpropylsulfonyl group, a 3-phenylpropylsulfonyl group, a 1-methyl-1-phenylethylsulfonyl group, and the like.

Examples of the "C7-C9 phenylalkylsulfonyl group wherein a benzene ring portion may have optionally one or more groups selected from the group Y" in the compound of the present invention include a benzylsulfonyl group, a 2-fluorobenzylsulfonyl group, a 3-chlorobenzylsulfonyl group, a 4-bromobenzylsulfonyl group, a 2-cyanobenzylsulfonyl group, a 3-nitrobenzylsulfonyl group, a 3-methoxybenzylsulfonyl group, a 4-trifluoromethoxybenzylsulfonyl group, a 1-(3-chlorophenyl)ethylsulfonyl group, a 2-(4-bromophenyl)ethylsulfonyl group, a 1-(2-cyanophenyl)propylsulfonyl group, a 2-(3-nitrophenyl)propylsulfonyl group, a 3-(3-methoxyphenyl)propylsulfonyl group, a 1-methyl-1-(4-trifluoromethoxyphenyl)ethylsulfonyl group, and the like.

Examples of the "benzylsulfonyl group wherein a benzene ring portion may have optionally one or more groups selected from the group Y" in the compound of the present invention include a benzylsulfonyl group, a 2-fluorobenzylsulfonyl group, a 3-chlorobenzylsulfonyl group, a 4-bromobenzylsulfonyl group, a 2-cyanobenzylsulfonyl group, a 3-nitrobenzylsulfonyl group, a 3-methoxybenzylsulfonyl group, a 4-trifluoromethoxybenzylsulfonyl group, and the like.

Examples of the "C1-C6 alkoxy group" in the compound of the present invention include a methoxy group, an ethoxy group, a propoxy group, an isopropoxy group, a butoxy group, an isobutoxy group, a sec-butoxy group, a tert-butoxy group, a pentyloxy group, a 2,2-dimethylpropoxy group, a 3-methylbutoxy group, a 2,3-dimethylbutoxy group, a 3,3-dimethylbutoxy group, a hexyloxy group, and the like.

Examples of the "C1-C6 alkoxy group optionally having one or more halogen atoms" in the compound of the present invention include a methoxy group, an ethoxy group, a propoxy group, an isopropoxy group, a butoxy group, an isobutoxy group, a sec-butoxy group, a tert-butoxy group, a pentyloxy group, a 2,2-dimethylpropoxy group, a 3-methylbutoxy group, a 2,3-dimethylbutoxy group, a 3,3-dimethylbutoxy group, a hexyloxy group, a trichloromethoxy group, a difluoromethoxy group, a trifluoromethoxy group, a 2,2,2-trifluoroethoxy group, a pentafluoroethoxy group, a heptafluoropropoxy group, a heptafluoroisopropoxy group, and the like.

Examples of the compound of the present invention include the following compounds.

A compound represented by Formula (1) wherein $R^1$ represents a hydrogen atom;

a compound represented by Formula (1) wherein $R^1$ represents a halogen atom;

a compound represented by Formula (1) wherein $R^1$ represents a nitro group;

a compound represented by Formula (1) wherein $R^1$ represents a C1-C6 alkyl group;

a compound represented by Formula (1) wherein $R^1$ represents a C1-C6 alkyl group optionally having one or more groups selected from the group X;

a compound represented by Formula (1) wherein $R^1$ represents a C2-C6 alkenyl group;

a compound represented by Formula (1) wherein $R^1$ represents a C2-C6 alkenyl group optionally having one or more groups selected from the group X;

a compound represented by Formula (1) wherein $R^1$ represents a C2-C6 alkynyl group;

a compound represented by Formula (1) wherein $R^1$ represents a C2-C6 alkynyl group optionally having one or more groups selected from the group X;

a compound represented by Formula (1) wherein $R^1$ represents a phenyl group;

a compound represented by Formula (1) wherein $R^1$ represents a phenyl group optionally having one or more groups selected from the group Y;

a compound represented by Formula (1) wherein $R^1$ represents a 6-membered aromatic heterocyclic group;

a compound represented by Formula (1) wherein $R^1$ represents a 6-membered aromatic heterocyclic group optionally having one or more groups selected from the group Y;

a compound represented by Formula (1) wherein $R^1$ represents a 5-membered aromatic heterocyclic group;

a compound represented by Formula (1) wherein $R^1$ represents a 5-membered aromatic heterocyclic group optionally having one or more groups selected from the group Y;

a compound represented by Formula (1) wherein $R^1$ represents a carboxy group;

a compound represented by Formula (1) wherein $R^1$ represents a C2-C6 alkylcarbonyl group;

a compound represented by Formula (1) wherein $R^1$ represents a C2-C6 alkylcarbonyl group optionally having one or more halogen atoms;

a compound represented by Formula (1) wherein $R^1$ represents a benzoyl group;

a compound represented by Formula (1) wherein $R^1$ represents a benzoyl group optionally having one or more groups selected from the group Y;

a compound represented by Formula (1) wherein $R^1$ represents a C2-C6 alkoxycarbonyl group;

a compound represented by Formula (1) wherein $R^1$ represents a aminocarbonyl group;

a compound represented by Formula (1) wherein $R^1$ represents $-NR^{11}R^{12}$;

a compound represented by Formula (1) wherein $R^1$ represents $-S(O)_2NR^7R^{11}$;

a compound represented by Formula (1) wherein $R^1$ represents $-OR^{11}$;

a compound represented by Formula (1) wherein $R^1$ represents $-S(O)_mR^{11}$;

a compound represented by Formula (1) wherein $R^1$ represents $-SF_5$;

a compound represented by Formula (1) wherein $R^1$ represents a C1-C4 alkyl group optionally having one or more halogen atoms;

a compound represented by Formula (1) wherein $R^1$ represents a C2-C4 alkenyl group optionally having one or more halogen atoms;

a compound represented by Formula (1) wherein $R^1$ represents a C2-C4 alkynyl group optionally having one or more halogen atoms;

a compound represented by Formula (1) wherein $R^1$ represents a pyridyl group optionally having one or more groups selected from the group Y;

a compound represented by Formula (1) wherein $R^1$ represents a pyrimidinyl group optionally having one or more groups selected from the group Y;

a compound represented by Formula (1) wherein $R^1$ represents a thienyl group optionally having one or more groups selected from the group Y;

a compound represented by Formula (1) wherein $R^1$ represents a pyrrolyl group optionally having one or more groups selected from the group Y;

a compound represented by Formula (1) wherein $R^1$ represents a C2-C5 alkylcarbonyl group optionally having one or more halogen atoms;

a compound represented by Formula (1) wherein $R^2$ represents a hydrogen atom;

a compound represented by Formula (1) wherein $R^2$ represents a halogen atom;

a compound represented by Formula (1) wherein $R^2$ represents a cyano group;

a compound represented by Formula (1) wherein $R^2$ represents a nitro group;

a compound represented by Formula (1) wherein $R^2$ represents a C1-C6 alkyl group;

a compound represented by Formula (1) wherein $R^2$ represents a C1-C6 alkyl group optionally having one or more groups selected from the group X;

a compound represented by Formula (1) wherein $R^2$ represents a C2-C6 alkenyl group;

a compound represented by Formula (1) wherein $R^2$ represents a C2-C6 alkenyl group optionally having one or more groups selected from the group X;

a compound represented by Formula (1) wherein $R^2$ represents a C2-C6 alkynyl group;

a compound represented by Formula (1) wherein $R^2$ represents a C2-C6 alkynyl group optionally having one or more groups selected from the group X;

a compound represented by Formula (1) wherein $R^2$ represents a phenyl group;

a compound represented by Formula (1) wherein $R^2$ represents a phenyl group optionally having one or more groups selected from the group Y;

a compound represented by Formula (1) wherein $R^2$ represents a 6-membered aromatic heterocyclic group;

a compound represented by Formula (1) wherein $R^2$ represents a 6-membered aromatic heterocyclic group optionally having one or more groups selected from the group Y;

a compound represented by Formula (1) wherein $R^2$ represents a 5-membered aromatic heterocyclic group;

a compound represented by Formula (1) wherein $R^2$ represents a 5-membered aromatic heterocyclic group optionally having one or more groups selected from the group Y;

a compound represented by Formula (1) wherein $R^2$ represents a carboxy group;

a compound represented by Formula (1) wherein $R^2$ represents a C2-C6 alkylcarbonyl group;

a compound represented by Formula (1) wherein $R^1$ represents a C2-C6 alkylcarbonyl group optionally having one or more halogen atoms;

a compound represented by Formula (1) wherein $R^2$ represents a benzoyl group;

a compound represented by Formula (1) wherein $R^2$ represents a benzoyl group optionally having one or more groups selected from the group Y;

a compound represented by Formula (1) wherein $R^2$ represents a C2-C6 alkoxycarbonyl group;

a compound represented by Formula (1) wherein $R^2$ represents a aminocarbonyl group;

a compound represented by Formula (1) wherein $R^2$ represents —$NR^{12}R^{13}$;

a compound represented by Formula (1) wherein $R^2$ represents —$S(O)_2NR^7R^{11}$;

a compound represented by Formula (1) wherein $R^2$ represents —$OR^{13}$;

a compound represented by Formula (1) wherein $R^2$ represents —$S(O)_mR^{13}$;

a compound represented by Formula (1) wherein $R^2$ represents —$SF_5$;

a compound represented by Formula (1) wherein $R^2$ represents a C1-C4 alkyl group;

a compound represented by Formula (1) wherein $R^2$ represents a C1-C4 alkyl group optionally having one or more halogen atoms;

a compound represented by Formula (1) wherein $R^2$ represents a C2-C4 alkenyl group;

a compound represented by Formula (1) wherein $R^2$ represents a C2-C4 alkenyl group optionally having one or more halogen atoms;

a compound represented by Formula (1) wherein $R^2$ represents a C2-C4 alkynyl group;

a compound represented by Formula (1) wherein $R^2$ represents a C2-C4 alkynyl group optionally having one or more halogen atoms;

a compound represented by Formula (1) wherein $R^2$ represents a pyridyl group;

a compound represented by Formula (1) wherein $R^2$ represents a pyridyl group optionally having one or more groups selected from the group Y;

a compound represented by Formula (1) wherein $R^2$ represents a pyrimidinyl group;

a compound represented by Formula (1) wherein $R^2$ represents a pyrimidinyl group optionally having one or more groups selected from the group Y;

a compound represented by Formula (1) wherein $R^2$ represents a thienyl group;

a compound represented by Formula (1) wherein $R^2$ represents a thienyl group optionally having one or more groups selected from the group Y;

a compound represented by Formula (1) wherein $R^2$ represents a pyrrolyl group;

a compound represented by Formula (1) wherein $R^2$ represents a pyrrolyl group optionally having one or more groups selected from the group Y;

a compound represented by Formula (1) wherein $R^2$ represents a C2-C5 alkylcarbonyl group;

a compound represented by Formula (1) wherein $R^2$ represents a C2-C5 alkylcarbonyl group optionally having one or more halogen atoms;

a compound represented by Formula (1) wherein $R^2$ represents a C2-C4 alkoxycarbonyl group;

a compound represented by Formula (1) wherein $R^3$ represents a hydrogen atom;

a compound represented by Formula (1) wherein $R^3$ represents a halogen atom;

a compound represented by Formula (1) wherein $R^3$ represents a cyano group;

a compound represented by Formula (1) wherein $R^3$ represents a nitro group;

a compound represented by Formula (1) wherein $R^3$ represents a C1-C6 alkyl group;

a compound represented by Formula (1) wherein $R^3$ represents a C1-C6 alkyl group optionally having one or more groups selected from the group X;

a compound represented by Formula (1) wherein $R^3$ represents a C2-C6 alkenyl group;

a compound represented by Formula (1) wherein $R^3$ represents a C2-C6 alkenyl group optionally having one or more groups selected from the group X;

a compound represented by Formula (1) wherein $R^3$ represents a C2-C6 alkynyl group;

a compound represented by Formula (1) wherein $R^3$ represents a C2-C6 alkynyl group optionally having one or more groups selected from the group X;

a compound represented by Formula (1) wherein $R^3$ represents a phenyl group;

a compound represented by Formula (1) wherein $R^3$ represents a phenyl group optionally having one or more groups selected from the group Y;

a compound represented by Formula (1) wherein $R^3$ represents a 6-membered aromatic heterocyclic group;

a compound represented by Formula (1) wherein $R^3$ represents a 6-membered aromatic heterocyclic group optionally having one or more groups selected from the group Y;

a compound represented by Formula (1) wherein $R^3$ represents a 5-membered aromatic heterocyclic group;

a compound represented by Formula (1) wherein $R^3$ represents a 5-membered aromatic heterocyclic group optionally having one or more groups selected from the group Y;

a compound represented by Formula (1) wherein $R^3$ represents a carboxy group;

a compound represented by Formula (1) wherein $R^3$ represents a C2-C6 alkylcarbonyl group;

a compound represented by Formula (1) wherein $R^3$ represents a C2-C6 alkylcarbonyl group optionally having one or more halogen atoms;

a compound represented by Formula (1) wherein $R^3$ represents a benzoyl group optionally having one or more groups selected from the group Y;

a compound represented by Formula (1) wherein $R^3$ represents a C2-C6 alkoxycarbonyl group;

a compound represented by Formula (1) wherein $R^3$ represents a aminocarbonyl group;

a compound represented by Formula (1) wherein $R^3$ represents —$NR^{11}R^{12}$;

a compound represented by Formula (1) wherein $R^3$ represents —$S(O)_2NR^7R^{11}$;

a compound represented by Formula (1) wherein $R^3$ represents —$OR^{11}$;

a compound represented by Formula (1) wherein $R^3$ represents —$S(O)_mR^{11}$;

a compound represented by Formula (1) wherein $R^3$ represents —$SF_5$;

a compound represented by Formula (1) wherein $R^3$ represents a C1-C4 alkyl group;

a compound represented by Formula (1) wherein $R^3$ represents a C1-C4 alkyl group optionally having one or more halogen atoms;

a compound represented by Formula (1) wherein $R^3$ represents a C2-C4 alkenyl group;

a compound represented by Formula (1) wherein $R^3$ represents a C2-C4 alkenyl group optionally having one or more halogen atoms;

a compound represented by Formula (1) wherein $R^3$ represents a C2-C4 alkynyl group;

a compound represented by Formula (1) wherein $R^3$ represents a C2-C4 alkynyl group optionally having one or more halogen atoms;

a compound represented by Formula (1) wherein $R^3$ represents a pyridyl group;

a compound represented by Formula (1) wherein $R^3$ represents a pyridyl group optionally having one or more groups selected from the group Y;

a compound represented by Formula (1) wherein $R^3$ represents a pyrimidinyl group;

a compound represented by Formula (1) wherein $R^3$ represents a pyrimidinyl group optionally having one or more groups selected from the group Y;

a compound represented by Formula (1) wherein $R^3$ represents a thienyl group;

a compound represented by Formula (1) wherein $R^3$ represents a thienyl group optionally having one or more groups selected from the group Y;

a compound represented by Formula (1) wherein $R^3$ represents a pyrrolyl group;

a compound represented by Formula (1) wherein $R^3$ represents a pyrrolyl group optionally having one or more groups selected from the group Y;

a compound represented by Formula (1) wherein $R^3$ represents a pyrazolyl group;

a compound represented by Formula (1) wherein $R^3$ represents a pyrazolyl group optionally having one or more groups selected from the group Y;

a compound represented by Formula (1) wherein $R^3$ represents a C2-C5 alkylcarbonyl group;

a compound represented by Formula (1) wherein $R^3$ represents a C2-C5 alkylcarbonyl group optionally having one or more halogen atoms;

a compound represented by Formula (1) wherein $R^3$ represents a C2-C4 alkoxycarbonyl group;

a compound represented by Formula (1) wherein $R^4$ represents a hydrogen atom;

a compound represented by Formula (1) wherein $R^4$ represents a halogen atom;

a compound represented by Formula (1) wherein $R^4$ represents a cyano group;

a compound represented by Formula (1) wherein $R^4$ represents a nitro group;

a compound represented by Formula (1) wherein $R^4$ represents a C1-C6 alkyl group;

a compound represented by Formula (1) wherein $R^4$ represents a C1-C6 alkyl group optionally having one or more groups selected from the group X;

a compound represented by Formula (1) wherein $R^1$ represents a C2-C6 alkenyl group;

a compound represented by Formula (1) wherein $R^1$ represents a C2-C6 alkenyl group optionally having one or more groups selected from the group X;

a compound represented by Formula (1) wherein $R^4$ represents a C2-C6 alkynyl group;

a compound represented by Formula (1) wherein $R^4$ represents a C2-C6 alkynyl group optionally having one or more groups selected from the group X;

a compound represented by Formula (1) wherein $R^4$ represents a phenyl group;

a compound represented by Formula (1) wherein $R^4$ represents a phenyl group optionally having one or more groups selected from the group Y;

a compound represented by Formula (1) wherein $R^4$ represents a 6-membered aromatic heterocyclic group;

a compound represented by Formula (1) wherein $R^4$ represents a 6-membered aromatic heterocyclic group optionally having one or more groups selected from the group Y;

a compound represented by Formula (1) wherein $R^4$ represents a 5-membered aromatic heterocyclic group;

a compound represented by Formula (1) wherein $R^4$ represents a 5-membered aromatic heterocyclic group optionally having one or more groups selected from the group Y;

a compound represented by Formula (1) wherein $R^4$ represents a carboxy group;

a compound represented by Formula (1) wherein $R^4$ represents a C2-C6 alkylcarbonyl group;

a compound represented by Formula (1) wherein $R^4$ represents a C2-C6 alkylcarbonyl group optionally having one or more halogen atoms;

a compound represented by Formula (1) wherein $R^4$ represents a benzoyl group optionally having one or more groups selected from the group Y;

a compound represented by Formula (1) wherein $R^4$ represents a C2-C6 alkoxycarbonyl group;

a compound represented by Formula (1) wherein $R^4$ represents an aminocarbonyl group;

a compound represented by Formula (1) wherein $R^4$ represents —$NR^{11}R^{12}$;

a compound represented by Formula (1) wherein $R^4$ represents —$S(O)_2NR^7R^{11}$;

a compound represented by Formula (1) wherein $R^4$ represents —$OR^{11}$;

a compound represented by Formula (1) wherein $R^4$ represents —$S(O)_mR^{11}$;

a compound represented by Formula (1) wherein $R^4$ represents —$SF_5$;

a compound represented by Formula (1) wherein $R^4$ represents a C1-C4 alkyl group;

a compound represented by Formula (1) wherein $R^4$ represents a C1-C4 alkyl group optionally having one or more halogen atoms;

a compound represented by Formula (1) wherein $R^4$ represents a C2-C4 alkenyl group;

a compound represented by Formula (1) wherein $R^4$ represents a C2-C4 alkenyl group optionally having one or more halogen atoms;

a compound represented by Formula (1) wherein $R^4$ represents a C2-C4 alkynyl group;

a compound represented by Formula (1) wherein $R^4$ represents a C2-C4 alkynyl group optionally having one or more halogen atoms;

a compound represented by Formula (1) wherein $R^4$ represents a pyridyl group;

a compound represented by Formula (1) wherein $R^4$ represents a pyridyl group optionally having one or more groups selected from the group Y;

a compound represented by Formula (1) wherein $R^4$ represents a pyrimidinyl group;

a compound represented by Formula (1) wherein $R^4$ represents a pyrimidinyl group optionally having one or more groups selected from the group Y;

a compound represented by Formula (1) wherein $R^4$ represents a thienyl group;

a compound represented by Formula (1) wherein $R^4$ represents a thienyl group optionally having one or more groups selected from the group Y;

a compound represented by Formula (1) wherein $R^4$ represents a pyrrolyl group;

a compound represented by Formula (1) wherein $R^4$ represents a pyrrolyl group optionally having one or more groups selected from the group Y;

a compound represented by Formula (1) wherein $R^4$ represents a C2-C5 alkylcarbonyl group;

a compound represented by Formula (1) wherein $R^4$ represents a C2-C5 alkylcarbonyl group optionally having one or more halogen atoms;

a compound represented by Formula (1) wherein $R^4$ represents a C2-C4 alkoxycarbonyl group;

a compound represented by Formula (1) wherein $R^5$ represents a hydrogen atom;

a compound represented by Formula (1) wherein $R^5$ represents a halogen atom;

a compound represented by Formula (1) wherein $R^5$ represents a cyano group;

a compound represented by Formula (1) wherein $R^5$ represents a nitro group;

a compound represented by Formula (1) wherein $R^5$ represents a C1-C6 alkyl group;

a compound represented by Formula (1) wherein $R^5$ represents a C1-C6 alkyl group optionally having one or more groups selected from the group X;

a compound represented by Formula (1) wherein $R^5$ represents a carboxy group;

a compound represented by Formula (1) wherein $R^5$ represents a C2-C6 alkoxycarbonyl group;

a compound represented by Formula (1) wherein $R^5$ represents —$NR^{11}R^{12}$;

a compound represented by Formula (1) wherein $R^5$ represents —$S(O)_2NR^7R^{11}$;

a compound represented by Formula (1) wherein $R^5$ represents —$OR^{14}$;

a compound represented by Formula (1) wherein $R^5$ represents a phenyl group;

a compound represented by Formula (1) wherein $R^5$ represents a phenyl group optionally having one or more groups selected from the group Y;

a compound represented by Formula (1) wherein $R^5$ represents a 6-membered aromatic heterocyclic group;

a compound represented by Formula (1) wherein $R^5$ represents a 6-membered aromatic heterocyclic group optionally having one or more groups selected from the group Y;

a compound represented by Formula (1) wherein $R^5$ represents a 5-membered aromatic heterocyclic group;

a compound represented by Formula (1) wherein $R^5$ represents a 5-membered aromatic heterocyclic group optionally having one or more groups selected from the group Y;

a compound represented by Formula (1) wherein $R^5$ represents a C1-C4 alkyl group;

a compound represented by Formula (1) wherein $R^5$ represents a C1-C4 alkyl group optionally having one or more halogen atoms;

a compound represented by Formula (1) wherein $R^5$ represents a C2-C5 alkoxycarbonyl group;

a compound represented by Formula (1) wherein $R^5$ represents a pyrrolyl group;

a compound represented by Formula (1) wherein $R^5$ represents a pyrrolyl group optionally having one or more groups selected from the group Y;

a compound represented by Formula (1) wherein $R^1$ represents a halogen atom, and $R^5$ represents a hydrogen atom;

a compound represented by Formula (1) wherein $R^1$ represents a halogen atom, and $R^5$ represents a halogen atom;

a compound represented by Formula (1) wherein $R^1$ represents a halogen atom, and $R^5$ represents a C1-C6 alkyl group optionally having one or more groups selected from the group X;

a compound represented by Formula (1) wherein $R^1$ represents a halogen atom, and $R^5$ represents a carboxy group;

a compound represented by Formula (1) wherein $R^1$ represents a halogen atom, and $R^5$ represents a C2-C6 alkoxycarbonyl group;

a compound represented by Formula (1) wherein $R^1$ represents a halogen atom, and $R^5$ represents —$NR^{11}R^{12}$;

a compound represented by Formula (1) wherein $R^1$ represents a halogen atom, and $R^5$ represents —$OR^{14}$;

a compound represented by Formula (1) wherein $R^1$ represents a halogen atom, and $R^5$ represents a phenyl group optionally having one or more groups selected from the group Y;

a compound represented by Formula (1) wherein $R^1$ represents a halogen atom, and $R^5$ represents a C1-C4 alkyl group optionally having one or more halogen atoms;

a compound represented by Formula (1) wherein $R^1$ represents a C1-C6 alkyl group optionally having one or more groups selected from the group X, and $R^5$ represents a hydrogen atom;

a compound represented by Formula (1) wherein $R^1$ represents a C1-C6 alkyl group optionally having one or more groups selected from the group X, and $R^5$ represents a halogen atom;

a compound represented by Formula (1) wherein $R^1$ represents a C1-C6 alkyl group optionally having one or more groups selected from the group X, and $R^5$ represents a C1-C6 alkyl group optionally having one or more groups selected from the group X;

a compound represented by Formula (1) wherein $R^1$ represents a C1-C6 alkyl group optionally having one or more groups selected from the group X, and $R^5$ represents a carboxy group;

a compound represented by Formula (1) wherein $R^1$ represents a C1-C6 alkyl group optionally having one or more groups selected from the group X, and $R^5$ represents a C2-C6 alkoxycarbonyl group;

a compound represented by Formula (1) wherein $R^1$ represents a C1-C6 alkyl group optionally having one or more groups selected from the group X, and $R^5$ represents —$NR^{11}R^{12}$;

a compound represented by Formula (1) wherein R-represents a C1-C6 alkyl group optionally having one or more groups selected from the group X, and $R^5$ represents —$OR^{14}$;

a compound represented by Formula (1) wherein $R^1$ represents a C1-C6 alkyl group optionally having one or more groups selected from the group X, and $R^5$ represents a phenyl group optionally having one or more groups selected from the group Y;

a compound represented by Formula (1) wherein $R^1$ represents a C1-C6 alkyl group optionally having one or more groups selected from the group X, and $R^5$ represents a C1-C4 alkyl group optionally having one or more halogen atoms;

a compound represented by Formula (1) wherein $R^1$ represents a phenyl group optionally having one or more groups selected from the group Y, and $R^5$ represents a hydrogen atom;

a compound represented by Formula (1) wherein $R^1$ represents a phenyl group optionally having one or more groups selected from the group Y, and $R^5$ represents a halogen atom;

a compound represented by Formula (1) wherein R: represents a phenyl group optionally having one or more groups selected from the group Y, and $R^5$ represents a C1-C6 alkyl group optionally having one or more groups selected from the group X;

a compound represented by Formula (1) wherein $R^1$ represents a phenyl group optionally having one or more groups selected from the group Y, and $R^5$ represents a carboxy group;

a compound represented by Formula (1) wherein $R^1$ represents a phenyl group optionally having one or more groups selected from the group Y, and $R^3$ represents a C2-C6 alkoxycarbonyl group;

a compound represented by Formula (1) wherein $R^1$ represents a phenyl group optionally having one or more groups selected from the group Y, and $R^5$ represents —$NR^{11}R^{12}$;

a compound represented by Formula (1) wherein $R^1$ represents a phenyl group optionally having one or more groups selected from the group Y, and $R^5$ represents —$OR^{14}$;

a compound represented by Formula (1) wherein $R^1$ represents a phenyl group optionally having one or more groups selected from the group Y, and $R^5$ represents a phenyl group optionally having one or more groups selected from the group Y;

a compound represented by Formula (1) wherein $R^1$ represents a phenyl group optionally having one or more groups selected from the group Y, and $R^5$ represents a C1-C4 alkyl group optionally having one or more halogen atoms;

a compound represented by Formula (1) wherein $R^1$ represents a 6-membered aromatic heterocyclic group optionally having one or more groups selected from the group Y, and $R^5$ represents a halogen atom;

a compound represented by Formula (1) wherein $R^1$ represents a 6-membered aromatic heterocyclic group optionally having one or more groups selected from the group Y, and $R^5$ represents a C1-C6 alkyl group optionally having one or more groups selected from the group X;

a compound represented by Formula (1) wherein $R^1$ represents a 6-membered aromatic heterocyclic group optionally having one or more groups selected from the group Y, and $R^5$ represents a carboxy group;

a compound represented by Formula (1) wherein R-represents a 6-membered aromatic heterocyclic group optionally having one or more groups selected from the group Y, and $R^5$ represents a C2-C6 alkoxycarbonyl group;

a compound represented by Formula (1) wherein $R^1$ represents a 6-membered aromatic heterocyclic group optionally having one or more groups selected from the group Y, and $R^5$ represents —$NR^{11}R^{12}$;

a compound represented by Formula (1) wherein $R^1$ represents a 6-membered aromatic heterocyclic group optionally having one or more groups selected from the group Y, and $R^5$ represents —$OR^{14}$;

a compound represented by Formula (1) wherein $R^1$ represents a 6-membered aromatic heterocyclic group optionally having one or more groups selected from the group Y, and $R^5$ represents a phenyl group optionally having one or more groups selected from the group Y;

a compound represented by Formula (1) wherein $R^1$ represents a 6-membered aromatic heterocyclic group optionally having one or more groups selected from the group Y, and $R^5$ represents a C1-C4 alkyl group optionally having one or more halogen atoms;

a compound represented by Formula (1) wherein $R^1$ represents a 5-membered aromatic heterocyclic group optionally having one or more groups selected from the group Y, and $R^5$ represents a hydrogen atom;

a compound represented by Formula (1) wherein $R^1$ represents a thienyl group optionally having one or more groups selected from the group Y, and $R^5$ represents a hydrogen atom;

a compound represented by Formula (1) wherein $R^1$ represents a 5-membered aromatic heterocyclic group optionally having one or more groups selected from the group Y, and $R^5$ represents a halogen atom;

a compound represented by Formula (1) wherein $R^1$ represents a 5-membered aromatic heterocyclic group optionally having one or more groups selected from the group Y, and $R^5$ represents a C1-C6 alkyl group optionally having one or more groups selected from the group X;

a compound represented by Formula (1) wherein $R^1$ represents a 5-membered aromatic heterocyclic group optionally having one or more groups selected from the group Y, and $R^5$ represents a carboxy group;

a compound represented by Formula (1) wherein $R^1$ represents a 5-membered aromatic heterocyclic group optionally having one or more groups selected from the group Y, and $R^5$ represents a C2-C6 alkoxycarbonyl group;

a compound represented by Formula (1) wherein $R^1$ represents a 5-membered aromatic heterocyclic group optionally having one or more groups selected from the group Y, and $R^5$ represents —$NR^{11}R^{12}$;

a compound represented by Formula (1) wherein $R^1$ represents a 5-membered aromatic heterocyclic group optionally having one or more groups selected from the group Y, and $R^5$ represents —$OR^{14}$;

a compound represented by Formula C1) wherein $R^1$ represents a 5-membered aromatic heterocyclic group optionally having one or more groups selected from the group Y, and $R^5$ represents a phenyl group optionally having one or more groups selected from the group Y;

a compound represented by Formula (1) wherein $R^1$ represents a 5-membered aromatic heterocyclic group optionally having one or more groups selected from the group Y, and $R^5$ represents a C1-C4 alkyl group optionally having one or more halogen atoms;

a compound represented by Formula (1) wherein $R^1$ represents a carboxy group, and $R^5$ represents a hydrogen atom;

a compound represented by Formula (1) wherein $R^1$ represents a carboxy group, and $R^5$ represents a halogen atom;

a compound represented by Formula (1) wherein $R^1$ represents a carboxy group, and $R^5$ represents a C1-C6 alkyl group optionally having one or more groups selected from the group X;

a compound represented by Formula (1) wherein $R^1$ represents a carboxy group, and $R^5$ represents carboxy group;

a compound represented by Formula (1) wherein $R^1$ represents a carboxy group, and $R^5$ represents a C2-C6 alkoxycarbonyl group;

a compound represented by Formula (1) wherein $R^1$ represents a carboxy group, and $R^5$ represents —$NR^{11}R^{12}$;

a compound represented by Formula (1) wherein $R^1$ represents a carboxy group, and $R^5$ represents —$OR^{14}$;

a compound represented by Formula (1) wherein $R^1$ represents a carboxy group, and $R^5$ represents a phenyl group optionally having one or more groups selected from the group Y;

a compound represented by Formula (1) wherein $R^1$ represents a carboxy group, and $R^5$ represents a C1-C4 alkyl group optionally having one or more halogen atoms;

a compound represented by Formula (1) wherein $R^1$ represents a C2-C6 alkylcarbonyl group optionally having one or more halogen atoms, and $R^5$ represents a hydrogen atom;

a compound represented by Formula (1) wherein $R^1$ represents a C2-C6 alkylcarbonyl group optionally having one or more halogen atoms, and $R^5$ represents a halogen atom;

a compound represented by Formula (1) wherein $R^1$ represents a C2-C6 alkylcarbonyl group which may have optionally one or more halogen atoms, and $R^5$ represents a C1-C6 alkyl group optionally having one or more groups selected from the group X;

a compound represented by Formula (1) wherein $R^1$ represents a C2-C6 alkylcarbonyl group optionally having one or more halogen atoms, and $R^5$ represents a carboxy group;

a compound represented by Formula (1) wherein $R^1$ represents a C2-C6 alkylcarbonyl group optionally having one or more halogen atoms, and $R^5$ represents a C2-C6 alkoxycarbonyl group;

a compound represented by Formula (1) wherein $R^1$ represents a C2-C6 alkylcarbonyl group optionally having one or more halogen atoms, and $R^5$ represents —$NR^{11}R^{12}$;

a compound represented by Formula (1) wherein $R^1$ represents a C2-C6 alkylcarbonyl group optionally having one or more halogen atoms, and $R^5$ represents —$OR^{14}$;

a compound represented by Formula (1) wherein $R^1$ represents a C2-C6 alkylcarbonyl group optionally having one or more halogen atoms, and $R^5$ represents a phenyl group optionally having one or more groups selected from the group Y;

a compound represented by Formula (1) wherein $R^1$ represents a C2-C6 alkylcarbonyl group optionally having one or more halogen atoms, and $R^5$ represents C1-C4 alkyl group optionally having one or more halogen atoms;

a compound represented by Formula (1) wherein $R^1$ represents a C2-C6 alkoxycarbonyl group, and $R^5$ represents a hydrogen atom;

a compound represented by Formula (1) wherein $R^1$ represents a C2-C5 alkoxycarbonyl group, and $R^5$ represents a hydrogen atom;

a compound represented by Formula (1) wherein $R^1$ represents a C2-C6 alkoxycarbonyl group, and $R^5$ represents a halogen atom;

a compound represented by Formula (1) wherein R-represents a C2-C6 alkoxycarbonyl group, and $R^5$ represents a C1-C6 alkyl group optionally having one or more groups selected from the group X;

a compound represented by Formula (1) wherein $R^1$ represents a C2-C6 alkoxycarbonyl group, and $R^5$ represents a carboxy group;

a compound represented by Formula (1) wherein $R^1$ represents a C2-C6 alkoxycarbonyl group, and $R^5$ represents a C2-C6 alkoxycarbonyl group;

a compound represented by Formula (1) wherein $R^1$ represents a C2-C6 alkoxycarbonyl group, and $R^5$ represents $NR^{11}R^{12}$;

a compound represented by Formula (1) wherein $R^1$ represents a C2-C6 alkoxycarbonyl group, and $R^5$ represents —$OR^{14}$;

a compound represented by Formula (1) wherein $R^1$ represents a C2-C6 alkoxycarbonyl group, and $R^3$ represents a phenyl group optionally having one or more groups selected from the group Y;

a compound represented by Formula (1) wherein $R^1$ represents a C2-C6 alkoxycarbonyl group, and $R^5$ represents a C1-C4 alkyl group optionally having one or more halogen atoms;

a compound represented by Formula (1) wherein $R^1$ represents an aminocarbonyl group, and $R^5$ represents a halogen atom;

a compound represented by Formula (1) wherein $R^1$ represents an aminocarbonyl group, and $R^5$ represents a C1-C6 alkyl group optionally having one or more groups selected from the group X;

a compound represented by Formula (1) wherein $R^1$ represents an aminocarbonyl group, and $R^5$ represents a carboxy group;

a compound represented by Formula (1) wherein $R^1$ represents an aminocarbonyl group, and $R^5$ represents a C2-C6 alkoxycarbonyl group;

a compound represented by Formula (1) wherein $R^1$ represents an aminocarbonyl group, and $R^5$ represents —$NR^{11}R^{12}$;

a compound represented by Formula (1) wherein $R^1$ represents an aminocarbonyl group, and $R^5$ represents —$OR^{14}$;

a compound represented by Formula (1) wherein $R^1$ represents an aminocarbonyl group, and $R^5$ represents a phenyl group optionally having one or more groups selected from the group Y;

a compound represented by Formula (1) wherein $R^1$ represents an aminocarbonyl group, and $R^5$ represents a C1-C4 alkyl group optionally having one or more halogen atoms;

a compound represented by Formula (1) wherein $R^1$ represents —$NR^{11}R^{12}$, and $R^5$ represents a hydrogen atom;

a compound represented by Formula (1) wherein $R^1$ represents —$OR^{11}$, and $R^5$ represents a hydrogen atom;

a compound represented by Formula (1) wherein $R^1$ represents —$OR^{11}$, and $R^5$ represents a halogen atom;

a compound represented by Formula (1) wherein $R^1$ represents —$OR^{11}$, and $R^5$ represents a C1-C6 alkyl group optionally having one or more groups selected from the group X;

a compound represented by Formula (1) wherein $R^1$ represents —$OR^{11}$, and $R^5$ represents a carboxy group;

a compound represented by Formula (1) wherein $R^1$ represents —$OR^{11}$, and $R^5$ represents a C2-C6 alkoxycarbonyl group;

a compound represented by Formula (1) wherein $R^1$ represents —$OR^{11}$, and $R^5$ represents —$NR^{11}R^{12}$;

a compound represented by Formula (1) wherein $R^1$ represents —$OR^{11}$, and $R^5$ represents —$OR^{14}$;

a compound represented by Formula (1) wherein $R^1$ represents —$OR^{11}$, and $R^5$ represents a phenyl group optionally having one or more groups selected from the group Y;

a compound represented by Formula (1) wherein $R^1$ represents —$OR^{11}$, and $R^5$ represents a C1-C4 alkyl group optionally having one or more halogen atoms;

a compound represented by Formula (1) wherein $R^1$ represents —$S(O)_nR^{11}$, and $R^5$ represents a hydrogen atom;

a compound represented by Formula (1) wherein $R^1$ represents —$S(O)_mR^{11}$, and $R^5$ represents a halogen atom;

a compound represented by Formula (1) wherein $R^1$ represents —$S(O)_mR^{11}$, and $R^5$ represents a C1-C6 alkyl group optionally having one or more groups selected from the group X;

a compound represented by Formula (1) wherein $R^1$ represents —$S(O)_mR^{11}$, and $R^5$ represents a carboxy group;

a compound represented by Formula (1) wherein $R^1$ represents —$S(O)_mR^{11}$, and $R^5$ represents a C2-C6 alkoxycarbonyl group;

a compound represented by Formula (1) wherein $R^1$ represents —$S(O)_mR^{11}$, and $R^5$ represents —$NR^{11}R^{12}$;

a compound represented by Formula (1) wherein $R^1$ represents —$S(O)_mR^{11}$, and $R^5$ represents —$OR^{14}$;

a compound represented by Formula (1) wherein $R^1$ represents —$S(O)_mR^{11}$, and $R^5$ represents a phenyl group optionally having one or more groups selected from the group Y;

a compound represented by Formula (1) wherein $R^1$ represents —$S(O)_mR^{11}$, and $R^5$ represents a C1-C4 alkyl group optionally having one or more halogen atoms;

a compound represented by Formula (1) wherein $R^1$ represents —$SF_5$, and $R^5$ represents a hydrogen atom;

a compound represented by Formula (1) wherein $R^1$ represents —$SF_5$, and $R^5$ represents a halogen atom;

a compound represented by Formula (1) wherein $R^1$ represents —$SF_5$, and $R^5$ represents a C1-C6 alkyl group optionally having one or more groups selected from the group X;

a compound represented by Formula (1) wherein $R^1$ represents —$SF_5$, and $R^5$ represents a carboxy group;

a compound represented by Formula (1) wherein $R^1$ represents —$SF_5$, and $R^5$ represents a C2-C6 alkoxycarbonyl group;

a compound represented by Formula (1) wherein $R^1$ represents —$SF_5$, and $R^5$ represents —$NR^{11}R^{12}$;

a compound represented by Formula (1) wherein $R^1$ represents —$SF_5$, and $R^5$ represents —$OR^{14}$;

a compound represented by Formula (1) wherein $R^1$ represents —$SF_5$, and $R^5$ represents a phenyl group optionally having one or more groups selected from the group Y;

a compound represented by Formula (1) wherein $R^1$ represents —$SF_5$, and $R^5$ represents a C1-C4 alkyl group optionally having one or more halogen atoms;

a compound represented by Formula (12 wherein $R^1$ represents a C1-C4 alkyl group optionally having one cr more halogen atoms, and $R^5$ represents a hydrogen atom;

a compound represented by Formula (1) wherein $R^1$ represents a C1-C4 alkyl group optionally having one or more halogen atoms, and $R^5$ represents a halogen atom;

a compound represented by Formula (1) wherein $R^1$ represents a C1-C4 alkyl group optionally having one or more halogen atoms, and $R^5$ represents a C1-C6 alkyl group optionally having one or more groups selected from the group X;

a compound represented by Formula (1) wherein $R^1$ represents a C1-C4 alkyl group optionally having one or more halogen atoms, and $R^5$ represents a carboxy group;

a compound represented by Formula (1) wherein $R^1$ represents a C1-C4 alkyl group optionally having one or more halogen atoms, and $R^5$ represents a C2-C6 alkoxycarbonyl group;

a compound represented by Formula (1) wherein $R^1$ represents a C1-C4 alkyl group optionally having one or more halogen atoms, and $R^5$ represents —$NR^{11}R^{12}$;

a compound represented by Formula (1) wherein $R^1$ represents a C1-C4 alkyl group optionally having one or more halogen atoms, and $R^5$ represents —$OR^{14}$;

a compound represented by Formula (1) wherein R-represents a C1-C4 alkyl group optionally having one or more halogen atoms, and $R^5$ represents a phenyl group optionally having one or more groups selected from the group Y;

a compound represented by Formula (1) wherein $R^1$ represents a C1-C4 alkyl group optionally having one or more halogen atoms, and $R^5$ represents a C1-C4 alkyl group optionally having one or more halogen atoms;

a compound represented by Formula (1) wherein $R^1$ represents a hydrogen atom, and $R^5$ represents a halogen atom;

a compound represented by Formula (1) wherein $R^1$ represents a hydrogen atom, and $R^5$ represents a C1-C6 alkyl group optionally having one or more groups selected from the group X;

a compound represented by Formula (1) wherein $R^1$ represents a hydrogen atom, and $R^5$ represents a C1-C4 alkyl group optionally having one or more halogen atoms;

a compound represented by Formula (1) wherein $R^1$ represents a hydrogen atom, and $R^5$ represents a phenyl group optionally having one or more groups selected from the group Y;

a compound represented by Formula (1) wherein $R^1$ represents a hydrogen atom, and $R^5$ represents a 5-membered aromatic heterocyclic group optionally having one or more groups selected from the group Y;

a compound represented by Formula (1) wherein $R^1$ represents a hydrogen atom, and $R^5$ represents a pyrrolyl group optionally having one or more groups selected from the group Y;

a compound represented by Formula (1) wherein $R^1$ represents a hydrogen atom, and $R^5$ represents —$NR^{11}R^{12}$;

a compound represented by Formula (1) wherein $R^1$ represents a hydrogen atom, and $R^5$ represents —$OR^{14}$;

a compound represented by Formula (1) wherein $R^1$ represents a hydrogen atom, and $R^5$ represents a C2-C6 alkoxycarbonyl group;

a compound represented by Formula (1) wherein $R^1$ represents a hydrogen atom, and $R^5$ represents a C2-C5 alkoxycarbonyl group;

a compound represented by Formula (1) wherein $R^2$ represents a halogen atom, and $R^5$ represents a hydrogen atom;

a compound represented by Formula (1) wherein $R^2$ represents a halogen atom, and $R^5$ represents a halogen atom;

a compound represented by Formula (1) wherein $R^2$ represents a halogen atom, and $R^5$ represents a C1-C6 alkyl group optionally having one or more groups selected from the group X;

a compound represented by Formula (1) wherein $R^2$ represents a halogen atom, and $R^5$ represents a carboxy group;

a compound represented by Formula (1) wherein $R^2$ represents a halogen atom, and $R^5$ represents a C2-C6 alkoxycarbonyl group;

a compound represented by Formula (1) wherein $R^2$ represents a halogen atom, and $R^5$ represents $-NR^{11}R^{12}$;

a compound represented by Formula (1) wherein $R^2$ represents a halogen atom, and $R^5$ represents $-OR^{14}$;

a compound represented by Formula (1) wherein $R^2$ represents a halogen atom, and $R^5$ represents a phenyl group optionally having one or more groups selected from the group Y;

a compound represented by Formula (1) wherein $R^2$ represents a halogen atom, and $R^5$ represents a C1-C4 alkyl group optionally having one or more halogen atoms;

a compound represented by Formula (1) wherein $R^2$ represents a C1-C6 alkyl group optionally having one or more groups selected from the group X, and $R^5$ represents a hydrogen atom;

a compound represented by Formula (1) wherein $R^2$ represents a C1-C6 alkyl group optionally having one or more groups selected from the group X, and $R^5$ represents a halogen atom;

a compound represented by Formula (1) wherein $R^2$ represents a C1-C6 alkyl group optionally having one or more groups selected from the group X, and $R^5$ represents a C1-C6 alkyl group optionally having one or more groups selected from the group X;

a compound represented by Formula (1) wherein $R^2$ represents a C1-C6 alkyl group optionally having one or more groups selected from the group X, and $R^5$ represents a carboxy group;

a compound represented by Formula (1) wherein $R^2$ represents a C1-C6 alkyl group optionally having one or more groups selected from the group X, and $R^5$ represents a C2-C6 alkoxycarbonyl group;

a compound represented by Formula (1) wherein $R^2$ represents a C1-C6 alkyl group optionally having one or more groups selected from the group X, and $R^5$ represents $-NR^{11}R^{12}$;

a compound represented by Formula (1) wherein $R^2$ represents a C1-C6 alkyl group optionally having one or more groups selected from the group X, and $R^5$ represents $-OR^{14}$;

a compound represented by Formula (1) wherein $R^2$ represents a C1-C6 alkyl group optionally having one or more groups selected from the group X, and $R^5$ represents a phenyl group optionally having one or more groups selected from the group Y;

a compound represented by Formula (1) wherein $R^2$ represents a C1-C6 alkyl group optionally having one or more groups selected from the group X, and $R^5$ represents a C1-C4 alkyl group optionally having one or more halogen atoms;

a compound represented by Formula (1) wherein $R^2$ represents a phenyl group optionally having one or more groups selected from the group Y, and $R^5$ represents a hydrogen atom;

a compound represented by Formula (1) wherein $R^2$ represents a phenyl group optionally having one or more groups selected from the group Y, and $R^5$ represents a halogen atom;

a compound represented by Formula (1) wherein $R^2$ represents a phenyl group optionally having one or more groups selected from the group Y, and $R^5$ represents a C1-C6 alkyl group optionally having one or more groups selected from the group X;

a compound represented by Formula (1) wherein $R^2$ represents a phenyl group optionally having one or more groups selected from the group Y, and $R^5$ represents a carboxy group;

a compound represented by Formula (1) wherein $R^2$ represents a phenyl group optionally having one or more groups selected from the group Y, and $R^5$ represents a C2-C6 alkoxycarbonyl group;

a compound represented by Formula (1) wherein $R^2$ represents a phenyl group optionally having one or more groups selected from the group Y, and $R^5$ represents $-NR^{11}R^{12}$;

a compound represented by Formula (1) wherein $R^2$ represents a phenyl group optionally having one or more groups selected from the group Y, and $R^5$ represents $-OR^{14}$;

a compound represented by Formula (1) wherein $R^2$ represents a phenyl group optionally having one or more groups selected from the group Y, and $R^5$ represents a phenyl group optionally having one or more groups selected from the group Y;

a compound represented by Formula (1) wherein $R^2$ represents a phenyl group optionally having one or more groups selected from the group Y, and $R^5$ represents a C1-C4 alkyl group optionally having one or more halogen atoms;

a compound represented by Formula (1) wherein $R^2$ represents a 6-membered aromatic heterocyclic group optionally having one or more groups selected from the group Y, and $R^5$ represents a hydrogen atom;

a compound represented by Formula (1) wherein $R^2$ represents a 6-membered aromatic heterocyclic group optionally having one or more groups selected from the group Y, and $R^5$ represents a halogen atom;

a compound represented by Formula (1) wherein $R^2$ represents a 6-membered aromatic heterocyclic group optionally having one or more groups selected from the group Y, and $R^5$ represents a C1-C6 alkyl group optionally having one or more groups selected from the group X;

a compound represented by Formula (1) wherein $R^2$ represents a 6-membered aromatic heterocyclic group optionally having one or more groups selected from the group Y, and $R^5$ represents a carboxy group;

a compound represented by Formula (1) wherein $R^2$ represents a 6-membered aromatic heterocyclic group optionally having one or more groups selected from the group Y, and $R^5$ represents a C2-C6 alkoxycarbonyl group;

a compound represented by Formula (1) wherein $R^2$ represents a 6-membered aromatic heterocyclic group optionally having one or more groups selected from the group Y, and $R^5$ represents $-NR^{11}R^{12}$;

a compound represented by Formula (1) wherein $R^2$ represents a 6-membered aromatic heterocyclic group optionally having one or more groups selected from the group Y, and $R^5$ represents $-OR^{14}$;

a compound represented by Formula (1) wherein $R^2$ represents a 6-membered aromatic heterocyclic group optionally having one or more groups selected from the group Y, and $R^5$ represents a phenyl group optionally having one or more groups selected from the group Y;

a compound represented by Formula (1) wherein $R^2$ represents a 6-membered aromatic heterocyclic group which may have optionally one or more groups selected from the group Y, and $R^5$ represents a C1-C4 alkyl group optionally having one or more halogen atoms;

a compound represented by Formula (1) wherein $R^2$ represents a 5-membered aromatic heterocyclic group optionally having one or more groups selected from the group Y, and $R^5$ represents a hydrogen atom;

a compound represented by Formula (1) wherein $R^2$ represents a 5-membered aromatic heterocyclic group optionally having one or more groups selected from the group Y, and $R^5$ represents a halogen atom;

a compound represented by Formula (1) wherein $R^2$ represents a 5-membered aromatic heterocyclic group optionally having one or more groups selected from the group Y, and $R^5$ represents a C1-C6 alkyl group optionally having one or more groups selected from the group X;

a compound represented by Formula (1) wherein $R^2$ represents a 5-membered aromatic heterocyclic group optionally having one or more groups selected from the group Y, and $R^5$ represents a carboxy group;

a compound represented by Formula (1) wherein $R^2$ represents a 5-membered aromatic heterocyclic group optionally having one or more groups selected from the group Y, and $R^5$ represents a C2-C6 alkoxycarbonyl group;

a compound represented by Formula (1) wherein $R^2$ represents a 5-membered aromatic heterocyclic group optionally having one or more groups selected from the group Y, and $R^5$ represents —$NR^{11}R^{12}$;

a compound represented by Formula (1) wherein $R^2$ represents a 5-membered aromatic heterocyclic group optionally having one or more groups selected from the group Y, and $R^5$ represents —$OR^{14}$;

a compound represented by Formula (1) wherein $R^2$ represents a 5-membered aromatic heterocyclic group optionally having one or more groups selected from the group Y, and $R^5$ represents a phenyl group optionally having one or more groups selected from the group Y;

a compound represented by Formula (1) wherein $R^2$ represents a 5-membered aromatic heterocyclic group optionally having one or more groups selected from the group Y, and $R^5$ represents a C1-C4 alkyl group optionally having one or more halogen atoms;

a compound represented by Formula (1) wherein $R^2$ represents a carboxy group, and $R^5$ represents a hydrogen atom;

a compound represented by Formula (1) wherein $R^2$ represents a carboxy group, and $R^5$ represents a halogen atom;

a compound represented by Formula (1) wherein $R^2$ represents a carboxy group, and $R^5$ represents a C1-C6 alkyl group optionally having one or more groups selected from the group X;

a compound represented by Formula (1) wherein $R^2$ represents a carboxy group, and $R^5$ represents a carboxy group;

a compound represented by Formula (1) wherein $R^2$ represents a carboxy group, and $R^5$ represents a C2-C6 alkoxycarbonyl group;

a compound represented by Formula (1) wherein $R^2$ represents a carboxy group, and $R^5$ represents —$NR^{11}R^{12}$;

a compound represented by Formula (1) wherein $R^2$ represents a carboxy group, and $R^5$ represents —$OR^{14}$;

a compound represented by Formula (1) wherein $R^2$ represents a carboxy group, and $R^5$ represents a phenyl group optionally having one or more groups selected from the group Y;

a compound represented by Formula (1) wherein $R^2$ represents a carboxy group, and $R^5$ represents a C1-C4 alkyl group optionally having one or more halogen atoms;

a compound represented by Formula (1) wherein $R^2$ represents a C2-C6 alkylcarbonyl group optionally having one or more halogen atoms, and $R^5$ represents a hydrogen atom;

a compound represented by Formula (1) wherein $R^2$ represents a C2-C6 alkylcarbonyl group optionally having one or more halogen atoms, and $R^5$ represents a halogen atom;

a compound represented by Formula (1) wherein $R^2$ represents a C2-C6 alkylcarbonyl group optionally having one or more halogen atoms, and $R^5$ represents a C1-C6 alkyl group optionally having one or more groups selected from the group X;

a compound represented by Formula (1) wherein $R^2$ represents a C2-C6 alkylcarbonyl group optionally having one or more halogen atoms, and $R^5$ represents a carboxy group;

a compound represented by Formula (1) wherein $R^2$ represents a C2-C6 alkylcarbonyl group optionally having one or more halogen atoms, and $R^5$ represents a C2-C6 alkoxycarbonyl group;

a compound represented by Formula (1) wherein $R^2$ represents a C2-C6 alkylcarbonyl group optionally having one or more halogen atoms, and $R^5$ represents —$NR^{11}R^{12}$;

a compound represented by Formula (1) wherein R represents a C2-C6 alkylcarbonyl group optionally having one or more halogen atoms, and $R^5$ represents —$OR^{14}$;

a compound represented by Formula (1) wherein $R^2$ represents a C2-C6 alkylcarbonyl group optionally having one or more halogen atoms, and $R^5$ represents a phenyl group optionally having one or more groups selected from the group Y;

a compound represented by Formula (1) wherein $R^2$ represents a C2-C6 alkylcarbonyl group optionally having one or more halogen atoms, and $R^5$ represents a C1-C4 alkyl group optionally having one or more halogen atoms;

a compound represented by Formula (1) wherein $R^2$ represents a benzoyl group optionally having one or more groups selected from the group Y, and $R^5$ represents a hydrogen atom;

a compound represented by Formula (1) wherein $R^2$ represents a benzoyl group optionally having one or more groups selected from the group Y, and $R^5$ represents a halogen atom;

a compound represented by Formula (1) wherein $R^2$ represents a benzoyl group optionally having one or more groups selected from the group Y, and $R^5$ represents a C1-C6 alkyl group optionally having one or more groups selected from the group X;

a compound represented by Formula (1) wherein $R^2$ represents a benzoyl group optionally having one or more groups selected from the group Y, and $R^5$ represents a carboxy group;

a compound represented by Formula (1) wherein $R^2$ represents a benzoyl group optionally having one or more groups selected from the group Y, and $R^5$ represents a C2-C6 alkoxycarbonyl group;

a compound represented by Formula (1) wherein $R^2$ represents a benzoyl group optionally having one or more groups selected from the group Y, and $R^5$ represents —$NR^{11}R^{12}$;

a compound represented by Formula (1) wherein $R^2$ represents a benzoyl group optionally having one or more groups selected from the group Y, and $R^5$ represents —$OR^{14}$;

a compound represented by Formula (1) wherein $R^2$ represents a benzoyl group optionally having one or more groups selected from the group Y, and $R^5$ represents a phenyl group optionally having one or more groups selected from the group Y;

a compound represented by Formula (1) wherein $R^2$ represents a benzoyl group optionally having one or more groups selected from the group Y, and $R^5$ represents a C1-C4 alkyl group optionally having one or more halogen atoms;

a compound represented by Formula (1) wherein $R^2$ represents a C2-C6 alkoxycarbonyl group, and $R^5$ represents a hydrogen atom;

a compound represented by Formula (1) wherein $R^2$ represents a C2-C6 alkoxycarbonyl group, and $R^5$ represents a halogen atom;

a compound represented by Formula (1) wherein $R^2$ represents a C2-C6 alkoxycarbonyl group, and $R^5$ represents a C1-C6 alkyl group optionally having one or more groups selected from the group X;

a compound represented by Formula (1) wherein $R^2$ represents a C2-C6 alkoxycarbonyl group, and $R^5$ represents a carboxy group;

a compound represented by Formula (1) wherein $R^2$ represents a C2-C6 alkoxycarbonyl group, and $R^5$ represents a C2-C6 alkoxycarbonyl group;

a compound represented by Formula (1) wherein $R^2$ represents a C2-C6 alkoxycarbonyl group, and $R^5$ represents —$NR^{11}R^{12}$;

a compound represented by Formula (1) wherein $R^2$ represents a C2-C6 alkoxycarbonyl group, and $R^5$ represents —$OR^{14}$;

a compound represented by Formula (1) wherein $R^2$ represents a C2-C6 alkoxycarbonyl group, and $R^5$ represents a phenyl group optionally having one or more groups selected from the group Y;

a compound represented by Formula (1) wherein $R^2$ represents a C2-C6 alkoxycarbonyl group, and $R^5$ represents a C1-C4 alkyl group optionally having one or more halogen atoms;

a compound represented by Formula (1) wherein $R^2$ represents an aminocarbonyl group, and $R^5$ represents a hydrogen atom;

a compound represented by Formula (1) wherein $R^2$ represents an aminocarbonyl group, and $R^5$ represents a halogen atom;

a compound represented by Formula (1) wherein $R^2$ represents an aminocarbonyl group, and $R^5$ represents a C1-C6 alkyl group optionally having one or more groups selected from the group X;

a compound represented by Formula (1) wherein $R^2$ represents an aminocarbonyl group, and $R^5$ represents a carboxy group;

a compound represented by Formula (1) wherein $R^2$ represents an aminocarbonyl group, and $R^5$ represents a C2-C6 alkoxycarbonyl group;

a compound represented by Formula (1) wherein $R^2$ represents an aminocarbonyl group, and $R^5$ represents —$NR^{11}R^{12}$;

a compound represented by Formula (1) wherein $R^2$ represents an aminocarbonyl group, and $R^5$ represents —$OR^{14}$;

a compound represented by Formula (1) wherein $R^2$ represents an aminocarbonyl group, and $R^5$ represents a phenyl group optionally having one or more groups selected from the group Y;

a compound represented by Formula (1) wherein $R^2$ represents an aminocarbonyl group, and $R^5$ represents a C1-C4 alkyl group optionally having one or more halogen atoms;

a compound represented by Formula (1) wherein $R^2$ represents —$NR^{12}R^{13}$, and $R^5$ represents a hydrogen atom;

a compound represented by Formula (1) wherein $R^2$ represents —$NR^{12}R^{13}$, and $R^5$ represents a halogen atom;

a compound represented by Formula (1) wherein $R^2$ represents —$NR^{12}R^{13}$, and $R^5$ represents a C1-C6 alkyl group optionally having one or more groups selected from the group X;

a compound represented by Formula (1) wherein $R^2$ represents —$NR^{12}R^{13}$, and $R^5$ represents a carboxy group;

a compound represented by Formula (1) wherein $R^2$ represents —$NR^{12}R^{13}$, and $R^5$ represents a C2-C6 alkoxycarbonyl group;

a compound represented by Formula (1) wherein $R^2$ represents —$NR^{12}R^{13}$, and $R^5$ represents —$NR^{11}R^{12}$;

a compound represented by Formula (1) wherein $R^2$ represents —$NR^{12}R^{13}$, and $R^5$ represents —$OR^{14}$;

a compound represented by Formula (1) wherein $R^2$ represents —$NR^{12}R^{13}$, and $R^5$ represents phenyl group optionally having one or more groups selected from the group Y;

a compound represented by Formula (1) wherein $R^2$ represents —$NR^{12}R^{13}$, and $R^5$ represents a C1-C4 alkyl group optionally having one or more halogen atoms;

a compound represented by Formula (1) wherein $R^2$ represents —$S(O)_2NR^7R^{11}$, and $R^5$ represents a hydrogen atom;

a compound represented by Formula (1) wherein $R^2$ represents —$S(O)_2NR^7R^{11}$, and $R^5$ represents a halogen atom;

a compound represented by Formula (1) wherein $R^2$ represents —$S(O)_2NR^7R^{11}$, and $R^5$ represents a C1-C6 alkyl group optionally having one or more groups selected from the group X;

a compound represented by Formula (1) wherein $R^2$ represents —$S(O)_2NR^7R^{11}$, and $R^5$ represents a carboxy group;

a compound represented by Formula (1) wherein $R^2$ represents —$S(O)_2NR^7R^{11}$, and $R^5$ represents a C2-C6 alkoxycarbonyl group;

a compound represented by Formula (1) wherein $R^2$ represents —$S(O)_2NR^7R^{11}$, and $R^5$ represents —$NR^{11}R^{12}$;

a compound represented by Formula (1) wherein $R^2$ represents —$S(O)_2NR^7R^{11}$, and $R^5$ represents —$OR^{14}$;

a compound represented by Formula (1) wherein $R^2$ represents —$S(O)_2NR^7R^{11}$, and $R^5$ represents a phenyl group optionally having one or more groups selected from the group Y;

a compound represented by Formula (1) wherein $R^2$ represents —$S(O)_2NR^7R^{11}$, and $R^5$ represents a C1-C4 alkyl group optionally having one or more halogen atoms;

a compound represented by Formula (1) wherein $R^2$ represents —$OR^{13}$, and $R^5$ represents a hydrogen atom;

a compound represented by Formula (1) wherein $R^2$ represents —$OR^{13}$, and $R^5$ represents a halogen atom;

a compound represented by Formula (1) wherein $R^2$ represents —$OR^{13}$, and $R^5$ represents a C1-C6 alkyl group optionally having one or more groups selected from the group X;

a compound represented by Formula (1) wherein $R^2$ represents —$OR^{13}$, and $R^5$ represents a carboxy group;

a compound represented by Formula (1) wherein $R^2$ represents —$OR^{13}$, and $R^5$ represents a C2-C6 alkoxycarbonyl group;

a compound represented by Formula (1) wherein $R^2$ represents —$OR^{13}$, and $R^5$ represents —$NR^{11}R^{12}$;

a compound represented by Formula (1) wherein $R^2$ represents —$OR^{13}$, and $R^5$ represents —$OR^{14}$;

a compound represented by Formula (1) wherein $R^2$ represents —$OR^{13}$, and $R^5$ represents a phenyl group optionally having one or more groups selected from the group Y;

a compound represented by Formula (1) wherein $R^2$ represents —$OR^{13}$, and $R^5$ represents a C1-C4 alkyl group optionally having one or more halogen atoms;

a compound represented by Formula (1) wherein $R^2$ represents —$S(O)_mR^{13}$, and $R^5$ represents a hydrogen atom;

a compound represented by Formula (1) wherein $R^2$ represents —$S(O)_mR^{13}$, and $R^5$ represents a halogen atom;

a compound represented by Formula (1) wherein $R^2$ represents —$S(O)_mR^{13}$, and $R^5$ represents a C1-C6 alkyl group optionally having one or more groups selected from the group X;

a compound represented by Formula (1) wherein $R^2$ represents —$S(O)_mR^{13}$, and $R^5$ represents a carboxy group;

a compound represented by Formula (1) wherein $R^2$ represents —$S(O)_mR^{13}$, and $R^5$ represents a C2-C6 alkoxycarbonyl group;

a compound represented by Formula (1) wherein $R^2$ represents —$S(O)_mR^{13}$, and $R^5$ represents —$NR^{11}R^{12}$;

a compound represented by Formula (1) wherein $R^2$ represents —$S(O)_mR^{13}$, and $R^5$ represents —$OR^{14}$;

a compound represented by Formula (1) wherein $R^2$ represents —$S(O)_mR^{13}$, and $R^5$ represents a phenyl group optionally having one or more groups selected from the group Y;

a compound represented by Formula (1) wherein $R^2$ represents —$S(O)_mR^{13}$, and $R^5$ represents a C1-C4 alkyl group optionally having one or more halogen atoms;

a compound represented by Formula (1) wherein $R^2$ represents —$SF_5$, and $R^5$ represents a hydrogen atom;

a compound represented by Formula (1) wherein $R^2$ represents —$SF_5$, and $R^5$ represents a halogen atom;

a compound represented by Formula (1) wherein $R^2$ represents —$SF_5$, and $R^5$ represents a C1-C6 alkyl group optionally having one or more groups selected from the group X;

a compound represented by Formula (1) wherein $R^2$ represents —$SF_5$, and $R^5$ represents a carboxy group;

a compound represented by Formula (1) wherein $R^2$ represents —$SF_5$, and $R^5$ represents C2-C6 alkoxycarbonyl group;

a compound represented by Formula (1) wherein $R^2$ represents —$SF_5$, and $R^5$ represents —$NR^{11}R^{12}$;

a compound represented by Formula (1) wherein $R^2$ represents —$SF_5$, and $R^5$ represents —$OR^{14}$;

a compound represented by Formula (1) wherein $R^2$ represents —$SF_5$, and $R^5$ represents a phenyl group optionally having one or more groups selected from the group Y;

a compound represented by Formula (1) wherein $R^2$ represents —$SF_5$, and $R^5$ represents a C1-C4 alkyl group optionally having one or more halogen atoms;

a compound represented by Formula (1) wherein $R^2$ represents a C1-C4 alkyl group optionally having one or more halogen atoms, and $R^5$ represents a hydrogen atom;

a compound represented by Formula (1) wherein $R^2$ represents a C1-C4 alkyl group optionally having one or more halogen atoms, and $R^5$ represents a halogen atom;

a compound represented by Formula (1) wherein $R^2$ represents a C1-C4 alkyl group optionally having one or more halogen atoms, and $R^5$ represents a C1-C6 alkyl group optionally having one or more groups selected from the group X;

a compound represented by Formula (1) wherein $R^2$ represents a C1-C4 alkyl group optionally having one or more halogen atoms, and $R^5$ represents a carboxy group;

a compound represented by Formula (1) wherein $R^2$ represents a C1-C4 alkyl group optionally having one or more halogen atoms, and $R^5$ represents a C2-C6 alkoxycarbonyl group;

a compound represented by Formula (1) wherein $R^2$ represents a C1-C4 alkyl group optionally having one or more halogen atoms, and $R^5$ represents —$NR^{11}R^{12}$;

a compound represented by Formula (1) wherein $R^2$ represents a C1-C4 alkyl group optionally having one or more halogen atoms, and $R^5$ represents —$OR^{14}$;

a compound represented by Formula (1) wherein $R^2$ represents a C1-C4 alkyl group optionally having one or more halogen atoms, and $R^5$ represents a C1-C4 alkyl group which may have optionally one or more halogen atoms;

a compound represented by Formula (1) wherein $R^2$ represents a C1-C4 alkyl group optionally having one or more halogen atoms, and $R^5$ represents a phenyl group optionally having one or more groups selected from the group Y;

a compound represented by Formula (1) wherein $R^2$ represents a hydrogen atom, and $R^5$ represents a hydrogen atom;

a compound represented by Formula (1) wherein $R^2$ represents a pyridyl group optionally having one or more groups selected from the group Y, and $R^5$ represents a hydrogen atom;

a compound represented by Formula (1) wherein $R^2$ represents a pyrimidinyl group optionally having one or more groups selected from the group Y, and $R^5$ represents a hydrogen atom;

a compound represented by Formula (1) wherein $R^2$ represents a thienyl group optionally having one or more groups selected from the group Y, and $R^5$ represents a hydrogen atom;

a compound represented by Formula (1) wherein $R^2$ represents a C2-C5 alkylcarbonyl group optionally having one or more halogen atoms, and $R^5$ represents a hydrogen atom;

a compound represented by Formula (1) wherein $R^2$ represents a benzoyl group optionally having one or more groups selected from the group Y, and $R^5$ represents a hydrogen atom;

a compound represented by Formula (1) wherein $R^2$ represents a hydrogen atom, and $R^5$ represents a halogen atom;

a compound represented by Formula (1) wherein $R^2$ represents a hydrogen atom, and $R^5$ represents a C1-C6 alkyl group optionally having one or more groups selected from the group X;

a compound represented by Formula (1) wherein $R^2$ represents a hydrogen atom, and $R^5$ represents a C1-C4 alkyl group optionally having one or more halogen atoms;

a compound represented by Formula (1) wherein $R^2$ represents a hydrogen atom, and $R^5$ represents a phenyl group optionally having one or more groups selected from the group Y;

a compound represented by Formula (1) wherein $R^2$ represents a hydrogen atom, and $R^5$ represents a 5-membered aromatic heterocyclic group optionally having one or more groups selected from the group Y;

a compound represented by Formula (1) wherein $R^2$ represents a hydrogen atom, and $R^5$ represents a pyrrolyl group optionally having one or more groups selected from the group Y;

a compound represented by Formula (1) wherein $R^2$ represents a hydrogen atom, and $R^5$ represents —$NR^{11}R^{12}$;

a compound represented by Formula (1) wherein $R^2$ represents a hydrogen atom, and $R^5$ represents —$OR^{14}$;

a compound represented by Formula (1) wherein $R^2$ represents a hydrogen atom, and $R^5$ represents —$S(O)_2NR^7R^{11}$, a compound represented by Formula (1) wherein $R^2$ represents a nitro group, and $R^5$ represents —$OR^{14}$;

a compound represented by Formula (1) wherein $R^3$ represents a halogen atom, and $R^5$ represents a hydrogen atom;

a compound represented by Formula (1) wherein $R^3$ represents a halogen atom, and $R^5$ represents a halogen atom;

a compound represented by Formula (1) wherein $R^3$ represents a halogen atom, and $R^5$ represents a C1-C6 alkyl group optionally having one or more groups selected from the group X;

a compound represented by Formula (1) wherein $R^3$ represents a halogen atom, and $R^5$ represents a carboxy group;

a compound represented by Formula (1) wherein $R^3$ represents a halogen atom, and $R^5$ represents a C2-C6 alkoxycarbonyl group;

a compound represented by Formula (1) wherein $R^3$ represents a halogen atom, and $R^5$ represents —$NR^{11}R^{12}$;

a compound represented by Formula (1) wherein $R^3$ represents a halogen atom, and $R^5$ represents —$OR^{14}$;

a compound represented by Formula (1) wherein $R^3$ represents a halogen atom, and $R^5$ represents a phenyl group optionally having one or more groups selected from the group Y;

a compound represented by Formula (1) wherein $R^3$ represents a halogen atom, and $R^5$ represents a C1-C4 alkyl group optionally having one or more halogen atoms;

a compound represented by Formula (1) wherein $R^3$ represents a carboxy group, and $R^5$ represents a hydrogen atom;

a compound represented by Formula (1) wherein $R^3$ represents a carboxy group, and $R^5$ represents a halogen atom;

a compound represented by Formula (1) wherein $R^3$ represents a carboxy group, and $R^5$ represents a C1-C6 alkyl group optionally having one or more groups selected from the group X;

a compound represented by Formula (1) wherein $R^3$ represents a carboxy group, and $R^5$ represents a carboxy group;

a compound represented by Formula (1) wherein $R^3$ represents a carboxy group, and $R^5$ represents a C2-C6 alkoxycarbonyl group;

a compound represented by Formula (1) wherein $R^3$ represents a carboxy group, and $R^5$ represents —$NR^{11}R^{12}$;

a compound represented by Formula (1) wherein $R^3$ represents a carboxy group, and $R^5$ represents —$OR^{14}$;

a compound represented by Formula (1) wherein $R^3$ represents a carboxy group, and $R^5$ represents a phenyl group optionally having one or more groups selected from the group Y;

a compound represented by Formula (1) wherein $R^3$ represents a carboxy group, and $R^5$ represents a C1-C4 alkyl group optionally having one or more halogen atoms;

a compound represented by Formula (1) wherein $R^3$ represents a C2-C6 alkoxycarbonyl group, and $R^5$ represents a hydrogen atom;

a compound represented by Formula (1) wherein $R^3$ represents a C2-C6 alkoxycarbonyl group, and $R^5$ represents a halogen atom;

a compound represented by Formula (1) wherein $R^3$ represents a C2-C6 alkoxycarbonyl group, and $R^5$ represents a C1-C6 alkyl group optionally having one or more groups selected from the group x;

a compound represented by Formula (1) wherein $R^3$ represents a C2-C6 alkoxycarbonyl group, and $R^5$ represents a carboxy group;

a compound represented by Formula (1) wherein $R^3$ represents a C2-C6 alkoxycarbonyl group, and $R^5$ represents a C2-C6 alkoxycarbonyl group;

a compound represented by Formula (1) wherein $R^3$ represents a C2-C6 alkoxycarbonyl group, and $R^5$ represents —$NR^{11}R^{12}$;

a compound represented by Formula (1) wherein $R^3$ represents a C2-C6 alkoxycarbonyl group, and $R^5$ represents —$OR^{14}$;

a compound represented by Formula (1) wherein $R^3$ represents a C2-C6 alkoxycarbonyl group, and $R^5$ represents a phenyl group optionally having one or more groups selected from the group Y;

a compound represented by Formula (1) wherein $R^3$ represents a C2-C6 alkoxycarbonyl group, and $R^5$ represents a C1-C4 alkyl group optionally having one or more halogen atoms;

a compound represented by Formula (1) wherein $R^3$ represents an aminocarbonyl group, and $R^5$ represents a hydrogen atom;

a compound represented by Formula (1) wherein $R^3$ represents an aminocarbonyl group, and $R^5$ represents a halogen atom;

a compound represented by Formula (1) wherein $R^3$ represents an aminocarbonyl group, and $R^5$ represents a CL-C6 alkyl group optionally having one or more groups selected from the group X;

a compound represented by Formula (1) wherein $R^3$ represents an aminocarbonyl group, and $R^5$ represents a carboxy group;

a compound represented by Formula (1) wherein $R^3$ represents an aminocarbonyl group, and $R^5$ represents a C2-C6 alkoxycarbonyl group;

a compound represented by Formula (1) wherein $R^3$ represents an aminocarbonyl group, and $R^5$ represents —$NR^{11}R^{12}$;

a compound represented by Formula (1) wherein $R^3$ represents an aminocarbonyl group, and $R^5$ represents —$OR^{14}$;

a compound represented by Formula (1) wherein $R^3$ represents an aminocarbonyl group, and $R^5$ represents a phenyl group optionally having one or more groups selected from the group Y;

a compound represented by Formula (1) wherein $R^3$ represents an aminocarbonyl group, and $R^5$ represents a C1-C4 alkyl group optionally having one or more halogen atoms;

a compound represented by Formula (1) wherein $R^3$ represents a C1-C6 alkyl group optionally having one or more groups selected from the group X, and $R^5$ represents a hydrogen atom;

a compound represented by Formula (1) wherein $R^3$ represents a C1-C4 alkyl group optionally having one or more halogen atoms, and $R^5$ represents a hydrogen atom;

a compound represented by Formula (1) wherein $R^3$ represents a C1-C4 alkyl group optionally having one or more halogen atoms, and $R^5$ represents a halogen atom;

a compound represented by Formula (1) wherein $R^3$ represents a C1-C4 alkyl group optionally having one or more halogen atoms, and $R^5$ represents a C1-C6 alkyl group optionally having one or more groups selected from the group X;

a compound represented by Formula (1) wherein $R^3$ represents a C1-C4 alkyl group optionally having one or more halogen atoms, and $R^5$ represents a carboxy group;

a compound represented by Formula (1) wherein $R^3$ represents a C1-C4 alkyl group optionally having one or more halogen atoms, and $R^5$ represents a C2-C6 alkoxycarbonyl group;

a compound represented by Formula (1) wherein $R^3$ represents a C1-C4 alkyl group optionally having one or more halogen atoms, and $R^5$ represents —$NR^{11}R^{12}$;

a compound represented by Formula (1) wherein $R^3$ represents a C1-C4 alkyl group optionally having one or more halogen atoms, and $R^5$ represents —$OR^{14}$;

a compound represented by Formula (1) wherein $R^3$ represents a C1-C4 alkyl group optionally having one or more halogen atoms, and $R^5$ represents a phenyl group optionally having one or more groups selected from the group Y;

a compound represented by Formula (1) wherein $R^3$ represents a C1-C4 alkyl group optionally having one or more halogen atoms, and $R^5$ represents a C1-C4 alkyl group optionally having one or more halogen atoms;

a compound represented by Formula (1) wherein $R^3$ represents a hydrogen atom, and $R^5$ represents a hydrogen atom;

a compound represented by Formula (1) wherein $R^3$ represents a C2-C4 alkenyl group optionally having one or more halogen atoms, and $R^5$ represents a hydrogen atom;

a compound represented by Formula (1) wherein $R^3$ represents a C2-C4 alkynyl group optionally having one or more halogen atoms, and $R^5$ represents a hydrogen atom;

a compound represented by Formula (1) wherein $R^3$ represents a phenyl group optionally having one or more groups selected from the group Y, and $R^5$ represents a hydrogen atom;

a compound represented by Formula (1) wherein $R^3$ represents a 6-membered aromatic heterocyclic group optionally having one or more groups selected from the group Y, and $R^5$ represents a hydrogen atom;

a compound represented by Formula (1) wherein $R^3$ represents a pyridyl group optionally having one or more groups selected from the group Y, and $R^5$ represents a hydrogen atom;

a compound represented by Formula (1) wherein $R^3$ represents —$NR^{11}R^{12}$, and $R^5$ represents a hydrogen atom;

a compound represented by Formula (1) wherein $R^3$ represents —$OR^{14}$, and $R^5$ represents a hydrogen atom;

a compound represented by Formula (1) wherein $R^3$ represents a hydrogen atom, and $R^5$ represents a halogen atom;

a compound represented by Formula (1) wherein $R^3$ represents a hydrogen atom, and $R^5$ represents a C1-C6 alkyl group optionally having one or more groups selected from the group X;

a compound represented by Formula (1) wherein $R^3$ represents a hydrogen atom, and $R^5$ represents a C1-C4 alkyl group optionally having one or more halogen atoms;

a compound represented by Formula 1) wherein $R^3$ represents a hydrogen atom, and $R^5$ represents a 5-membered aromatic heterocyclic group optionally having one or more groups selected from the group Y;

a compound represented by Formula (1) wherein $R^3$ represents a hydrogen atom, and $R^5$ represents a pyrrolyl group optionally having one or more groups selected from the group Y;

a compound represented by Formula (1) wherein $R^3$ represents a hydrogen atom, and $R^5$ represents —$NR^{11}R^{12}$;

a compound represented by Formula (1) wherein $R^3$ represents a hydrogen atom, and $R^5$ represents —$OR^{14}$;

a compound represented by Formula (1) wherein $R^4$ represents a halogen atom, and $R^5$ represents a hydrogen atom;

a compound represented by Formula (1) wherein $R^4$ represents a halogen atom, and $R^5$ represents a halogen atom;

a compound represented by Formula (1) wherein $R^4$ represents a halogen atom, and $R^5$ represents a C1-C6 alkyl group optionally having one or more groups selected from the group X;

a compound represented by Formula (1) wherein $R^4$ represents a halogen atom, and $R^5$ represents a carboxy group;

a compound represented by Formula (1) wherein $R^4$ represents a halogen atom, and $R^5$ represents a C2-C6 alkoxycarbonyl group;

a compound represented by Formula (1) wherein $R^4$ represents a halogen atom, and $R^5$ represents —$NR^{11}R^{12}$;

a compound represented by Formula (1) wherein $R^4$ represents a halogen atom, and $R^5$ represents —$OR^{14}$;

a compound represented by Formula (1) wherein $R^4$ represents a halogen atom, and $R^5$ represents a phenyl group optionally having one or more groups selected from the group Y;

a compound represented by Formula (1) wherein $R^4$ represents a halogen atom, and $R^5$ represents a C1-C4 alkyl group optionally having one or more halogen atoms;

a compound represented by Formula (1) wherein $R^4$ represents a carboxy group, and $R^5$ represents a hydrogen atom;

a compound represented by Formula (1) wherein $R^4$ represents a carboxy group, and $R^5$ represents a halogen atom;

a compound represented by Formula (1) wherein $R^4$ represents a carboxy group, and $R^5$ represents a C1-C6 alkyl group optionally having one or more groups selected from the group X;

a compound represented by Formula (1) wherein $R^4$ represents a carboxy group, and $R^5$ represents a carboxy group;

a compound represented by Formula (1) wherein $R^4$ represents a carboxy group, and $R^5$ represents a C2-C6 alkoxycarbonyl group;

a compound represented by Formula (1) wherein $R^4$ represents a carboxy group, and $R^5$ represents —$NR^{11}R^{12}$;

a compound represented by Formula (1) wherein $R^4$ represents a carboxy group, and $R^5$ represents —$OR^{14}$;

a compound represented by Formula (1) wherein $R^4$ represents a carboxy group, and $R^5$ represents a phenyl group optionally having one or more groups selected from the group Y;

a compound represented by Formula (1) wherein $R^4$ represents a carboxy group, and $R^5$ represents a C1-C4 alkyl group optionally having one or more halogen atoms;

a compound represented by Formula (1) wherein $R^4$ represents a C2-C6 alkoxycarbonyl group, and $R^5$ represents a hydrogen atom;

a compound represented by Formula (1) wherein $R^4$ represents a C2-C6 alkoxycarbonyl group, and $R^5$ represents a halogen atom;

a compound represented by Formula (1) wherein $R^4$ represents a C2-C6 alkoxycarbonyl group, and $R^5$ represents a C1-C6 alkyl group optionally having one or more groups selected from the group X;

a compound represented by Formula (1) wherein $R^4$ represents a C2-C6 alkoxycarbonyl group, and $R^5$ represents a carboxy group;

a compound represented by Formula (1) wherein $R^4$ represents a C2-C6 alkoxycarbonyl group, and $R^5$ represents a C2-C6 alkoxycarbonyl group;

a compound represented by Formula (1) wherein $R^4$ represents a C2-C6 alkoxycarbonyl group, and $R^5$ represents —$NR^{11}R^{12}$;

a compound represented by Formula (1) wherein $R^4$ represents a C2-C6 alkoxycarbonyl group, and $R^5$ represents —$OR^{14}$;

a compound represented by Formula (1) wherein $R^4$ represents a C2-C6 alkoxycarbonyl group, and $R^5$ represents a phenyl group optionally having one or more groups selected from the group Y;

a compound represented by Formula (1) wherein $R^4$ represents a C2-C6 alkoxycarbonyl group, and $R^5$ represents a C1-C4 alkyl group optionally having one or more halogen atoms;

a compound represented by Formula (1) wherein $R^4$ represents an aminocarbonyl group, and $R^5$ represents a hydrogen atom;

a compound represented by Formula (1) wherein $R^4$ represents an aminocarbonyl group, and $R^5$ represents a halogen atom;

a compound represented by Formula (1) wherein $R^4$ represents an aminocarbonyl group, and $R^5$ represents a C1-C6 alkyl group optionally having one or more groups selected from the group X;

a compound represented by Formula (1) wherein $R^4$ represents an aminocarbonyl group, and $R^5$ represents a carboxy group;

a compound represented by Formula (1) wherein $R^4$ represents an aminocarbonyl group, and $R^5$ represents a C2-C6 alkoxycarbonyl group;

a compound represented by Formula (1) wherein $R^4$ represents an aminocarbonyl group, and $R^5$ represents —$NR^{11}R^{12}$;

a compound represented by Formula (1) wherein $R^4$ represents an aminocarbonyl group, and $R^5$ represents —$OR^{14}$;

a compound represented by Formula (1) wherein $R^4$ represents an aminocarbonyl group, and $R^5$ represents a phenyl group optionally having one or more groups selected from the group Y;

a compound represented by Formula (1) wherein $R^4$ represents an aminocarbonyl group, and $R^3$ represents a C1-C4 alkyl group optionally having one or more halogen atoms;

a compound represented by Formula (1) wherein $R^4$ represents a C1-C6 alkyl group optionally having one or more groups selected from the group X, and $R^5$ represents a hydrogen atom;

a compound represented by Formula (1) wherein $R^4$ represents a C1-C4 alkyl group optionally having one or more halogen atoms, and $R^5$ represents a hydrogen atom;

a compound represented by Formula (1) wherein $R^4$ represents a C1-C4 alkyl group optionally having one or more halogen atoms, and $R^5$ represents a halogen atom;

a compound represented by Formula (1) wherein $R^4$ represents a C1-C4 alkyl group optionally having one or more halogen atoms, and $R^5$ represents a C1-C6 alkyl group optionally having one or more groups selected from the group X;

a compound represented by Formula (1) wherein $R^4$ represents a C1-C4 alkyl group optionally having one or more halogen atoms, and $R^5$ represents a carboxy group;

a compound represented by Formula (1) wherein $R^4$ represents a C1-C4 alkyl group optionally having one or more halogen atoms, and $R^5$ represents a C2-C6 alkoxycarbonyl group;

a compound represented by Formula (1) wherein $R^4$ represents a C1-C4 alkyl group optionally having one or more halogen atoms, and $R^5$ represents —$NR^{11}R^{12}$;

a compound represented by Formula (1) wherein $R^4$ represents a C1-C4 alkyl group optionally having one or more halogen atoms, and $R^5$ represents —$OR^{14}$;

a compound represented by Formula (1) wherein $R^4$ represents a C1-C4 alkyl group optionally having one or more halogen atoms, and $R^5$ represents a phenyl group optionally having one or more groups selected from the group Y;

a compound represented by Formula (1) wherein $R^4$ represents a C1-C4 alkyl group optionally having one or more halogen atoms, and $R^5$ represents a C1-C4 alkyl group optionally having one or more halogen atoms;

a compound represented by Formula (1) wherein $R^4$ represents a phenyl group optionally having one or more groups selected from the group Y, and $R^5$ represents a hydrogen atom;

a compound represented by Formula (1) wherein $R^4$ represents a phenyl group optionally having one or more groups selected from the group Y, and $R^5$ represents a halogen atom;

a compound represented by Formula (1) wherein $R^4$ represents a phenyl group optionally having one or more groups selected from the group Y, and $R^5$ represents a C1-C6 alkyl group optionally having one or more groups selected from the group X;

a compound represented by Formula (1) wherein $R^4$ represents a phenyl group optionally having one or more groups selected from the group Y, and $R^5$ represents —$NR^{11}R^{12}$;

a compound represented by Formula (1) wherein $R^4$ represents a phenyl group optionally having one or more groups selected from the group Y, and $R^5$ represents —$OR^{14}$;

a compound represented by Formula (1) wherein $R^4$ represents a hydrogen atom, and $R^5$ represents a hydrogen atom;

a compound represented by Formula (1) wherein $R^4$ represents a phenyl group optionally having one or more groups selected from the group Y, and $R^3$ represents a hydrogen atom;

a compound represented by Formula (1) wherein $R^4$ represents —$OR^{11}$, and $R^5$ represents a hydrogen atom;

a compound represented by Formula (1) wherein $R^4$ represents a hydrogen atom, and $R^5$ represents a halogen atom;

a compound represented by Formula C1) wherein $R^4$ represents a hydrogen atom, and $R^5$ represents a C1-C6 alkyl group optionally having one or more groups selected from the group X;

a compound represented by Formula (1) wherein $R^4$ represents a hydrogen atom, and $R^5$ represents a C1-C4 alkyl group optionally having one or more halogen atoms;

a compound represented by Formula (1) wherein $R^4$ represents a hydrogen atom, and $R^5$ represents a phenyl group optionally having one or more groups selected from the group Y;

a compound represented by Formula (1) wherein $R^4$ represents a hydrogen atom, and $R^5$ represents a 5-membered aromatic heterocyclic group optionally having one or more groups selected from the group Y;

a compound represented by Formula (1) wherein $R^4$ represents a hydrogen atom, and $R^5$ represents a pyrrolyl group optionally having one or more groups selected from the group Y;

a compound represented by Formula (1) wherein $R^4$ represents a hydrogen atom, and $R^5$ represents a C2-C6 alkoxycarbonyl group;

a compound represented by Formula (1) wherein $R^4$ represents a hydrogen atom, and $R^5$ represents a C2-C4 alkoxycarbonyl group;

a compound represented by Formula (1) wherein $R^4$ represents a hydrogen atom, and $R^5$ represents —$NR^{11}R^{12}$;

a compound represented by Formula (1) wherein $R^4$ represents a hydrogen atom, and $R^5$ represents —$OR^{14}$;

a compound represented by Formula (1) wherein $R^4$ represents a hydrogen atom, and $R^5$ represents —$S(O)_2NR^7R^{11}$;

a compound represented by Formula (1) wherein $R^1$ represents a trifluoromethyl group, and $R^5$ represents a hydrogen atom;

a compound represented by Formula (1) wherein $R^1$ represents a trifluoromethyl group, and $R^5$ represents a halogen atom;

a compound represented by Formula (1) wherein $R^1$ represents a trifluoromethyl group, and $R^5$ represents a C1-C6 alkyl group optionally having one or more groups selected from the group X;

a compound represented by Formula (1) wherein $R^1$ represents a trifluoromethyl group, and $R^5$ represents a carboxy group;

a compound represented by Formula (1) wherein $R^1$ represents a trifluoromethyl group, and $R^5$ represents a C2-C6 alkoxycarbonyl group;

a compound represented by Formula (1) wherein $R^1$ represents a trifluoromethyl group, and $R^5$ represents —$NR^{11}R^{12}$;

a compound represented by Formula (1) wherein $R^1$ represents a trifluoromethyl group, and $R^5$ represents —$OR^{14}$;

a compound represented by Formula (1) wherein $R^1$ represents a trifluoromethyl group, and $R^5$ represents a phenyl group optionally having one or more groups selected from the group Y;

a compound represented by Formula (1) wherein $R^1$ represents a trifluoromethyl group, and $R^5$ represents a C1-C4 alkyl group optionally having one or more halogen atoms;

a compound represented by Formula (1) wherein $R^2$ represents a trifluoromethyl group, and $R^5$ represents a halogen atom;

a compound represented by Formula (1) wherein $R^2$ represents a trifluoromethyl group, and $R^5$ represents a C1-C6 alkyl group optionally having one or more groups selected from the group X;

a compound represented by Formula (1) wherein $R^2$ represents a trifluoromethyl group, and $R^5$ represents a carboxy group;

a compound represented by Formula (1) wherein $R^2$ represents a trifluoromethyl group, and $R^5$ represents a C2-C6 alkoxycarbonyl group;

a compound represented by Formula (1) wherein $R^2$ represents a trifluoromethyl group, and $R^5$ represents —$NR^{11}R^{12}$;

a compound represented by Formula (1) wherein $R^2$ represents a trifluoromethyl group, and $R^5$ represents —$OR^{14}$;

a compound represented by Formula (1) wherein $R^2$ represents a trifluoromethyl group, and $R^5$ represents a phenyl group optionally having one or more groups selected from the group Y;

a compound represented by Formula (1) wherein $R^2$ represents a trifluoromethyl group, and $R^5$ represents a C1-C4 alkyl group optionally having one or more halogen atoms;

a compound represented by Formula (1) wherein $R^3$ represents a trifluoromethyl group, and $R^5$ represents a hydrogen atom;

a compound represented by Formula (1) wherein $R^3$ represents a trifluoromethyl group, and $R^5$ represents a halogen atom;

a compound represented by Formula (1) wherein $R^3$ represents a trifluoromethyl group, and $R^5$ represents a C1-C6 alkyl group optionally having one or more groups selected from the group X;

a compound represented by Formula (1) wherein $R^3$ represents a trifluoromethyl group, and $R^5$ represents a carboxy group;

a compound represented by Formula (1) wherein $R^3$ represents a trifluoromethyl group, and $R^5$ represents a C2-C6 alkoxycarbonyl group;

a compound represented by Formula (1) wherein $R^3$ represents a trifluoromethyl group, and $R^5$ represents —$NR^{11}R^{12}$;

a compound represented by Formula (1) wherein $R^3$ represents a trifluoromethyl group, and $R^5$ represents —$OR^{14}$;

a compound represented by Formula (1) wherein $R^3$ represents a trifluoromethyl group, and $R^5$ represents a phenyl group optionally having one or more groups selected from the group Y;

a compound represented by Formula (1) wherein $R^3$ represents a trifluoromethyl group, and $R^5$ represents a C1-C4 alkyl group optionally having one or more halogen atoms;

a compound represented by Formula (1) wherein $R^4$ represents a trifluoromethyl group, and $R^5$ represents a hydrogen atom;

a compound represented by Formula (1) wherein $R^4$ represents a trifluoromethyl group, and $R^5$ represents a halogen atom;

a compound represented by Formula (1) wherein R⁴ represents a trifluoromethyl group, and R⁵ represents a C1-C6 alkyl group optionally having one or more groups selected from the group X;

a compound represented by Formula (1) wherein R⁴ represents a trifluoromethyl group, and R⁵ represents a carboxy group;

a compound represented by Formula (1) wherein R⁴ represents a trifluoromethyl group, and R⁵ represents a C2-C6 alkoxycarbonyl group;

a compound represented by Formula (1) wherein R⁴ represents a trifluoromethyl group, and R⁵ represents —NR¹¹R¹²;

a compound represented by Formula (1) wherein R⁴ represents a trifluoromethyl group, and R⁵ represents —OR¹⁴;

a compound represented by Formula (1) wherein R⁴ represents a trifluoromethyl group, and R⁵ represents a phenyl group optionally having one or more groups selected from the group Y;

a compound represented by Formula (1) wherein R⁴ represents a trifluoromethyl group, and R⁵ represents a C1-C4 alkyl group optionally having one or more halogen atoms;

a compound represented by Formula (1) wherein R=represents a halogen atom, and R⁵ represents a trifluoromethyl group;

a compound represented by Formula (1) wherein R¹ represents a C1-C6 alkyl group optionally having one or more groups selected from the group X, and R⁵ represents a trifluoromethyl group;

a compound represented by Formula (1) wherein R¹ represents a phenyl group optionally having one or more groups selected from the group Y, and R⁵ represents a trifluoromethyl group;

a compound represented by Formula (1) wherein R¹ represents a 6-membered aromatic heterocyclic group optionally having one or more groups selected from the group Y, and R³ represents a trifluoromethyl group;

a compound represented by Formula (1) wherein R¹ represents a 5-membered aromatic heterocyclic group optionally having one or more groups selected from the group Y, and R⁵ represents a trifluoromethyl group;

a compound represented by Formula (1) wherein R¹ represents a carboxy group, and R⁵ represents a trifluoromethyl group;

a compound represented by Formula (1) wherein R¹ represents a C2-C6 alkylcarbonyl group optionally having one or more halogen atoms, and R⁵ represents a trifluoromethyl group;

a compound represented by Formula (1) wherein R¹ represents a C2-C6 alkoxycarbonyl group, and R⁵ represents a trifluoromethyl group;

a compound represented by Formula (1) wherein R¹ represents an aminocarbonyl group, and R⁵ represents a trifluoromethyl group;

a compound represented by Formula (1) wherein R¹ represents —OR¹¹, and R⁵ represents a trifluoromethyl group;

a compound represented by Formula (1) wherein R¹ represents —S(O)ₙR¹¹, and R⁵ represents a trifluoromethyl group;

a compound represented by Formula (1) wherein R¹ represents —SF₅, and R⁵ represents a trifluoromethyl group;

a compound represented by Formula (1) wherein R¹ represents a C1-C4 alkyl group optionally having one or more halogen atoms, and R⁵ represents a trifluoromethyl group;

a compound represented by Formula (1) wherein R² represents a halogen atom, and R⁵ represents a trifluoromethyl group;

a compound represented by Formula (1) wherein R² represents a C1-C6 alkyl group optionally having one or more groups selected from the group X, and R⁵ represents a trifluoromethyl group;

a compound represented by Formula (1) wherein R² represents a phenyl group optionally having one or more groups selected from the group Y, and R⁵ represents a trifluoromethyl group;

a compound represented by Formula (1) wherein R² represents a 6-membered aromatic heterocyclic group optionally having one or more groups selected from the group Y, and R⁵ represents a trifluoromethyl group;

a compound represented by Formula (1) wherein R² represents a 5-membered aromatic heterocyclic group optionally having one or more groups selected from the group Y, and R⁵ represents a trifluoromethyl group;

a compound represented by Formula (1) wherein R² represents a carboxy group, and R⁵ represents a trifluoromethyl group;

a compound represented by Formula (1) wherein R² represents a C2-C6 alkylcarbonyl group optionally having one or more halogen atoms, and R⁵ represents a trifluoromethyl group;

a compound represented by Formula (1) wherein R² represents a benzoyl group optionally having one or more groups selected from the group Y, and R⁵ represents a trifluoromethyl group;

a compound represented by Formula (1) wherein R² represents a C2-C6 alkoxycarbonyl group, and R⁵ represents a trifluoromethyl group;

a compound represented by Formula (1) wherein R² represents an aminocarbonyl group, and R⁵ represents a trifluoromethyl group;

a compound represented by Formula (1) wherein R² represents —NR¹²R¹³, and R⁵ represents a trifluoromethyl group;

a compound represented by Formula (1) wherein R² represents —S(O)₂NR⁷R¹¹, and R⁵ represents a trifluoromethyl group;

a compound represented by Formula (1) wherein R² represents —OR¹³, and R⁵ represents a trifluoromethyl group;

a compound represented by Formula (1) wherein R² represents —S(O)ₘR¹³, and R⁵ represents a trifluoromethyl group;

a compound represented by Formula (1) wherein R² represents —SF₅, and R⁵ represents a trifluoromethyl group;

a compound represented by Formula (1) wherein R² represents a C1-C4 alkyl group optionally having one or more halogen atoms, and R⁵ represents a trifluoromethyl group;

a compound represented by Formula (1) wherein R³ represents a halogen atom, and R⁵ represents a trifluoromethyl group;

a compound represented by Formula (1) wherein R³ represents a carboxy group, and R⁵ represents a trifluoromethyl group;

a compound represented by Formula (1) wherein R³ represents a C2-C6 alkoxycarbonyl group, and R⁵ represents a trifluoromethyl group;

a compound represented by Formula (1) wherein R³ represents an aminocarbonyl group, and R⁵ represents a trifluoromethyl group;

a compound represented by Formula (1) wherein R³ represents a C1-C4 alkyl group optionally having one or more halogen atoms, and R⁵ represents a trifluoromethyl group;

a compound represented by Formula (1) wherein R⁴ represents a halogen atom, and R⁵ represents a trifluoromethyl group;

a compound represented by Formula (1) wherein R⁴ represents a carboxy group, and R⁵ represents a trifluoromethyl group;

a compound represented by Formula (1) wherein R⁴ represents a C2-C6 alkoxycarbonyl group, and R⁵ represents a trifluoromethyl group;

a compound represented by Formula (1) wherein R⁴ represents a aminocarbonyl group, and R⁵ represents a trifluoromethyl group;

a compound represented by Formula (1) wherein R⁴ represents a C1-C4 alkyl group optionally having one or more halogen atoms, and R⁵ represents a trifluoromethyl group;

a compound represented by Formula (1) wherein R¹ represents a hydrogen atom;

a compound represented by Formula (1) wherein R² represents a hydrogen atom;

a compound represented by Formula (1) wherein R³ represents a hydrogen atom;

a compound represented by Formula (1) wherein R⁴ represents a hydrogen atom;

a compound represented by Formula (1) wherein R⁵ represents a hydrogen atom;

a compound represented by Formula (1) wherein R¹ represents a fluorine atom;

a compound represented by Formula (1) wherein R² represents a fluorine atom;

a compound represented by Formula (1) wherein R³ represents a fluorine atom;

a compound represented by Formula (1) wherein R⁴ represents a fluorine atom;

a compound represented by Formula (1) wherein R⁵ represents a fluorine atom;

a compound represented by Formula (1) wherein R¹ represents a chlorine atom;

a compound represented by Formula (1) wherein R² represents a chlorine atom;

a compound represented by Formula (1) wherein R³ represents a chlorine atom;

a compound represented by Formula (1) wherein R⁴ represents a chlorine atom;

a compound represented by Formula (1) wherein R⁵ represents a chlorine atom;

a compound represented by Formula (1) wherein R¹ represents a bromine atom;

a compound represented by Formula (1) wherein R² represents a bromine atom;

a compound represented by Formula (1) wherein R³ represents a bromine atom;

a compound represented by Formula (1) wherein R⁴ represents a bromine atom;

a compound represented by Formula (1) wherein R³ represents a bromine atom;

a compound represented by Formula (1) wherein R¹ represents a iodine atom;

a compound represented by Formula (1) wherein R² represents a iodine atom;

a compound represented by Formula (1) wherein R³ represents a iodine atom;

a compound represented by Formula (1) wherein R⁴ represents a iodine atom;

a compound represented by Formula (1: wherein R⁵ represents a iodine atom;

a compound represented by Formula (1) wherein R¹ represents a methyl group;

a compound represented by Formula (1) wherein R² represents a methyl group;

a compound represented by Formula (1) wherein R³ represents a methyl group;

a compound represented by Formula (1) wherein R⁴ represents a methyl group;

a compound represented by Formula (1) wherein R⁵ represents a methyl group;

a compound represented by Formula (1) wherein R¹ represents an ethyl group;

a compound represented by Formula (1) wherein R² represents an ethyl group;

a compound represented by Formula (1) wherein R³ represents an ethyl group;

a compound represented by Formula (1) wherein R⁴ represents an ethyl group;

a compound represented by Formula (1) wherein R⁵ represents an ethyl group;

a compound represented by Formula (1) wherein R¹ represents an isopropyl group;

a compound represented by Formula (1) wherein R² represents an isopropyl group;

a compound represented by Formula (1) wherein R³ represents an isopropyl group;

a compound represented by Formula (1) wherein R⁴ represents an isopropyl group;

a compound represented by Formula (1) wherein R⁵ represents an isopropyl group;

a compound represented by Formula (1) wherein R¹ represents a tert-butyl group;

a compound represented by Formula (1) wherein R² represents a tert-butyl group;

a compound represented by Formula (1) wherein R³ represents a tert-butyl group;

a compound represented by Formula (1) wherein R⁴ represents a tert-butyl group;

a compound represented by Formula (1) wherein R⁵ represents a tert-butyl group;

a compound represented by Formula (1) wherein R¹ represents a difluoromethyl group;

a compound represented by Formula (1) wherein R² represents a difluoromethyl group;

a compound represented by Formula (1) wherein R³ represents a difluoromethyl group;

a compound represented by Formula (1) wherein R⁴ represents a difluoromethyl group;

a compound represented by Formula (1) wherein R⁵ represents a difluoromethyl group;

a compound represented by Formula (1) wherein R¹ represents a trifluoromethyl group;

a compound represented by Formula (1) wherein R² represents a trifluoromethyl group;

a compound represented by Formula (1) wherein R³ represents a trifluoromethyl group;

a compound represented by Formula (1) wherein R⁴ represents a trifluoromethyl group;

a compound represented by Formula (1) wherein R⁵ represents a trifluoromethyl group;

a compound represented by Formula (1) wherein $R^1$ represents a 2,2,2-trifluoroethyl group;

a compound represented by Formula (1) wherein $R^2$ represents a 2,2,2-trifluoroethyl group;

a compound represented by Formula (1) wherein $R^3$ represents a 2,2,2-trifluoroethyl group;

a compound represented by Formula (1) wherein $R^4$ represents a 2,2,2-trifluoroethyl group;

a compound represented by Formula (1) wherein $R^5$ represents a 2,2,2-trifluoroethyl group;

a compound represented by Formula (1) wherein $R^1$ represents a pentafluoroethyl group;

a compound represented by Formula (1) wherein $R^2$ represents a pentafluoroethyl group;

a compound represented by Formula (1) wherein $R^3$ represents a pentafluoroethyl group;

a compound represented by Formula (1) wherein $R^4$ represents a pentafluoroethyl group;

a compound represented by Formula (1) wherein $R^5$ represents a pentafluoroethyl group;

a compound represented by Formula (1) wherein $R^1$ represents a heptafluoropropyl group;

a compound represented by Formula (1) wherein $R^2$ represents a heptafluoropropyl group;

a compound represented by Formula (1) wherein $R^3$ represents a heptafluoropropyl group;

a compound represented by Formula (1) wherein $R^4$ represents a heptafluoropropyl group;

a compound represented by Formula (1) wherein $R^5$ represents a heptafluoropropyl group;

a compound represented by Formula (1) wherein $R^1$ represents a heptafluoroisopropyl group;

a compound represented by Formula (1) wherein $R^2$ represents a heptafluoroisopropyl group;

a compound represented by Formula (1) wherein $R^3$ represents a heptafluoroisopropyl group;

a compound represented by Formula (1) wherein $R^4$ represents a heptafluoroisopropyl group;

a compound represented by Formula (1) wherein $R^5$ represents a heptafluoroisopropyl group;

a compound represented by Formula (1) wherein $R^1$ represents a methoxycarbonyl group;

a compound represented by Formula (1) wherein $R^2$ represents a methoxycarbonyl group;

a compound represented by Formula (1) wherein $R^3$ represents a methoxycarbonyl group;

a compound represented by Formula (1) wherein $R^4$ represents a methoxycarbonyl group;

a compound represented by Formula (1) wherein $R^5$ represents a methoxycarbonyl group;

a compound represented by Formula (1) wherein $R^1$ represents an ethoxycarbonyl group;

a compound represented by Formula (1) wherein $R^2$ represents an ethoxycarbonyl group;

a compound represented by Formula (1) wherein $R^3$ represents an ethoxycarbonyl group;

a compound represented by Formula (1) wherein $R^4$ represents an ethoxycarbonyl group;

a compound represented by Formula (1) wherein $R^5$ represents an ethoxycarbonyl group;

a compound represented by Formula (1) wherein $R^1$ represents a difluoromethoxycarbonyl group;

a compound represented by Formula (1) wherein $R^2$ represents a difluoromethoxycarbonyl group;

a compound represented by Formula (1) wherein $R^3$ represents a difluoromethoxycarbonyl group;

a compound represented by Formula (1) wherein $R^4$ represents a difluoromethoxycarbonyl group;

a compound represented by Formula (1) wherein $R^5$ represents a difluoromethoxycarbonyl group;

a compound represented by Formula (1) wherein $R^1$ represents a trifluoroethoxycarbonyl group;

a compound represented by Formula (1) wherein $R^2$ represents a trifluoroethoxycarbonyl group;

a compound represented by Formula (1) wherein $R^3$ represents a trifluoromethoxycarbonyl group;

a compound represented by Formula (1) wherein $R^4$ represents a trifluoromethoxycarbonyl group;

a compound represented by Formula (1) wherein $R^5$ represents a trifluoromethoxycarbonyl group;

a compound represented by Formula (1) wherein $R^1$ represents a 2,2,2-trifluoroethoxycarbonyl group;

a compound represented by Formula (1) wherein $R^2$ represents a 2,2,2-trifluoroethoxycarbonyl group;

a compound represented by Formula (1) wherein $R^3$ represents a 2,2,2-trifluoroethoxycarbonyl group;

a compound represented by Formula (1) wherein $R^4$ represents a 2,2,2-trifluoroethoxycarbonyl group;

a compound represented by Formula (1) wherein $R^5$ represents a 2,2,2-trifluoroethoxycarbonyl group;

a compound represented by Formula (1) wherein $R^1$ represents a hydroxy group;

a compound represented by Formula (1) wherein $R^1$ represents a methoxy group;

a compound represented by Formula (1) wherein $R^1$ represents an amino group;

a compound represented by Formula (1) wherein $R^1$ represents a dimethylamino group;

a compound represented by Formula C1) wherein $R^1$ represents a 2-thienyl group;

a compound represented by Formula (1) wherein $R^2$ represents a 2-chlorophenyl croup;

a compound represented by Formula (1) wherein $R^2$ represents a 3-chlorophenyl group;

a compound represented by Formula (1) wherein $R^2$ represents a 4-chlorophenyl group;

a compound represented by Formula (1) wherein $R^2$ represents a 4-trifluoromethylphenyl group;

a compound represented by Formula (1) wherein $R^2$ represents a 2-pyridyl group;

a compound represented by Formula (1) wherein $R^2$ represents a 3-pyridyl group;

a compound represented by Formula (1) wherein $R^2$ represents a 4-pyridyl group;

a compound represented by Formula (1) wherein $R^2$ represents a 2-pyrimidinyl group;

a compound represented by Formula (1) wherein $R^2$ represents a 2-thienyl group;

a compound represented by Formula (1) wherein $R^2$ represents an acetyl group;

a compound represented by Formula (1) wherein $R^2$ represents a trifluoroacetyl group;

a compound represented by Formula (1) wherein $R^2$ represents an amino group;

a compound represented by Formula (1) wherein $R^2$ represents an acetylamino group;

a compound represented by Formula (1) wherein $R^2$ represents a trifluoroacetylamino group;

a compound represented by Formula (1) wherein $R^2$ represents a benzoylamino group;

a compound represented by Formula (1) wherein $R^2$ represents a 2-thienylcarbonylamino group;

a compound represented by Formula (1) wherein $R^2$ represents a 3-(2-chlorophenyl)ureido group;

a compound represented by Formula (1) wherein $R^2$ represents a methylsulfonylamino group;

a compound represented by Formula (1) wherein $R^2$ represents a trifluoromethylsulfonylamino group;

a compound represented by Formula (1) wherein $R^2$ represents a 4-methylphenylsulfonylamino group;

a compound represented by Formula (1) wherein $R^2$ represents a 4-chlorophenylsulfonylamino group;

a compound represented by Formula (1) wherein $R^2$ represents a benzylsulfonylamino group;

a compound represented by Formula (1) wherein $R^2$ represents a hydroxy group;

a compound represented by Formula (1) wherein $R^2$ represents a methoxy group;

a compound represented by Formula (1) wherein $R^2$ represents a trifluoromethoxy group;

a compound represented by Formula (1) wherein $R^2$ represents a methylthio group;

a compound represented by Formula (1) wherein $R^2$ represents a trifluoromethylthio group;

a compound represented by Formula (1) wherein $R^2$ represents a trifluoromethylsulfinyl group;

a compound represented by Formula (1) wherein $R^2$ represents a trifluoromethylsulfonyl group;

a compound represented by Formula (1) wherein $R^3$ represents a vinyl group;

a compound represented by Formula (1) wherein $R^3$ represents an ethynyl group;

a compound represented by Formula (1) wherein $R^3$ represents a 4-trifluoromethoxyphenyl group;

a compound represented by Formula (1) wherein $R^3$ represents a 6-trifluoromethyl-3-pyridyl group;

a compound represented by Formula (1) wherein $R^3$ represents a 1-difluoromethyl-3-pyrazolidyl group;

a compound represented by Formula (1) wherein $R^3$ represents an amino group;

a compound represented by Formula (1) wherein $R^3$ represents a hydroxy group;

a compound represented by Formula (1) wherein $R^3$ represents a methoxy group;

a compound represented by Formula (1) wherein $R^3$ represents a propargyloxy group;

a compound represented by Formula (1) wherein $R^3$ represents a 3-methoxybenzyloxy group;

a compound represented by Formula (1) wherein $R^3$ represents a 4-trifluoromethylbenzyloxy group;

a compound represented by Formula (1) wherein $R^4$ represents a 3-methylphenyl group;

a compound represented by Formula (1) wherein $R^4$ represents a 2-methoxyphenyl group;

a compound represented by Formula (1) wherein $R^4$ represents a hydroxy group;

a compound represented by Formula (1) wherein $R^4$ represents a methoxy group;

a compound represented by Formula (1) wherein $R^4$ represents a 2-methylphenoxy group;

a compound represented by Formula (1) wherein $R^4$ represents a 4-trifluoromethylphenoxy group;

a compound represented by Formula (1) wherein $R^4$ represents a 4-trifluoromethoxyphenoxy group;

a compound represented by Formula (1) wherein $R^5$ represents a 1-pyrrolyl group;

a compound represented by Formula (1) wherein $R^5$ represents an amino group;

a compound represented by Formula (1) wherein $R^5$ represents a methylamino group;

a compound represented by Formula (1) wherein $R^5$ represents a dimethylamino group;

a compound represented by Formula (1) wherein $R^5$ represents a formylamino group;

a compound represented by Formula (1) wherein $R^5$ represents an acetylamino group;

a compound represented by Formula (1) wherein $R^5$ represents a trifluoroacetylamino group;

a compound represented by Formula (1) wherein $R^5$ represents a benzoylamino group;

a compound represented by Formula (1) wherein $R^5$ represents a 5-bromo-2-thienylcarbonylamino group;

a compound represented by Formula (1) wherein $R^5$ represents a 2,5-dichloro-3-thienylcarbonylamino group;

a compound represented by Formula (1) wherein $R^3$ represents a 1-methyl-3-pyrazolylcarbonylamino group;

a compound represented by Formula (1) wherein $R^5$ represents a 1,5-dimethyl-5-pyrazolylcarbonylamino group;

a compound represented by Formula (1) wherein $R^5$ represents a 1,4-dimethyl-5-pyrazolylcarbonylamino group;

a compound represented by Formula (1) wherein $R^5$ represents a 3-methyl-5-isoxazolylcarbonylamino group compound represented by Formula (1) wherein $R^5$ represents a hydroxy group;

a compound represented by Formula (1) wherein $R^5$ represents a methoxy group;

a compound represented by Formula (1) wherein $R^5$ represents an ethoxy group;

a compound represented by Formula (1) wherein $R^5$ represents an isopropoxy group;

a compound represented by Formula (1) wherein $R^5$ represents an allyloxy group;

a compound represented by Formula (1) wherein $R^5$ represents a benzyloxy group;

a compound represented by Formula (1) wherein $R^5$ represents an acetyloxy group;

a compound represented by Formula (1) wherein $R^5$ represents a 2-chlorobenzoyloxy group;

a compound represented by Formula (1) wherein $R^5$ represents a 4-methylphenylsulfonyloxy group;

a compound represented by Formula (1) wherein $R^5$ represents an N-methyl-aminosulfonyl group;

a compound represented by Formula (1) wherein $R^5$ represents an N-(3-chlorobenzyl)-aminosulfonyl group;

a compound represented by Formula (1) wherein $R^5$ represents an N-(4-methylphenyl)-aminosulfonyl group;

a compound represented by Formula (1) wherein $R^5$ represents an N-(4-methylphenyl)-aminosulfonyl group;

a compound represented by Formula (1) wherein $R^5$ represents an N-(2-pyridylmethyl)-aminosulfonyl group;

a compound represented by Formula (1) wherein $R^1$ represents a hydrogen atom, and $R^5$ represents a hydrogen atom;

a compound represented by Formula (1) wherein $R^1$ represents a fluorine atom, and $R^5$ represents a hydrogen atom;

a compound represented by Formula (1) wherein $R^1$ represents a chlorine atom, and $R^5$ represents a hydrogen atom;

a compound represented by Formula (1) wherein $R^1$ represents a bromine atom, and $R^5$ represents a hydrogen atom;

a compound represented by Formula (1) wherein $R^1$ represents an iodine atom, and $R^5$ represents a hydrogen atom;

a compound represented by Formula (1) wherein $R^1$ represents a nitro group, and $R^5$ represents a hydrogen atom;

a compound represented by Formula (1) wherein $R^1$ represents an amino group, and $R^5$ represents a hydrogen atom;

a compound represented by Formula (1) wherein $R^1$ represents a dimethylamino group, and $R^5$ represents a hydrogen atom;

a compound represented by Formula (1) wherein $R^1$ represents a methoxy group, and $R^5$ represents a hydrogen atom;

a compound represented by Formula (1) wherein $R^1$ represents a methyl group, and $R^5$ represents a hydrogen atom;

a compound represented by Formula (1) wherein $R^1$ represents a difluoromethyl group, and $R^5$ represents a hydrogen atom;

a compound represented by Formula (1) wherein $R^1$ represents a pentafluoroethyl group, and $R^5$ represents a hydrogen atom;

a compound represented by Formula (1) wherein $R^1$ represents a methoxycarbonyl group, and $R^5$ represents a hydrogen atom;

a compound represented by Formula (1) wherein $R^1$ represents a phenyl group, and $R^5$ represents a hydrogen atom;

a compound represented by Formula (1) wherein $R^1$ represents a 2-thienyl group, and $R^5$ represents a hydrogen atom;

a compound represented by Formula (1) wherein $R^1$ represents a hydrogen atom, and $R^5$ represents a chlorine atom;

a compound represented by Formula (1) wherein $R^1$ represents a hydrogen atom, and $R^5$ represents a nitro group;

a compound represented by Formula (1) wherein $R^1$ represents a hydrogen atom, and $R^5$ represents an amino group;

a compound represented by Formula (1) wherein $R^1$ represents a hydrogen atom, and $R^5$ represents a formylamino group;

a compound represented by Formula (1) wherein $R^1$ represents a hydrogen atom, and $R^5$ represents an acetylamino group;

a compound represented by Formula (1) wherein $R^1$ represents a hydrogen atom, and $R^5$ represents a trifluoroacetylamino group;

a compound represented by Formula (1) wherein $R^1$ represents a hydrogen atom, and $R^5$ represents a benzoylamino group;

a compound represented by Formula (1) wherein $R^1$ represents a hydrogen atom, and $R^5$ represents a 5-bromo-2-thienylcarbonylamino group;

a compound represented by Formula (1) wherein $R^1$ represents a hydrogen atom, and $R^5$ represents a 2,5-dichloro-3-thienylcarbonylamino group;

a compound represented by Formula (1) wherein $R^1$ represents a hydrogen atom, and $R^5$ represents a 1-methyl-3-pyrazolylcarbonylamino group;

a compound represented by Formula (1) wherein $R^1$ represents a hydrogen atom, and $R^5$ represents a 1,5-dimethyl-3-pyrazolylcarbonylamino group;

a compound represented by Formula (1) wherein $R^1$ represents a hydrogen atom, and $R^5$ represents a 1,4-dimethyl-5-pyrazolylcarbonylamino group;

a compound represented by Formula (1) wherein $R^1$ represents a hydrogen atom, and $R^5$ represents a 3-methyl-5-isoxazolylcarbonylamino group;

a compound represented by Formula (1) wherein $R^1$ represents a hydrogen atom, and $R^5$ represents a hydroxy group;

a compound represented by Formula (1) wherein $R^1$ represents a hydrogen atom, and $R^5$ represents a methoxy group;

a compound represented by Formula (1) wherein $R^1$ represents a hydrogen atom, and $R^5$ represents an ethoxy group;

a compound represented by Formula (1) wherein R-represents a hydrogen atom, and $R^5$ represents an isopropoxy group;

a compound represented by Formula (1) wherein $R^1$ represents a hydrogen atom, and $R^5$ represents an allyloxy group;

a compound represented by Formula (1) wherein $R^1$ represents a hydrogen atom, and $R^5$ represents a benzyloxy group;

a compound represented by Formula (1) wherein $R^1$ represents a hydrogen atom, and $R^5$ represents an acetyloxy group;

a compound represented by Formula (1) wherein $R^1$ represents a hydrogen atom, and $R^5$ represents a 2-chlorobenzoyloxy group;

a compound represented by Formula (1) wherein $R^1$ represents a hydrogen atom, and $R^5$ represents a 4-methylphenylsulfonyloxy group;

a compound represented by Formula (1) wherein $R^1$ represents a hydrogen atom, and $R^5$ represents an N-methylaminosulfonyl group;

a compound represented by Formula (1) wherein $R^1$ represents a hydrogen atom, and $R^3$ represents an N-(3-chlorobenzyl)-aminosulfonyl group;

a compound represented by Formula (1) wherein $R^1$ represents a hydrogen atom, and $R^5$ represents an N-(4-methylphenyl)-aminosulfonyl group;

a compound represented by Formula (1) wherein $R^1$ represents a hydrogen atom, and $R^5$ represents an N-(4-methylbenzyl)-aminosulfonyl group;

a compound represented by Formula (1) wherein $R^1$ represents a hydrogen atom, and $R^5$ represents an N-(2-pyridylmethyl)-aminosulfonyl group;

a compound represented by Formula (1) wherein $R^1$ represents a hydrogen atom, and $R^5$ represents an acetyloxy group;

a compound represented by Formula (1) wherein $R^1$ represents a hydrogen atom, and $R^5$ represents a methyl group;

a compound represented by Formula (1) wherein $R^1$ represents a hydrogen atom, and $R^5$ represents a trifluoromethyl group;

a compound represented by Formula (1) wherein $R^1$ represents a hydrogen atom, and $R^5$ represents a heptafluoropropyl group;

a compound represented by Formula (1) wherein $R^1$ represents a hydrogen atom, and $R^5$ represents a methoxycarbonyl group;

a compound represented by Formula (1) wherein $R^1$ represents a hydrogen atom, and $R^5$ represents a prenyl group;

a compound represented by Formula (1) wherein $R^1$ represents a hydrogen atom, and $R^5$ represents a 1-pyrrolyl group;

a compound represented by Formula (1) wherein R-represents a chlorine atom, and $R^5$ represents an amino group;

a compound represented by Formula (1) wherein $R^2$ represents a hydrogen atom, and $R^5$ represents a hydrogen atom;

a compound represented by Formula (1) wherein $R^2$ represents a cyano group, and $R^5$ represents a hydrogen atom;

a compound represented by Formula (1) wherein $R^2$ represents a nitro group, and $R^5$ represents a hydrogen atom;

a compound represented by Formula (1) wherein $R^2$ represents a fluorine atom, and $R^5$ represents a hydrogen atom;

a compound represented by Formula (1) wherein $R^2$ represents a chlorine atom, and $R^5$ represents a hydrogen atom;

a compound represented by Formula (1) wherein $R^2$ represents a bromine atom, and $R^5$ represents a hydrogen atom;

a compound represented by Formula (1) wherein $R^2$ represents an iodine atom, and $R^5$ represents a hydrogen atom;

a compound represented by Formula (1) wherein $R^2$ represents a methyl group, and $R^5$ represents a hydrogen atom;

a compound represented by Formula (1) wherein $R^2$ represents a difluoromethyl group, and $R^5$ represents a hydrogen atom;

a compound represented by Formula (1) wherein $R^2$ represents a trifluoromethyl group, and $R^5$ represents a hydrogen atom;

a compound represented by Formula (1) wherein $R^2$ represents a pentafluoroethyl group, and $R^5$ represents a hydrogen atom;

a compound represented by Formula (1) wherein $R^2$ represents a heptafluoropropyl group, and $R^5$ represents a hydrogen atom;

a compound represented by Formula (1) wherein $R^2$ represents a tert-butyl group, and $R^5$ represents a hydrogen atom;

a compound represented by Formula (1) wherein $R^2$ represents a 2-chlorophenyl group, and $R^5$ represents a hydrogen atom;

a compound represented by Formula (1) wherein $R^2$ represents a 3-chlorophenyl group, and $R^5$ represents a hydrogen atom;

a compound represented by Formula (1) wherein $R^2$ represents a 4-chlorophenyl group, and $R^5$ represents a hydrogen atom;

a compound represented by Formula (1) wherein $R^2$ represents a 4-trifluoromethylphenyl group, and $R^5$ represents a hydrogen atom;

a compound represented by Formula (1) wherein $R^2$ represents a 2-pyridyl group, and $R^3$ represents a hydrogen atom;

a compound represented by Formula (1) wherein $R^2$ represents a 3-pyridyl group, and $R^5$ represents a hydrogen atom;

a compound represented by Formula (1) wherein $R^2$ represents a 4-pyridyl group, and $R^5$ represents a hydrogen atom;

a compound represented by Formula (1) wherein $R^2$ represents a 2-pyrimidinyl group, and $R^5$ represents a hydrogen atom;

a compound represented by Formula (1) wherein $R^2$ represents a 2-thienyl group, and $R^5$ represents a hydrogen atom;

a compound represented by Formula (1) wherein $R^2$ represents an acetyl group, and $R^5$ represents a hydrogen atom;

a compound represented by Formula (1) wherein $R^2$ represents a trifluoroacetyl group, and $R^5$ represents a hydrogen atom;

a compound represented by Formula (1) wherein $R^2$ represents a benzoyl group, and $R^3$ represents a hydrogen atom;

a compound represented by Formula (1) wherein $R^2$ represents a methoxycarbonyl group, and $R^5$ represents a hydrogen atom;

a compound represented by Formula (1) wherein $R^2$ represents an amino group, and $R^5$ represents a hydrogen atom;

a compound represented by Formula (1) wherein $R^2$ represents an acetylamino group, and $R^5$ represents a hydrogen atom;

a compound represented by Formula (1) wherein $R^2$ represents a chloroacetylamino group, and $R^5$ represents a hydrogen atom;

a compound represented by Formula (1) wherein $R^2$ represents a trifluoroacetylamino group, and $R^5$ represents a hydrogen atom;

a compound represented by Formula (1) wherein $R^2$ represents a benzoylamino group, and $R^5$ represents a hydrogen atom;

a compound represented by Formula (1) wherein $R^2$ represents a 2-thienylcarbonylamino group, and $R^5$ represents a hydrogen atom;

a compound represented by Formula (1) wherein $R^2$ represents a methylsulfonylamino group, and $R^5$ represents a hydrogen atom;

a compound represented by Formula (1) wherein $R^2$ represents a trifluoromethylsulfonylamino group, and $R^5$ represents a hydrogen atom;

a compound represented by Formula (1) wherein $R^2$ represents a 4-chlorophenylsulfonylamino group, and $R^5$ represents a hydrogen atom;

a compound represented by Formula (1) wherein $R^2$ represents a 4-methylphenylsulfonylamino group, and $R^5$ represents a hydrogen atom;

a compound represented by Formula (1) wherein $R^2$ represents a benzylsulfonylamino group, and $R^5$ represents a hydrogen atom;

a compound represented by Formula (1) wherein $R^2$ represents a hydroxy group, and $R^5$ represents a hydrogen atom;

a compound represented by Formula (1) wherein $R^2$ represents a methoxy group, and $R^5$ represents a hydrogen atom;

a compound represented by Formula (1) wherein $R^2$ represents a trifluoromethoxy group, and $R^5$ represents a hydrogen atom;

a compound represented by Formula (1) wherein $R^2$ represents a methylthio group, and $R^5$ represents a hydrogen atom;

a compound represented by Formula (1) wherein $R^2$ represents a trifluoromethylthio group, and $R^5$ represents a hydrogen atom;

a compound represented by Formula (1) wherein $R^2$ represents a trifluoromethylsulfinyl group, and $R^5$ represents a hydrogen atom;

a compound represented by Formula (1) wherein $R^2$ represents a trifluoromethylsulfonyl group, and $R^5$ represents a hydrogen atom;

a compound represented by Formula (1) wherein $R^2$ represents a hydrogen atom, and $R^5$ represents a chlorine atom;

a compound represented by Formula (1) wherein $R^2$ represents a hydrogen atom, and $R^5$ represents a nitro group;

a compound represented by Formula (1) wherein $R^2$ represents a hydrogen atom, and $R^5$ represents a methyl group;

a compound represented by Formula (1) wherein $R^2$ represents a hydrogen atom, and $R^5$ represents a trifluoromethyl group;

a compound represented by Formula (1) wherein $R^2$ represents a hydrogen atom, and $R^5$ represents a methoxycarbonyl group;

a compound represented by Formula (1) wherein $R^2$ represents a hydrogen atom, and $R^5$ represents a phenyl group;

a compound represented by Formula (1) wherein $R^2$ represents a hydrogen atom, and $R^5$ represents a 1-pyrrolyl group;

a compound represented by Formula (1) wherein $R^2$ represents a hydrogen atom, and $R^5$ represents an amino group;

a compound represented by Formula (1) wherein $R^2$ represents a hydrogen atom, and $R^5$ represents a formylamino group;

a compound represented by Formula (1) wherein $R^2$ represents a hydrogen atom, and $R^5$ represents an acetylamino group;

a compound represented by Formula (1) wherein $R^2$ represents a hydrogen atom, and $R^5$ represents a trifluoroacetylamino group;

a compound represented by Formula (1) wherein $R^2$ represents a hydrogen atom, and $R^5$ represents a benzoylamino group;

a compound represented by Formula (1) wherein $R^2$ represents a hydrogen atom, and $R^5$ represents a 5-bromo-2-thienylcarbonylamino group;

a compound represented by Formula (1) wherein $R^2$ represents a hydrogen atom, and $R^5$ represents a 2,5-dichloro-3-thienylcarbonylamino group;

a compound represented by Formula (1) wherein $R^2$ represents a hydrogen atom, and $R^5$ represents a 1-methyl-3-pyrazolylcarbonylamino group;

a compound represented by Formula (1) wherein $R^2$ represents a hydrogen atom, and $R^5$ represents a 1,5-dimethyl-3-pyrazolylcarbonylamino group;

a compound represented by Formula (1) wherein $R^1$ represents a hydrogen atom, and $R^5$ represents a 1,4-dimethyl-5-pyrazolylcarbonylamino group;

a compound represented by Formula (1) wherein $R^2$ represents a hydrogen atom, and $R^5$ represents a 3-methyl-5-isoxazolylcarbonylamino group;

a compound represented by Formula (1) wherein $R^2$ represents a hydrogen atom, and $R^5$ represents an N-methylaminosulfonyl group;

a compound represented by Formula (1) wherein $R^2$ represents a hydrogen atom, and $R^5$ represents an N-(3-chlorobenzyl)-aminosulfonyl group;

a compound represented by Formula (1) wherein $R^2$ represents a hydrogen atom, and $R^5$ represents an N-(4-methylphenyl)-aminosulfonyl group;

a compound represented by Formula (1) wherein $R^2$ represents a hydrogen atom, and $R^5$ represents an N-(4-methylbenzyl)-aminosulfonyl group;

a compound represented by Formula (1) wherein $R^2$ represents a hydrogen atom, and $R^5$ represents an N-(2-pyridylmethyl)-aminosulfonyl group;

a compound represented by Formula (1) wherein $R^2$ represents a hydrogen atom, and $R^5$ represents a hydroxy group;

a compound represented by Formula (1) wherein $R^2$ represents a hydrogen atom, and $R^5$ represents a methoxy group;

a compound represented by Formula (1) wherein $R^2$ represents a hydrogen atom, and $R^5$ represents an ethoxy group;

a compound represented by Formula (1) wherein $R^2$ represents a hydrogen atom, and $R^5$ represents an isopropoxy group;

a compound represented by Formula (1) wherein $R^2$ represents a hydrogen atom, and $R^5$ represents a benzyloxy group;

a compound represented by Formula (1) wherein $R^2$ represents a hydrogen atom, and $R^5$ represents an acetyloxy group;

a compound represented by Formula (1) wherein $R^2$ represents a hydrogen atom, and $R^5$ represents a 2-chlorobenzoyloxy group;

a compound represented by Formula (1) wherein $R^2$ represents a hydrogen atom, and $R^5$ represents a 4-methylphenylsulfonyloxy group;

a compound represented by Formula (1) wherein $R^2$ represents a trifluoromethyl group, and $R^5$ represents a chlorine atom;

a compound represented by Formula (1) wherein $R^2$ represents a trifluoromethyl group, and $R^5$ represents a methyl group;

a compound represented by Formula (1) wherein $R^2$ represents a trifluoromethyl group, and $R^5$ represents a trifluoromethyl group;

a compound represented by Formula (1) wherein $R^2$ represents a trifluoromethyl group, and $R^5$ represents an amino group;

a compound represented by Formula (1) wherein $R^2$ represents a trifluoromethyl group, and $R^5$ represents a methylamino group;

a compound represented by Formula (1) wherein $R^2$ represents a trifluoromethyl group, and $R^5$ represents a dimethylamino group;

a compound represented by Formula (1) wherein $R^2$ represents a trifluoromethyl group, and $R^5$ represents a formylamino group;

a compound represented by Formula (1) wherein $R^2$ represents a trifluoromethyl group, and $R^5$ represents an acetylamino group;

a compound represented by Formula (1) wherein $R^2$ represents a trifluoromethyl group, and $R^5$ represents a trifluoroacetylamino group;

a compound represented by Formula (1) wherein $R^2$ represents a trifluoromethyl group, and $R^5$ represents a hydroxy group;

a compound represented by Formula (1) wherein $R^2$ represents a trifluoromethyl group, and $R^5$ represents an ethoxy group;

a compound represented by Formula (1) wherein $R^2$ represents a trifluoromethyl group, and $R^5$ represents a methoxy group;

a compound represented by Formula (1) wherein $R^2$ represents a trifluoromethyl group, and $R^5$ represents an isopropoxy group;

a compound represented by Formula (1) wherein $R^2$ represents a trifluoromethyl group, and $R^5$ represents an allyloxy group;

a compound represented by Formula (1) wherein $R^2$ represents a trifluoromethyl group, and $R^5$ represents a benzyloxy group;

a compound represented by Formula (1) wherein $R^2$ represents a trifluoromethyl group, and $R^5$ represents an acetyloxy group;

a compound represented by Formula (1) wherein $R^2$ represents a nitro group, and $R^5$ represents a hydroxy group;

a compound represented by Formula (1) wherein $R^2$ represents a 3-(2-chlorophenyl)ureido group, and $R^5$ represents a methoxy group;

a compound represented by Formula (1) wherein $R^3$ represents a nitro group, and $R^5$ represents a hydrogen atom;

a compound represented by Formula (1) wherein $R^3$ represents a fluorine atom, and $R^5$ represents a hydrogen atom;

a compound represented by Formula (1) wherein $R^3$ represents a chlorine atom, and $R^5$ represents a hydrogen atom;

a compound represented by Formula (1) wherein $R^3$ represents a bromine atom, and $R^5$ represents a hydrogen atom;

a compound represented by Formula (1) wherein $R^3$ represents a methyl group, and $R^5$ represents a hydrogen atom;

a compound represented by Formula (1) wherein $R^3$ represents a vinyl group, and $R^5$ represents a hydrogen atom;

a compound represented by Formula (1) wherein $R^3$ represents an ethynyl group, and $R^5$ represents a hydrogen atom;

a compound represented by Formula (1) wherein $R^3$ represents a methoxycarbonyl group, and $R^5$ represents a hydrogen atom;

a compound represented by Formula (1) wherein $R^3$ represents a phenyl group, and $R^5$ represents a hydrogen atom;

a compound represented by Formula (1) wherein $R^3$ represents a 4-trifluoromethoxyphenyl group, and R represents a hydrogen atom;

a compound represented by Formula (1) wherein $R^3$ represents a 6-trifluoromethyl-3-pyridyl group, and R represents a hydrogen atom;

a compound represented by Formula (1) wherein $R^3$ represents an amino group, and $R^5$ represents a hydrogen atom;

a compound represented by Formula (1) wherein $R^3$ represents a hydroxy group, and $R^5$ represents a hydrogen atom;

a compound represented by Formula (1) wherein $R^3$ represents a methoxy group, and $R^5$ represents a hydrogen atom;

a compound represented by Formula (1) wherein $R^3$ represents a propargyloxy group, and $R^5$ represents a hydrogen atom;

a compound represented by Formula (1) wherein $R^3$ represents a 3-methoxybenzyloxy group, and $R^5$ represents a hydrogen atom;

a compound represented by Formula (1) wherein $R^3$ represents a 4-trifluoromethylbenzyloxy group, and $R^5$ represents a hydrogen atom;

a compound represented by Formula (1) wherein $R^3$ represents a hydrogen atom, and $R^5$ represents an acetyloxy group;

a compound represented by Formula (1) wherein $R^3$ represents a hydrogen atom, and R; represents a 2-chlorobenzoyloxy group;

a compound represented by Formula (1) wherein $R^3$ represents a hydrogen atom, and $R^5$ represents a 4-methylphenylsulfonyloxy group;

a compound represented by Formula (1) wherein $R^3$ represents a hydrogen atom, and $R^5$ represents a nitro group;

a compound represented by Formula (1) wherein $R^3$ represents a hydrogen atom, and $R^5$ represents a chlorine atom;

a compound represented by Formula (1) wherein $R^3$ represents a hydrogen atom, and $R^5$ represents a methyl group;

a compound represented by Formula (1) wherein $R^3$ represents a hydrogen atom, and $R^5$ represents a trifluoromethyl group;

a compound represented by Formula (1) wherein $R^3$ represents a hydrogen atom, and $R^5$ represents a heptafluoropropyl group;

a compound represented by Formula (1) wherein $R^3$ represents a hydrogen atom, and $R^5$ represents a methoxycarbonyl group;

a compound represented by Formula (1) wherein $R^3$ represents a hydrogen atom, and $R^5$ represents a phenyl group;

a compound represented by Formula (1) wherein $R^1$ represents a hydrogen atom, and $R^5$ represents a 1-pyrrolyl group;

a compound represented by Formula (1) wherein $R^3$ represents a hydrogen atom, and $R^5$ represents an amino group;

a compound represented by Formula (1) wherein $R^3$ represents a hydrogen atom, and $R^5$ represents a methylamino group;

a compound represented by Formula (1) wherein $R^3$ represents a hydrogen atom, and $R^5$ represents a dimethylamino group;

a compound represented by Formula (1) wherein $R^3$ represents a hydrogen atom, and $R^5$ represents a formylamino group;

a compound represented by Formula (1) wherein $R^3$ represents a hydrogen atom, and $R^5$ represents an acetylamino group;

a compound represented by Formula (1) wherein $R^3$ represents a hydrogen atom, and $R^5$ represents a trifluoroacetylamino group;

a compound represented by Formula (1) wherein $R^3$ represents a hydrogen atom, and $R^5$ represents a benzoylamino group;

a compound represented by Formula (1) wherein $R^3$ represents a hydrogen atom, and $R^5$ represents a hydroxy group;

a compound represented by Formula (1) wherein $R^3$ represents a hydrogen atom, and $R^5$ represents a methoxy group;

a compound represented by Formula (1) wherein $R^3$ represents a hydrogen atom, and $R^5$ represents an ethoxy group;

a compound represented by Formula (1) wherein $R^3$ represents a hydrogen atom, and $R^5$ represents an isopropoxy group;

a compound represented by Formula (1) wherein $R^3$ represents a hydrogen atom, and $R^5$ represents an allyloxy group;

a compound represented by Formula (1) wherein $R^3$ represents a hydrogen atom, and $R^5$ represents a benzyloxy group;

a compound represented by Formula (1) wherein $R^3$ represents a hydrogen atom, and $R^5$ represents a 5-bromo-2-thienylcarbonylamino group;

a compound represented by Formula (1) wherein $R^3$ represents a hydrogen atom, and $R^5$ represents a 2,5-dichloro-3-thienylcarbonylamino group;

a compound represented by Formula (1) wherein $R^3$ represents a hydrogen atom, and $R^5$ represents a 1-methyl-3-pyrazolylcarbonylamino group;

a compound represented by Formula (1) wherein $R^3$ represents a hydrogen atom, and $R^5$ represents a 1,5-dimethyl-3-pyrazolylcarbonylamino group;

a compound represented by Formula (1) wherein $R^3$ represents a hydrogen atom, and $R^5$ represents a 1,4-dimethyl-5-pyrazolylcarbonylamino group;

a compound represented by Formula (1) wherein $R^3$ represents a hydrogen atom, and $R^5$ represents a 3-methyl-5-isoxazolylcarbonylamino group;

a compound represented by Formula (1) wherein $R^3$ represents a hydrogen atom, and $R^5$ represents an N-methylaminosulfonyl group;

a compound represented by Formula (1) wherein $R^3$ represents a hydrogen atom, and $R^5$ represents an N-(3-chlorobenzyl)-aminosulfonyl group;

a compound represented by Formula (1) wherein $R^3$ represents a hydrogen atom, and $R^5$ represents an N-(4-methylphenyl)-aminosulfonyl group;

a compound represented by Formula (1) wherein $R^3$ represents a hydrogen atom, and $R^5$ represents an N-(4-methylbenzyl)-aminosulfonyl group;

a compound represented by Formula (1) wherein $R^3$ represents a hydrogen atom, and $R^5$ represents an N-(2-pyridylmethyl)-aminosulfonyl group;

a compound represented by Formula (1) wherein $R^3$ represents a 1-difluoromethyl-3-pyrazolyl group, and $R^5$ represents a chlorine atom;

a compound represented by Formula (1) wherein $R^3$ represents a trifluoromethyl group, and $R^5$ represents an amino group;

a compound represented by Formula (1) wherein $R^4$ represents a fluorine atom, and $R^5$ represents a hydrogen atom;

a compound represented by Formula (1) wherein $R^4$ represents a chlorine atom, and $R^5$ represents a hydrogen atom;

a compound represented by Formula (1) wherein $R^4$ represents a bromine atom, and $R^5$ represents a hydrogen atom;

a compound represented by Formula (1) wherein $R^4$ represents a methyl group, and $R^5$ represents a hydrogen atom;

a compound represented by Formula (1) wherein $R^4$ represents a phenyl group, and $R^5$ represents a hydrogen atom;

a compound represented by Formula (1) wherein $R^4$ represents a hydroxy group, and $R^5$ represents a hydrogen atom;

a compound represented by Formula (1) wherein $R^4$ represents a methoxy group, and $R^5$ represents a hydrogen atom;

a compound represented by Formula (1) wherein $R^4$ represents a 2-methylphenoxy group, and $R^5$ represents a hydrogen atom;

a compound represented by Formula (1) wherein $R^4$ represents a 4-trifluoromethylphenoxy group, and $R^5$ represents a hydrogen atom;

a compound represented by Formula (1) wherein $R^4$ represents a hydrogen atom, and $R^5$ represents a nitro group;

a compound represented by Formula (1) wherein $R^4$ represents a hydrogen atom, and $R^5$ represents a chlorine atom;

a compound represented by Formula (1) wherein $R^4$ represents a hydrogen atom, and $R^5$ represents a methyl group;

a compound represented by Formula (1) wherein $R^4$ represents a hydrogen atom, and $R^5$ represents a trifluoromethyl group;

a compound represented by Formula (1) wherein $R^4$ represents a hydrogen atom, and $R^5$ represents a heptafluoropropyl group;

a compound represented by Formula (1) wherein $R^4$ represents a hydrogen atom, and $R^5$ represents a methoxycarbonyl group;

a compound represented by Formula (1) wherein $R^4$ represents a hydrogen atom, and $R^5$ represents a phenyl group;

a compound represented by Formula (1) wherein $R^4$ represents a hydrogen atom, and $R^5$ represents a 1-pyrrolyl group;

a compound represented by Formula (1) wherein $R^4$ represents a hydrogen atom, and $R^5$ represents an amino group;

a compound represented by Formula (1) wherein $R^4$ represents a hydrogen atom, and $R^5$ represents a methylamino group;

a compound represented by Formula (1) wherein $R^4$ represents a hydrogen atom, and $R^5$ represents a dimethylamino group;

a compound represented by Formula (1) wherein $R^4$ represents a hydrogen atom, and $R^5$ represents a formylamino group;

a compound represented by Formula (1) wherein $R^4$ represents a hydrogen atom, and $R^5$ represents an acetylamino group;

a compound represented by Formula (1) wherein $R^4$ represents a hydrogen atom, and $R^5$ represents a trifluoroacetylamino group;

a compound represented by Formula (1) wherein $R^4$ represents a hydrogen atom, and $R^5$ represents a benzoylamino group;

a compound represented by Formula (1) wherein $R^4$ represents a hydrogen atom, and $R^5$ represents a hydroxy group;

a compound represented by Formula (1) wherein $R^4$ represents a hydrogen atom, and $R^5$ represents a methoxy group;

a compound represented by Formula (1) wherein $R^4$ represents a hydrogen atom, and $R^5$ represents an ethoxy group;

a compound represented by Formula (1) wherein $R^4$ represents a hydrogen atom, and $R^5$ represents an isopropoxy group;

a compound represented by Formula (1) wherein $R^4$ represents a hydrogen atom, and $R^5$ represents an allyloxy group;

a compound represented by Formula (1) wherein $R^4$ represents a hydrogen atom, and $R^5$ represents a benzyloxy group;

a compound represented by Formula (1) wherein $R^4$ represents a 4-trifluoromethoxyphenoxy group, and $R^5$ represents a hydrogen atom;

a compound represented by Formula (1) wherein $R^4$ represents a hydrogen atom, and $R^5$ represents an acetyloxy group;

a compound represented by Formula (1) wherein $R^4$ represents a hydrogen atom, and $R^5$ represents a 2-chlorobenzoyloxy group;

a compound represented by Formula (1) wherein $R^4$ represents a hydrogen atom, and $R^5$ represents a 4-methylphenylsulfonyloxy group;

a compound represented by Formula (1) wherein $R^4$ represents a hydrogen atom, and $R^5$ represents a 5-bromo-2-thienylcarbonylamino group;

a compound represented by Formula (1) wherein $R^4$ represents a hydrogen atom, and $R^5$ represents a 2,5-dichloro-3-thienylcarbonylamino group;

a compound represented by Formula (1) wherein $R^4$ represents a hydrogen atom, and $R^5$ represents a 1-methyl-3-pyrazolylcarbonylamino group;

a compound represented by Formula (1) wherein $R^4$ represents a hydrogen atom, and $R^5$ represents a 1,5-dimethyl-3-pyrazolylcarbonylamino group;

a compound represented by Formula (1) wherein $R^4$ represents a hydrogen atom, and $R^5$ represents a 1,4-dimethyl-5-pyrazolylcarbonylamino group;

a compound represented by Formula (1) wherein $R^4$ represents a hydrogen atom, and $R^5$ represents a 3-methyl-5-isoxazolylcarbonylamino group;

a compound represented by Formula (1) wherein $R^4$ represents a hydrogen atom, and $R^5$ represents an N-methylaminosulfonyl group;

a compound represented by Formula (1) wherein $R^4$ represents a hydrogen atom, and $R^5$ represents an N-(3-chlorobenzyl)-aminosulfonyl group;

a compound represented by Formula (1) wherein $R^4$ represents a hydrogen atom, and $R^5$ represents an N-(4-methylphenyl)-aminosulfonyl group;

a compound represented by Formula (1) wherein $R^4$ represents a hydrogen atom, and $R^5$ represents an N-(4-methylbenzyl)-aminosulfonyl group;

a compound represented by Formula (1) wherein $R^4$ represents a hydrogen atom, and $R^5$ represents an N-(2-pyridylmethyl)-aminosulfonyl group;

a compound represented by Formula (1) wherein $R^3$ and $R^4$ each represents a hydrogen atom;

a compound represented by Formula (1) wherein $R^1$ and $R^4$ each represents a hydrogen atom;

a compound represented by Formula (1) wherein $R^2$ and $R^3$ each represents a hydrogen atom;

a compound represented by Formula (1) wherein $R^2$ and $R^4$ each represents a hydrogen atom;

a compound represented by Formula (1) wherein $R^1$ and $R^2$ each represents a hydrogen atom;

a compound represented by Formula (1) wherein $R^1$ and $R^3$ each represents a hydrogen atom;

a compound represented by Formula (1) wherein $R^3$, $R^4$, and $R^5$ each represents a hydrogen atom;

a compound represented by Formula (1) wherein $R^1$, $R^4$, and $R^5$ each represents a hydrogen atom;

a compound represented by Formula (1) wherein $R^2$, $R^3$, and $R^5$ each represents a hydrogen atom;

a compound represented by Formula (1) wherein $R^2$, $R^4$, and $R^5$ each represents a hydrogen atom;

a compound represented by Formula (1) wherein $R^1$, $R^2$, and $R^5$ each represents a hydrogen atom;

a compound represented by Formula (1) wherein $R^1$, $R^3$, and $R^5$ each represents a hydrogen atom;

a compound represented by Formula (1) wherein $R^2$, $R^3$, and $R^4$ each represents a hydrogen atom;

a compound represented by Formula (1) wherein $R^1$, $R^3$, and $R^4$ each represents a hydrogen atom;

a compound represented by Formula (1) wherein $R^1$, $R^2$, and $R^4$ each represents a hydrogen atom;

a compound represented by Formula (1) wherein $R^1$, $R^2$, and $R^3$ each represents a hydrogen atom;

a compound represented by Formula (1) wherein $R^1$, $R^3$, and $R^4$ each represents a hydrogen atom, and $R^2$ represents a C1-C4 alkyl group optionally having one or more halogen atoms;

a compound represented by Formula (1) wherein $R^2$, $R^3$, and $R^4$ each represents a hydrogen atom, and $R^5$ represents a C1-C4 alkyl group optionally having one or more halogen atoms;

a compound represented by Formula (1) wherein $R^3$, $R^4$, and $R^5$ each represents a hydrogen atom, and $R^5$ represents a C1-C4 alkyl group optionally having one or more halogen atoms;

a compound represented by Formula (1) wherein $R^3$, $R^4$, and $R^5$ each represents a hydrogen atom, and $R^2$ represents a C1-C4 alkyl group optionally having one or more halogen atoms;

a compound represented by Formula (1) wherein $R^2$, $R^3$, and $R^4$ each represents a hydrogen atom, and $R^1$ represents a methyl group;

a compound represented by Formula (1) wherein $R^2$, $R^3$, and $R^4$ each represents a hydrogen atom, and $R^1$ represents a difluoromethyl group;

a compound represented by Formula (1) wherein $R^2$, $R^3$, and $R^4$ each represents a hydrogen atom, and $R^1$ represents a trifluoromethyl group;

a compound represented by Formula (1) wherein $R^2$, $R^3$, and $R^1$ each represents a hydrogen atom, and $R^1$ represents a pentafluoroethyl group;

a compound represented by Formula (1) wherein $R^3$, $R^4$, and $R^5$ each represents a hydrogen atom, and $R^1$ represents a methyl group;

a compound represented by Formula (1) wherein $R^3$, $R^4$, and $R^5$ each represents a hydrogen atom, and $R^1$ represents a difluoromethyl group;

a compound represented by Formula (1) wherein $R^3$, $R^4$, and $R^5$ each represents a hydrogen atom, and $R^1$ represents a trifluoromethyl group;

a compound represented by Formula (1) wherein $R^3$, $R^4$, and $R^5$ each represents a hydrogen atom, and $R^2$ represents a pentafluoroethyl group;

a compound represented by Formula (1) wherein $R^1$, $R^3$, and $R^4$ each represents a hydrogen atom, and $R^2$ represents a methyl group;

a compound represented by Formula (1) wherein $R^1$, R, and $R^4$ each represents a hydrogen atom, and $R^2$ represents a difluoromethyl group;

a compound represented by Formula (1) wherein $R^1$, $R^3$, and $R^4$ each represents a hydrogen atom, and $R^2$ represents a trifluoromethyl group;

a compound represented by Formula (1) wherein $R^1$, $R^3$, and $R^4$ each represents a hydrogen atom, and $R^2$ represents a pentafluoroethyl group;

a compound represented by Formula (1) wherein $R^1$, $R^3$, and $R^4$ each represents a hydrogen atom, and $R^2$ represents a heptafluoropropyl group;

a compound represented by Formula (1) wherein $R^1$, $R^3$, and $R^4$ each represents a hydrogen atom, and $R^2$ represents a tert-butyl group;

a compound represented by Formula (1) wherein $R^3$, $R^4$, and $R^5$ each represents a hydrogen atom, and $R^2$ represents a methyl group;

a compound represented by Formula (1) wherein $R^3$, $R^4$, and $R^5$ each represents a hydrogen atom, and $R^2$ represents a difluoromethyl group;

a compound represented by Formula (1) wherein $R^3$, $R^4$, and $R^5$ each represents a hydrogen atom, and $R^2$ represents a trifluoromethyl group;

a compound represented by Formula (1) wherein $R^3$, $R^4$, and $R^5$ each represents a hydrogen atom, and $R^2$ represents a pentafluoroethyl group;

a compound represented by Formula (1) wherein $R^3$, $R^4$, and $R^5$ each represents a hydrogen atom, and $R^2$ represents a heptafluoropropyl group;

a compound represented by Formula (1) wherein $R^3$, $R^4$, and $R^5$ each represents a hydrogen atom, and $R^2$ represents a tert-butyl group;

a compound represented by Formula (1) wherein $R^1$, $R^3$, and $R^4$ each represents a hydrogen atom, and $R^2$ represents a trifluoromethyl group;

a compound represented by Formula (1) wherein $R^2$, $R^3$, and $R^4$ each represents a hydrogen atom, and $R^1$ represents a trifluoromethyl group;

a compound represented by Formula (1) wherein $R^3$, $R^4$, and $R^5$ each represents a hydrogen atom, and $R^1$ represents a trifluoromethyl group;

a compound represented by Formula (1) wherein $R^3$, $R^4$, and $R^5$ each represents a hydrogen atom, and $R^2$ represents a trifluoromethyl group;

a compound represented by Formula (1) wherein $R^2$, $R^3$, and $R^4$ each represents a hydrogen atom, and $R^1$ represents a phenyl group optionally having one or more groups selected from the group Y;

a compound represented by Formula (1) wherein $R^1$, $R^3$, and $R^4$ each represents a hydrogen atom, and $R^2$ represents a phenyl group optionally having one or more groups selected from the group Y;

a compound represented by Formula (1) wherein $R^3$, $R^4$, and $R^5$ each represents a hydrogen atom, and $R^1$ represents a phenyl group optionally having one or more groups selected from the group Y;

a compound represented by Formula (1) wherein $R^3$, $R^4$, and $R^5$ each represents a hydrogen atom, and $R^2$ represents a phenyl group optionally having one or more groups selected from the group Y;

a compound represented by Formula (1) wherein $R^2$, $R^3$, and $R^4$ each represents a hydrogen atom, and $R^1$ represents a phenyl group;

a compound represented by Formula (1) wherein $R^3$, $R^4$, and $R^5$ each represents a hydrogen atom, and $R^1$ represents a phenyl group;

a compound represented by Formula (1) wherein $R^1$, $R^3$, and $R^4$ each represents a hydrogen atom, and $R^2$ represents a phenyl group;

a compound represented by Formula (1) wherein $R^1$, $R^3$, and $R^4$ each represents a hydrogen atom, and $R^2$ represents a 2-chlorophenyl group;

a compound represented by Formula (1) wherein $R^1$, $R^3$, and $R^4$ each represents a hydrogen atom, and $R^2$ represents a 3-chlorophenyl group;

a compound represented by Formula (1) wherein $R^1$, $R^3$, and $R^4$ each represents a hydrogen atom, and $R^2$ represents a 4-chlorophenyl group;

a compound represented by Formula (1) wherein $R^1$, $R^3$, and $R^4$ each represents a hydrogen atom, and $R^2$ represents a 4-trifluoromethylphenyl group;

a compound represented by Formula (1) wherein $R^3$, $R^4$, and $R^5$ each represents a hydrogen atom, and $R^2$ represents a phenyl group;

a compound represented by Formula (1) wherein $R^3$, $R^4$, and $R^5$ each represents a hydrogen atom, and $R^2$ represents a 2-chlorophenyl group;

a compound represented by Formula (1) wherein $R^3$, $R^4$, and $R^5$ each represents a hydrogen atom, and $R^2$ represents a 3-chlorophenyl group;

a compound represented by Formula (1) wherein $R^3$, $R^4$, and $R^5$ each represents a hydrogen atom, and $R^2$ represents a 4-chlorophenyl group;

a compound represented by Formula (1) wherein $R^3$, $R^4$, and $R^5$ each represents a hydrogen atom, and $R^2$ represents a 4-trifluoromethylphenyl group;

a compound represented by Formula (1) wherein $R^2$, $R^3$, $R^4$, and $R^5$ each represents a hydrogen atom;

a compound represented by Formula (1) wherein $R^1$, $R^3$, $R^4$, and $R^5$ each represents a hydrogen atom;

a compound represented by Formula (1) wherein $R^1$, $R^2$, $R^4$, and $R^5$ each represents a hydrogen atom;

a compound represented by Formula (1) wherein $R^1$, $R^2$, $R^3$, and $R^5$ each represents a hydrogen atom;

a compound represented by Formula (1) wherein $R^1$, $R^2$, $R^3$, and $R^4$ each represents a hydrogen atom;

a compound represented by Formula (1) wherein $R^2$, $R^3$, $R^4$, and $R^5$ each represents a hydrogen atom, and $R^1$ represents a phenyl group optionally having one or more groups selected from the group Y;

a compound represented by Formula (1) wherein $R^1$, $R^3$, $R^4$, and $R^5$ each represents a hydrogen atom, and $R^2$ represents a phenyl group optionally having one or more groups selected from the group Y;

a compound represented by Formula (1) wherein $R^1$, $R^2$, $R^4$, and $R^5$ each represents a hydrogen atom, and $R^3$ represents a phenyl group optionally having one or more groups selected from the group Y;

a compound represented by Formula (1) wherein $R^1$, $R^2$, $R^3$, and $R^5$ each represents a hydrogen atom, and $R^4$ represents a phenyl group optionally having one or more groups selected from the group Y;

a compound represented by Formula (1) wherein $R^1$, $R^2$, $R^3$, and $R^4$ each represents a hydrogen atom, and $R^5$ represents a phenyl group optionally having one or more groups selected from the group Y;

a compound represented by Formula (1) wherein $R^2$, $R^3$, $R^4$, and $R^5$ each represents a hydrogen atom, and $R^1$ represents a C1-C4 alkyl group optionally having one or more halogen atoms;

a compound represented by Formula (1) wherein $R^1$, $R^3$, $R^4$, and $R^5$ each represents a hydrogen atom, and $R^2$ represents a C1-C4 alkyl group optionally having one or more halogen atoms;

a compound represented by Formula (1) wherein $R^1$, $R^2$, $R^4$, and $R^5$ each represents a hydrogen atom, and $R^3$ represents a C1-C4 alkyl group optionally having one or more halogen atoms;

a compound represented by Formula (1) wherein $R^1$, $R^2$, $R^3$, and $R^5$ each represents a hydrogen atom, and $R^4$ represents a C1-C4 alkyl group optionally having one or more halogen atoms;

a compound represented by Formula (1) wherein $R^1$, $R^2$, $R^3$, and $R^4$ each represents a hydrogen atom, and $R^5$ represents a C1-C4 alkyl group optionally having one or more halogen atoms;

a compound represented by Formula (1) wherein W represents —$OR^6$;

a compound represented by Formula (1) wherein W represents —$OR^6$, —$ON=CR^7R^8$, or —$SR^9$;

a compound represented by Formula (1) wherein W represents —$NR^7R^{10}$;

a compound represented by Formula (1) wherein W represents —$ON=CR^7R^8$;

a compound represented by Formula (1) wherein W represents —$SR^9$;

a compound represented by Formula (1) wherein W represents —$OR^6$ or —$SR^9$;

a compound represented by Formula (1) wherein W represents —$OR^6$ or —$ON=CR^7R^8$;

a compound represented by Formula (1) wherein W represents —$OR^6$ or —$NR^7R^{10}$;

a compound represented by Formula (1) wherein W represents —$SR^9$ or —$NR^7R^{10}$;

a compound represented by Formula (1) wherein $R^6$ and $R^9$ each represents a C1-C6 alkyl group optionally having one or more groups selected from the group Z, a C3-C6 alkynyl group optionally having one or more groups selected from the group X, a C7-C9 phenylalkyl group optionally having one or more groups selected from the group X, or a phenyl group optionally having one or more groups selected from the group Y;

a compound represented by Formula (1) wherein $R^6$ and $R^9$ each represents a C1-C6 alkyl group optionally having one or more groups selected from the group Z;

a compound represented by Formula (1) wherein $R^6$ and $R^9$ each represents a C1-C6 alkyl group;

a compound represented by Formula (1) wherein W represents —$OR^6$ or —$SR^9$, and $R^6$ and $R^9$ each represents a C1-C6 alkyl group optionally having one or more groups selected from the group Z, a C3-C6 alkynyl group optionally having one or more groups selected from the group X, a C7-C9 phenylalkyl group optionally having one or more groups selected from the group Y, or a phenyl group optionally having one or more groups selected from the group Y;

a compound represented by Formula (1) wherein W represents —$OR^6$ or —$SR^9$, and $R^6$ and $R^9$ each represents a C1-C6 alkyl group optionally having one or more groups selected from the group Z;

a compound represented by Formula (1) wherein W represents —$OR^6$ or —$SR^9$, and $R^6$ and $R^9$ each represents a C1-C6 alkyl group;

a compound represented by Formula (1) wherein W represents —$OR^6$, and $R^6$ represents a C1-C6 alkyl group optionally having one or more groups selected from the group Z, a C3-C6 alkynyl group optionally having one or more groups selected from the group X, a C7-C9 phenylalkyl group optionally having one or more groups selected from the group Y, or a phenyl group optionally having one or more groups selected from the group Y;

a compound represented by Formula (1) wherein W represents —$OR^6$, and $R^6$ represents a C1-C6 alkyl group optionally having one or more groups selected from the group Z;

a compound represented by Formula (1) wherein W represents —$OR^6$, and $R^6$ represents C1-C6 alkyl group;

a compound represented by Formula (1) wherein W represents —$SR^9$, and $R^9$ represents a C1-C6 alkyl group optionally having one or more groups selected from the group Z, or a phenyl group optionally having one or more groups selected from the group Y;

a compound represented by Formula (1) wherein W represents —$SR^9$, and $R^9$ represents a C1-C6 alkyl group optionally having one or more groups selected from the group Z;

a compound represented by Formula (1) wherein W represents —$SR^9$, and $R^9$ represents a C1-C6 alkyl group;

a compound represented by Formula (1) wherein W represents —$NR^7R^{10}$, and $R^7$ represents a hydrogen atom;

a compound represented by Formula (1) wherein W represents —$NR^7R^{10}$, $R^7$ represents a hydrogen atom, and $R^{10}$ represents a hydrogen atom, a cyano group, a C1-C6 alkyl group optionally having one or more groups selected from the group Z, a phenyl group optionally having one or more groups selected from the group Y, a benzyl group wherein a benzene ring portion may have optionally one or more groups selected from the group Y, —OH, or —$NH_2$;

a compound represented by Formula (1) wherein W represents —$NR^7R^{10}$, $R^7$ represents a hydrogen atom, and $R^{10}$ represents a hydrogen atom, a cyano group, a C1-C6 alkyl group optionally having one or more groups selected from the group Z, a phenyl group optionally having one or more groups selected from the group Y, —OH, or —$NH_2$;

a compound represented by Formula (1) wherein W represents —$NR^7R^{10}$, $R^7$ represents a hydrogen atom, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein W represents —$NR^7R^{10}$, $R^7$ represents a hydrogen atom, and $R^{10}$ represents a hydrogen atom or a C1-C6 alkyl group optionally having one or more groups selected from the group Z;

a compound represented by Formula (1) wherein W represents —$NR^7R^{10}$, $R^7$ represents a hydrogen atom, and $R^{10}$ represents a hydrogen atom or a C1-C6 alkyl group;

a compound represented by Formula (1) wherein W represents —$NR^7R^{10}$, and $R^{10}$ represents a hydrogen atom, a cyano group, a C1-C6 alkyl group optionally having one or more groups selected from the group Z, a phenyl group optionally having one or more groups selected from the group Y, —OH, or —$NH_2$;

a compound represented by Formula (1) wherein W represents —$NR^7R^{10}$, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein W represents —$NR^7R^{10}$, and $R^{10}$ represents a hydrogen atom or a C1-C6 alkyl group optionally having one or more groups selected from the group Z;

a compound represented by Formula (1) wherein W represents —$NR^7R^{10}$, and $R^{10}$ represents a hydrogen atom or a C1-C6 alkyl group;

a compound represented by Formula (1) wherein W represents —$NR^7R^{10}$, and $R^{10}$ represents a cyano group, —OH, or —$NH_2$;

a compound represented by Formula (1) wherein W represents —$NR^7R^{10}$, $R^7$ represents a hydrogen atom, and $R^{10}$ represents a cyano group, —OH, or —$NH_2$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, and R$^5$ represents a halogen atom, a nitro group, a C1-C4 alkyl group optionally having one or more halogen atoms, a C2-C6 alkoxycarbonyl group, —NR$^{11}$R$^{12}$, —S(O)$_2$NR$^7$R$^{11}$, —OR$^{14}$, a phenyl group optionally having one or more groups selected from the group Y, or a 5-membered aromatic heterocyclic group optionally having one or more groups selected from the group Y, a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^5$ represents a halogen atom, a C1-C4 alkyl group optionally having one or more halogen atoms, —NR$^{11}$R$^{12}$, —OR$^{14}$, or a phenyl group optionally having one or more groups selected from the group Y;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a halogen atom, a C1-C4 alkyl group optionally having one or more halogen atoms, —OR$^{14}$, or a phenyl group optionally having one or more groups selected from the group Y, R$^{11}$ represents a C1-C3 alkyl group optionally having one or more halogen atoms, R$^{13}$ represents a C1-C3 alkyl group optionally having one or more halogen atoms, and R$^{14}$ represents a C1-C4 alkyl group optionally having one or more groups selected from the group X or a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a halogen atom, a nitro group, a C1-C4 alkyl group optionally having one or more halogen atoms, a C2-C6 alkoxycarbonyl group, —NR$^{11}$R$^{12}$, or —S(O)$_2$NR$^7$R$^{11}$, —OR$^{14}$, a phenyl group optionally having one or more groups selected from the group Y, or a 5-membered aromatic heterocyclic group optionally having one or more groups selected from the group Y, and W represents —OR$^6$ or —SR$^9$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^5$ represents a halogen atom, a C1-C4 alkyl group optionally having one or more halogen atoms, a C2-C6 alkoxycarbonyl group, —NR$^{11}$R$^{12}$, —OR$^{14}$, or a phenyl group optionally having one or more groups selected from the group Y, W represents —OR$^6$ or —SR$^9$, and $R^6$ and $R^9$ each represents a C1-C6 alkyl group optionally having one or more groups selected from the group Z, or a phenyl group optionally having one or more groups selected from the group Y;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^2$ represents a hydrogen atom, a halogen atom, a nitro group, a CL-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^5$ represents a halogen atom, a C1-C4 alkyl group optionally having one or more halogen atoms, a C2-C6 alkoxycarbonyl group, —NR$^{11}$R$^{12}$, —OR$^{14}$, or a phenyl group optionally having one or more groups selected from the group Y, W represents —OR$^6$ or —SR$^9$, and $R^6$ and $R^9$ each represents a C1-C6 alkyl group optionally having one or more groups selected from the group Z;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^5$ represents a halogen atom, a C1-C4 alkyl group optionally having one or more halogen atoms, a C2-C6 alkoxycarbonyl group, —NR$^{11}$R$^{12}$, —OR$^{14}$, or a phenyl group optionally having one or more groups selected from the group Y, W represents —OR$^6$ or —SR$^9$, and $R^6$ and $R^9$ represent a C1-C6 alkyl group;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^5$ represents a halogen atom, a nitro group, a C1-C4 alkyl group optionally having one or more halogen atoms, a C2-C6 alkoxycarbonyl group, —NR$^{11}$R$^{12}$, —S(O)$_2$NR$^7$R$^{11}$, —OR$^{14}$, a phenyl group optionally having one or more groups selected from the group Y, or a 5-membered aromatic heterocyclic group optionally having one or more groups selected from the group Y, W represents —OR$^6$, and $R^6$ represents a C1-C6 alkyl group optionally having one or more groups selected from the group Z;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^5$ represents a halogen atom, a nitro group, a C1-C4 alkyl group optionally having one or more halogen atoms, a C2-C6 alkoxycarbonyl group, $-NR^{11}R^{12}$, $-S(O)_2 NR^7R^{11}$, $-OR^{14}$, a phenyl group optionally having one or more groups selected from the group Y, or a 5-membered aromatic heterocyclic group optionally having one or more groups selected from the group Y, W represents $-OR^6$, and $R^6$ represents a C1-C6 alkyl group;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^5$ represents a halogen atom, a C1-C4 alkyl group optionally having one or more halogen atoms, a C2-C6 alkoxycarbonyl group, $-NR^{11}R^{12}$, $-OR^{14}$, or a phenyl group optionally having one or more groups selected from the group Y, and W represents $-NR^7R^{10}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m{}^{11}$, $R^5$ represents a halogen atom, a C1-C4 alkyl group optionally having one or more halogen atoms, a C2-C6 alkoxycarbonyl group, $-NR^{11}R^{12}$, $-OR^{14}$, or a phenyl group optionally having one or more groups selected from the group Y, W represents $-NR^7R^{10}$, and $R^7$ represents a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^5$ represents a halogen atom, a C1-C4 alkyl group optionally having one or more halogen atoms, a C2-C6 alkoxycarbonyl group, $-NR^{11}R^{12}$, $-OR^{14}$, or a phenyl group optionally having one or more groups selected from the group Y, W represents $-NR^7R^{10}$, $R^7$ represents a hydrogen atom, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein $R^1$ represents a hydrogen atom, a halogen atom, a nitro group, a C1-C alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, R³ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR¹¹R¹², —OR¹¹, or —S(O)$_m$R¹¹, R⁴ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR¹¹R¹², —OR¹¹, or —S(O)$_m$R¹¹, R⁵ represents a halogen atom, a C1-C4 alkyl group optionally having one or more halogen atoms, a C2-C6 alkoxycarbonyl group, —NR¹¹R¹², —OR¹⁴, or a phenyl group optionally having one or more groups selected from the group Y, W represents —NR⁷R¹⁰, R⁷ represents a hydrogen atom, and R¹⁰ represents a hydrogen atom or a C1-C6 alkyl group;

a compound represented by Formula (1) wherein R¹ represents a hydrogen atom, a halogen atom, a nitro group, a C1-C6 alkyl group optionally having one or more groups selected from the group X, a phenyl group optionally having one or more groups selected from the group Y, —OR¹¹, or —S(O)$_m$R¹¹, R² represents a hydrogen atom, a halogen atom, a nitro group, a C1-C6 alkyl group optionally having one or more groups selected from the group X, a phenyl group optionally having one or more groups selected from the group Y, —OR¹³, or —S(O)$_m$R¹³, R³ represents a hydrogen atom, a halogen atom, a nitro group, a C1-C6 alkyl group optionally having one or more groups selected from the group X, a phenyl group optionally having one or more groups selected from the group Y, —OR¹¹, or —S(O)$_m$R¹¹, R⁴ represents a hydrogen atom, a halogen atom, a nitro group, a C1-C6 alkyl group optionally having one or more groups selected from the group X, a phenyl group optionally having one or more groups selected from the group Y, —OR¹¹, or —S(O)$_m$R¹¹, R⁵ represents a halogen atom, a nitro group, a C1-C4 alkyl group optionally having one or more halogen atoms, —NR¹¹R¹², —S(O)₂NR⁷R¹¹, —OR¹⁴, a phenyl group optionally having one or more groups selected from the group Y, or a 5-membered aromatic heterocyclic group optionally having one or more groups selected from the group Y, W represents —OR⁶, and R⁶ represents a C1-C6 alkyl group;

a compound represented by Formula (1) wherein R¹ represents a hydrogen atom, a halogen atom, a nitro group, a C1-C6 alkyl group optionally having one or more groups selected from the group X, a phenyl group optionally having one or more groups selected from the group Y, —OR¹¹, or —S(O)$_m$R¹¹, R² represents a hydrogen atom, a halogen atom, a nitro group, a C1-C6 alkyl group optionally having one or more groups selected from the group X, a phenyl group optionally having one or more groups selected from the group Y, —OR¹³, or —S(O)$_m$R¹³, R³ represents a hydrogen atom, a halogen atom, a nitro group, a C1-C6 alkyl group optionally having one or more groups selected from the group X, a phenyl group optionally having one or more groups selected from the group Y, —OR¹¹, or —S(O)$_m$R¹¹, R⁴ represents a hydrogen atom, a halogen atom, a nitro group, a C1-C6 alkyl group optionally having one or more groups selected from the group X, a phenyl group optionally having one or more groups selected from the group Y, —OR¹¹, or —S(O)$_m$R¹¹, R⁵ represents a halogen atom, a C1-C4 alkyl group optionally having one or more halogen atoms, —NR¹¹R¹², —OR¹⁴, or a phenyl group optionally having one or more groups selected from the group Y, W represents —NR⁷R¹⁰, R⁷ represents a hydrogen atom; and R¹⁰ represents a hydrogen atom or a C1-C6 alkyl group;

a compound represented by Formula (1) wherein R¹ represents a halogen atom, a nitro group, a C1-C6 alkyl group optionally having one or more groups selected from the group X, a phenyl group optionally having one or more groups selected from the group Y, a 5-membered aromatic heterocyclic group optionally having one or more groups selected from the group Y, a C2-C6 alkoxycarbonyl group, —NR¹¹R¹², —OR¹¹, or —S(O)$_m$R¹¹, and R², R³, and R⁴ each represents a hydrogen atom;

a compound represented by Formula (1) wherein R¹, R³, and R⁴ each represents a hydrogen atom, and R² represents a halogen atom, a cyano group, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a C2-C6 alkylcarbonyl group optionally having one or more halogen atoms, a benzoyl group optionally having one or more groups selected from the group Y, a C2-C6 alkoxycarbonyl group, an amino carbonyl group, —NR¹²R¹³, —OR¹³, —S(O)$_m$R¹³, or —SF₅;

a compound represented by Formula (1) wherein R¹, R², and R⁴ represent a hydrogen atom, and R³ represents a halogen atom, a nitro group, a C1-C6 alkyl group optionally having one or more groups selected from the group X, C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a C2-C6 alkoxycarbonyl group, —NR¹¹R¹², —OR¹¹, or —S(O)$_m$R¹¹;

a compound represented by Formula (1) wherein R¹, R², and R³ each represents a hydrogen atom, and R⁴ represents a halogen atom, a nitro group, a C1-C6 alkyl group optionally having one or more groups selected from the group X, a phenyl group optionally having one or more groups selected from the group Y, a C2-C6 alkoxycarbonyl group, —NR¹¹R¹², —OR¹¹, or —S(O)$_m$R¹¹;

a compound represented by Formula (1) wherein R¹ represents a halogen atom, a nitro group, a C1-C6 alkyl group optionally having one or more groups selected from the group X, a phenyl group optionally having one or more groups selected from the group Y, a 5-membered aromatic heterocyclic group optionally having one or more groups selected from the group Y, a C2-C6 alkoxycarbonyl group, —NR¹¹R¹², —OR¹¹, or —S(O)$_m$R¹¹, and R², R³, R⁴, and R⁵ each represents a hydrogen atom;

a compound represented by Formula (1) wherein R¹, R², R⁴, and R⁵ each represents a hydrogen atom, and $R^2$ represents a halogen atom, a cyano group, a nitro group, a C1-C6 alkyl group optionally having one or more groups selected from the group X, a 6-membered aromatic heterocyclic group optionally having one or more groups selected from the group Y, a 5-membered aromatic heterocyclic group optionally having one or more groups selected from the group Y, a C2-C6 alkylcarbonyl group optionally having one or more halogen atoms, a benzoyl group optionally having one or more groups selected from the group Y, a phenyl group optionally having one or more groups selected from the group Y, a C2-C6 alkoxycarbonyl group, an aminocarbonyl group, —$NR^{12}R^{13}$, —$OR^{13}$, —$S(O)_mR^{13}$, or —$SF_5$;

a compound represented by Formula (1) wherein $R^1$, $R^2$, $R^4$, and $R^5$ each represents a hydrogen atom, and $R^3$ represents a halogen atom, a nitro group, a C1-C6 alkyl group optionally having one or more groups selected from the group X, a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, a C2-C6 alkoxycarbonyl group, —$NR^{11}R^{12}$, —$OR^{11}$, or —$S(O)_mR^{11}$;

a compound represented by Formula (1) wherein $R^1$, $R^2$, $R^3$, and $R^5$ each represents a hydrogen atom, and $R^4$ represents a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$;

a compound represented by Formula (1) wherein $R^1$, $R^2$, $R^3$, and $R^4$ each represents a hydrogen atom, and $R^5$ represents a halogen atom, a nitro group, a C1-C4 alkyl group optionally having one or more halogen atoms, a C2-C6 alkoxycarbonyl group, —$NR^{11}R^{12}$, —$OR^{14}$, a phenyl group optionally having one or more groups selected from the group Y, or a 5-membered aromatic heterocyclic group optionally having one or more groups selected from the group Y;

a compound represented by Formula (1) wherein $R^1$, $R^2$, $R^3$, and $R^4$ each represents a hydrogen atom, and $R^5$ represents a C1-C4 alkyl group optionally having one or more halogen atoms, —$NR^{11}R^{12}$, or —$OR^{14}$;

a compound represented by Formula (1) wherein $R^1$, $R^2$, $R^3$, and $R^4$ each represents a hydrogen atom, $R^5$ represents a C1-C4 alkyl group optionally having one or more halogen atoms or —$OR^{14}$, and $R^{14}$ represents a C1-C4 alkyl group optionally having one or more groups selected from the group X, a C7-C9 phenylalkyl group wherein a benzene ring portion may have optionally one or more groups selected from the group Y, a C2-C6 alkylcarbonyl group optionally having one or more halogen atoms, a benzoyl group optionally having one or more groups selected from the group Y, a phenylsulfonyl group optionally having one or more groups selected from the group Y, or a hydrogen atom;

a compound represented by Formula (1) wherein $R^1$, $R^2$, $R^3$, and $R^4$ each represents a hydrogen atom, $R^5$ represents a C1-C4 alkyl group optionally having one or more halogen atoms or —$OR^{14}$, and $R^{14}$ represents a C1-C4 alkyl group optionally having one or more halogen atoms or a hydrogen atom;

a compound represented by Formula (1) wherein $R^1$, $R^2$, $R^3$, and $R^4$ each represents a hydrogen atom, and $R^5$ represents a C1-C4 alkyl group optionally having one or more halogen atoms;

a compound represented by Formula (1) wherein $R^1$, $R^2$, $R^3$, and $R^4$ each represents a hydrogen atom, $R^5$ represents —$OR^{14}$, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^5$ represents a C1-C4 alkyl group optionally having one or more halogen atoms;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{12}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^5$ represents —$OR^{14}$, and $R^{14}$ represents a C1-C4 alkyl group optionally having one or more groups selected from the group X or a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, and R$^5$ represents a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^5$ represents a C1-C4 alkyl group optionally having one or more halogen atoms;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents —OR$^{14}$, and R$^{14}$ represents a C1-C4 alkyl group optionally having one or more groups selected from the group X or a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$ or —S(O)$_m$R$^{11}$, R$^5$ represents a C1-C4 alkyl group optionally having one or more halogen atoms, R$^{11}$ represents a C1-C3 alkyl group optionally having one or more halogen atoms, and R$^{13}$ represents a C1-C3 alkyl group optionally having one or more halogen atoms;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a hydrogen atom, R$^{11}$ represents a C1-C3 alkyl group optionally having one or more halogen atoms, and R$^{13}$ represents a C1-C3 alkyl group optionally having one or more halogen atoms;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, and R$^5$ represents a trifluoromethyl group;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a trifluoromethyl group, W represents —OR$^6$, and R$^6$ represents a C1-C6 alkyl group optionally having one or more groups selected from the group Z;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a trifluoromethyl group, and W represents —NR$^7$R$^{10}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a trifluoromethyl group, W represents —NR$^7$R$^{10}$, R$^7$ represents a hydrogen atom, and R$^{10}$ represents a hydrogen atom, a C1-C6 alkyl group optionally having one or more groups selected from the group Z, or a phenyl group optionally having one or more groups selected from the group Y;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a trifluoromethyl group, and W represents —SR$^9$, R$^9$ represents a C1-C6 alkyl group optionally having one or more groups selected from the group Z;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{11}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^5$ represents a trifluoromethyl group;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a trifluoromethyl group, R$^{11}$ represents a C1-C3 alkyl group optionally having one or more halogen atoms, and R$^{13}$ represents a C1-C3 alkyl group optionally having one or more halogen atoms;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a hydrogen atom, a halogen atom, a nitro group, a methyl group, a trifluoromethyl group, a phenyl group optionally having one or more groups selected from the group Y, —OR$^{13}$, or —S(O)$_m$R$^{13}$, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a trifluoromethyl group, R$^{11}$ represents a methyl group or a trifluoromethyl group, and R$^{13}$ represents a methyl group or a trifluoromethyl group;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a hydrogen atom, a halogen atom, a nitro group, a methyl group, a trifluoromethyl group, a phenyl group optionally having one or more groups selected from the group Y, —OR$^{13}$, or —S(O)$_m$R$^{13}$, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, R$^{11}$ represents a methyl group or a trifluoromethyl group, and R$^{13}$ represents a methyl group or a trifluoromethyl group;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a hydrogen atom, a halogen atom, a nitro group, a methyl group, a trifluoromethyl group, a phenyl group optionally having one or more groups selected from the group Y, —OR$^{13}$, or —S(O)$_m$R$^{13}$, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, $R^5$ represents a trifluoromethyl group,
$R^{11}$ represents a methyl group, and
$R^{13}$ represents a methyl group;

a compound represented by Formula (1) wherein $R^1$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^4$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^5$ represents a hydrogen atom,
$R^{11}$ represents a methyl group, and
$R^{13}$ represents a methyl group;

a compound represented by Formula (1) wherein $R^1$ represents a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^2$, $R^3$, and $R^4$ each represents a hydrogen atom, and $R^5$ represents a halogen atom, a C1-C4 alkyl group optionally having one or more halogen atoms, a C2-C6 alkoxycarbonyl group, —$NR^{11}R^{12}$, —$OR^{11}$, or a phenyl group optionally having one or more groups selected from the group Y;

a compound represented by Formula (1) wherein $R^1$, $R^3$, and $R^4$ each represents a hydrogen atom, $R^2$ represents a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, and $R^5$ represents a halogen atom, a C1-C4 alkyl group optionally having one or more halogen atoms, a C2-C6 alkoxycarbonyl group, —$NR^{11}R^{12}$, —$OR^{14}$, or a phenyl group optionally having one or more groups selected from the group Y;

a compound represented by Formula (1) wherein $R^1$, $R^2$, and $R^4$ each represents a hydrogen atom, $R^3$ represents a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^5$ represents a halogen atom, a C1-C4 alkyl group optionally having one or more halogen atoms, a C2-C6 alkoxycarbonyl group, —$NR^{11}R^{12}$, —$OR^{14}$, or a phenyl group optionally having one or more groups selected from the group Y;

a compound represented by Formula (1) wherein $R^1$, $R^2$, and $R^3$ represent a hydrogen atom, $R^4$ represents a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^5$ represents a halogen atom, a C1-C4 alkyl group optionally having one or more halogen atoms, a C2-C6 alkoxycarbonyl group, —$NR^{11}R^{12}$, —$OR^{14}$, or a phenyl group optionally having one or more groups selected from the group Y;

a compound represented by Formula (1) wherein $R^1$ represents a halogen atom, a C1-C6 alkyl group optionally having one or more groups selected from the group X, a phenyl group optionally having one or more groups selected from the group Y, —$OR^{11}$, or —$S(O)_mR^{11}$, and $R^2$, $R^3$, $R^4$, and $R^5$ each represents a hydrogen atom;

a compound represented by Formula (1) wherein $R^1$, $R^3$, $R^4$, and $R^5$ each represents a hydrogen atom, and $R^2$ represents a halogen atom, a C1-C6 alkyl group optionally having one or more groups selected from the group X, a phenyl group optionally having one or more groups selected from the group Y, —$OR^{13}$, or —$S(O)_mR^{13}$;

a compound represented by Formula (1) wherein $R^1$, $R^2$, $R^4$, and $R^5$ each represents a hydrogen atom, and $R^3$ represents a halogen atom, a C1-C6 alkyl group optionally having one or more groups selected from the group X, a phenyl group optionally having one or more groups selected from the group Y, —$OR^{11}$, or —$S(O)_mR^{11}$;

a compound represented by Formula (1) wherein $R^1$, $R^2$, $R^3$, and $R^5$ each represents a hydrogen atom, and $R^4$ represents a halogen atom, a C1-C6 alkyl group optionally having one or more groups selected from the group X, a phenyl group optionally having one or more groups selected from the group Y, —$OR^{11}$, or —$S(O)_mR^{11}$;

a compound represented by Formula (1) wherein $R^1$ represents a halogen atom, a C1-C6 alkyl group optionally having one or more groups selected from the group X, a phenyl group optionally having one or more groups selected from the group Y, —$OR^{11}$, or —$S(O)_mR^{11}$, $R^2$, $R^3$, and $R^4$ each represents a hydrogen atom, and $R^5$ represents a C1-C4 alkyl group optionally having one or more halogen atoms, —$NR^{11}R^{12}$, or —$OR^{14}$;

a compound represented by Formula (1) wherein $R^1$, $R^3$, and $R^4$ each represents a hydrogen atom, $R^2$ represents a halogen atom, a C1-C6 alkyl group optionally having one or more groups selected from the group X, a phenyl group optionally having one or more groups selected from the group Y, —$OR^{13}$, or —$S(O)_mR^{13}$, and $R^5$ represents a C1-C4 alkyl group optionally having one or more halogen atoms, —$NR^{11}R^{12}$, or —$OR^{14}$;

a compound represented by Formula (1) wherein $R^1$, $R^2$, and $R^4$ each represents a hydrogen atom, $R^3$ represents a halogen atom, a C1-C6 alkyl group optionally having one or more groups selected from the group X, a phenyl group optionally having one or more groups selected from the group Y, —$OR^{11}$, or —$S(O)_mR^{11}$, and $R^5$ represents a C1-C4 alkyl group optionally having one or more halogen atoms, —$NR^{11}R^{12}$, or —$OR^{14}$;

a compound represented by Formula (1) wherein $R^1$, $R^2$, and $R^3$ each represents a hydrogen atom, $R^4$ represents a halogen atom, a C1-C6 alkyl group optionally having one or more groups selected from the group X, a phenyl group optionally having one or more groups selected from the group Y, —$OR^{11}$, or —$S(O)_mR^{11}$, and $R^5$ represents a C1-C4 alkyl group optionally having one or more halogen atoms, —$NR^{11}R^{12}$, or —$OR^{14}$;

a compound represented by Formula (1) wherein $R^1$ represents a halogen atom, and $R^2$, $R^3$, $R^4$, and $R^5$ each represents a hydrogen atom;

a compound represented by Formula (1) wherein $R^1$, $R^3$, $R^4$, and R each represents a hydrogen atom, and $R^2$ represents a halogen atom;

a compound represented by Formula (1) wherein $R^1$, $R^2$, $R^4$, and $R^5$ each represents a hydrogen atom, and $R^3$ represents a halogen atom;

a compound represented by Formula (1) wherein $R^1$, $R^2$, $R^3$, and $R^5$ each represents a hydrogen atom, and $R^4$ represents a halogen atom;

a compound represented by Formula (1) wherein $R^1$ represents a C1-C6 alkyl group optionally having one or more groups selected from the group X, and $R^2$, $R^3$, $R^4$, and $R^5$ each represents a hydrogen atom;

a compound represented by Formula (1) wherein $R^1$, $R^3$, $R^4$, and $R^5$ each represents a hydrogen atom, and $R^2$ represents a C1-C6 alkyl group optionally having one or more groups selected from the group X;

a compound represented by Formula (1) wherein $R^1$, $R^2$, $R^4$, and $R^5$ each represents a hydrogen atom, and $R^3$ represents a C1-C6 alkyl group optionally having one or more groups selected from the group X;

a compound represented by Formula (1) wherein $R^1$, $R^2$, $R^3$, and $R^5$ each represents a hydrogen atom, and $R^4$ represents a C1-C6 alkyl group optionally having one or more groups selected from the group X;

a compound represented by Formula (1) wherein $R^1$ represents a C1-C4 alkyl group optionally having one or more halogen atoms, and $R^2$, $R^3$, $R^4$, and $R^5$ each represents a hydrogen atom;

a compound represented by represented by Formula (1) wherein $R^1$, $R^3$, $R^4$, and $R^5$ each represents a hydrogen atom, and R represents a C1-C4 alkyl group optionally having one or more halogen atoms;

a compound represented by represented by Formula (1) wherein $R^1$, $R^2$, $R^4$, and $R^5$ each represents a hydrogen atom, and $R^3$ represents a C1-C4 alkyl group optionally having one or more halogen atoms;

a compound represented by represented by Formula (1) wherein $R^1$, $R^2$, $R^3$, and $R^5$ each represents a hydrogen atom, and $R^4$ represents a C1-C4 alkyl group optionally having one or more halogen atoms;

a compound represented by Formula (1) wherein $R^1$ represents a trifluoromethyl group, and $R^2$, $R^3$, $R^4$, and $R^5$ each represents a hydrogen atom;

a compound represented by Formula (1) wherein $R^1$ represents a trifluoromethyl group,
$R^2$, $R^3$, $R^4$, and $R^5$ each represents a hydrogen atom,
W represents a —$OR^6$, and
$R^6$ represents a C1-C6 alkyl group optionally having one or more groups selected from the group Z;

a compound represented by Formula (1) wherein $R^1$ represents a trifluoromethyl group,
$R^2$, $R^3$, $R^4$, and $R^5$ each represents a hydrogen atom,
W represents a —$OR^6$, and
$R^6$ represents a C3-C6 alkyl group;

a compound represented by Formula (1) wherein $R^1$ represents a trifluoromethyl group,
$R^2$, $R^3$, $R^4$, and $R^5$ each represents a hydrogen atom, and
W represents —ON=$CR^7R^8$, —$SR^9$, or —$NR^7R^{10}$;

a compound represented by Formula (1) wherein $R^1$ represents a trifluoromethyl group,
$R^2$, $R^3$, $R^4$, and $R^5$ each represents a hydrogen atom, and
W represents —ON=$CR^7R^8$;

a compound represented by Formula (1) wherein $R^1$ represents a trifluoromethyl group,
$R^2$, $R^3$, $R^4$, and $R^5$ each represents a hydrogen atom, and
W represents —$SR^9$;

a compound represented by Formula (1) wherein $R^1$ represents a trifluoromethyl group,
$R^2$, $R^3$, $R^4$, and $R^5$ each represents a hydrogen atom,
W represents —$SR^9$, and
$R^9$ represents a C1-C6 alkyl group optionally having one or more groups selected from the group Z;

a compound represented by Formula (1) wherein $R^1$ represents a trifluoromethyl group,
$R^2$, $R^3$, $R^4$, and $R^5$ each represents a hydrogen atom, and
W represents —$NR^7R^{10}$;

a compound represented by Formula (1) wherein $R^1$ represents a trifluoromethyl group,
$R^2$, $R^3$, $R^4$, and $R^5$ each represents a hydrogen atom,
W represents —$NR^7R^{10}$, $R^7$ represents a hydrogen atom, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein $R^1$, $R^3$, $R^4$, and $R^5$ each represents a hydrogen atom, and $R^2$ represents a trifluoromethyl group;

a compound represented by Formula (1) wherein $R^1$, $R^3$, $R^4$, and $R^5$ each represents a hydrogen atom, $R^2$ represents a trifluoromethyl group, W represents —$OR^6$, and $R^6$ represents a C1-C6 alkyl group optionally having one or more groups selected from the group Z;

a compound represented by Formula (1) wherein $R^1$, $R^3$, $R^4$, and $R^5$ each represents a hydrogen atom, $R^2$ represents a trifluoromethyl group, W represents —$OR^6$, and $R^6$ represents a C3-C6 alkyl group;

a compound represented by Formula (1) wherein $R^1$, $R^3$, $R^4$, and $R^5$ each represents a hydrogen atom, R represents a trifluoromethyl group, and W represents —ON=$CR^7R^8$, —$SR^9$, or —$NR^7R^{10}$;

a compound represented by Formula (1) wherein $R^1$, $R^3$, $R^4$, and $R^5$ each represents a hydrogen atom, $R^2$ represents a trifluoromethyl group, and W represents —ON=$CR^7R^8$;

a compound represented by Formula (1) wherein $R^1$, $R^3$, $R^4$, and $R^5$ each represents a hydrogen atom, $R^2$ represents a trifluoromethyl group, and W represents —$SR^9$;

a compound represented by Formula (1) wherein $R^1$, $R^3$, $R^4$, and $R^5$ each represents a hydrogen atom, $R^2$ represents a trifluoromethyl group, W represents —$SR^9$, and $R^9$ represents a C1-C6 alkyl group optionally having one or more groups selected from the group Z;

a compound represented by Formula (1) wherein $R^1$, $R^3$, $R^4$, and $R^5$ each represents a hydrogen atom, $R^2$ represents a trifluoromethyl group, and W represents —$NR^7R^{10}$;

a compound represented by Formula (1) wherein $R^1$, $R^3$, $R^4$, and $R^5$ each represents a hydrogen atom, $R^2$ represents a trifluoromethyl group, W represents —$NR^7R^{10}$, $R^7$ represents a hydrogen atom, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein $R^1$, $R^2$, $R^4$, and $R^5$ each represents a hydrogen atom, and $R^3$ represents a trifluoromethyl group;

a compound represented by Formula (1) wherein $R^1$, $R^2$, $R^4$, and $R^5$ each represents a hydrogen atom, $R^3$ represents a trifluoromethyl group, W represents —$OR^6$, and $R^6$ represents a CL-C6 alkyl group optionally having one or more groups selected from the group Z;

a compound represented by Formula (1) wherein $R^1$, $R^2$, $R^4$, and $R^5$ each represents a hydrogen atom, $R^3$ represents a trifluoromethyl group, W represents —$OR^6$, and $R^6$ represents a C3-C6 alkyl group;

a compound represented by Formula (1) wherein $R^1$, $R^2$, $R^4$, and $R^5$ each represents a hydrogen atom, $R^3$ represents a trifluoromethyl group, and W represents —$ON=CR^7R^8$, —$SR^9$, or —$NR^7R^{10}$;

a compound represented by Formula (1) wherein $R^1$, $R^2$, $R^4$, and $R^5$ each represents a hydrogen atom, $R^3$ represents a trifluoromethyl group, and W represents —$ON=CR^7R^8$;

a compound represented by Formula (1) wherein $R^1$, $R^2$, $R^4$, and $R^5$ each represents a hydrogen atom, $R^3$ represents a trifluoromethyl group, and W represents —$SR^9$;

a compound represented by Formula (1) wherein $R^1$, $R^2$, $R^4$, and $R^5$ each represents a hydrogen atom, $R^3$ represents a trifluoromethyl group, W represents —$SR^9$, and $R^9$ represents a C1-C6 alkyl group optionally having one or more groups selected from the group Z;

a compound represented by Formula (1) wherein $R^1$, $R^2$, $R^4$, and $R^5$ each represents a hydrogen atom, $R^3$ represents a trifluoromethyl group, and W represents —$NR^7R^{10}$;

a compound represented by Formula (1) wherein $R^1$, $R^2$, $R^1$, and $R^5$ each represents a hydrogen atom, $R^3$ represents a trifluoromethyl group, W represents —$NR^7R^{10}$, $R^7$ represents a hydrogen atom, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein $R^1$, $R^2$, $R^3$, and $R^5$ each represents a hydrogen atom, and $R^4$ represents a trifluoromethyl group;

a compound represented by Formula (1) wherein $R^1$, $R^2$, $R^3$, and $R^5$ each represents a hydrogen atom, $R^4$ represents a trifluoromethyl group, W represents —$OR^6$, and $R^6$ represents a C1-C6 alkyl group optionally having one or more groups selected from the group Z;

a compound represented by Formula (1) wherein $R^1$, $R^2$, $R^3$, and $R^5$ each represents a hydrogen atom, $R^4$ represents a trifluoromethyl group, W represents —$OR^6$, and $R^6$ represents a C3-C6 alkyl group;

a compound represented by Formula (1) wherein $R^1$, $R^2$, $R^3$, and $R^5$ each represents a hydrogen atom, $R^4$ represents a trifluoromethyl group, and W represents —$ON=CR^7R^8$, —$SR^9$, or —$NR^7R^{10}$;

a compound represented by Formula (1) wherein $R^1$, $R^2$, $R^3$, and $R^5$ each represents a hydrogen atom, $R^4$ represents a trifluoromethyl group, and W represents —$ON=CR^7R^8$;

a compound represented by Formula (1) wherein $R^1$, $R^2$, $R^3$, and $R^5$ each represents a hydrogen atom, $R^4$ represents a trifluoromethyl group, and W represents —$SR^9$;

a compound represented by Formula (1) wherein $R^1$, $R^2$, $R^3$, and $R^5$ each represents a hydrogen atom, $R^4$ represents a trifluoromethyl group, W represents —$SR^9$, and $R^9$ represents a C1-C6 alkyl group optionally having one or more groups selected from the group Z;

a compound represented by Formula (1) wherein $R^1$, $R^2$, $R^3$, and $R^5$ each represents a hydrogen atom, $R^4$ represents a trifluoromethyl group, and W represents —$NR^7R^{10}$;

a compound represented by Formula (1) wherein $R^1$, $R^2$, $R^3$, and $R^5$ each represents a hydrogen atom, $R^4$ represents a trifluoromethyl group, W represents —$NR^7R^{10}$, $R^7$ represents a hydrogen atom, and $R^{10}$ represents a C1-C6 alkyl group optionally having one or more groups selected from the group Z, or a phenyl group optionally having one or more groups selected from the group Y;

a compound represented by Formula (1) wherein $R^1$, $R^2$, $R^3$, and $R^4$ represent a hydrogen atom, and $R^5$ represents a trifluoromethyl group;

a compound represented by Formula (1) wherein $R^1$, $R^2$, $R^3$, and $R^4$ each represents a hydrogen atom, $R^5$ represents a trifluoromethyl group, W represents —$OR^6$, and $R^6$ represents a C1-C6 alkyl group optionally having one or more groups selected from the group Z;

a compound represented by Formula (1) wherein $R^1$, $R^2$, $R^3$, and $R^4$ each represents a hydrogen atom, $R^5$ represents a trifluoromethyl group, and W represents —$ON=CR^7R^8$;

a compound represented by Formula (1) wherein $R^1$, $R^2$, $R^3$, and $R^4$ each represents a hydrogen atom, $R^5$ represents a trifluoromethyl group, and W represents —$SR^9$;

a compound represented by Formula (1) wherein $R^1$, $R^2$, $R^3$, and $R^4$ each represents a hydrogen atom, $R^5$ represents a trifluoromethyl group, W represents —$SR^9$, and $R^9$ represents a C1-C6 alkyl group optionally having one or more groups selected from the group Z;

a compound represented by Formula (1) wherein $R^1$, $R^2$, $R^3$, and $R^4$ each represents a hydrogen atom, $R^5$ represents a trifluoromethyl group, and W represents —$NR^7R^{10}$;

a compound represented by Formula (1) wherein $R^1$, $R^2$, $R^3$, and $R^4$ each represents a hydrogen atom, $R^5$ represents a trifluoromethyl group, W represents —$NR^7R^{10}$, and $R^7$ represents a hydrogen atom, and $R^{10}$ represents a C1-C6 alkyl group optionally having one or more groups selected from the group Z, or a phenyl group optionally having one or more groups selected from the group Y;

a compound represented by Formula (1) wherein $R^1$ represents a phenyl group optionally having one or more groups selected from the group Y, and $R^2$, $R^3$, $R^4$, and $R^5$ each represents a hydrogen atom;

a compound represented by Formula (1) wherein $R^1$, $R^3$, $R^4$, and $R^5$ each represents a hydrogen atom, and $R^2$ represents a phenyl group optionally having one or more groups selected from the group Y;

a compound represented by Formula (1) wherein $R^1$, $R^2$, $R^4$, and $R^5$ each represents a hydrogen atom, and $R^3$ represents a phenyl group optionally having one or more groups selected from the group Y;

a compound represented by Formula (1) wherein $R^1$, $R^2$, $R^3$, and R each represents a hydrogen atom, and $R^4$ represents a phenyl group optionally having one or more groups selected from the group Y;

a compound represented by Formula (1) wherein $R^1$ represents —$OR^{11}$, and $R^2$, $R^3$, $R^4$, and $R^5$ each represents a hydrogen atom;

a compound represented by Formula (1) wherein $R^1$, $R^3$, $R^4$, and $R^5$ each represents a hydrogen atom, and $R^2$ represents —$OR^{13}$;

a compound represented by Formula (1) wherein $R^1$, $R^2$, $R^4$, and $R^5$ each represents a hydrogen atom, and $R^3$ represents —$OR^{11}$;

a compound represented by Formula (1) wherein $R^1$, $R^2$, $R^3$, and $R^5$ each represents a hydrogen atom, and $R^4$ represents —$OR^{11}$;

a compound represented by Formula (1) wherein $R^1$ represents —$S(O)_mR^6$, and $R^2$, $R^3$, $R^4$, and $R^5$ each represents a hydrogen atom;

a compound represented by Formula (1) wherein $R^1$, $R^3$, $R^4$, and $R^5$ each represents a hydrogen atom, and $R^2$ represents or —$S(O)_mR^{13}$;

a compound represented by Formula (1) wherein $R^1$, $R^2$, $R^4$, and $R^5$ each represents a hydrogen atom, and $R^3$ represents or —$S(O)_mR^{11}$, a compound represented by Formula (1) wherein $R^1$, $R^2$, $R^3$, and $R^5$ each represents a hydrogen atom, and $R^4$ represents or $-S(O)_m R^{11}$;

a compound represented by Formula (1) wherein $R^1$ represents $-OR^{10}$, $R^2$, $R^3$, $R^4$, and $R^5$ each represents a hydrogen atom, and $R^{11}$ represents a C1-C3 alkyl group optionally having one or more halogen atoms;

a compound represented by Formula (1) wherein $R^1$, $R^3$, $R^4$, and $R^5$ each represents a hydrogen atom, $R^2$ represents $-OR^{13}$, and $R^{13}$ represents a C1-C3 alkyl group optionally having one or more halogen atoms;

a compound represented by Formula (1) wherein $R^1$, $R^2$, $R^4$, and $R^5$ each represents a hydrogen atom, $R^3$ represents $-OR^{11}$, and $R^{11}$ represents a C1-C3 alkyl group optionally having one or more halogen atoms;

a compound represented by Formula (1) wherein $R^1$, $R^2$, $R^3$, and $R^5$ each represents a hydrogen atom, $R^4$ represents $-OR^{11}$, and $R^{11}$ represents a C1-C3 alkyl group optionally having one or more halogen atoms;

a compound represented by Formula (1) wherein $R^1$ represents $-S(O)_m R^{11}$, $R^2$, $R^3$, $R^4$, and $R^5$ each represents a hydrogen atom, and $R^{11}$ represents a C1-C3 alkyl group optionally having one or more halogen atoms;

a compound represented by Formula (1) wherein $R^1$, $R^3$, $R^4$, and $R^5$ each represents a hydrogen atom, $R^2$ represents $-S(O)_m R^{13}$, and $R^{13}$ represents a C1-C3 alkyl group optionally having one or more halogen atoms;

a compound represented by Formula (1) wherein $R^1$, $R^2$, $R^4$, and $R^5$ each represents a hydrogen atom, $R^3$ represents $-S(O)_m R^{11}$, and $R^{11}$ represents a C1-C3 alkyl group optionally having one or more halogen atoms;

a compound represented by Formula (1) wherein $R^1$, $R^2$, $R^3$, and $R^5$ each represents a hydrogen atom, $R^4$ represents $-S(O)_m R^{11}$, and $R^{11}$ represents a C1-C3 alkyl group optionally having one or more halogen atoms;

a compound represented by Formula (1) wherein $R^1$ represents a halogen atom, $R^2$, $R^3$, and $R^4$ each represents a hydrogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^3$, and $R^4$ each represents a hydrogen atom, $R^2$ represents a halogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^4$ each represents a hydrogen atom, $R^3$ represents a halogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^3$ each represents a hydrogen atom, $R^4$ represents a halogen atom, and $R^5$ represents a C1-C4 alkyl group optionally having one or more halogen atoms, $-NR^{11}R^{12}$, or $-OR^{14}$;

a compound represented by Formula (1) wherein $R^1$ represents a C1-C6 alkyl group optionally having one or more groups selected from the group X, $R^2$, $R^3$, and $R^4$ each represents a hydrogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^3$, and $R^4$ each represents a hydrogen atom, $R^2$ represents a C1-C6 alkyl group optionally having one or more groups selected from the group X, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^4$ each represents a hydrogen atom, $R^3$ represents a C1-C6 alkyl group optionally having one or more groups selected from the group X, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^3$ each represents a hydrogen atom, $R^4$ represents a C1-C6 alkyl group optionally having one or more groups selected from the group X, and $R^5$ represents a C1-C4 alkyl group optionally having one or more halogen atoms, $-NR^{11}R^{12}$, or $-OR^{14}$;

a compound represented by Formula (1) wherein $R^1$ represents a C1-C4 alkyl group optionally having one or more halogen atoms, $R^2$, $R^3$, and $R^4$ each represents a hydrogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^3$, and $R^4$ each represents a hydrogen atom, $R^2$ represents a C1-C4 alkyl group optionally having one or more halogen atoms, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^4$ each represents a hydrogen atom, $R^3$ represents a C1-C4 alkyl group optionally having one or more halogen atoms, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^3$ each represents a hydrogen atom, $R^4$ represents a C1-C4 alkyl group optionally having one or more halogen atoms, and $R^5$ represents a C1-C4 alkyl group optionally having one or more halogen atoms, $-NR^{11}R^{12}$, or $-OR^{14}$;

a compound represented by Formula (1) wherein $R^1$ represents a trifluoromethyl group, $R^2$, $R^3$, and $R^4$ each represents a hydrogen atom, and $R^1$ represents a halogen atom, a cyano group, a nitro group, a C1-C4 alkyl group optionally having one or more halogen atoms, a C2-C5 alkoxycarbonyl group, $-NR^{11}R^{12}$, $-S(O)_2NR^7R^{11}$, $-OR^{14}$, or a phenyl group optionally having one or more groups selected from the group Y;

a compound represented by Formula (1) wherein $R^1$, $R^3$, and $R^4$ each represents a hydrogen atom, $R^2$ represents a trifluoromethyl group, and $R^5$ represents a halogen atom, a cyano group, a nitro group, a C1-C4 alkyl group optionally having one or more halogen atoms, a C2-C5 alkoxycarbonyl group, $-NR^{11}R^{12}$, $-S(O)_2NR^7R^{11}$, $-OR^{14}$, or a phenyl group optionally having one or more groups selected from the group Y;

a compound represented by Formula (1) wherein $R^1$, $R^2$, and $R^4$ each represents a hydrogen atom, $R^3$ represents a trifluoromethyl group, and $R^5$ represents a halogen atom, a cyano group, a nitro group, a C1-C4 alkyl group optionally having one or more halogen atoms, a C2-C5 alkoxycarbonyl group, $-NR^{11}R^{12}$, $-S(O)_2NR^7R^{11}$, $-OR^{14}$, or a phenyl group optionally having one or more groups selected from the group Y;

a compound represented by Formula (1) wherein $R^1$, R, and $R^3$ each represents a hydrogen atom, $R^4$ represents a trifluoromethyl group, and $R^5$ represents a halogen atom, a cyano group, a nitro group, a C1-C4 alkyl group optionally having one or more halogen atoms, a C2-C5 alkoxycarbonyl group, $-NR^{11}R^{12}$, $-S(O)_2NR^7R^{11}$, $-OR^{14}$, or a phenyl group optionally having one or more groups selected from the group Y;

a compound represented by Formula (1) wherein $R^1$ represents a trifluoromethyl group, $R^2$, $R^3$, and $R^4$ each represents a hydrogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^3$, and $R^4$ each represents a hydrogen atom, $R^2$ represents a trifluoromethyl group, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^4$ each represents a hydrogen atom, $R^3$ represents a trifluoromethyl group, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^3$ each represents a hydrogen atom, $R^4$ represents a trifluoromethyl group, and $R^5$ represents a C1-C4 alkyl group optionally having one or more halogen atoms, $-NR^{11}R^{12}$, or $-OR^{14}$;

a compound represented by Formula (1) wherein $R^1$ represents a trifluoromethyl group, $R^2$, $R^3$, and $R^4$ each represents a hydrogen atom, $R^5$ represents a C1-C4 alkyl group optionally having one or more halogen atoms or $-OR^{14}$, and $R^{14}$ represents a C1-C4 alkyl group optionally having one or more groups selected from the group X or a hydrogen atom;

a compound represented by Formula (1) wherein $R^1$, $R^3$, and $R^4$ each represents a hydrogen atom, $R^2$ represents a trifluoromethyl group, $R^5$ represents a C1-C4 alkyl group optionally having one or more halogen atoms or $-OR^{14}$, and $R^{14}$ represents a C1-C4 alkyl group optionally having one or more groups selected from the group X or a hydrogen atom;

a compound represented by Formula (1) wherein $R^1$, $R^2$, and $R^4$ each represents a hydrogen atom, $R^3$ represents a trifluoromethyl group, $R^5$ represents a C1-C4 alkyl group optionally having one or more halogen atoms or $-OR^{14}$, and $R^{14}$ represents a C1-C4 alkyl group optionally having one or more groups selected from the group X or a hydrogen atom;

a compound represented by Formula (1) wherein $R^1$, $R^2$, and $R^3$ each represents a hydrogen atom, $R^4$ represents a trifluoromethyl group, $R^5$ represents a C1-C4 alkyl group optionally having one or more halogen atoms or $-OR^{14}$, and $R^{14}$ represents a C1-C4 alkyl group optionally having one or more groups selected from the group X or a hydrogen atom;

a compound represented by Formula (1) wherein $R^1$ represents a trifluoromethyl group, $R^2$, $R^3$, and $R^4$ each represents a hydrogen atom, $R^5$ represents a trifluoromethyl group, $R^5$ represents a C1-C4 alkyl group optionally having one or more halogen atoms or $-OR^{14}$, and $R^{14}$ represents a C1-C4 alkyl group optionally having one or more halogen atoms or a hydrogen atom;

a compound represented by Formula (1) wherein $R^1$, $R^3$, and $R^4$ each represents a hydrogen atom, $R^2$ represents a trifluoromethyl group, $R^5$ represents a C1-C4 alkyl group optionally having one or more halogen atoms or $-OR^{14}$, and $R^{14}$ represents a C1-C4 alkyl group optionally having one or more halogen atoms or a hydrogen atom;

a compound represented by Formula (1) wherein $R^1$, $R^2$, and $R^4$ each represents a hydrogen atom, $R^3$ represents a trifluoromethyl group, $R^5$ represents a C1-C4 alkyl group optionally having one or more halogen atoms or $-OR^{14}$, and $R^{14}$ represents a C1-C4 alkyl group optionally having one or more halogen atoms or a hydrogen atom;

a compound represented by Formula (1) wherein $R^1$, $R^2$, and $R^3$ each represents a hydrogen atom, $R^4$ represents a trifluoromethyl group, $R^5$ represents a C1-C4 alkyl group optionally having one or more halogen atoms or $-OR^{14}$, and $R^{14}$ represents a C1-C4 alkyl group optionally having one or more halogen atoms or a hydrogen atom;

a compound represented by Formula (1) wherein $R^1$ represents a phenyl group optionally having one or more groups selected from the group Y, $R^2$, $R^3$, and $R^4$ each represents a hydrogen atom, and $R^5$ represents a C1-C4 alkyl group optionally having one or more halogen atoms, $-NR^{11}R^{12}$, or $-OR^{14}$;

a compound represented by Formula (1) wherein $R^1$, $R^3$, and $R^4$ each represents a hydrogen atom, $R^2$ represents a phenyl group optionally having one or more groups selected from the group Y, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^4$ each represents a hydrogen atom, $R^3$ represents a phenyl group optionally having one or more groups selected from the group Y, and $R^5$ represents a C1-C4 alkyl group optionally having one or more halogen atoms, $-NR^{11}R^{12}$, or $-OR^{14}$;

a compound represented by Formula (1) wherein $R^1$, $R^2$, and $R^3$ each represents a hydrogen atom, $R^4$ represents a phenyl group optionally having one or more groups selected from the group Y, and $R^5$ represents a C1-C4 alkyl group optionally having one or more halogen atoms, $-NR^1R^{12}$, or $-OR^{14}$;

a compound represented by Formula (1) wherein $R^1$ represents $-OR^{11}$, $R^2$, $R^3$, and $R^4$ each represents a hydrogen atom, $R^5$ represents a C1-C4 alkyl group optionally having one or more halogen atoms, $-NR^{11}R^{12}$, or $-OR^{14}$, and $R^{11}$ represents a C1-C3 alkyl group optionally having one or more halogen atoms;

a compound represented by Formula (1) wherein $R^1$, $R^3$, and $R^4$ each represents a hydrogen atom, $R^2$ represents $-OR^{13}$, $R^5$ represents a C1-C4 alkyl group optionally having one or more halogen atoms, $-NR^{11}R^{12}$, or $-OR^{14}$, and $R^{13}$ represents a C1-C3 alkyl group optionally having one or more halogen atoms;

a compound represented by Formula (1) wherein $R^1$, $R^2$, and $R^4$ each represents a hydrogen atom, $R^3$ represents $-OR^{11}$, $R^5$ represents a C1-C4 alkyl group optionally having one or more halogen atoms, $-NR^{11}R^{12}$, or $-OR^{14}$, and $R^{11}$, represents a C1-C3 alkyl group optionally having one or more halogen atoms;

a compound represented by Formula (1) wherein $R^1$, $R^2$, and $R^3$ each represents a hydrogen atom, $R^4$ represents $-OR^{11}$, $R^5$ represents a C1-C4 alkyl group optionally having one or more halogen atoms, $-NR^{11}R^{12}$, or $-OR^{14}$, and $R^1$ represents a C1-C3 alkyl group optionally having one or more halogen atoms;

a compound represented by Formula (1) wherein $R^1$ represents $-S(O)_mR^{11}$, $R^2$, $R^3$, and $R^4$ each represents a hydrogen atom, $R^5$ represents a C1-C4 alkyl group optionally having one or more halogen atoms, $-NR^{11}R^{12}$, or $-OR^{14}$, and $R^{11}$ represents a C1-C3 alkyl group optionally having one or more halogen atoms;

a compound represented by Formula (1) wherein $R^1$, $R^3$, and $R^4$ each represents a hydrogen atom, $R^2$ represents $-S(O)_mR^{13}$, $R^5$ represents a C1-C4 alkyl group optionally having one or more halogen atoms, $-NR^{11}R^{12}$, or $-OR^{14}$, and $R^{13}$ represents a C1-C3 alkyl group optionally having one or more halogen atoms;

a compound represented by Formula (1) wherein $R^1$, $R^2$, and $R^4$ each represents a hydrogen atom, $R^3$ represents $-S(O)_mR^{11}$, $R^5$ represents a C1-C4 alkyl group optionally having one or more halogen atoms, —NR$^{11}$R$^{12}$, or —OR$^{14}$, and R$^{11}$ represents a C1-C3 alkyl group optionally having one or more halogen atoms;

a compound represented by Formula (1) wherein R$^1$, R$^2$, and R$^3$ each represents a hydrogen atom, R$^1$ represents —S(O)$_m$R$^{11}$, R$^5$ represents a C1-C4 alkyl group optionally having one or more halogen atoms, —NR$^{11}$R$^{12}$, or —OR$^{14}$, and R$^{11}$ represents a C1-C3 alkyl group optionally having one or more halogen atoms;

a compound represented by Formula (1) wherein R$^1$ represents a halogen atom, R$^2$, R$^3$, and R$^4$ each represents a hydrogen atom, R$^5$ represents a C1-C4 alkyl group optionally having one or more halogen atoms or —OR, and R$^{14}$ represents a C1-C4 alkyl group optionally having one or more halogen atoms or a hydrogen atom;

a compound represented by Formula (1) wherein R$^1$, R$^3$, and R$^4$ each represents a hydrogen atom, R$^2$ represents a halogen atom, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (1) wherein R$^1$, R$^2$, and R$^4$ each represents a hydrogen atom, R$^3$ represents a halogen atom, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (1) wherein R$^1$, R$^2$, and R$^3$ each represents a hydrogen atom, R$^4$ represents a halogen atom, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (l) wherein R$^1$ represents a phenyl group optionally having one or more groups selected from the group Y, R$^2$, R$^3$, and R$^4$ each represents a hydrogen atom, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (1) wherein R$^1$, R$^3$, and R$^4$ each represents a hydrogen atom, R$^2$ represents a phenyl group optionally having one or more groups selected from the group Y, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (1) wherein R$^1$, R$^2$, and R$^4$ each represents a hydrogen atom, R$^3$ represents a phenyl group optionally having one or more groups selected from the group Y, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (1) wherein R$^1$, R$^2$, and R$^3$ each represents a hydrogen atom, R$^4$ represents a phenyl group optionally having one or more groups selected from the group Y, R$^5$ represents a C1-C4 alkyl group optionally having one or more halogen atoms or —OR$^{14}$, and R$^{14}$ represents a C1-C4 alkyl group optionally having one or more halogen atoms or a hydrogen atom;

a compound represented by Formula (1) wherein R-represents —OR$^{11}$, R$^2$, R$^3$, and R$^4$ each represents a hydrogen atom, R$^5$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$, R$^3$, and R$^4$ each represents a hydrogen atom, R$^2$ represents —OR$^{13}$, R$^5$ represents a C1-C4 alkyl group optionally having one or more halogen atoms or —OR$^{14}$, R$^{13}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$, R$^2$, and R$^4$ each represents a hydrogen atom, R$^3$ represents —OR, R$^5$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$, R$^2$, and R$^3$ each represents a hydrogen atom, R$^4$ represents —OR$^{11}$, R$^5$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$ represents —S(O)$_m$R$^{11}$, R$^2$, R$^3$, and R$^4$ each represents a hydrogen atom, R$^5$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$, R$^3$, and R$^4$ each represents a hydrogen atom, R$^2$ represents —S(O)$_m$R$^{13}$, R$^5$ represents a C1-C4 alkyl group optionally having one or more halogen atoms or —OR$^{14}$, R$^{13}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$, R$^2$, and R$^4$ each represents a hydrogen atom, R$^3$ represents —S(O)$_m$R$^{11}$, R$^3$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$, R$^2$, and R$^3$ each represents a hydrogen atom, R$^4$ represents —S(O)$_m$R$^{11}$, R$^5$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$ represents a trifluoromethyl group, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^1$ represents a hydrogen atom, a C1-C4 alkyl group, a C1-C4 alkyl group optionally having one or more halogen atoms, or —$OR^{14}$;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^5$ represents a hydrogen atom, a C1-C4 alkyl group, a C1-C4 alkyl group optionally having one or more halogen atoms, or —$OR^{14}$, W represents —$OR^6$, and $R^6$ represents a C1-C6 alkyl group optionally having one or more groups selected from the group Z;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^1$ represents a hydrogen atom, a C1-C4 alkyl group optionally having one or more halogen atoms, or —$OR^{14}$, and W represents —$NR^7R^{10}$;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^1$ represents a hydrogen atom, a C1-C4 alkyl group optionally having one or more halogen atoms, or —$OR^{14}$, W represents —$NR^7R^{10}$, $R^7$ represents a hydrogen atom, and $R^{10}$ represents a hydrogen atom, a C1-C6 alkyl group optionally having one or more groups selected from the group Z or a phenyl group optionally having one or more groups selected from the group Y;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{11}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^1$ represents a hydrogen atom, a C1-C4 alkyl group optionally having one or more halogen atoms, or —$OR^{14}$, W represents —$SR^9$, and $R^9$ represents a C1-C6 alkyl group optionally having one or more groups selected from the group Z;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, and $R^1$ represents a hydrogen atom, a C1-C4 alkyl group optionally having one or more halogen atoms, or —$OR^{14}$;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^5$ represents a hydrogen atom, a C1-C4 alkyl group optionally having one or more halogen atoms, or —$OR^{14}$, $R^{11}$ represents a C1-C3 alkyl group optionally having one or more halogen atoms, $R^{13}$ represents a C1-C3 alkyl group optionally having one or more halogen atoms, and $R^{14}$ represents a C1-C4 alkyl group optionally having one or more halogen atoms or a hydrogen atom;

a compound represented by Formula (1) wherein $R^1$ represents a trifluoromethyl group, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^5$ represents a hydrogen atom, a methyl group, a trifluoromethyl group, or —$OR^{14}$, $R^{11}$ represents a methyl group or a trifluoromethyl group, $R^{13}$ represents a methyl group or a trifluoromethyl group, and $R^{14}$ represents a C1-C4 alkyl group optionally having one or more halogen atoms or a hydrogen atom;

a compound represented by Formula (1) wherein $R^1$ represents a trifluoromethyl group, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^5$ represents a hydrogen atom, a methyl group, a trifluoromethyl group, or —$OR^{14}$, $R^{11}$ represents a methyl group, $R^{13}$ represents a methyl group, and $R^{14}$ represents a C1-C4 alkyl group optionally having one or more halogen atoms or a hydrogen atom;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{12}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, and $R^5$ represents a hydrogen atom;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, and $R^5$ represents a hydrogen atom;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^5$ represents a hydrogen atom, $R^{11}$ represents a C1-C3 alkyl group optionally having one or more halogen atoms, and $R^{13}$ represents a C1-C3 alkyl group optionally having one or more halogen atoms;

a compound represented by Formula (1) wherein $R^1$ represents a trifluoromethyl group, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^5$ represents a hydrogen atom, $R^{11}$ represents a methyl group or a trifluoromethyl group, and $R^{13}$ represents a methyl group or a trifluoromethyl group;

a compound represented by Formula (1) wherein R-represents a trifluoromethyl group, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^5$ represents a hydrogen atom, $R^1$ represents a methyl group, and $R^{13}$ represents a methyl group;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, C2-C6 alkoxycarbonyl group, $-NR^{11}R^{12}$, $-OR^{11}$, or $-S(O)_mR^{11}$, and $R^5$ represents a C1-C4 alkyl group optionally having one or more halogen atoms or $-OR^{14}$;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, and $R^5$ represents a C1-C4 alkyl group optionally having one or more halogen atoms or $-OR^{14}$;

a compound represented by Formula (1) wherein $R^1$ represents a trifluoromethyl group, $R^2$ represents a hydrogen atom, a halogen atom, a nitro group, a C1-C6 alkyl group optionally having one or more groups selected from the group X, a phenyl group optionally having one or more groups selected from the group Y, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, and $R^5$ represents a C1-C4 alkyl group optionally having one or more halogen atoms or $-OR^{14}$, $R^{11}$ represents C1-C3 alkyl group optionally having one or more halogen atoms, $R^{13}$ represents a C1-C3 alkyl group optionally having one or more halogen atoms, and $R^{14}$ represents a C1-C4 alkyl group optionally having one or more halogen atoms or a hydrogen atom;

a compound represented by Formula (1) wherein $R^1$ represents a trifluoromethyl group, $R^2$ represents a hydrogen atom, a halogen atom, a nitro group, a methyl group, a trifluoromethyl group, a phenyl group which may have optionally one or more groups selected from the group Y, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^5$ represents a methyl group, a trifluoromethyl group, or $-OR^{14}$, $R^{11}$ represents a methyl group or a trifluoromethyl group, $R^{13}$ represents a methyl group or a trifluoromethyl group, and $R^{14}$ represents a C1-C4 alkyl group optionally having one or more halogen atoms or a hydrogen atom;

a compound represented by Formula (1) wherein $R^1$ represents a trifluoromethyl group, $R^2$ represents a hydrogen atom, a halogen atom, a nitro group, a methyl group, a trifluoromethyl group, a phenyl group optionally having one or more groups selected from the group Y, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^5$ represents a methyl group, a trifluoromethyl group, or $-OR^{14}$, $R^{11}$ represents a methyl group, $R^{13}$ represents a methyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, $R^2$ represents a trifluoromethyl group, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, and $R^1$ represents a hydrogen atom, a C1-C4 alkyl group optionally having one or more halogen atoms, or $-OR^{14}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a trifluoromethyl group, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, $R^5$ represents a hydrogen atom, a C1-C4 alkyl group optionally having one or more halogen atoms, or $-OR^{14}$, W represents $-OR^6$, and $R^6$ represents a C1-C6 alkyl group optionally having one or more groups selected from the group Z;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a hydrogen atom, a C1-C4 alkyl group optionally having one or more halogen atoms, or —OR$^{14}$, and W represents —NR$^7$R$^{10}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a hydrogen atom, a C1-C4 alkyl group optionally having one or more halogen atoms, or —OR$^{14}$, W represents —NR$^7$R$^{10}$, R$^7$ represents a hydrogen atom, and R$^{10}$ represents a hydrogen atom, a C1-C6 alkyl group optionally having one or more groups selected from the group Z, or a phenyl group optionally having one or more groups selected from the group Y;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a hydrogen atom, a C1-C4 alkyl group which may have optionally one or more halogen atoms, or —OR$^{14}$, W represents —SR$^9$, and R$^3$ represents a C1-C6 alkyl group optionally having one or more groups selected from the group Z;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^7$, or —S(O)$_m$R$^{11}$, and R$^1$ represents a hydrogen atom, a C1-C4 alkyl group optionally having one or more halogen atoms, or —OR$^{14}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a hydrogen atom, a C1-C4 alkyl group optionally having one or more halogen atoms, or —OR$^{14}$, R$^{11}$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, a methyl group, a trifluoromethyl group, or —OR$^{14}$, R$^{11}$ represents a methyl group or a trifluoromethyl group, and R$^{14}$ represents a C1-C4 alkyl group optionally having one or more halogen atoms or a hydrogen atom;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, a methyl group, a trifluoromethyl group, or —OR$^{14}$, R$^{11}$ represents a methyl group, and R$^{14}$ represents a C1-C4 alkyl group optionally having one or more halogen atoms or a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, and R$^5$ represents a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^5$ represents a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a hydrogen atom, and R$^{11}$ represents a C1-C3 alkyl group optionally having one or more halogen atoms;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, and R$^{11}$ represents a methyl group or a trifluoromethyl group;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, and R$^1$ represents a methyl group;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, and R$^5$ represents a C1-C4 alkyl group optionally having one or more halogen atoms or —OR$^{14}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^5$ represents a C1-C4 alkyl group optionally having one or more halogen atoms or —OR$^{14}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a trifluoromethyl group, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a C1-C4 alkyl group optionally having one or more halogen atoms or —OR$^{14}$, R$^{11}$ represents a C1-C3 alkyl group optionally having one or more halogen atoms, and R$^{14}$ represents a C1-C4 alkyl group optionally having one or more halogen atoms;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_m R^{11}$, $R^2$ represents a trifluoromethyl group, $R^3$ represents a hydrogen atom, a halogen atom, a nitro group, a methyl group, a trifluoromethyl group, a phenyl group optionally having one or more groups selected from the group Y, $-OR^{11}$, or $-S(O)_m R^{11}$, $R^4$ represents a hydrogen atom, a halogen atom, a nitro group, a methyl group, a trifluoromethyl group, a phenyl group optionally having one or more groups selected from the group Y, $-OR^{11}$ or $-S(O)_m R^{11}$, $R^5$ represents a methyl group, a trifluoromethyl group, or $-OR^{14}$, $R^{11}$ represents a methyl group or a trifluoromethyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_m R^{11}$, $R^2$ represents a trifluoromethyl group, $R^3$ represents a hydrogen atom, a halogen atom, a nitro group, a methyl group, a trifluoromethyl group, a phenyl group optionally having one or more groups selected from the group Y, $-OR^{11}$, or $-S(O)_m R^{11}$, $R^4$ represents a hydrogen atom, a halogen atom, a nitro group, a methyl group, a trifluoromethyl group, a phenyl group optionally having one or more groups selected from the group Y, $-OR^{11}$, or $-S(O)_m R^{11}$, $R^5$ represents a methyl group, a trifluoromethyl group, or $-OR^{14}$, $R^{11}$ represents a methyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, and $R^5$ represents a hydrogen atom, a C1-C4 alkyl group optionally having one or more halogen atoms, or $-OR^{14}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^5$ represents a hydrogen atom, a C1-C4 alkyl group optionally having one or more halogen atoms, or $-OR^{14}$, W represents $-OR^6$, and $R^6$ represents a C1-C6 alkyl group optionally having one or more groups selected from the group Z;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^2R^{11}$, $-OR^{13}$, or $-S(O)_m R^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^5$ represents a hydrogen atom, a C1-C4 alkyl group optionally having one or more halogen atoms, or $-OR^{14}$, and W represents $-NR^7R^{10}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^5$ represents a hydrogen atom, a C1-C4 alkyl group optionally having one or more halogen atoms, or $-OR^{14}$, W represents $-NR^7R^{10}$, $R^7$ represents a hydrogen atom, and $R^{10}$ represents a hydrogen atom, a C1-C6 alkyl group optionally having one or more groups selected from the group Z, or a phenyl group optionally having one or more groups selected from the group Y;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_m R^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^5$ represents a hydrogen atom, a C1-C4 alkyl group optionally having one or more halogen atoms, or —OR$^{14}$, W represents a —SR$^9$, and R$^9$ represents a C1-C6 alkyl group optionally having one or more groups selected from the group Z;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a trifluoromethyl group, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^1$ represents a hydrogen atom, a C1-C4 alkyl group optionally having one or more halogen atoms, or —OR$^{14}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a trifluoromethyl group, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^9$ represents a hydrogen atom, a C1-C4 alkyl group optionally having one or more halogen atoms, or —OR$^{14}$, R$^6$ represents a C1-C3 alkyl group optionally having one or more halogen atoms, R$^9$ represents a C1-C3 alkyl group optionally having one or more halogen atoms, and R$^{14}$ represents a C1-C4 alkyl group optionally having one or more halogen atoms or a hydrogen atom;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a hydrogen atom, a halogen atom, a nitro group, a methyl group, a trifluoromethyl group, a phenyl group optionally having one or more groups selected from the group Y, —OR$^{13}$, or —S(O)$_m$R$^{13}$, R$^3$ represents a trifluoromethyl group, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, a methyl group, a trifluoromethyl group, or —OR$^{14}$, R$^{11}$ represents a methyl group or a trifluoromethyl group, R$^{13}$ represents a methyl group or a trifluoromethyl group, and R$^{14}$ represents a C1-C4 alkyl group optionally having one or more halogen atoms or a hydrogen atom;

a compound represented by Formula (1) wherein R$^1$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^2$ represents a hydrogen atom, a halogen atom, a nitro group, a methyl group, a trifluoromethyl group, a phenyl group optionally having one or more groups selected from the group Y, —OR$^{13}$, or —S(O)$_m$R$^{13}$, R$^3$ represents a trifluoromethyl group, R$^4$ represents a hydrogen atom, a halogen atom, a nitro group, a methyl group, a trifluoromethyl group, a phenyl group optionally having one or more groups selected from the group Y, —OR$^{11}$, or —S(O)$_m$R$^{11}$, R$^5$ represents a hydrogen atom, a methyl group, a trifluoromethyl group, or —OR$^{14}$, R$^{11}$ represents a methyl group, R$^{13}$ represents a methyl group, and R$^{14}$ represents a C1-C4 alkyl group optionally having one or more halogen atoms or a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a trifluoromethyl group, R$^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, and R$^5$ represents a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a trifluoromethyl group, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, and R$^5$ represents a hydrogen atom;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a trifluoromethyl group, R$^4$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^5$ represents a hydrogen atom, R$^{11}$ represents a C1-C3 alkyl group optionally having one or more halogen atoms, and $R^{13}$ represents a C1-C3 alkyl group optionally having one or more halogen atoms;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^2$ represents a hydrogen atom, a halogen atom, a nitro group, a methyl group, a trifluoromethyl group, a phenyl group optionally having one or more groups selected from the group Y, $-OR^{13}$, or $-S(O)_mR^{13}$, $R^3$ represents a trifluoromethyl group, $R^4$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^5$ represents a hydrogen atom, $R^1$ represents a methyl group or a trifluoromethyl group, and $R^{13}$ represents a methyl group or a trifluoromethyl group;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^2$ represents a hydrogen atom, a halogen atom, a nitro group, a methyl group, a trifluoromethyl group, a phenyl group optionally having one or more groups selected from the group Y, $-OR^{13}$, or $-S(O)_mR^{13}$, $R^3$ represents a trifluoromethyl group, $R^4$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^5$ represents a hydrogen atom, $R^{11}$ represents a methyl group, and $R^{13}$ represents a methyl group;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_mR^{13}$, R represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, and $R^5$ represents a C1-C4 alkyl group optionally having one or more halogen atoms or $-OR^{14}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, $-OR^{13}$, or $-S(O)_mR^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, and $R^5$ represents a C1-C4 alkyl group optionally having one or more halogen atoms or $-OR^{14}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, $-OR^{13}$, or $-S(O)_mR^{13}$, $R^3$ represents a trifluoromethyl group, $R^4$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^5$ represents a C1-C4 alkyl group optionally having one or more halogen atoms or $-OR^{14}$, $R^{11}$ represents a C1-C3 alkyl group optionally having one or more halogen atoms, $R^{13}$ represents a C1-C3 alkyl group optionally having one or more halogen atoms, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^2$ represents a hydrogen atom, a halogen atom, a nitro group, methyl group, a trifluoromethyl group, a phenyl group optionally having one or more groups selected from the group Y, $-OR^{13}$, or $-S(O)_mR^{13}$, $R^3$ represents a trifluoromethyl group, $R^4$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^5$ represents a methyl group, a trifluoromethyl group, or $-OR^{14}$, $R^{11}$ represents a methyl group or a trifluoromethyl group, $R^{13}$ represents a methyl group or a trifluoromethyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^2$ represents a hydrogen atom, a halogen atom, a nitro group, methyl group, a trifluoromethyl group, a phenyl group which may have optionally one or more groups selected from the group Y, $-OR^{13}$, or $-S(O)_mR^{13}$, $R^3$ represents a trifluoromethyl group, $R^4$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^5$ represents a methyl group, a trifluoromethyl group, or $-OR^{14}$, R represents a methyl group, $R^{13}$ represents a methyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_m R^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a trifluoromethyl group, and R$^1$ represents a hydrogen atom, a C1-C4 alkyl group optionally having one or more halogen atoms or —OR$^{14}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a trifluoromethyl group, R$^5$ represents a hydrogen atom, a C1-C4 alkyl group optionally having one or more halogen atoms or —OR$^{14}$, W represents —OR$^6$, and R$^6$ represents a C1-C6 alkyl group optionally having one or more groups selected from the group Z;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a trifluoromethyl group, R$^5$ represents a hydrogen atom, a C1-C4 alkyl group optionally having one or more halogen atoms or —OR$^{14}$, and W represents —NR$^7$R$^{10}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{13}$, —OR$^{11}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a trifluoromethyl group, R$^5$ represents a hydrogen atom, a C1-C4 alkyl group optionally having one or more halogen atoms or —OR$^{14}$, R$^7$ represents a hydrogen atom, and R$^{13}$ represents a hydrogen atom, a C1-C6 alkyl group optionally having one or more groups selected from the group Z, or a phenyl group optionally having one or more groups selected from the group Y;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{12}$R$^{13}$, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —NR$^{11}$R$^{12}$, —OR$^{11}$, or —S(O)$_m$R$^{11}$, R$^4$ represents a trifluoromethyl group, R$^5$ represents a hydrogen atom, a C1-C4 alkyl group optionally having one or more halogen atoms or —OR$^{14}$, W represents —SR$^9$, and R$^9$ represents a C1-C6 alkyl group optionally having one or more groups selected from the group Z;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group which may have optionally one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a trifluoromethyl group, and R$^1$ represents a hydrogen atom, a C1-C4 alkyl group optionally having one or more halogen atoms, or —OR$^{14}$;

a compound represented by Formula (1) wherein R$^1$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^2$ represents a hydrogen atom, a halogen atom, a nitro group, a C1-C6 alkyl group optionally having one or more groups selected from the group X, a phenyl group optionally having one or more groups selected from the group Y, —OR$^{13}$, or —S(O)$_m$R$^{13}$, R$^3$ represents a hydrogen atom, a halogen atom, a nitro group, a C1-C6 alkyl group optionally having one or more groups selected from the group X, a phenyl group optionally having one or more groups selected from the group Y, —OR$^{11}$, or —S(O)$_m$R$^{11}$, R$^4$ represents a trifluoromethyl group, R$^5$ represents a hydrogen atom, a C1-C4 alkyl group optionally having one or more halogen atoms, or —OR$^{14}$, R$^{11}$ represents a C1-C3 alkyl group optionally having one or more halogen atoms, $R^{13}$ represents a C1-C3 alkyl group optionally having one or more halogen atoms, and $R^4$ represents a C1-C4 alkyl group optionally having one or more halogen atoms or a hydrogen atom;

a compound represented by Formula (1) wherein $R^1$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^4$ represents a trifluoromethyl group, $R^3$ represents a hydrogen atom, a methyl group, a trifluoromethyl group, or —$OR^{14}$, $R^{11}$ represents a methyl group or a trifluoromethyl group, $R^{13}$ represents a methyl group or a trifluoromethyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^4$ represents a trifluoromethyl group, $R^5$ represents a hydrogen atom, a methyl group, a trifluoromethyl group, or —$OR^{14}$, $R^{11}$ represents a methyl group, $R^{13}$ represents a methyl group, and $R^{14}$ represents a C1-C4 alkyl group optionally having one or more halogen atoms or a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{13}$, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^4$ represents a trifluoromethyl group, and $R^5$ represents a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^2$ represents a hydrogen atom, a nitro group, a C1-C6 alkyl group optionally having one or more groups selected from the group X, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a trifluoromethyl group, and R=represents a hydrogen atom;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, —$OR^{13}$, or —$S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, —$OR^{11}$, or —$S(O)_mR^{11}$, $R^4$ represents a trifluoromethyl group, $R^5$ represents a hydrogen atom, $R^{11}$ represents a C1-C3 alkyl group optionally having one or more halogen atoms, and $R^{13}$ represents a C1-C3 alkyl group optionally having one or more halogen atoms;

a compound represented by Formula (1) wherein $R^1$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^4$ represents a trifluoromethyl group, $R^5$ represents a hydrogen atom, $R^{11}$ represents a methyl group or a trifluoromethyl group, and $R^{13}$ represents a methyl group or a trifluoromethyl group;

a compound represented by Formula (1) wherein $R^1$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^2$ represents a hydrogen atom, a halogen atom, a nitro group, a methyl group, a trifluoromethyl group, a phenyl group optionally having one or more groups selected from the group Y, —$OR^{13}$, or —$S(O)_mR^{13}$, $R^3$ represents a hydrogen atom, a halogen atom, a nitro group, a methyl group, a trifluoromethyl group, a phenyl group optionally having one or more groups selected from the group Y, —$OR^{11}$, or —$S(O)_mR^{11}$, $R^1$ represents a trifluoromethyl group, $R^5$ represents a hydrogen atom, $R^{11}$ represents a methyl group, and $R^{13}$ represents a methyl group;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, —$NR^{11}R^{12}$, —$OR^{11}$, or —$S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{12}R^{13}$, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, a C2-C6 alkoxycarbonyl group, $-NR^{11}R^{12}$, $-OR^{11}$, or $-S(O)_mR^{11}$, $R^4$ represents a trifluoromethyl group, and $R^5$ represents a C1-C4 alkyl group optionally having one or more halogen atoms or $-OR^{11}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, $-OR^{13}$, or $-S(O)_mR^{11}$, $R^3$ represents a hydrogen atom, a halogen atom, a nitro group, a C1-C6 alkyl group optionally having one or more groups selected from the group X, a phenyl group optionally having one or more groups selected from the group Y, $-OR^7$, or $-S(O)_mR^{11}$, $R^4$ represents a trifluoromethyl group, and $R^5$ represents a C1-C4 alkyl group optionally having one or more halogen atoms or $-OR^{14}$;

a compound represented by Formula (1) wherein $R^1$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^2$ represents a hydrogen atom, a halogen atom, a nitro group, a C1-C6 alkyl group optionally having one or more groups selected from the group X, a phenyl group optionally having one or more groups selected from the group Y, $-OR^{13}$, or $-S(O)_mR^{13}$, $R^3$ represents a hydrogen atom, a halogen atom, a nitro group, a C1-C6 alkyl group optionally having one or more groups selected from the group X, a phenyl group optionally having one or more groups selected from the group Y, $-OR^{11}$, or $-S(O)_mR^{11}$, $R^4$ represents a trifluoromethyl group, R represents a C1-C4 alkyl group optionally having one or more halogen atoms or $-OR^{14}$, $R^{11}$ represents a C1-C3 alkyl group optionally having one or more halogen atoms, $R^{13}$ represents a C1-C3 alkyl group optionally having one or more halogen atoms, and $R^{14}$ represents a C1-C4 alkyl group optionally having one or more halogen atoms, or a hydrogen atom;

a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^2$, represents a hydrogen atom, a halogen atom, a nitro group, a methyl group, a trifluoromethyl group, a phenyl group optionally having one or more groups selected from the group Y, $-OR^{13}$, or $-S(O)_mR^{13}$, $R^3$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^4$ represents a trifluoromethyl group, $R^5$ represents a methyl group, a trifluoromethyl group, or $-OR^{14}$, $R^{11}$ represents a methyl group or a trifluoromethyl group, $R^{13}$ represents a methyl group or a trifluoromethyl group, and $R^{14}$ represents a C1-C4 alkyl group optionally having one or more halogen atoms or a hydrogen atom a compound represented by Formula (1) wherein $R^1$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^2$ represents a hydrogen atom, a halogen atom, a nitro group, a methyl group, a trifluoromethyl group, a phenyl group optionally having one or more groups selected from the group Y, $-OR^{13}$, or $-S(O)_mR^{13}$, $R^3$ represents a hydrogen atom, a halogen atom, a nitro group, a methyl group, a trifluoromethyl group, a phenyl group optionally having one or more groups selected from the group Y, $-OR^{11}$, or $-S(O)_mR^{11}$, $R^4$ represents a trifluoromethyl group, $R^5$ represents a methyl group, a trifluoromethyl group, or $-OR^{14}$, $R^{11}$ represents a methyl group, $R^{13}$ represents a methyl group, and $R^{14}$ represents a C1-C4 alkyl group optionally having one or more halogen atoms or a hydrogen atom.

When the compound of the present invention is used in the method of the present invention, the compound of the present invention may be used alone. However, as described below, the compound may be used as a composition for promoting plant growth that is formulated using various inactive ingredients (solid carriers, liquid carriers, surfactants, other adjuvant for formulation, and the like).

Examples of the solid carriers used for formulation include fine powdery or granular materials and the like that formed of minerals such as kaolin clay, attapulgite clay, bentonite, montmorillonite, Japanese acid clay, pyrophyllite, talc, diatomaceous earth, and calcite, natural organic substances such as corn rachis powder and walnut shell powder, synthetic organic substances such as urea, salts such as calcium carbonate and ammonium sulfate, or synthetic inorganic substances such as synthetic hydrous silicon oxide. Examples of the liquid carriers include aromatic hydrocarbons such as xylene, alkylbenzene, and methylnaphthalene, alcohols such as 2-propanol, ethylene glycol, propylene glycol, and ethylene glycol monoethyl ether, ketones such as acetone, cyclohexanone, and isophorone, plant oil such as soybean oil and cotton seed oil, petroleum-based aliphatic hydrocarbons, esters, dimethylsulfoxide, acetonitrile, water, and the like.

Examples of the surfactants include anionic surfactants such as an alkyl sulfuric acid ester salt, an alkyl aryl sulfonic acid salt, a dialkyl sulfosuccinic acid salt, a polyoxyethylene alkyl aryl ether phosphoric acid ester salt, lignin sulfonic acid salt, and a naphthalene sulfonate formaldehyde polycondensate, nonionic surfactants such as polyoxyethylene alkyl aryl ether, a polyoxyethylene alkyl polyoxypropylene block copolymer, and a sorbitan aliphatic ester, and cationic surfactants such as an alkyl trimethyl ammonium salt.

Examples of other adjuvants for formulation include water-soluble polymers such as polyvinyl alcohol and polyvinyl pyrrolidone, gum Arabic, alginic acid and a salt thereof, polysaccharides such as carboxymethylcellulose (CMC) and xanthan gum, inorganic substances such as aluminum magnesium silicate and alumina sol, preservatives, colorants, and stabilizing agents such as isopropyl acid phosphate (PAP) and BHT.

In the method of the present invention, when a plant is treated with the compound of the present invention, the plant or the plantation thereof is treated with the compound of the present invention at an effective dose. When the plant or the plantation of the plant is treated, it is treated once or plural times with the compound of the present invention.

Specific examples of the application method of the present invention include treating of the foliage, flower organs, or ear of a plant by means of spraying the compound to the foliage, soil (plantation) treatment that is performed before or after a plant is planted, seed treatment such as seed sterilization, seed soaking, or seed coating, seedling treatment, treating of a bulb such as a seed tuber, and the like.

In the method of the present invention, examples of the treating of the foliage, flower organs, or ears of a plant include a treatment method by applying the compound onto the surface of a plant by means of spraying the compound to foliage, stem, and the like. The examples also include a method of performing spraying treatment on flower organs or the entire plant during the flowering period including a pre-flowering stage, a mid-flowering stage, and a post-flowering stage. Moreover, for grain and the like, the examples include a spraying method performed on the ears or the entire plant during the period of ear emergence.

Examples of the soil treatment method in the method of the present invention include spraying to soil, soil incorporation, and drenching soil with liquid chemical (liquid chemical irrigation, soil injection, or liquid chemical dripping). Examples of the place to be treated include planting holes, planting rows, the vicinity of planting holes, the vicinity of planting rows, the entire area of plantation, the vicinity of plantation, inter-row spaces, places under the stem, a ridge between main stems, culture soil, a seedling box, a seedling tray, a seedbed, and the like. The treatment is performed, for example, during a pre-seeding stage, a seeding stage, a stage immediately after seeding, and during the growing period including a seedling raising stage, a pre-planting stage, at a planting stage, and the post-planting stage. Further, in the soil treatment, a plant may be treated with plural kinds of compounds of the present invention at the same time, and a solid fertilizer such as a paste fertilizer containing the compound of the present invention may be applied to the soil. Moreover, the compound of the present invention may be mixed into a liquid for irrigation by means of, for example, by being injected into irrigation facilities (an irrigation tube, an irrigation pipe, a sprinkler, and the like), mixed into a liquid for inter-row space irrigation, or mixed into a hydroponic medium. In addition, the compound of the present invention may be mixed with the liquid for irrigation in advance to perform the treatment by means of, for example, the above irrigation method or other appropriate irrigation methods such as spraying of water and flooding.

In the present invention, the plant seed treated with the compound of the present invention retains the compound of the present invention at an effective dose, in the inside or surface of the plant seed or in the coated portion formed in the circumference of the plant seed. In the method of the present invention, the treating of seeds is a method of treating seeds or bulbs of a plant as a target with the compound of the present invention. Specific examples thereof include spraying treatment in which a suspension of the compound of the present invention is sprayed onto the seed surface or the bulb surface in the form of mist, smearing treatment in which wettable powder, an emulsion, or a flowable agent of the compound of the present invention is used as is or used by being supplemented with a small amount of water so as to coat the seed or bulb, a soaking treatment in which the seeds are soaked into the solution of the present compound for a certain time, film coating treatment, pellet coating treatment, and the like. Moreover, in the present invention, the plant seeds treated with the compound of the present invention are seeds of a plant that have not yet been seeded to soil or a culture medium.

In the method of the present invention, examples of the seedling treatment include spraying treatment in which the compound of the present invention is prepared by being diluted with water to yield an appropriate concentration of active ingredients, and the diluted solution is sprayed to the entire seedling, soaking treatment in which the seedling is soaked into the diluted solution, coating treatment in which the compound of the present invention that is prepared as a dust formulation is applied to the entire seedling, and seedling-growing box treatment in which the culture soil that is being used to raise seedling is treated with the compound of the present invention at an effective dose. Moreover, examples of the soil treatment performed before or after seedlings are planted include a method in which a diluted solution, which is prepared by diluting the compound of the present invention with water to yield an appropriate concentration of active ingredients, is sprayed to the seedlings or the surrounding soil after the seedlings are planted, and a method in which the compound of the present invention that is prepared as granules or a solid formulation such as granules is sprayed to the surrounding soil after the seedlings are planted.

Further, the compound of the present invention may be used by being mixed with a hydroponic medium in hydroponic culture, or used as one of medium components in tissue culture. Regarding hydroponic treatment method in the method of the present invention, when the compound is used for hydroponic culture, the compound may be used by being dissolved or suspended in a hydroponic medium for hydroponic culture that is generally used for a horticultural experiment and the like, within a range of a concentration thereof in the medium of 0.001 ppm to 1,000 ppm. Moreover, when the compound is used for tissue culture or cell culture, the compound may be used by being dissolved or suspended in a generally used medium for plant tissue culture, such as Murashige & Scoog medium, or a hydroponic medium such as Hoagland hydroponic culture solution, within a range of a concentration thereof in the medium of 0.001 ppm to 1,000 ppm. In this case, saccharides as a carbon source, various plant hormones, and the like may be appropriately added according to the conventional method.

When the compound of the present invention is used to treat a plant or a place where the plant grows, the amount of the compound used for the treatment varies with the type of plant to be treated, the form of formulation, the time of treatment, weather conditions, and the like. However, the amount is generally within a range of 0.1 g to 10,000 g and preferably within a range of 1 g to 1,000 g, in terms of the amount of active ingredients per 10,000 $m^2$. When the compound is mixed with the entire soil, the amount of the compound used for the treatment is generally 0.1 g to 10,000 g and preferably 1 g to 1,000 g, in terms of the amount of active ingredients per 10,000 $m^2$.

The emulsion, wettable powder, flowable agent, microcapsules, and the like are used for the treatment generally by being diluted with water and sprayed. In this case, the concentration of active ingredients is generally within a range of 0.1 ppm to 10,000 ppm, and preferably within a range of 1 ppm to 1,000 ppm. Powder, granules, and the like are generally used as they are without being diluted.

During the seed treatment, a weight of the compound of the present invention per 100 Kg of seeds is generally within a range of 0.01 g to 1,000 g and preferably within a range of 0.1 g to 100 g.

Examples of plants to which the method of the present invention is applicable include the following.

Crops: corn, rice, wheat, barley, rye, oat, sorghum, cotton, soybean, peanut, buckwheat, sugar beet, colza, sunflower, sugar cane, tobacco, hop, and the like Vegetables: vegetables from Solanaceae family (eggplant, tomato, potato, pepper, bell pepper, and the like), vegetables from Cucurbitaceous family (cucumber, squash, zucchini, watermelon, melon, oriental melon, and the like), vegetables from Cruciferous family (radish, turnip, horseradish, kohlrabi, napa cabbage, cabbage, rape, mustard, broccoli, cauliflower, and the like), vegetables from Compositae family (burdock, edible chrysanthemum, artichoke, lettuce, and the like), vegetables from Liliceae family (green onion, onion, garlic, asparagus, and the like), vegetables from Apiaceae family (carrot, parsley, celery, parsnip, and the like), vegetables from Chenopodiaceae family (spinach, chard, and the like), vegetables from Lamiaceae family (Japanese basil, mint, basil, and the like), crops from Laguminosae family (pea, common bean, azuki bean, broad bean, chickpea, and the like), strawberry, sweet potato, Japanese yam, taro, konjac, ginger, okra, and the like Fruit trees: pomaceous fruits (apple, pear, European pear, Chinese quince, quince, and the like), stone fruits (peach, plum, nectarine, Japanese apricot, cherry, apricot, prune, and the like), citrus (Citrus unshiu, orange, lemon, lime, grapefruit, and the like), nuts (chestnut, walnut, hazelnut, almond, pistachio, cashew nut, macadamia nut, and the like), berries (blueberry, cranberry, blackberry, raspberry, and the like), grape, persimmon, olive, loquat, banana, coffee, date, coconut, oil palm, and the like Trees other than fruit trees: tea, a mulberry tree, flowering trees (chive, camellia, hydrangea, sasanqua, Japanese star anise, cherry, tulip tree, crape myrtle, fragrant olive, and the like), roadside trees (ash, birch, dogwood, eucalyptus, gingko, lilac, maple, oak, poplar, cercis, liquidambar, plane, Japanese zelkova, Japanese arborvitae, fir, southern Japanese hemlock, juniper, pine, spruce, yew, elm, buckeye, and the like), sweet viburnum, yew plum pine, Japanese cedar, Japanese cypress, croton, Japanese spindle tree, Japanese photinia, and the like Lawn: grasses (zoysia grass, Zoysia Matrella, and the like), bermuda grasses (Cynodon Dactylon, and the like), bentgrasses (wood medowgrass, creeping bentgrass, colonial bent, and the like), bluegrasses (Kentucky bluegrass, Poa compressa, and the like), fescues (fescue grass, *Festuca rubra*, and the like), ryegrasses (*Lolium multiporum* Lam, *Lolium pererne*, and the like), orchardgrass, timothy grass, and the like Others: flowers and ornamental plants (rose, carnation, chrysanthemum, Russell prairie gentian, gypsophila, gerbera, marigold, salvia, petunia, verbena, tulip, aster, gentian, lily, pansy, cyclamen, orchid, lily of valley, lavender, stock, ornamental cabbage, primula, poinsettia, gladiolus, cattleya, daisy, cymbidium, begonia, and the like), biofuel plants (jatropha, safflower, camelinas, switchgrass, miscanthus, reed canarygrass, Arundo donax, Ambry hemp, cassava, withy, and the like), foliage plants, and the like Examples of plants applicable to the present invention preferably include tea, apple, pear, grape, cherry, peach, nectarine, persimmon, Japanese apricot, plum, soybean, lettuce, cabbage, tomato, eggplant, cucumber, watermelon, melon, common bean, peas, azuki bean, grasses, colza, strawberry, almond, corn, sorghum, broad beans, napa, potato, peanut, rice, wheat, taro, konjac, Japanese yam, radish, turnip, parsley, oriental melon, okra, ginger, lemon, orange, grapefruit, lime, blueberry, chestnut, hop, basil, more preferably include plants from the Poaceae family or plants from the Solanaceae family, even more preferably include plants from the Poaceae family, and still more preferably include rice, wheat, corn, and the like.

The above "plant" may be a plant into which a gene which imparts herbicide resistance to a plant, a gene which selectively produces toxicity for harmful insects, a gene which imparts disease resistance to a plant, a gene which relieve abiotic stress, and the like have been introduced by gene recombination or cross-breeding, or may be a stacked GM plant composed of plural kinds of combinations of these.

The compound of the present invention may be used simultaneously with an insecticide, a fungicide, or a safener for a certain herbicide to treat seeds, or may be applied to the plant simultaneously with the above agents.

In the method of the present invention, the plant to be treated with the compound of the present invention may be a plant that has been or will be exposed to abiotic stress. The degree of the abiotic stress that is indicated by the value of "stress intensity" described in the following formula may be 105 to 200, preferably 110 to 180, and more preferably 120 to 160.

Formula (1): "stress intensity"=100×"one of the plant phenotypes in a plant that has not yet been exposed to abiotic stress conditions"/"one of the plant phenotypes in the above plant that has been exposed to abiotic stress conditions"

The term "abiotic stress" as used herein means the stress that causes a decline in physiological functions of cells of a plant, when the plant is exposed to an abiotic stress condition, and then deterioration in the physiological state of the plant, leading to its growth inhibition, such as temperature stress, i.e. high-temperature stress or low-temperature stress, water stress, i.e. drought stress or excess water stress, and salt stress. The high-temperature stress refers to the stress that a plant suffers from when the plant is exposed to a temperature higher than the temperature appropriate for the growth or germination of the plant. Specifically, for example, this type of stress may be caused when an average cultivation temperature of the environment in which a plant is cultured is under condition of 25° C. or higher, more strictly 30° C. or higher, and even more strictly 35° C. or higher. The low-temperature stress refers to the stress that a plant suffers from when the plant is exposed to a temperature lower than the temperature appropriate for the growth or germination of the plant. Specifically, for example, this type of stress may be caused when an average cultivation temperature of the environment in which a plant is cultured is under condition of 15° C. or lower, more strictly 10° C. or lower, and even more strictly 5° C. or lower. Moreover, the drought stress refers to the stress that a plant suffers from when the water content in soil is reduced by the decrease in precipitation or watering amount, water absorption of the plant is hindered, and the plant is exposed to a water environment that may hinder the growth of the plant. Specifically, for example, this type of stress may be caused when a moisture content of soil in which the plant is cultured is under the condition of 15% by weight or less, more strictly 10% by weight or less, and even more strictly 7.5% by weight or less which may causes water stress, or a pF value of soil in which the plant is cultured is under the condition of 2.3 or higher, strictly 2.7 or higher, and even more strictly 3.0 or higher, though these values may vary with the type of soil. The excess water stress refers to the stress that a plant suffers from when the plant is exposed to a water environment in which a water content in the soil becomes excessive, and the growth of the plant may be hindered. The excess water stress refers to the stress that a plant suffers from when a water content in the soil becomes excessive, and the growth of the plant may be hindered. Specifically, for example, this type of stress may be caused when a moisture content of the soil in which the plant is cultured is under the condition of 30% by weight or more, more strictly 40% by weight or more, and even more strictly 50% by weight or more, or a pF value of the soil in which the plant is cultured is under the condition of 1.7 or less, strictly 1.0 or less, and even more strictly 0.3 or less, though these values may vary with the type of soil. Further, the pF value of soil may be measured according to the principle described in "Dictionary of Soil-Plant Nutrition•Environment" (TAIYOSHA, CO., LTD., 1994, Matsusaka et al.), pp 61-62, "pF value measurement method". In addition, the salt stress refers to the stress that a plant suffers from when salts accumulate in the soil or hydroponic medium in which a plant is cultured, the osmotic pressure increases, water absorption of the plant is hindered, and accordingly, the plant is exposed to the environment which may hinder the growth of the plant. Specifically, for example, this type of stress may be caused when an osmotic potential resulting from a salt in the soil or hydroponic medium is under the condition of 0.2 MPa (2,400 ppm in terms of a NaCl concentration) or higher, strictly 0.25 MPa or higher, and even more strictly 0.30 MPa or higher. The osmotic pressure in soil may be determined based on the following Raoult's equation, by diluting the soil with water and analyzing a salt concentration of the supernatant liquid.

Laoult's equation $\pi$ (atm)$=cRT$

R=0.082 (L·atm/mol·K)
T=absolute temperature (K)
c=molar concentration of ion (mol/L)
1 atm=0.1 MPa Production processes of the compound of the present invention is described below.

The compound of the present invention may be prepared according to, for example, the following (Production process 1) to (Production process 18).

(Production Process 1)

A compound represented by Formula (3) may be prepared according to, for example, the following scheme.

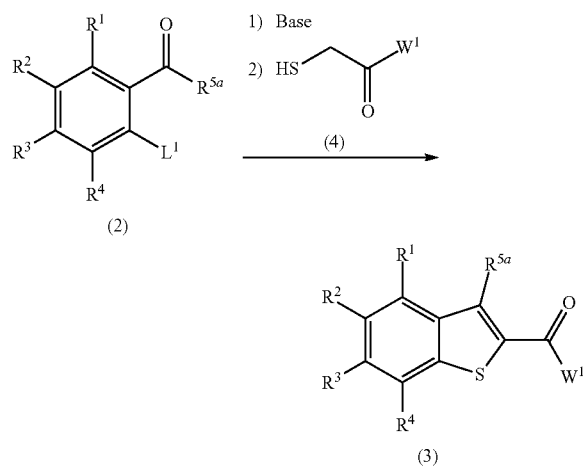

[wherein, $W^1$ represents a hydroxy group, $-OR^6$, or $-NR^7R^{10}$, $L^1$ represents a halogen atom or a nitro group, $R^{5a}$ represents a hydrogen atom, a C1-C6 alkyl group optionally having one or more groups selected from the group X, or a phenyl group optionally having one or more groups selected from the group Y, and $R^1$, $R^2$, $R^3$, $R^4$, $R^6$, $R^7$, and $R^{10}$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane; and a mixture of these.

In this reaction, a compound represented by Formula (4) is used in an amount of 1 mole or more in general and preferably in an amount of 1 mol to 1.2 moles, based on 1 mole of the compound represented by Formula (2).

Examples of the base used in this reaction include inorganic bases such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like.

In this reaction, the base is used in an amount of 1 mole to 5 moles in general, and preferably in an amount of 1 mole to 1.2 moles, based on 1 mole of the compound represented by Formula (2).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, a post-treatment operation in which acid is added to the reaction mixture, extraction is performed using an organic solvent, and the obtained organic layer is dried and concentrated is performed, whereby the compound represented by Formula (3) may be isolated. The isolated compound that is represented by Formula (3) may also be purified by chromatography, recrystallization, and the like.

(Production Process 2)

The compound represented by Formula (3) may be prepared by according to, for example, the following scheme.

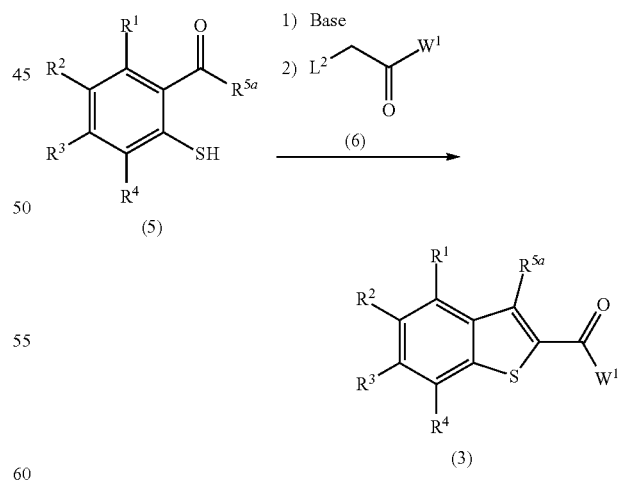

[wherein, $L^2$ represents a halogen atom, and $W^1$, $R^1$, $R^2$, $R^3$, $R^4$, and $R^{5a}$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane, and a mixture of these.

In this reaction, a compound represented by Formula (6) is used in an amount of 1 mole or more in general and preferably in an amount of 1 mole to 2 moles, based on 1 mole of a compound represented by Formula (5).

This reaction is generally performed in the presence of a base. Examples of the base used in this reaction include inorganic bases such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. In this reaction, the base is used in an amount of 1 mole or more in general, and preferably in an amount of 1 mole to 2 moles, based on 1 mole of the compound represented by Formula (5).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, a post-treatment operation in which water is added to the reaction mixture, extraction is performed using an organic solvent, and the obtained organic layer is dried and concentrated is performed, whereby the compound represented by Formula (3) may be isolated. The isolated compound that is represented by Formula (3) may also be purified by chromatography, recrystallization, and the like.

(Production Process 3)

A compound represented by Formula (8) may be prepared according to, for example, the following scheme.

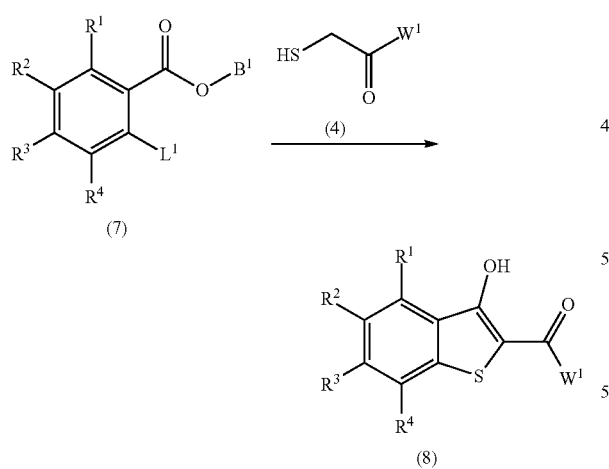

[wherein, $B^1$ represents a C1-C6 alkyl group, and PC $L^1$, $W^1$, $R^1$, $R^2$, $R^3$, and $R^4$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane, and a mixture of these.

In this reaction, a compound represented by Formula (4) is used in an amount of 1 mole or more in general and preferably in an amount of 1 mole to 1.2 moles, based on 1 mole of a compound represented by Formula (7).

This reaction is generally performed in the presence of a base. Examples of the base used in this reaction include inorganic bases such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. In this reaction, the base is used in an amount of 1 mole to 5 moles in general, and preferably in an amount of 1 mole to 1.2 moles, based on 1 mole of the compound represented by Formula (7).

The reaction temperature of this reaction is generally 0° C. to 200° C. and preferably 30° C. to 10° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, a post-treatment operation in which an acid is added to the reaction mixture, and then the precipitated solids are collected by filtration, washed with water and hexane, and then dried is performed, whereby a compound represented by Formula (8) may be isolated. The isolated compound that is represented by Formula (8) may also be purified by chromatography, recrystallization, and the like.

(Production Process 4)

A compound represented by Formula (10) may be prepared according to, for example, the following scheme.

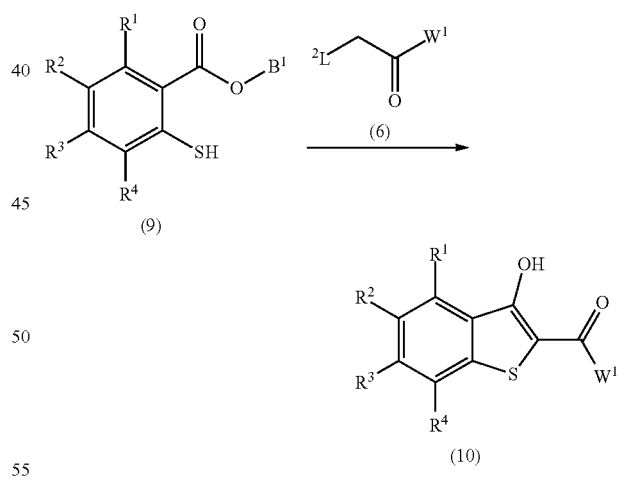

[wherein, B, $L^2$, $W^1$, $R^1$, $R^2$, $R^3$, and $R^4$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane, and a mixture of these.

In this reaction, a compound represented by Formula (6) is used in an amount of 1 mole or more in general and preferably in an amount of 1 mole to 2 moles, based on 1 mole of a compound represented by Formula (9).

This reaction is generally performed in the presence of a base. Examples of the base used in this reaction include inorganic bases such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. In this reaction, the base is used in an amount of 1 mole to 10 moles in general, and preferably in an amount of 1 mole to 2 moles, based on 1 mole of the compound represented by Formula (9).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, a post-treatment operation in which an acid is added to the reaction mixture, and then the precipitated solids are collected by filtration, washed with water and hexane, and then dried is performed, whereby a compound represented by Formula (10) may be isolated. The isolated compound that is represented by Formula (10) may also be purified by chromatography, recrystallization, and the like.

(Production Process 5)

A compound represented by Formula (12) may be prepared by according to, for example, the following scheme.

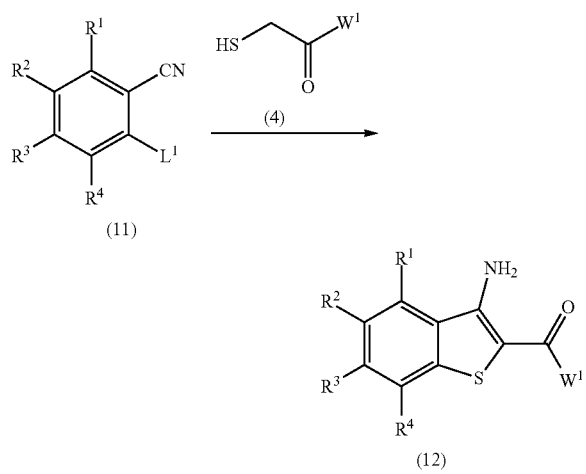

[wherein, $L^1$, $W^1$, $R^1$, $R^2$, $R^3$, and $R^4$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane, and a mixture of these.

In this reaction, a compound represented by Formula (4) is used in an amount of 1 mole or more in general and preferably in an amount of 1 mole to 1.2 moles, based on 1 mole of a compound represented by Formula (11).

This reaction is generally performed in the presence of a base. Examples of the base used in this reaction include inorganic bases such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. In this reaction, the base is used in an amount of 1 mole to 10 moles in general, and preferably in an amount of 1 mole to 1.2 moles, based on 1 mole of the compound represented by Formula (11).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-Layer chromatography and high-performance liquid chromatography. After this reaction is completed, for example, water is added to the reaction mixture, extraction is then performed using an organic solvent, and then the obtained organic layer is dried and concentrated, followed by chromatography, recrystallization, and the like, whereby a compound represented by Formula (12) may be isolated.

(Production Process 6)

A compound represented by Formula (14) may be prepared by according to, for example, the following scheme.

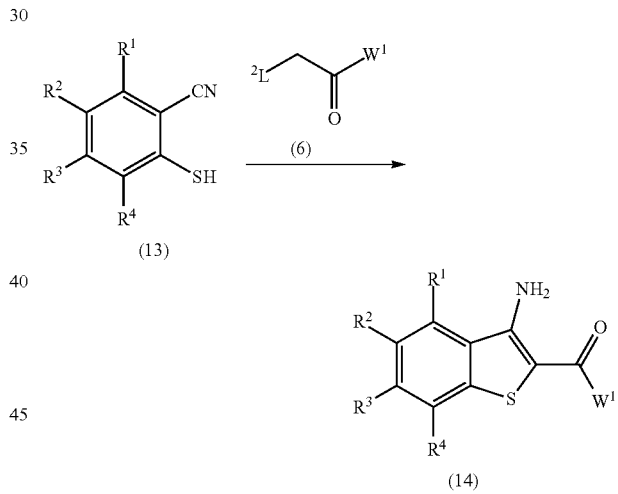

[wherein, $L^2$, $W^1$, $R^1$, $R^2$, $R^3$, and $R^4$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane, and a mixture of these.

In this reaction, a compound represented by Formula (6) is used in an amount of 1 mole or more in general and preferably in an amount of 1 mol to 2 moles, based on 1 mole of a compound represented by Formula (13).

This reaction is generally performed in the presence of a base. Examples of the base used in this reaction include inorganic bases such as sodium, carbonate and potassium carbonate; metal alkoxides such as sodium methoxide; alkaline metal hydrides such as sodium hydride; organic bases such as triethylamine, tributylamine, and N,N-diisopropylethylamine; and the like. In this reaction, the base is used in an amount of 1 mole to 5 moles in general, and preferably in an amount of 1 mole to 2 moles, based on 1 mole of the compound represented by Formula (13).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, water is added to the reaction mixture, extraction is then performed using an organic solvent, and then the obtained organic layer is dried and concentrated, followed by chromatography, recrystallization, and the like, whereby a compound represented by Formula (14) may be isolated.

(Production Process 7)

A compound represented by Formula (16) may be prepared by according to, for example, the following scheme.

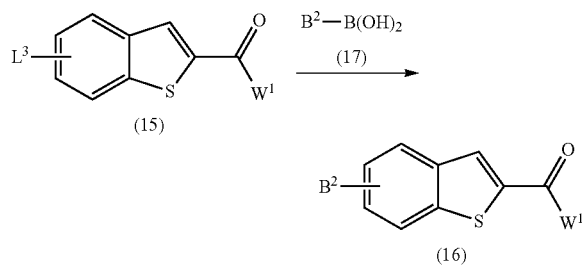

[wherein, $L^3$ represents a leaving group (for example, a halogen atom such as a chlorine atom, a bromine atom, or an iodine atom, and the pseudohalogen) substituted at position 3, 4, 5, 6, or 7, $B^2$ represents a C1-C6 alkyl group optionally having one or more groups selected from the group X, a C2-C6 alkenyl group optionally having one or more groups selected from the group X, a C2-C6 alkynyl group which may have optionally one or more groups selected from the group X, a phenyl group optionally having one or more groups selected from the group Y, a 6-membered aromatic heterocyclic group optionally having one or more groups selected from the group Y, or a 5-membered aromatic heterocyclic group optionally having one or more groups selected from the group Y, and $W^1$ has the same definition as described above]

In this reaction, a compound represented by Formula (17) is used in an amount of 1 mole or more in general, and preferably in an amount of 1 mole to 3 moles, based on 1 mol of a compound represented by (15).

This reaction is performed in a solvent. Examples of the solvent used in this reaction include aromatic hydrocarbons such as benzene, toluene, and xylene; alcohols such as methanol, ethanol, and propanol; ethers such as diethylether, diisopropylether, 1,4-dioxane, tetrahydrofuran, and 1,2-dimethoxyethane; ketones such as acetone and methyl ethyl ketone; nitriles such as acetonitrile; amides such as N,N-dimethylformamide and N,N-dimethylacetamide; sulfoxides such as dimethyl sulfoxide; sulfones such as sulfolane; water; and a mixture of these.

Moreover, this reaction is performed in the presence of a base. Examples of the base used in this reaction include organic bases such as triethylamine, tripropylamine, pyridine, dimethylaniline, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and potassium phosphate. In this reaction, the base is used in an amount of 0.5 mole to 10 moles in general, and preferably in an amount of 1 mole to 5 moles, based on 1 mole of the compound represented by Formula (15).

This reaction is generally performed in the presence of a catalyst such as tetrakis(triphenylphosphine)palladium (0), dichlorobis(triphenylphosphine)palladium (II), dichlorobis(tricyclohexylphosphine)palladium (II), or a [1,1'-bis(diphenylphosphino)ferrocene palladium] (II) dichloride dichloromethane adduct. This catalyst is used in an amount of 0.001 moles to 0.5 moles in general and preferably in an amount of 0.01 moles to 0.2 moles, based on 1 mol of the compound represented by Formula (15).

In this reaction, lithium chloride or the like is optionally used in an amount of 1 mole to 20 moles and preferably in an amount of 2 mole to 10 moles, based on 1 mole of the compound represented by Formula (15).

The reaction temperature of this reaction is generally 20° C. to 180° C. and preferably 60° C. to 150° C. The reaction time of this reaction is generally 30 minutes to 100 hours. The progress of this reaction may be confirmed by analyzing a portion of the reaction mixture by thin-layer chromatography, high-performance liquid chromatography, and the like.

After this reaction is completed, for example, an operation in which the reaction mixture is mixed with water, extraction is performed using an organic solvent, and the obtained organic layer is dried and concentrated is performed, whereby the compound represented by Formula (16) may be isolated. The isolated compound that is represented by Formula (16) may also be purified by chromatography, recrystallization, and the like.

(Production Process 8)

A compound represented by Formula (19) may be prepared according to, for example, the following scheme.

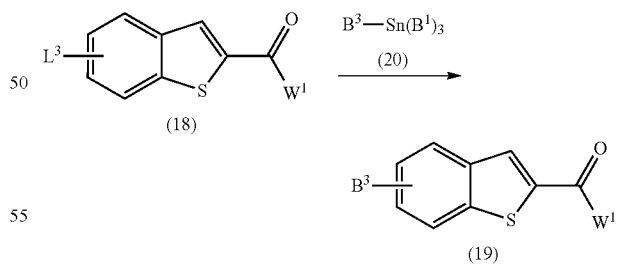

[wherein, $B^3$ represents a C2-C6 alkenyl group optionally having one or more groups selected from the group X, a C2-C6 alkynyl group optionally having one or more groups selected from the group X, a phenyl group optionally having one or more groups selected from the group Y, a 6-membered aromatic heterocyclic group optionally having one or more groups selected from the group Y, or a 5-membered aromatic heterocyclic group optionally having one or more groups selected from the group Y, and $B^1$, $L^3$, and $W^1$ have the same definition as described above respectively]

In this reaction, a compound represented by Formula (20) is used in an amount of 1 mole or more in general, and preferably in an amount of 1 mole to 3 moles, based on 1 mole of a compound represented by Formula (18).

This reaction is performed in a solvent. Examples of the solvent used in this reaction include aromatic hydrocarbons such as benzene, toluene, and xylene; ethers such as diethylether, diisopropylether, 1,4-dioxane, tetrahydrofuran, and 1,2-dimethoxyethane; amides such as N,N-dimethylformamide and N,N-dimethylacetamide; sulfoxides such as dimethyl sulfoxide; and a mixture of these.

This reaction is generally performed in the presence of a catalyst such as tetrakis(triphenylphosphine)palladium (0) or dichlorobis(triphenylphosphine)palladium (II). This catalyst is used in an amount of 0.001 moles to 0.5 moles in general, and preferably in an amount of 0.01 moles to 0.2 moles, based on 1 mole of the compound represented by Formula 18).

The reaction temperature of this reaction is generally −80° C. to 180° C. and preferably −30° C. to 150#C. The reaction time of this reaction is generally 30 minutes to 100 hours. The progress of this reaction may be confirmed by analyzing a portion of the reaction mixture by thin-layer chromatography, high-performance liquid chromatography, and the like. After this reaction is completed, for example, an operation in which the reaction mixture is mixed with water, extraction is performed using an organic solvent, and the obtained organic layer is dried and concentrated is performed, whereby the compound represented by Formula (19) may be isolated. The isolated compound that is represented by Formula (19) may also be purified by chromatography, recrystallization, and the like.

(Production Process 9)

A compound represented by Formula (22) may be prepared according to, for example, the following scheme.

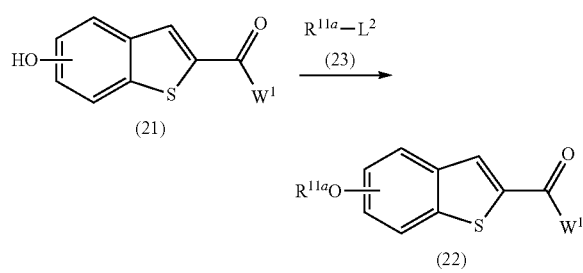

[wherein, HO represents a hydroxy group substituted at a position 3, 4, 5, 6, or 7, $R^{11a}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C7-C9 phenylalkyl group wherein a benzene ring portion may have optionally one or more groups selected from the group Y, a 6-membered aromatic heterocyclic-C1-C3 alkyl group wherein a 6-membered aromatic heterocyclic portion may have optionally one or more groups selected from the group Y, or a C3-C6 cycloalkyl group optionally having one or more halogen atoms, and $W^1$ and $L^2$ have the same definition as described above respectively]

This reaction is performed in a solvent. Examples of the solvent used in this reaction include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; ketones such as acetone and methyl ethyl ketone; nitriles such as acetonitrile; esters such as ethyl acetate; amides such as N,N-dimethylformamide and N,N-dimethylacetamide; sulfoxides such as dimethyl sulfoxide; sulfones such as sulfolane; and a mixture of these.

In this reaction, a compound represented by Formula (23) is used in an amount of 1 mole or more in general, and preferably in an amount of 1 mole to 3 moles, based on 1 mole of the compound represented by Formula (21).

This reaction is generally performed in the presence of a base. Examples of the base used in this reaction include organic bases such as triethylamine, tripropylamine, pyridine, dimethylaminopyridine, and 1,8-diazabicyclo[5.4.0]-7-undecene; inorganic bases such as sodium hydroxide, potassium hydroxide, calcium hydroxide, sodium carbonate, potassium carbonate, sodium hydrogen carbonate, and calcium carbonate; metal hydrides such as sodium hydride; and metal alkoxides such as sodium methylate, sodium ethylate, and potassium t-butoxide. In this reaction, the base is used in an amount of 0.5 molar equivalents to 10 molar equivalents in general, and preferably in an amount of 1 molar equivalent to 5 molar equivalents, based on 1 mole of the compound represented by Formula (21).

The reaction temperature of this reaction is generally −30° C. to 180° C. and preferably 0° C. to 100° C. The reaction time of this reaction is generally 10 minutes to 30 hours.

The progress of this reaction may be confirmed by analyzing a portion of the reaction mixture by thin-layer chromatography, high-performance liquid chromatography, and the like. After this reaction is completed, for example, an operation in which the reaction mixture is mixed with water, extraction is performed using an organic solvent, and the obtained organic layer is dried and concentrated is performed, whereby the compound represented by Formula (22) may be isolated. The isolated compound that is represented by Formula (22) may also be purified by chromatography, recrystallization, and the like.

(Production Process 10)

A compound represented by Formula (25) may be prepared according to, for example, the following scheme.

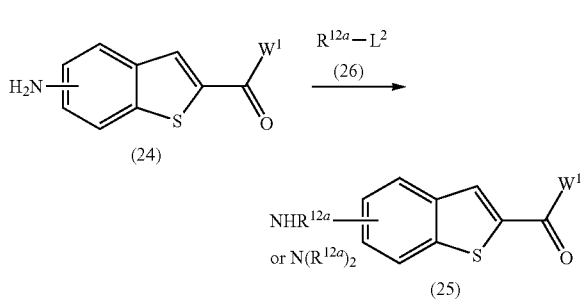

[wherein, $H_2N$ represents an amino group substituted at a position 3, 4, 5, 6, or 7, $R^{12a}$ represents a C1-C4 alkyl group optionally having one or more halogen atoms, a C1-C4 alkylsulfonyl group optionally having one or more halogen atoms, a phenylsulfonyl group optionally having one or more groups selected from the group Y, a C7-C9 phenylalkylsulfonyl group wherein a benzene ring portion may have optionally one or more groups selected from the group Y, a C2-C6 alkoxycarbonyl group, —C(O)R$^{15}$, or —C(O)NR$^{7}$R$^{8}$, and W$^{1}$, L$^{2}$, R, R$^{8}$, and R$^{15}$ have the same definition as described above respectively]

This reaction may be performed in a solvent. Examples of the usable solvent include aromatic hydrocarbons such as benzene, and toluene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfoxides such as dimethyl sulfoxide; sulfones such as sulfolane; and a mixture of these.

The amount of a compound represented by Formula (26) used in this reaction is generally 1 molar equivalent or more, and preferably 1 molar equivalent to 3 molar equivalents, based on the compound represented by Formula (24).

This reaction is generally performed in the presence of a base. Examples of the base used in this reaction include organic bases such as triethylamine, tripropylamine, pyridine, dimethylaminopyridine, diisopropyl ethylamine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, and sodium hydride. In this reaction, the base is used in an amount of 0.5 moles to 10 moles in general, and preferably in an amount of 1 mole to 5 moles, based on 1 mole of the compound represented by Formula (24).

The reaction temperature of this reaction is generally −30° C. to 180° C. and preferably −10° C. to 50° C. The reaction time of this reaction is generally 10 minutes to 30 hours.

The completion of this reaction may be confirmed by sampling a portion of the reaction mixture and using analysis means such as thin-layer chromatography and high-performance liquid chromatography. After this reaction is completed, for example, an operation in which the reaction mixture is mixed with water, extraction is performed using an organic solvent, and the obtained organic layer is dried and concentrated is performed, whereby the compound represented by Formula (25) may be isolated. The isolated compound that is represented by Formula (25) may also be purified by chromatography, recrystallization, and the like.

(Production Process 11)

A compound represented by Formula (28) may be prepared according to, for example, the following scheme.

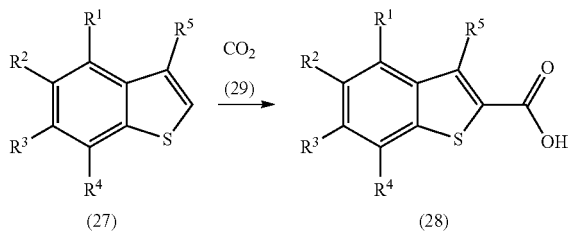

[wherein, R$^{1}$, R$^{2}$, R$^{3}$, R$^{4}$, and R$^{5}$ have the same definition as described above respectively]

This reaction is generally performed in a solvent. Examples of the usable solvent include aromatic hydrocarbons such as benzene, toluene, and xylene; ethers such as diethylether, diisopropylether, 1,4-dioxane, tetrahydrofuran, and 1,2-dimethoxyethane; and a mixture of these.

This reaction is performed in the presence of a base. Examples of the base used in this reaction include n-butyllithium, lithium diisopropylamide, and the like. In this reaction, the base is used in an amount of 1 mole to 2 moles in general, and preferably in an amount of 1 mole to 1.1 moles, based on 1 mole of a compound represented by Formula (27).

In this reaction, the compound represented by Formula (29) is used in an amount of 10 moles or more in general, and preferably in an amount of 10 moles to 1,000 moles, based on 1 mol of the compound represented by Formula (27).

The reaction temperature of this reaction is generally −100° C. to 0° C., and the reaction time of this reaction is generally 5 minutes to 5 hours.

The completion of this reaction may be confirmed by sampling a portion of the reaction mixture and using analysis means such as thin-layer chromatography and high-performance liquid chromatography. After this reaction is completed, for example, an operation in which water is added to the reaction mixture, the residue is washed with an organic solvent, concentrated hydrochloric acid is then added to the aqueous layer, extraction is performed using an organic solvent, and the obtained organic layer is dried and concentrated is performed, whereby the compound represented by Formula (28) may be isolated.

(Production Process 12)

A compound represented by Formula (30) may be prepared according to, for example, the following scheme.

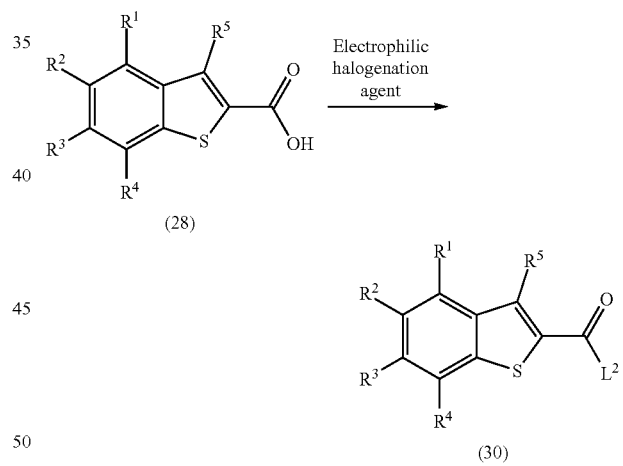

[wherein, L$^{2}$, R$^{1}$, R$^{2}$, R$^{3}$, R$^{4}$, and R$^{5}$ have the same definition as described above respectively]

This reaction is generally performed in a solvent. Examples of the usable solvent include aromatic hydrocarbons such as benzene and toluene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; sulfoxides such as dimethyl sulfoxide, sulfones such as sulfolane; and a mixture of these.

Examples of the electrophilic halogenation agent used in this reaction include thionyl chloride, oxalyl chloride, phosphoryl chloride, sulfuryl chloride, phosphorus trichloride, phosphorus pentachloride, phosphorus tribromide, phosgene, and the like.

In this reaction, the electrophilic halogenation agent is used in an amount of 1 mole to 100 moles in general, and preferably in an amount of 2 moles to 20 moles, based on 1 mole of a compound represented by Formula (28).

In this reaction, N,N-dimethylformamide and the like are also optionally used in an amount of 0.001 moles to 1,000 moles, and preferably in an amount of 0.01 moles to 50 moles, based on 1 mole of the compound represented by Formula (28). The reaction temperature of this reaction is generally in a range of room temperature to a boiling point of the solvent used, preferably 60° C. to a boiling point of the solvent. This reaction may be performed in a sealed tube or a pressure-resistant sealed container.

The reaction time of this reaction is generally about 5 minutes to several days.

The progress of this reaction may be confirmed by analyzing a portion of the reaction mixture by thin-layer chromatography, high-performance liquid chromatography, and the like. After this reaction is completed, for example, an operation in which the reaction mixture is concentrated is performed, whereby the compound represented by Formula (30) may be isolated.

(Production Process 13)

The compound represented by Formula (1) may be prepared by according to, for example, the following scheme.

line metal hydrides such as sodium hydride; organic bases such as triethylamine, tributylamine, and N,N-diisopropylethylamine; and the like.

In this reaction, the base is used in an amount of 1 mole to 50 moles in general, and preferably in an amount of 1 mole to 5 moles, based on 1 mole of the compound represented by Formula (30).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, a post-treatment operation in which water is added to the reaction mixture, extraction is performed using an organic solvent, and the obtained organic layer is dried and concentrated is performed, whereby the compound represented by Formula (1) may be isolated. The isolated compound that is represented by Formula (1) may also be purified by chromatography, recrystallization, and the like.

(Production Process 14)

Among the compounds of the present invention, the compound represented by Formula (1) may be prepared according to the following scheme.

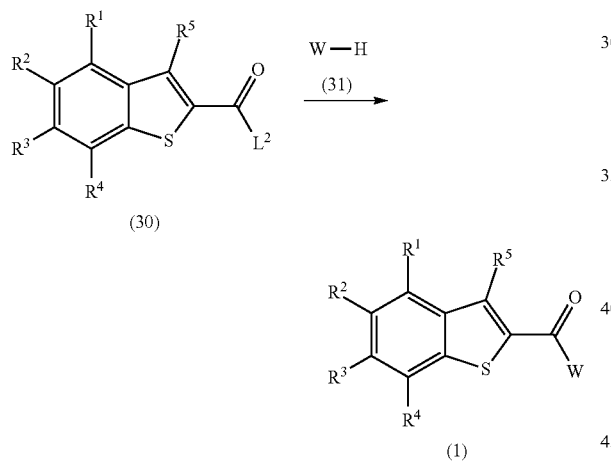

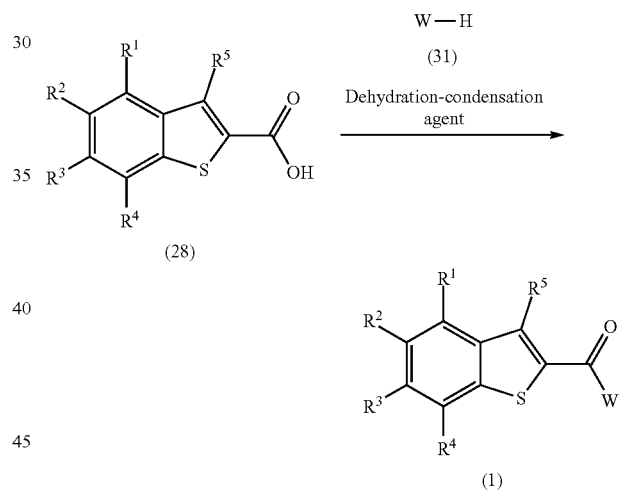

[wherein, W, $L^2$, $R^1$, $R^2$, $R^3$, $R^4$, and $R^5$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane; ketones such as acetone, methyl ethyl ketone, and methyl isobutyl ketone; and a mixture of these.

In this reaction, a compound represented by Formula (31) is used in an amount of 1 mole or more in general, and preferably in an amount of 1 mole to 50 moles, based on 1 mole of a compound represented by Formula (30).

This reaction is generally performed in the presence of a base. Examples of the base used in this reaction include metal carbonates such as sodium carbonate and potassium carbonate; metal alkoxides such as sodium methoxide; alka-

[wherein, W, $R^1$, $R^2$, $R^3$, $R^4$, and $R^5$ have the same definition as described above respectively]

This reaction is generally performed in a solvent. Examples of usable solvents include aromatic hydrocarbons such as benzene, toluene, and xylene; ethers such as diethylether, diisopropylether, 1,4-dioxane, tetrahydrofuran, and 1,2-dimethoxyethane; halogenated hydrocarbons such as dichloromethane, chloroform, and 1,2-dichloroethane; amides such as N,N-dimethylformamide and N,N-dimethylacetamide; sulfones such as sulfolane; esters such as ethyl acetate and butyl acetate; and a mixture of these.

In this reaction, a compound represented by Formula (31) is used in an amount of 1 mole or more in general, and preferably in an amount of 1 mole to 10 moles, based on 1 mole of the compound represented by Formula (28).

Examples of the dehydration-condensation agent used in this reaction include carbodiimide-based agents such as N,N-dicyclohexylcarbodiimide, and 1-ethyl-3-(3-dimethylaminopropyl)carbodiimide hydrochloride; phosphonium salt-based agents such as a benzotriazol-1-yloxytris(dimethylamino)phosphonium salt; and the like.

In this reaction, the dehydration-condensation agent is used in an amount of 1 mole to 50 moles in general, and preferably in an amount of 1 mole to 10 moles, based on 1 mole of the compound represented by Formula (28).

In this reaction, 4,4-dimethylaminopyridine and the like are also optionally used in an amount of 0.001 moles to 10 moles, and preferably in an amount of 0.01 moles to 0.5 moles, based on 1 mole of the compound represented by Formula (28).

This reaction is optionally performed in the presence of a base. Examples of the base used in this reaction include metal carbonate such as sodium carbonate and potassium carbonate; metal alkoxides such as sodium methoxide; alkaline metal hydrides such as sodium hydride; organic bases such as triethylamine, tributylamine, and N,N-diisopropylethylamine; and the like. These bases are used in an amount of 1 mole to 50 moles in general, and preferably in an amount of 1 mole to 10 moles, based on 1 mole of the compound represented by Formula (28).

The reaction temperature of this reaction is generally 0° C. to 200° C. and preferably 30° C. to 100° C. The reaction time of this reaction is generally 30 minutes to 30 hours.

The completion of this reaction may be confirmed by sampling a portion of the reaction mixture and using analysis means such as thin-layer chromatography and high-performance liquid chromatography. After this reaction is completed, for example, a post-treatment operation in which water is added to the reaction mixture, extraction is performed using an organic solvent, and the obtained organic layer is dried and concentrated is performed, whereby the compound represented by Formula (1) may be isolated. The isolated compound that is represented by Formula (1) may also be purified by chromatography, recrystallization, and the like.

(Production Process 15)

A compound represented by Formula (33) may be prepared according to, for example, the following scheme.

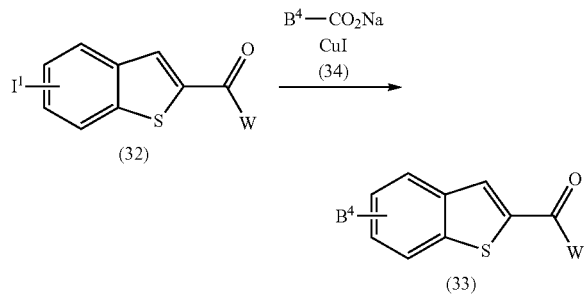

[wherein, $I^1$ represents an iodine atom substituted at a position 3, 4, 5, 6, or 7, $B^4$ represents a C1-C6 alkyl group optionally having one or more halogen atoms, and W has the same definition as described above]

In this reaction, a compound represented by Formula (34) is used in an amount of 2 moles or more in general, and preferably in an amount of 2 moles to 20 moles, based on 1 mole of a compound represented by Formula (32).

This reaction is performed in a solvent. Examples of the solvent used in this reaction include aromatic hydrocarbons such as benzene, toluene, and xylene; amides such as N,N-dimethylformamide, N,N-dimethylacetamide, and N-methyl-2-pyrrolidone; sulfoxides such as dimethyl sulfoxide; and a mixture of these.

This reaction is generally performed in the presence of a catalyst such as copper (I) iodide. In this reaction, the catalyst is used in an amount of 1 mole or more in general, and preferably in an amount of 1 mole to 10 moles, based on 1 mole of the compound represented by Formula (32).

The reaction temperature of this reaction is generally 0° C. to 300° C. and preferably 120° C. to 250° C. The reaction time of this reaction is generally 30 minutes to 100 hours. The progress of this reaction may be confirmed by analyzing a portion of the reaction mixture by thin-layer chromatography, high-performance liquid chromatography, and the like.

After this reaction is completed, an operation such as silica gel chromatography is performed, whereby a compound represented by Formula (33) may be isolated.

(Production Process 16)

A compound represented by Formula (33) may be prepared according to, for example, the following scheme.

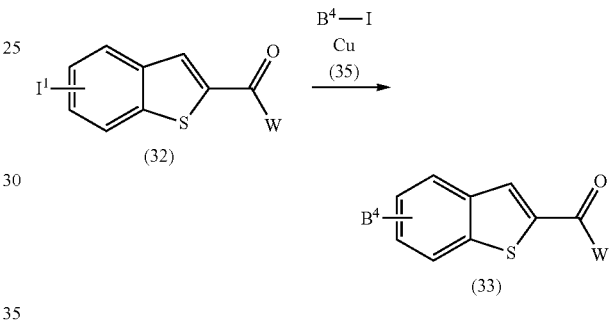

[wherein, $I^1$, $B^4$, and $W^2$ have the same definition as described above respectively]

In this reaction, a compound represented by Formula (35) is used in an amount of 1 mole or more in general, and preferably in an amount of 1 mole to 20 moles, based on 1 mole of the compound represented by Formula (32).

This reaction is performed in a solvent. Examples of the solvent used in this reaction include aromatic hydrocarbons such as benzene, toluene, and xylene; amides such as N,N-dimethylformamide, N,N-dimethylacetamide, and N-methyl-2-pyrrolidone; sulfoxides such as dimethyl sulfoxide; and a mixture of these.

This reaction is generally performed in the presence of a catalyst such as copper (0). In this reaction, the catalyst is used in an amount of 1 mole or more in general, and preferably in an amount of 1 mole to 20 moles, based on 1 mole of the compound represented by Formula (32).

The reaction temperature of this reaction is generally 0° C. to 300° C. and preferably 120° C. to 250° C. The reaction time of this reaction is generally 30 minutes to 100 hours. The progress of this reaction may be confirmed by analyzing a portion of the reaction mixture by thin-layer chromatography, high-performance liquid chromatography, and the like.

After this reaction is completed, an operation such as silica gel chromatography is performed, whereby the compound represented by Formula (33) may be isolated.

(Production Process 17)

A compound represented by Formula (36) may be prepared by, for example, reacting (15) with (37) in the presence of a palladium compound, a base, and a copper salt.

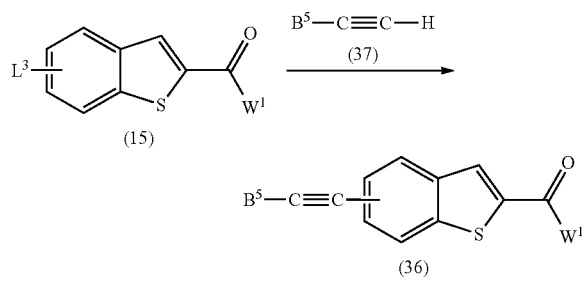

[wherein, $B^5$ represents a hydrogen atom, a C1-C4 alkyl group optionally having one or more groups selected from the group X, or a trimethylsilyl group, and $W^1$ and $L^3$ have the same definition as described above respectively]

In this reaction, the compound represented by Formula (37) is used in an amount of 1 mole or more, and preferably in an amount of 1 mole to 10 moles, based on 1 mole of the compound represented by Formula (15).

This reaction is generally performed using a base as a solvent. However, an auxiliary solvent may also be used.

Examples of the base used in this reaction include organic bases such as triethylamine, diethylamine, diisopropylamine, tripropylamine, pyridine, dimethylaniline, dimethylaminopyridine, and 1,8-diazabicyclo[5.4.0]-7-undecene. In this reaction, the base is used in an amount of 1 mole to 1,000 moles in general, and preferably in an amount of 1 mole to 100 moles, based on 1 mole of the compound represented by (15).

Examples of the auxiliary solvent used in this reaction include aromatic hydrocarbons such as benzene, toluene, xylene; ethers such as diethylether, diisopropylether, 1,4-dioxane, tetrahydrofuran, and 1,2-dimethoxyethane; nitriles such as acetonitrile; amides such as N,N-dimethylformamide and N,N-dimethylacetamide; sulfoxides such as dimethyl sulfoxide; sulfones such as sulfolane; and a mixture of these.

Examples of the palladium compound used in this reaction include tetrakis(triphenylphosphine)paladium, dichlorobis(triphenylphosphine)palladium, dichlorobis(tricyclohexylphosphine)palladium, or a [1,1'-bis(diphenylphosphino)ferrocene]palladium (II) dichloride dichloromethane adduct. In this reaction, the palladium compound is used in an amount of 0.001 moles or more, and preferably in an amount of 0.001 moles to 0.5 moles, based on 1 mole of the compound represented by Formula (15).

Examples of the copper salt used in this reaction include copper (I) iodide, copper (I) bromide, and the like. In this reaction, the copper salt is used in an amount of 0.001 moles or more and preferably in an amount of 0.031 moles to 0.5 moles, based on 1 mole of the compound represented by Formula (15).

The reaction temperature of this reaction is generally 0° C. to 180° C. and preferably 10° C. to 100° C. The reaction time of this reaction is generally 30 minutes to 100 hours. The progress of this reaction may be confirmed by analyzing a portion of the reaction mixture by thin-layer chromatography, high-performance liquid chromatography, and the like. After this reaction is completed, for example, an operation in which water is added to the reaction mixture, extraction is performed using an organic solvent, and the obtained organic layer is dried and concentrated is performed, whereby the compound represented by Formula (36) may be isolated. The isolated compound that is represented by Formula (36) may also be purified by chromatography, recrystallization, and the like.

Moreover, a compound represented by Formula (37) wherein $B^5$ represents a trimethylsilyl group is reacted with the compound (15) in the presence of a palladium compound, a base, and a copper salt, and a desilylation reaction is performed on the compound obtained by the above reaction based on the method described in "GREENE'S PROTECTIVE GROUPS IN ORGANIC SYNTHESIS Fourth Edition, Wiley Interscience, 2007", whereby a compound represented by Formula (36) wherein $B^5$ represents a hydrogen atom may be obtained.

The compound represented by Formula (16) may be prepared according to, for example, the following scheme.

(Production Process 18)

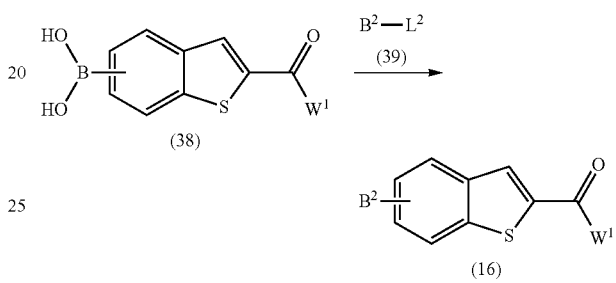

[wherein, —$B(OH)_2$ represents —$B(OH)_2$ substituted at a position 3, 4, 5, 6, or 7, and $B^2$, $L^2$, and $W^1$ have the same definition as described above respectively]

In this reaction, a compound represented by Formula (39) is used in an amount of 1 mole or more, and preferably in an amount of 1 mole to 3 moles, based on 1 mole of a compound represented by Formula (38).

This reaction is performed in a solvent. Examples of the solvent used in this reaction include aromatic hydrocarbons such as benzene, toluene, and xylene; alcohols such as methanol, ethanol, and propanol; ethers such as diethylether, diisopropylether, 1,4-dioxane, tetrahydrofuran, and 1,2-dimethoxyethane; ketones such as acetone, methyl ethyl ketone, and methyl isobutyl ketone; nitriles such as acetonitrile; amides such as N,N-dimethylformamide and N,N-dimethylacetamide; sulfoxides such as dimethyl sulfoxide; sulfones such as sulfolane; water; and a mixture of these.

Moreover, this reaction is performed in the presence of a base. Examples of the base used in this reaction include organic bases such as triethylamine, tripropylamine, pyridine, dimethylaniline, dimethylaminopyridine, and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate, and potassium phosphate. In this reaction, the base is used in an amount of 0.5 moles to 10 moles in general, and preferably in an amount of 1 mole to 5 moles, based on 1 mole of the compound represented by Formula (38).

This reaction is generally performed in the presence of a catalyst such as tetrakis(triphenylphosphine)palladium, dichlorobis(triphenylphosphine)palladium, dichlorobis(tricyclohexylphosphine)palladium, or a [1,1'-bis(diphenylphosphino)ferrocene]palladium (II) dichloride dichloromethane adduct. In this reaction, the catalyst is used in an amount of 0.001 moles to 0.5 moles, and preferably in an amount of 0.01 moles to 0.2 moles, based on 1 mole of the compound represented by Formula (38).

In this reaction, lithium chloride or the like is optionally used in an amount of 1 mole to 20 moles, and preferably in an amount of 2 moles to 10 moles, based on 1 mole of the compound represented by (38).

The reaction temperature of this reaction is generally 20° C. to 180° C. and preferably 60° C. to 150° C. The reaction time of this reaction is generally 30 minutes to 100 hours. The progress of this reaction may be confirmed by analyzing a portion of the reaction mixture by thin-layer chromatography, high-performance liquid chromatography, and the like.

After this reaction is completed, for example, an operation in which the reaction mixture is mixed with water, extraction is performed using an organic solvent, and the obtained organic layer is dried and concentrated is performed, whereby the compound represented by Formula (16) may be isolated. The isolated compound that is represented by Formula (16) may also be purified by chromatography, recrystallization, and the like.

Reference Production Process 1

The compound represented by Formula (2) may be prepared according to, for example, the following scheme.

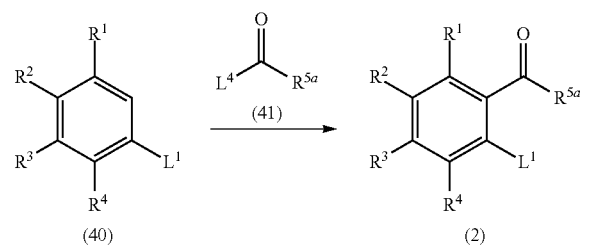

[wherein, $L^4$ represents a leaving group (for example, a halogen atom such as a chlorine atom, a bromine atom, or an iodine atom, a C1-C6 alkoxy group such as a methoxy group or an ethoxy group, and an N-methoxy-N-methylamino group), and $L^1$, $R^1$, $R^2$, $R^3$, $R^4$, and $R^{5a}$ have the same definition as described above respectively]

This reaction is generally performed in a solvent. Examples of the usable solvent include aromatic hydrocarbon such as benzene, toluene, and xylene; ethers such as diethylether, diisopropylether, 1,4-dioxane, tetrahydrofuran, and 1,2-dimethoxyethane; and a mixture of these.

This reaction is performed in the presence of a base. Examples of the base used in this reaction include n-butyllithium, lithium isopropylamide, and the like. In this reaction, the base is used in an amount of 1 mole to 2 moles in general, and preferably in an amount of 1 mole to 1.1 moles, based on 1 mole of the compound represented by Formula (40).

In this reaction, the compound represented by Formula (41) is used in an amount of 1 mole or more in general, and preferably in an amount of 1 mole to 10 moles, based on 1 mole of the compound represented by Formula (40).

The reaction temperature of this reaction is generally −100° C. to −30° C., and the reaction time of this reaction is generally 5 minutes to 5 hours.

The completion of this reaction may be confirmed by sampling a portion of the reaction mixture and using analysis means such as thin-layer chromatography and high-performance liquid chromatography. After this reaction is completed, for example, water is added to the reaction mixture, extraction is performed using an organic solvent, the obtained organic layer is dried and concentrated, and then chromatography, distillation, and the like are performed, whereby the compound represented by (2) may be isolated.

Reference Production Process 2

A compound represented by Formula (42) may be prepared by, for example, reacting the compound represented by Formula (1) with a metal hydroxide.

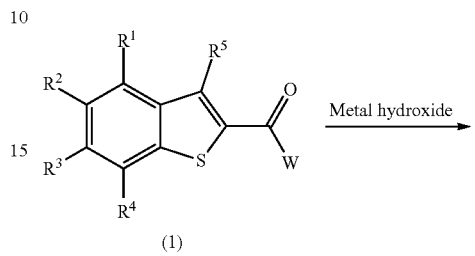

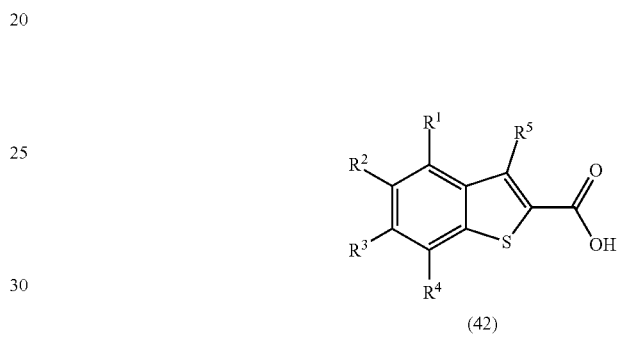

[wherein, W, $R^1$, $R^2$, $R^3$, $R^4$, and $R^5$ have the same definition as described above respectively]

This reaction is generally performed in a solvent. Examples of the solvent used in this reaction include water; ethers such as tetrahydrofuran and 1,4-dioxane; alcohols such as methanol and ethanol; and a mixture of these.

Examples of the metal hydroxide used in this reaction include hydroxides of alkaline metals, such as lithium hydroxide, sodium hydroxide, and potassium hydroxide. In this reaction, the metal hydroxide is used in an amount of 2 moles to 20 moles in general and preferably 2 moles to 4 moles, based on 1 mole of the compound represented by Formula (1).

The reaction temperature of this reaction is generally within a range of room temperature to a boiling point of the solvent, and preferably is a boiling point of the solvent. This reaction may also be performed in a sealed tube or a pressure-resistant sealed container. The reaction time of this reaction is generally about 5 minutes to 36 hours.

The progress of this reaction may be confirmed by analyzing a portion of the reaction mixture by thin-layer chromatography, high-performance liquid chromatography, and the like. After this reaction is completed, for example, an operation in which hydrochloric acid is added to the reaction mixture, extraction is performed using an organic solvent, and the obtained organic layer is dried and concentrated is performed, whereby the compound represented by Formula (42) may be isolated.

Reference Production Process 3

A compound represented by Formula (42) may be prepared according to, for example, the following scheme.

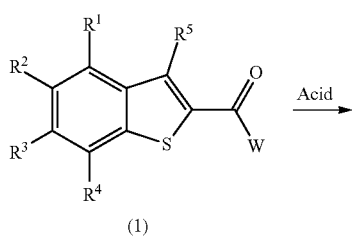

(1)

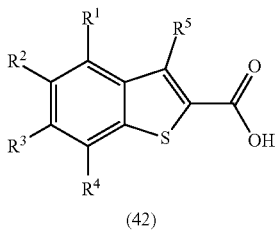

(42)

[wherein, W, $R^1$, $R^2$, $R^3$, $R^4$, and $R^5$ have the same PG definition as described above respectively]

This reaction is generally performed in a solvent. Examples of the solvent used in this reaction include water; organic carboxylic acids such as acetic acid and propionic acid; and a mixture of these.

Examples of the acid used in this reaction include hydrochloric acid, hydrobromic acid, trifluoromethanesulfonic acid, and the like.

In this reaction, the acid is used in an amount of 1 mole to 100 moles in general, and preferably in an amount of 2 moles to 20 moles, based on 1 mole of the compound represented by Formula (1).

The reaction temperature of this reaction is generally within a range of room temperature to a boiling point of the used solvent, and preferably is from 80° C. to a boiling point of the solvent. This reaction may also be performed in a sealed tube or a pressure-resistant sealed container. The reaction time of this reaction is generally about 5 minutes to several days.

The progress of this reaction may be confirmed by analyzing a portion of the reaction mixture by thin-layer chromatography, high-performance liquid chromatography, and the like. After this reaction is completed, for example, an operation in which water is added to the reaction mixture, extraction is performed using an organic solvent, and the obtained organic layer is dried and concentrated is performed, whereby the compound represented by Formula (42) may be isolated.

Reference Production Process 4

A compound represented by Formula (44) may be prepared according to, for example, the following scheme.

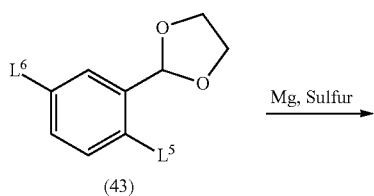

(43)

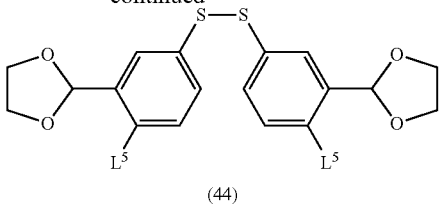

(44)

[wherein, $L^5$ represents a leaving group such as a fluorine atom, a chlorine atom, and a nitro group, and $L^6$ represents a bromine atom or a iodine atom]

This reaction is generally performed in a solvent. Examples of the solvent used in this reaction include aromatic hydrocarbons such as benzene, toluene, and xylene; ethers such as diethylether, diisopropylether, 1,4-dioxane, tetrahydrofuran, and 1,2-dichloroethane; and a mixture of these.

In this reaction, magnesium is used in an amount of 1 mole or more in general, and preferably in an amount of 1 molar equivalent to 2 molar equivalents, based on 1 mole of a compound represented by Formula (43).

In this reaction, sulfur is used in an amount of 0.125 moles or more in general, and preferably in an amount of 0.125 moles to 10 moles, based on 1 mole of the compound represented by Formula (43).

The reaction temperature of this reaction is generally −100° C. to 100° C., and the reaction time of this reaction is generally 5 minutes to 30 minutes.

The completion of this reaction may be confirmed by sampling a portion of the reaction mixture and using analysis means such as thin-layer chromatography and high-performance liquid chromatography. After this reaction is completed, purification is performed by silica gel column chromatography and the like, whereby the compound represented by Formula (44) may be isolated.

Reference Production Process 5

A compound represented by Formula (45) may be prepared according to, for example, the following scheme.

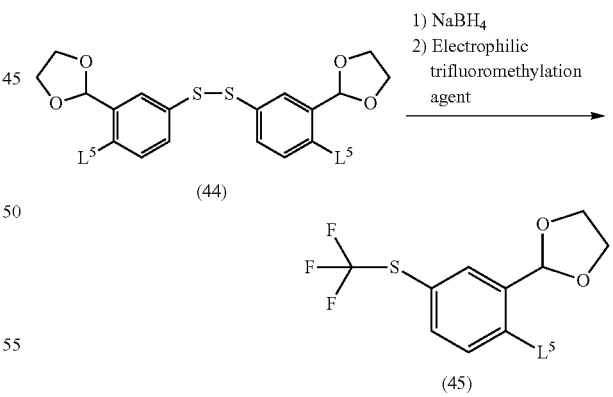

[wherein, $L^5$ has the same definition as described above]

This reaction is generally performed in a solvent. Examples of the usable solvent include aromatic hydrocarbons such as benzene, toluene, and xylene; ethers such as diethylether, diisopropylether, 1,4-dioxane, tetrahydrofuran, and 1,2-dimethoxyethane; alcohols such as methanol, ethanol, and propanol; halogenated hydrocarbons such as dichloromethane, chloroform, and 1,2-dichloroethane; and a mixture of these.

In this reaction, sodium borohydride is used in an amount of 1 mole or more, and preferably in an amount of 1 mole to 20 moles, based on 1 mole of a compound represented by (44).

Examples of the electrophilic trifluoromethylation agent used in this reaction include 1-trifluoromethyl-3,3-dimethyl-1,2-benziodoxole, and the like. In this reaction, the electrophilic trifluoromethylation agent is used in an amount of 1 mole or more in general, and preferably in an amount of 1 mole to 5 moles, based on 1 mole of the compound represented by (44).

The reaction temperature of this reaction is generally −100° C. to 150° C., and the reaction time of this reaction is generally 5 minutes to 30 hours.

The completion of this reaction may be confirmed by sampling a portion of the reaction mixture and using analysis means such as thin-layer chromatography and high-performance liquid chromatography. After this reaction is completed, purification is performed by silica gel chromatography and the like, whereby the compound represented by Formula (45) may be isolated.

Moreover, a deacetalization reaction is performed on the compound represented by Formula (45) based on the method described in "GREENE'S PROTECTIVE GROUPS IN ORGANIC SYNTHESIS Fourth Edition, Wiley Interscience, 2007", whereby a corresponding aldehyde may be obtained.

Reference Production Process 6

A compound represented by Formula (46) may be prepared according to, for example, the following scheme.

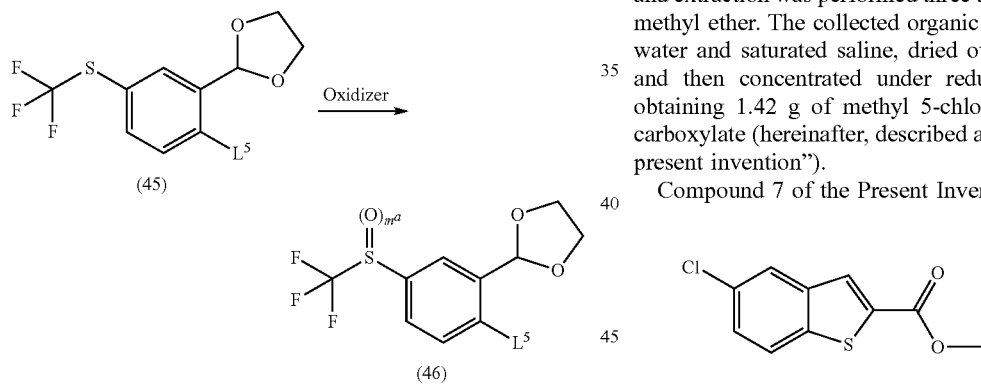

[wherein, $m^a$ represents 1 or 2, and $L^5$ has the same definition as described above]

This reaction is performed in a solvent. Examples of the solvent used in this reaction include alcohols such as methanol, ethanol, and propanol; ethers such as diethylether, diisopropylether, 1,4-dioxane, tetrahydrofuran, and 1,2-methoxyethane; nitriles such as acetonitrile; halogenated hydrocarbons such as dichloromethane, chloroform, 1,2-dichloroethane, organic acids such as acetic acid; water; and a mixture of these.

Examples of the oxidizer used in this reaction include m-chloroperbenzoic acid, aqueous hydrogen peroxide, and the like. In this reaction, the oxidizer is used in an amount of 1 mol or more in general, and preferably in an amount of 1 mol to 10 mol, based on 1 mol of the compound represented by Formula (45).

The reaction temperature of this reaction is generally −130° C. to 150° C., and the reaction time of this reaction is generally 5 minutes to 30 hours.

The completion of this reaction may be confirmed by sampling a portion of the reaction mixture and using analysis means such as thin-layer chromatography and high-performance liquid chromatography. After this reaction is completed, purification is performed by silica gel column chromatography and the like, whereby the compound represented by Formula (46) may be isolated.

Moreover, a deacetalization reaction is performed on the compound represented by Formula (46) based on the method described in "GREENE'S PROTECTIVE GROUPS IN ORGANIC SYNTHESIS Fourth Edition, Wiley Interscience, 2007", whereby a corresponding aldehyde may be obtained.

EXAMPLES

Hereinafter, the production examples, formulation examples, and test examples of the present invention are described in more detail, but the present invention is not limited to the following examples. Moreover, in the following examples, "part(s)" indicates "part(s) by weight" unless otherwise specified.

Production Example 1

A mixture of 1.10 g of 5-chloro-2-fluorobenzaldehyde, 803 mg of methyl thioglycolate, 956 mg of potassium carbonate, and 15 ml of N,N-dimethylformamide was stirred for 2 hours at 60° C. The reaction mixture was cooled to room temperature. Water was added to the reaction mixture, and extraction was performed three times by using tert-butyl methyl ether. The collected organic layer was washed with water and saturated saline, dried over magnesium sulfate, and then concentrated under reduced pressure, thereby obtaining 1.42 g of methyl 5-chlorobenzo[b]thiophene-2-carboxylate (hereinafter, described as a "compound 7 of the present invention").

Compound 7 of the Present Invention

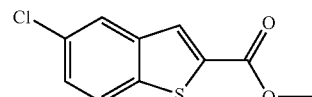

$^1$H-NMR (CDCl$_3$) δ: 7.99 (s, 1H), 7.86 (d, 1H, J=2.2 Hz), 7.79 (d, 1H, J=8.7 Hz), 7.42 (dd, 1H, J=8.7, 2.2 Hz), 3.95 (s, 3H).

Production Example 2

A mixture of 500 mg of methyl 4-bromobenzo[b]thiophene-2-carboxylate, 161 mg of methylboronic acid, 1.17 g of potassium phosphate, 151 mg of a [1,1′-bis(diphenylphosphino)ferrocene]palladium (II) dichloride dichloromethane adduct, 6 ml of 1,4-dioxane, and 0.1 ml of water was stirred for 3 hours at 100° C. under a nitrogen atmosphere. After being cooled to room temperature, the reaction mixture was concentrated under reduced pressure. Chloroform and water were added to the residues, and insoluble matter was separated by filtration. The filtrate was extracted using chloroform, and the organic layer was washed with saturated saline, dried over magnesium sulfate, and then concentrated under reduced pressure. The residues were subjected to silica gel column chromatography, thereby obtaining 340 mg of methyl 4-methylbenzo[b]thiophene-2-carboxylate (hereinafter, described as a "compound 22 of the present invention").

Compound 22 of the Present Invention

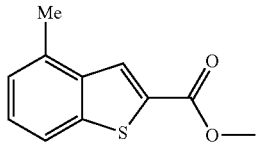

¹H-NMR (CDCl₃) δ: 8.17-8.16 (m, 1H), 7.71-7.69 (m, 1H), 7.37-7.35 (m, 1H), 7.20-7.18 (m, 1H), 3.95 (s, 3H), 2.64 (s, 3H).

Production Example 3

Step 1

A mixture of 5.2 g of bromoacetaldehyde diethylacetal and 10 ml of tetrahydrofuran was added to a mixture of 4.00 g of 4-methylbenzenethiol, 1.4 g of 60% sodium hydride, and 35 ml of tetrahydrofuran. The reaction mixture was stirred for 15 hours at room temperature. Ten (10) ml of aqueous saturated ammonium chloride solution was added to the reaction mixture, and extraction was performed three times by using tert-butyl methyl ether. The collected organic layer was washed with water and saturated saline, dried over magnesium sulfate, and then concentrated under reduced pressure. The residues were added to a mixture of 5 g of diphosphorus pentoxide and 10 g of phosphoric acid that had been stirred for 45 minutes at 175° C., and the residue was stirred for 5 minutes. The reaction mixture was poured into ice water, and extraction was performed three times by using tert-butyl methyl ether. The collected organic layer was washed with water and saturated saline, dried over magnesium sulfate, and then concentrated under reduced pressure. The residues were subjected to silica gel column chromatography, thereby obtaining 2.77 g of 5-methylbenzo[b] thiophene.

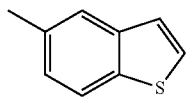

Step 2

A mixture of 2.77 g of 5-methylbenzo[b]thiophene and 40 ml of diethylether was stirred at 0° C., and 18 ml of n-butyllithium (2.6 M hexane solution) was added thereto. The reaction mixture was stirred for 2 hours, and then 1 g of dry ice was added thereto. After the temperature of the reaction mixture was set to room temperature, water was added thereto, and the residue was washed three times with tert-butyl methyl ether. Concentrated hydrochloric acid was added to the aqueous layer, and then and extraction was performed three times by using tert-butyl methyl ether. The collected organic layer was washed with saturated saline, dried over magnesium sulfate, and then concentrated under reduced pressure. Eight hundreds (800) mg of oxalyl chloride was added to a mixture of the residues and 20 ml of methanol under ice cooling. This mixture was stirred for 2 hours at 80° C. After being cooled to room temperature, the reaction mixture was concentrated under reduced pressure. The residues were subjected to silica gel column chroma-tography, thereby obtaining 387 mg of methyl 5-methyl-benzo[b]thiophene-2-carboxylate (hereinafter, described as a "compound 23 of the present invention").

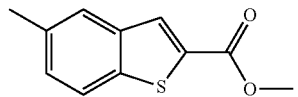

Compound 23 of the Present Invention
¹H-NMR (CDCl₃) δ: 7.99 (s, 1H), 7.75 (d, 1H, J=8.6 Hz), 7.67 (s, 1H), 7.29 (d, 1H, J=8.6 Hz), 3.94 (s, 3H), 2.48 (s, 3H).

Production Example 4

A mixture of 600 mg of methyl 7-bromobenzo[b]thio-phene-2-carboxylate, 199 mg of methylboronic acid, 1.41 g of potassium phosphate, 181 mg of a [1,1'-bis(diphenylphos-phino)ferrocene]palladium (II) dichloride dichloromethane adduct, 7 ml of 1,4-dioxane, and 0.12 ml of water was stirred for 2.5 hours at 100° C. under a nitrogen atmosphere. After being cooled to room temperature, the reaction mixture was concentrated under reduced pressure. Chloroform and water were added to the residues, and insoluble matter was sepa-rated by filtration. The filtrate was extracted using chloro-form, and the organic layer was washed with saturated saline, dried over magnesium sulfate, and then concentrated under reduced pressure. The residues were subjected to silica gel column chromatography, thereby obtaining 402 mg of methyl 7-methylbenzo[b]thiophene-2-carboxylate (hereinafter, described as a "compound 25 of the present invention").

Compound 25 of the Present Invention

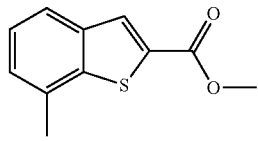

¹H-NMR (CDCl₃) δ: 8.09 (s, 1H), 7.74-7.72 (m, 1H), 7.35-7.33 (m, 1H), 7.27-7.25 (m, 1H), 3.95 (s, 3H), 2.57 (s, 3H).

Production Example 5

A mixture of 7.80 g of bromoacetaldehyde diethylacetal and 20 ml of tetrahydrofuran was added to a mixture of 8.00 g of 4-tert-butylbenzenthiol, 2.10 g of sodium hydride, and 70 ml of tetrahydrofuran. The reaction mixture was stirred for 15 hours at room temperature. Twenty (20) ml of an aqueous saturated ammonium chloride solution was added to the reaction mixture, and extraction was performed three times by using tert-butyl methyl ether. The collected organic layer was washed with water and saturated saline, dried over magnesium sulfate, and then concentrated under reduced pressure. The residues were added to a mixture of 10 g of diphosphorus pentoxide which had been stirred for 45 minutes at 175° C. and 20 g of phosphoric acid, and the residue was stirred for 5 minutes. The reaction mixture was poured into ice water, and extraction was performed three times by using tert-butyl methyl ether. The collected organic layer was washed with water and saturated saline, dried over magnesium sulfate, and then concentrated under reduced pressure. The residues were subjected to silica gel column chromatography, thereby obtaining 6.7 g of 5-tert-butyl-benzo[b]thiophene.

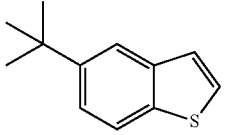

A mixture of 3.00 g of 5-tert-butylbenzo[b]thiophene and 40 ml of diethylether was stirred at 0° C., and 15 ml of n-butyllithium (2.6 M hexane solution) was added thereto. The reaction mixture was stirred for 2 hours, and then 1 g of dry ice was added thereto. After the temperature of the reaction mixture was set to room temperature, water was added thereto, and the residue was washed three times with using tert-butyl methyl ether. Concentrated hydrochloric acid was added to the aqueous layer, and extraction was performed three times by using tert-butyl methyl ether. The collected organic layer was washed with saturated saline, dried over magnesium sulfate, and then concentrated under reduced pressure. Four hundreds and two (402) mg of oxalyl chloride was added to a mixture of the residues and 30 ml of methanol under ice cooling. This mixture was stirred for 2 hours at 80° C. After being cooled to room temperature, the reaction mixture was concentrated under reduced pressure. The residues were subjected to silica gel column chromatography, thereby obtaining 416 mg of methyl 5-tert-butylbenzo[b]thiophene-2-carboxylate (hereinafter, described as a "compound 27 of the present invention").

Compound 27 of the Present Invention

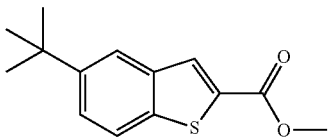 [SMILES: COC(=O)c1cc2cc(C(C)(C)C)ccc2s1]

$^1$H-NMR (CDCl$_3$) δ: 8.04 (s, 1H), 7.85-7.84 (m, 1H), 7.80-7.78 (m, 1H), 7.56-7.54 (m, 1H), 3.94 (s, 3H), 1.39 (s, 9H).

Production Example 6

A mixture of 1.00 g of 2-fluorophenyl(trifluoromethyl) ketone, 633 mg of methyl thioglycolate, 737 g of triethylamine, and 15 ml of acetonitrile was stirred for 18 hours at 90° C. After being cooled to room temperature, the reaction mixture was concentrated under reduced pressure. Water was added to the reaction mixture, and extraction was performed three times by using tert-butyl methyl ether. The collected organic layer was washed with a 1 M aqueous hydrochloric acid solution, a 1 M aqueous sodium hydroxide solution, and saturated saline, dried over magnesium sulfate, and then concentrated under reduced pressure. The residues were subjected to silica gel column chromatography, thereby obtaining 415 mg of methyl 3-trifluoromethylbenzo[b]thiophene-2-carboxylate (hereinafter, described as a "compound 28 of the present invention").

Compound 28 of the Present Invention

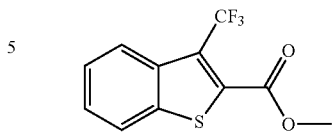

$^1$H-NMR (CDCl$_3$) δ: 8.15-8.14 (m, 1H), 7.90-7.87 (m, 1H), 7.53-7.51 (m, 2H), 3.99 (s, 3H).

Production Example 7

A mixture of 325 mg of methyl 4-iodobenzo[b]thiophene-2-carboxylate, 1.90 g of sodium pentafluoropropionate, 486 mg of copper (1) iodide, 5 ml of N-methyl-2-pyrrolidone, and 5 ml of xylene was stirred for 5 hours at 160° C. under a nitrogen atmosphere. After the reaction mixture was cooled to room temperature, chloroform and water were added thereto, and insoluble matter was separated by filtration. Extraction was performed on the filtrate by using chloroform, and then the collected organic layer was washed with saturated saline, dried over magnesium sulfate, and then concentrated under reduced pressure. The residues were subjected to silica gel column chromatography, thereby obtaining 80 mg of methyl 4-pentafluoroethylbenzo[b]thiophene-2-carboxylate (hereinafter, described as a "compound 29 of the present invention").

Compound 29 of the Present Invention

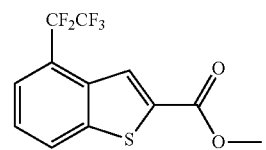

$^1$H-NMR (CDCl$_3$) δ: 8.26 (s, 1H), 8.09-8.07 (m, 1H), 7.70-7.68 (m, 1H), 7.58-7.56 (m, 1H), 3.98 (s, 3H).

Production Example 8

A mixture of 1.00 g of methyl 5-iodobenzo[b]thiophene-2-carboxylate, 2.92 g of sodium pentafluoropropionate, 1.50 g of copper (I) iodide, 15 ml of N,N-methyl-2-pyrrolidone, and 15 ml of N-dimethylformamide was stirred for 5 hours at 160° C. under a nitrogen atmosphere. After the reaction mixture was cooled to room temperature, an aqueous saturated sodium hydrogen carbonate solution and an aqueous saturated ammonia solution were added thereto, and extraction was performed three times by using tert-butyl methyl ether. The collected organic layer was washed with saturated saline, dried over magnesium sulfate, and then concentrated under reduced pressure. The residues were subjected to silica gel column chromatography, thereby obtaining 556 mg of methyl 5-pentafluoroethylbenzo[b]thiophene-2-carboxylate (hereinafter, described as a "compound 30 of the present invention").

Compound 30 of the Present Invention

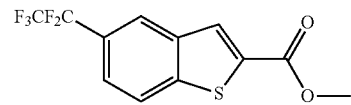

$^1$H-NMR (CDCl$_3$) δ: 8.15-8.12 (m, 2H), 8.00 (d, 1H, J=8.8 Hz), 7.64 (d, 1H, J=8.8 Hz), 3.99 (s, 3H).

Production Example 9

A mixture of 1,000 mg of methyl 5-iodobenzo[b]thiophene-2-carboxylate, 2.79 g of 1-iodoheptafluoropropane, 600 mg of copper (0), and 20 ml of N,N-dimethylformamide was stirred for 8 hours at 150° C. under a nitrogen atmosphere. After the reaction mixture was cooled to room temperature, tert-butyl methyl ether and an aqueous saturated ammonia solution were added thereto, and filtration was performed using Celite™. The filtrate was washed with water and saturated saline, dried over magnesium sulfate, and then concentrated under reduced pressure. The residues were subjected to silica gel column chromatography, thereby obtaining 351 mg of methyl 5-pentafluoropropylbenzo[b]thiophene-2-carboxylate (hereinafter, described as a "compound 31 of the present invention").

Compound 31 of the Present Invention

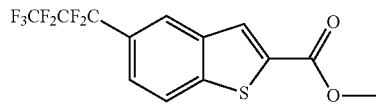

$^1$H-NMR (CDCl$_3$) δ: 8.14 (s, 1H), 8.12 (s, 1H), 8.00 (d, 1H, J=8.5 Hz), 7.63 (d, 1H, J=8.5 Hz), 3.97 (s, 3H).

Production Example 10

A mixture of 500 mg of methyl 6-bromobenzo[b]thiophene-2-carboxylate, 877 mg of tributyl vinyl tin, 213 mg of tetrakis(triphenylphosphine)palladium (0), and 4 ml of toluene was stirred for 5 hours at 110° C. under a nitrogen atmosphere. After the reaction mixture was cooled to room temperature, an aqueous saturated ammonium chloride solution and ethyl acetate were added thereto, and insoluble matter was separated by filtration. Extraction was performed on the filtrate by using ethyl acetate, and the organic layer was washed with saturated saline, dried over magnesium sulfate, and then concentrated under reduced pressure. The residues were subjected to silica gel column chromatography, thereby obtaining 229 mg of methyl 6-vinylbenzo[b]thiophene-2-carboxylate (hereinafter, described as a "compound 32 of the present invention").

Compound 32 of the Present Invention

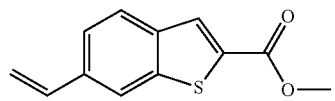

$^1$H-NMR (CDCl$_3$) δ: 8.03 (s, 1H), 7.84-7.81 (m, 2H), 7.52-7.50 (m, 1H), 6.82 (dd, 1H, J=17.6, 11.0 Hz), 5.87 (d, 1H, J=17.6 Hz), 5.36 (d, 1H, J=11.0 Hz), 3.95 (s, 3H).

Production Example 11

A mixture of 900 mg of methyl 6-bromobenzo[b]thiophene-2-carboxylate, 2.28 ml of diisopropylamine, 116 mg of dichlorobis(triphenylphosphine)palladium (II), 32 mg of copper iodide (1), 0.92 ml of trimethylsilyl acetylene, and 15 ml of toluene was stirred for 20 hours at room temperature under a nitrogen atmosphere. The reaction mixture was concentrated under reduced pressure, hexane was added to the residues, and insoluble matter was separated by filtration. The filtrate was concentrated under reduced pressure, and the residues were subjected to silica gel column chromatography, thereby obtaining 590 mg of methyl 6-(trimethylsilylethynyl)benzo[b]thiophene-2-carboxylate.

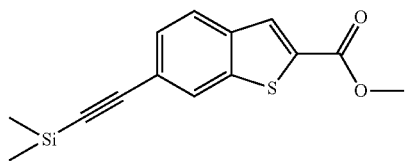

Step 2

A mixture of 590 mg of methyl 6-(trimethylsilylethynyl)benzo[b]thiophene-2-carboxylate, 215 mg of lithium hydroxide monohydrate, 4 ml of water, and 12 ml of methanol was stirred for 1 hour at 80° C. After the reaction mixture was cooled to room temperature, water and concentrated hydrochloric acid were added thereto, and the precipitated solids were collected by filtration and dried under reduced pressure, thereby obtaining 402 mg of 6-ethynylbenzo[b]thiophene-2-carboxylic acid.

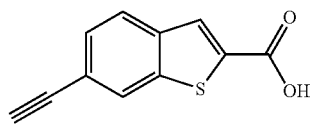

Step 3

Four point three (4.3) ml of trimethylsilyldiazomethane (2 M diethylether solution) was added dropwise at 0° C. to a mixture of 217 mg of 6-ethynylbenzo[b]thiophene-2-carboxylic acid and 10 ml of methanol. After being stirred for 15 hours at 0° C., the reaction mixture was stirred for 30 minutes at room temperature. The reaction mixture was concentrated under reduced pressure, methanol was added to the residues, and insoluble matter was collected by filtration, thereby obtaining 182 mg of methyl 6-ethynylbenzo[b]thiophene-2-carboxylate (hereinafter, described as a "compound 33 of the present invention").

Compound 33 of the Present Invention

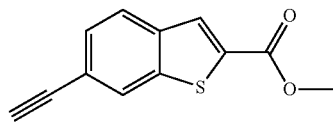

$^1$H-NMR (CDCl$_3$) δ: 6.04 (s, 1H), 8.01 (s, 1H), 7.83-7.81 (m, 1H), 7.51-7.48 (m, 1H), 3.95 (s, 3H), 3.19 (s, 1H).

Production Example 12

A mixture of 750 ng of methyl 4-bromobenzo[b]thiophene-2-carboxylate, 438 mg of phenyl boronic acid, 610 mg of lithium chloride, 528 mg of sodium carbonate, 160 mg of tetrakis(triphenylphosphine)palladium (0), 30 ml of 1,4-dioxane, and 15 ml of water was stirred for 4 hours at 100° C. under nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 477 mg of methyl 4-phenylbenzo[b]thiophene-2-carboxylate (hereinafter, described as a "compound 34 of the present invention").

Compound 34 of the Present Invention

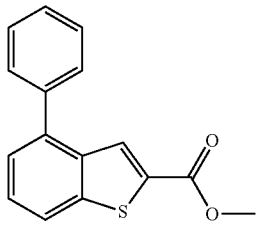 [SMILES: COC(=O)c1cc2c(-c3ccccc3)cccc2s1]

$^{1}$H-NMR (CDCl$_{3}$) δ: 8.17-8.16 (m, 1H), 7.87-7.85 (m, 1H), 7.57-7.48 (m, 5H), 7.47-7.42 (m, 1H), 7.41-7.39 (m, 1H), 3.93 (s, 3H).

Production Example 13

A mixture of 500 mg of methyl 5-bromobenzo[b]thiophene-2-carboxylate, 292 mg of phenyl boronic acid, 406 mg of lithium chloride, 351 mg of sodium carbonate, 106 mg of tetrakis(triphenylphosphine)palladium (0), 20 ml of 1,4-dioxane, and 10 ml of water was stirred for 3 hours at 100° C. After being cooled to room temperature, the reaction mixture was concentrated under reduced pressure. Water was added to the residues, and extraction was performed three times by using chloroform. The collected organic layer was washed with water and saturated saline, dried over magnesium sulfate, and then concentrated under reduced pressure. The residues were subjected to silica gel column chromatography, thereby obtaining 295 mg of methyl 5-phenylbenzo[b]thiophene-2-carboxylate (hereinafter, described as a "compound 35 of the present invention").

Compound 35 of the Present Invention

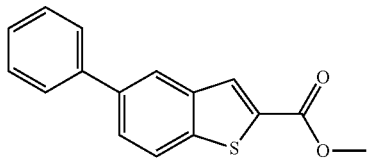

$^{1}$H-NMR (CDCl$_{3}$) δ: 8.11 (s, 1H), 8.07 (s, 1H), 7.93 (d, 1H, J=8.5 Hz), 7.71 (d, 1H, J=8.5 Hz), 7.66-7.64 (m, 2H), 7.49-7.47 (m, 2H), 7.40-7.38 (m, 1H), 3.97 (s, 3H).

Production Example 14

A mixture of 750 mg of methyl 6-bromobenzo[b]thiophene-2-carboxylate, 438 mg of phenyl boronic acid, 610 mg of lithium chloride, 528 mg of sodium carbonate, 160 mg of tetrakis(triphenylphosphine)palladium (0), 30 ml of 1,4-dioxane, and 15 ml of water was stirred for 4 hours at 100° C. under a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 475 mg of methyl 6-phenylbenzo[b]thiophene-2-carboxylate (hereinafter, described as a "compound 36 of the present invention").

Compound 36 of the present invention

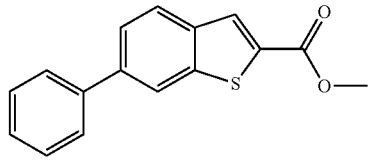 [SMILES: COC(=O)c1cc2ccc(-c3ccccc3)cc2s1]

$^{1}$H-NMR (CDCl$_{3}$) δ: 8.08 (s, 1H), 8.07-8.06 (m, 1H), 7.95-7.93 (m, 1H), 7.67-7.65 (m, 3H), 7.49-7.47 (m, 2H), 7.40-7.38 (m, 1H), 3.96 (s, 3H).

Production Example 15

A mixture of 750 mg of methyl 7-bromobenzo[b]thiophene-2-carboxylate, 438 mg of phenyl boronic acid, 610 mg of lithium chloride, 528 mg of sodium carbonate, 160 mg of tetrakis(triphenylphosphine)palladium (0), 30 ml of 1,4-dioxane, and 15 ml of water was stirred for 4 hours at 100° C. in a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 118 mg of methyl 7-phenylbenzo[b]thiophene-2-carboxylate (hereinafter, described as a "compound 37 of the present invention").

Compound 37 of the Present Invention

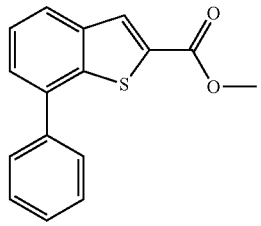 [SMILES: COC(=O)c1cc2cccc(-c3ccccc3)c2s1]

$^{1}$H-NMR (CDCl$_{3}$) δ: 8.14 (s, 1H), 7.88-7.86 (m, 1H), 7.72-7.71 (m, 2H), 7.54-7.41 (m, 5H), 3.94 (s, 3H).

Production Example 16

A mixture of 274 mg of methyl 3-chlorobenzo[b]thiophene-2-carboxylate, 221 mg of phenyl boronic acid, 541 mg of potassium, 31.7 mg of triphenyl phosphine, bis(triphenylphosphine)nickel (II) dichloride, 7 ml of toluene was stirred for 6 hours at 120° C. under a nitrogen atmosphere. After the reaction mixture was cooled to room temperature, water was added thereto, and extraction was performed using ethyl acetate. The collected organic layer was washed with saturated saline, dried over magnesium sulfate, and then concentrated under reduced pressure. The residues were subjected to silica gel column chromatography, thereby obtaining 260 mg of methyl 3-phenylbenzo[b]thiophene-2-carboxylate (hereinafter, described as a "compound 38 of the present invention".

Compound 38 of the Present Invention

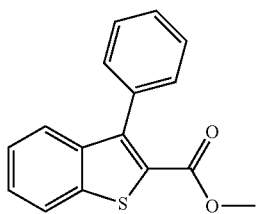 [SMILES: COC(=O)c1sc2ccccc2c1-c1ccccc1]

$^1$H-NMR (CDCl$_3$) δ: 7.90-7.88 (m, 1H), 7.56-7.35 (m, 8H), 3.78 (s, 3H).

Production Example 17

A mixture of 1.00 g of methyl 5-bromobenzo[b]thiophene-2-carboxylate, 750 mg of 2-chlorophenyl boronic acid, 813 mg of lithium chloride, 704 mg of sodium carbonate, 213 mg of tetrakis(triphenylphosphine)palladium (0), 40 ml of 1,4-dioxane, and 20 ml of water was stirred for 4 hours at 100° C. under a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 871 mg of methyl 5-(2-chlorophenyl)benzo[b]thiophene-2-carboxylate (hereinafter, described as a "compound 39 of the present invention").

Compound 39 of the Present Invention

$^1$H-NMR (CDCl$_3$) δ: 8.10 (s, 1H), 7.94-7.91 (m, 2H), 7.57-7.55 (m, 1H), 7.52-7.50 (m, 1H), 7.41-7.38 (m, 1H), 7.37-7.30 (m, 2H), 3.96 (s, 3H).

Production Example 18

A mixture of 1.00 g of methyl 5-bromobenzo[b]thiophene-2-carboxylate, 750 mg of 3-chlorophenyl boronic acid, 813 mg of lithium chloride, 704 mg of sodium carbonate, 213 mg of tetrakis(triphenylphosphine)palladium (0), 40 ml of 1,4-dioxane, and 20 ml of water was stirred for 4 hours at 100° C. in a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 870 mg of methyl 5-(3-chlorophenyl)benzo[b]thiophene-2-carboxylate (hereinafter, described as a "compound 40 of the present invention").

Compound 40 of the Present Invention

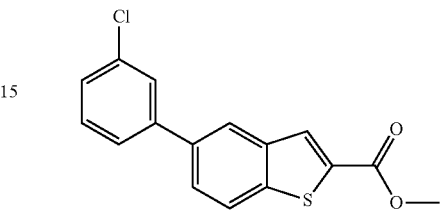

$^1$H-NMR (CDCl$_3$) δ: 8.11 (s, 1H), 8.04 (d, 1H, J=1.9 Hz), 7.94 (d, 1H, J=8.5 Hz), 7.67 (dd, 1H, J=8.5, 1.9 Hz), 7.64-7.63 (m, 1H), 7.53-7.51 (m, 1H), 7.42-7.40 (m, 1H), 7.37-7.35 (m, 1H), 3.97 (s, 3H).

Production Example 19

A mixture of 1.00 g of methyl 5-bromobenzo[b]thiophene-2-carboxylate, 750 mg of 4-chlorophenyl boronic acid, 813 mg of lithium chloride, 704 mg of sodium carbonate, 213 mg of tetrakis(triphenylphosphine)palladium (0), 40 ml of 1,4-dioxane, and 20 ml of water was stirred for 4 hours at 100° C. in a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 721 mg of methyl 5-(4-chlorophenyl)benzo[b]thiophene-2-carboxylate (hereinafter, described as a "compound 41 of the present invention").

Compound 41 of the Present Invention

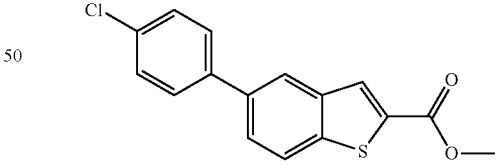

$^1$H-NMR (CDCl$_3$) δ: 8.11 (s, 1H), 8.03 (d, 1H, J=1.8 Hz), 7.93 (d, 1H, J=8.3 Hz), 7.66 (dd, 1H, J=8.3, 1.8 Hz), 7.57 (d, 2H, J=8.8 Hz), 7.44 (d, 2H, J=8.8 Hz), 3.97 (s, 3H).

Production Example 20

A mixture of 750 mg of methyl 7-bromobenzo[b]thiophene-2-carboxylate, 489 mg of 3-methylphenyl boronic acid, 610 mg of lithium chloride, 528 mg of sodium carbonate, 160 ng of tetrakis(triphenylphosphine)palladium (0), 30 ml of 1,4-dioxane, and 15 ml of water was stirred for 3 hours at 100° C. After being cooled to room temperature, the reaction mixture was concentrated under reduced pressure. Chloroform was added to the residues, and insoluble matter was separated by filtration. After water was added to the filtrate, extraction was performed by using chloroform. The organic layer was washed with saturated saline, dried over magnesium sulfate, and then concentrated under reduced pressure. The residues were subjected to silica gel column chromatography, thereby obtaining 385 mg of methyl 7-(3-methylphenyl)benzo[b]thiophene-2-carboxylate (hereinafter, described as a "compound 42 of the present invention").

Compound 42 of the Present Invention

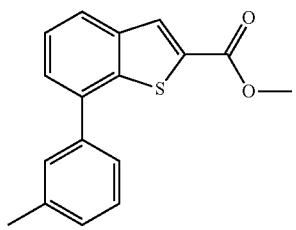

$^1$H-NMR (CDCl$_3$) δ: 8.13 (s, 1H), 7.86-7.84 (m, 1H), 7.52-7.46 (m, 4H), 7.41-7.39 (m, 1H), 7.26-7.23 (m, 1H), 3.94 (s, 3H), 2.45 (s, 3H).

Production Example 21

A mixture of 1.0 g of methyl 5-bromobenzo[b]thiophene-2-carboxylate, 911 mg of 4-trifluoromethylphenylboronic acid, 913 mg of lithium chloride, 704 mg of sodium carbonate, 213 mg of tetrakis(triphenylphosphine)palladium (0), 40 ml of 1,4-dioxane, and 20 ml of water was stirred for 2.5 hours at 100° C. After being cooled to room temperature, the reaction mixture was concentrated under reduced pressure. Chloroform was added to the residues, and insoluble matter was separated by filtration. After water was added to the filtrate, extraction was performed using chloroform. The organic layer was washed with water and saturated saline, dried over magnesium sulfate, and then concentrated under reduced pressure. Tert-butyl methyl ether was added to the residues, and insoluble matter was collected by filtration and dried under reduced pressure, thereby obtaining 845 mg of methyl 5-(4-trifluoromethylphenyl)benzo[b]thiophene-2-carboxylate (hereinafter, described as a "compound 43 of the present invention").

Compound 43 of the Present Invention

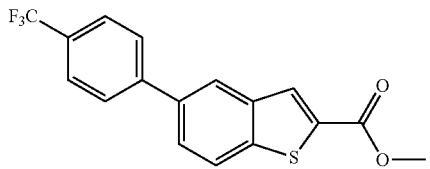 [SMILES: COC(=O)c1cc2cc(-c3ccc(C(F)(F)F)cc3)ccc2s1]

$^1$H-NMR (CDCl$_3$) δ: 8.13 (s, 1H), 8.09-8.08 (m, 1H), 7.98-7.95 (m, 1H), 7.76-7.75 (m, 4H), 7.71-7.69 (m, 1H), 3.97 (s, 3H).

Production Example 22

A mixture of 750 mg of methyl 7-bromobenzo[b]thiophene-2-carboxylate, 575 mg of 2-methoxyphenyl boronic acid, 610 mg of lithium chloride, 528 mg of sodium carbonate, 160 mg of tetrakis(triphenylphosphine)palladium (0), 30 ml of 1,4-dioxane, and 15 ml of water was stirred for 3 hours at 100° C. After being cooled to room temperature, the reaction mixture was concentrated under reduced pressure. Chloroform was added to the residues, and insoluble matter was separated by filtration. After water was added to the filtrate, extraction was performed using chloroform. The organic layer was washed with saturated saline, dried over magnesium sulfate, and then concentrated under reduced pressure. The residues were subjected to silica gel column chromatography, thereby obtaining 543 mg of methyl 7-(2-methoxyphenyl)benzo[b]thiophene-2-carboxylate (hereinafter, described as a "compound 44 of the present invention").

Compound 44 of the Present Invention

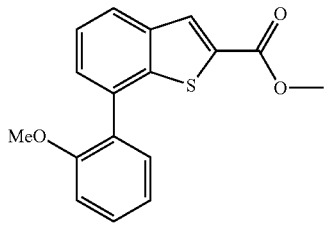 [SMILES: COC(=O)c1cc2cccc(-c3ccccc3OC)c2s1]

$^1$H-NMR (CDCl$_3$) δ: 8.11 (s, 1H), 7.87-7.85 (m, 1H), 7.50-7.41 (m, 4H), 7.08-7.05 (m, 2H), 3.91 (s, 3H), 3.79 (s, 3H).

Production Example 23

A mixture of 500 mg of methyl 6-bromobenzo[b]thiophene-2-carboxylate, 494 mg of 4-(trifluoromethoxy)phenylboronic acid, 407 mg of lithium chloride, 352 mg of sodium carbonate, 107 mg of tetrakis(triphenylphosphine) palladium (0), 20 ml of 1,4-dioxane, and 10 ml of water was stirred for 3.5 hours at 100° C. After being cooled to room temperature, the reaction mixture was concentrated under reduced pressure. Chloroform was added to the residues, and insoluble matter was separated by filtration. After water was added to the filtrate, extraction was performed using chloroform. The organic layer was washed with saturated saline, dried over magnesium sulfate, and then concentrated under reduced pressure. The residues were subjected to silica gel column chromatography, thereby obtaining 509 mg of methyl 6-(4-trifluoromethoxyphenyl)benzo[b]thiophene-2-carboxylate (hereinafter, described as a "compound 45 of the present invention")

Compound 45 of the Present Invention

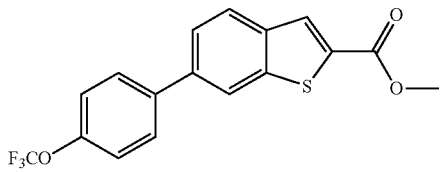 [SMILES: COC(=O)c1cc2ccc(-c3ccc(OC(F)(F)F)cc3)cc2s1]

$^1$H-NMR (CDCl$_3$) δ: 8.09 (s, 1H), 8.03 (s, 1H), 7.96-7.94 (n, 1H), 7.68-7.66 (m, 2H), 7.62-7.60 (m, 1H), 7.34-7.32 (m, 2H), 3.97 (s, 3H).

Production Example 24

A mixture of 500 mg of methyl 5-bromobenzo[b]thiophene-2-carboxylate, 679 mg of 2-(tributyl-stannyl)pyridine, 107 mg of tetrakis(triphenylphosphine)palladium (0), and 4 ml of toluene was stirred for 4.5 hours at 120° C. under a nitrogen atmosphere. After the reaction mixture was cooled to room temperature, ethyl acetate and water were added thereto. The aqueous layer was extracted twice by using ethyl acetate, and the collected organic layer was washed with saturated saline, dried over magnesium sulfate, and then concentrated under reduced pressure. The residues were subjected to silica gel column chromatography, thereby obtaining 368 mg of methyl 5-(2-pyridyl)benzo[b]thiophene-2-carboxylate (hereinafter, described as a "compound 46 of the present invention").

Compound 46 of the Present Invention

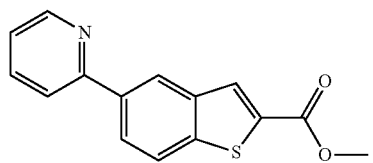 [SMILES: COC(=O)c1cc2cc(-c3ccccn3)ccc2s1]

$^1$H-NMR (CDCl$_3$) δ: 8.74-8.72 (m, 1H), 8.52-8.51 (m, 1), 8.14-8.11 (m, 2H), 7.97-7.95 (m, 1H), 7.83-7.77 (m, 2H), 7.29-7.27 (m, 1H), 3.97 (s, 3H).

Production Example 25

A mixture of 1.00 g of methyl 5-bromobenzo[b]thiophene-2-carboxylate, 623 mg of 3-pyridyl boronic acid, 813 mg of lithium chloride, 704 mg of sodium carbonate, 213 mg of tetrakis(triphenylphosphine)palladium (0), 40 ml of 1,4-dioxane, and 20 ml of water was stirred for 4 hours at 100° C. under a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 754 mg of methyl 5-(3-pyridyl)benzo[b]thiophene-2-carboxylate (hereinafter, described as a "compound 47 of the present invention").

Compound 47 of the Present Invention

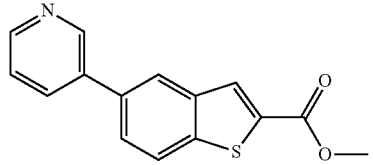 [SMILES: COC(=O)c1cc2cc(-c3cccnc3)ccc2s1]

$^1$H-NMR (CDCl$_3$) δ: 8.93-8.90 (m, 1H), 8.64-8.63 (m, 1H), 8.13 (s, —H), 8.07 (s, 1H), 7.99-7.97 (m, 1H), 7.95-7.93 (m, 1H), 7.70-7.67 (m, 1H), 7.42-7.40 (m, 1H), 3.97 (s, 3H).

Production Example 26

A mixture of 1.00 g of methyl 5-bromobenzo[b]thiophene-2-carboxylate, 623 mg of 4-pyridyl boronic acid, 813 mg of lithium chloride, 704 mg of sodium carbonate, 213 mg of tetrakis(triphenylphosphine)palladium (0), 40 ml of 1,4-dioxane, and 20 ml of water was stirred for 4 hours at 100° C. under a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 467 mg of methyl 5-(4-pyridyl)benzo[b]thiophene-2-carboxylate (hereinafter, described as a "compound 48 of the present invention").

Compound 48 of the Present Invention

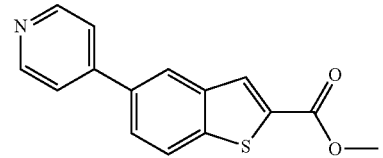 [SMILES: COC(=O)c1cc2cc(-c3ccncc3)ccc2s1]

$^1$H-NMR (CDCl$_3$) δ: 8.70 (dd, 2H, J=4.5, 1.5 Hz), 8.15-8.13 (m, 2H), 8.00-7.97 (m, 1H), 7.74-7.72 (m, 1H), 7.57 (dd, 2H, J=4.5, 1.5 Hz), 3.98 (s, 3H).

Production Example 27

A mixture of 500 mg of methyl 6-bromobenzo[b]thiophene-2-carboxylate, 458 mg of 2-trifluoromethyl-5-pyridyl boronic acid, 407 mg of lithium chloride, 352 mg of sodium carbonate, 107 mg of tetrakis(triphenylphosphine)palladium (0), 20 ml of 1,4-dioxane, and 10 ml of water was stirred for 2 hours at 100° C. After being cooled to room temperature, the reaction mixture was concentrated under reduced pressure. Chloroform was added to the residues, and insoluble matter was separated by filtration. After water was added to the filtrate, extraction was performed using chloroform. The organic layer was washed with saturated saline, dried over magnesium sulfate, and then concentrated under reduced pressure. The residues were subjected to silica gel column chromatography, thereby obtaining 366 mg of methyl 6-(6-trifluoromethyl-3-pyridyl)benzo[b]thiophene-2-carboxylate (hereinafter, described as a "compound 49 of the present invention").

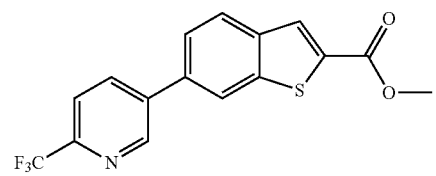 [SMILES: COC(=O)c1cc2ccc(-c3ccc(C(F)(F)F)nc3)cc2s1]

Compound 49 of the Present Invention $^1$H-NMR (CDCl$_3$) δ: 9.02 (s, 1H), 8.12-8.10 (m, 3H), 8.03-8.01 (m, 1H), 7.81-7.79 (m, 1H), 7.66-7.63 (m, 1H), 3.98 (s, 3H).

Production Example 28

A mixture of 1.00 g of 2-methoxycarbonylbenzo[b]thiophen-5-yl-boronic acid, 518 mg of 2-bromopyrimidine, 718 mg of lithium chloride, 622 mg of sodium carbonate, 188 mg of tetrakis(triphenylphosphine)palladium (0), 40 ml of 1,4- dioxane, and 20 ml of water was stirred for 3.5 hours at 100° C. in a nitrogen atmosphere. After being cooled to room temperature, the reaction mixture was concentrated under reduced pressure. Chloroform and water were added to the residue. The aqueous layer was extracted twice by using chloroform, and the collected organic layer was washed with saturated saline, dried over magnesium sulfate, and then concentrated under reduced pressure. The residues were recrystallized from chloroform and ethyl acetate, thereby obtaining 329 mg of methyl 5-(2-pyrimidinyl)benzo[b]thiophene-2-carboxylate (hereinafter, described as a "compound 50 of the present invention").

Compound 50 of the Present Invention

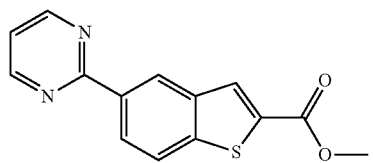 [SMILES: COC(=O)c1cc2cc(-c3ncccn3)ccc2s1]

$^1$H-NMR (CDCl$_3$) δ: 8.99 (d, 1H, J=1.8 Hz), 8.85 (d, 2H, J=4.8 Hz), 8.57 (dd, 1H, J=8.8, 1.8 Hz), 8.16 (s, 1H), 7.98 (d, 1H, J=8.8 Hz), 7.23 (t, 1H, C=4.8 Hz), 3.97 (s, 3H).

Production Example 29

A mixture of 353 mg of methyl 4-bromobenzo[b]thiophene-2-carboxylate, 217 mg of 2-thiophene boronic acid, 287 mg of lithium chloride, 248 mg of sodium carbonate, 75 mg of tetrakis(triphenylphosphine)palladium (0), 10 ml of 1,4-dioxane, and 5 ml of water was stirred for 3 hours at 100° C. under a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 350 mg of methyl 4-(2-thienyl)benzo[b]thiophene-2-carboxylate (hereinafter, described as a "compound 52 of the present invention").

Compound 52 of the Present Invention

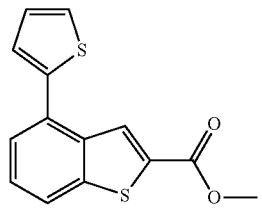 [SMILES: COC(=O)c1cc2c(-c3cccs3)cccc2s1]

$^1$H-NMR (CDCl$_3$) δ: 8.42 (s, 1H), 7.84-7.82 (m, 1H), 7.51-7.48 (m, 2H), 7.44-7.42 (m, 1H), 7.36-7.35 (m, 1H), 7.20-7.18 (m, 1H), 3.95 (s, 3H).

Production Example 30

A mixture of 1.00 g of methyl 5-bromobenzo[b]thiophene-2-carboxylate, 613 mg of 2-thiophene boronic acid, 813 mg of lithium chloride, 704 mg of sodium carbonate, 213 mg of tetrakis(triphenylphosphine)palladium (0), 40 ml of 1,4-dioxane, and 20 ml of water was stirred for 4 hours at 100° C. under a nitrogen atmosphere. After being cooled to room temperature, the reaction mixture was concentrated under reduced pressure. Chloroform and water were added to the residues, and insoluble matter was separated by filtration. The aqueous layer was extracted twice by using chloroform, and the collected organic layer was washed with saturated saline, dried over magnesium sulfate, and then concentrated under reduced pressure. The residues were subjected to silica gel column chromatography, thereby obtaining 607 mg of methyl 5-(2-thienyl)benzo[b]thiophene-2-carboxylate (hereinafter, described as a "compound 53 of the present invention").

Compound 53 of the Present Invention

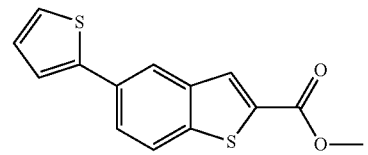 [SMILES: COC(=O)c1cc2cc(-c3cccs3)ccc2s1]

$^1$H-NMR (CDCl$_3$) δ: 8.09-8.08 (m, 1H), 8.07 (s, 1H), 7.87-7.85 (m, 1H), 7.74-7.71 (m, 1H), 7.38-7.37 (m, 1H), 7.32-7.31 (m, 1H), 7.12-7.11 (m, 1H), 3.96 (s, 3H).

Production Example 31

A mixture of 340 mg of 2-fluoro-5-acetylbenzaldehyde, 283 mg of methyl thioglycolate, 567 mg of potassium carbonate, and 10 ml of N,N-dimethylformamide was stirred for 2 hours at 80° C. After the reaction mixture was cooled to room temperature, water was added thereto, and the precipitated solids were collected by filtration. The obtained solids were washed with water and dried under reduced pressure, thereby obtaining 277 mg of methyl 5-acetylbenzo[b]thiophene-2-carboxylate (hereinafter, described as a "compound 54 of the present invention").

Compound 54 of the present invention

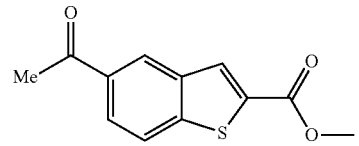 [SMILES: COC(=O)c1cc2cc(C(C)=O)ccc2s1]

$^1$H-NMR (CDCl$_3$) δ: 8.48 (d, 1H, J=1.8 Hz), 8.15 (s, 1H), 8.06 (dd, 1H, J=8.6, 1.8 Hz), 7.94 (d, 1H, J=8.6 Hz), 3.97 (s, 3H), 2.70 (s, 3H).

Production Example 32

Step 1

A mixture of 7.0 g of 2-(5-bromo-2-fluorophenyl)-1,3-dioxolane and 10 ml of tetrahydrofuran was added dropwise to a mixture of 895 mg of magnesium and 20 ml of tetrahydrofuran at 50° C., followed by stirring for 30 minutes. Thereafter, 3.82 g of N-methoxy-N-methyltrifluoroacetamide was added to the reaction mixture at 0° C., followed by stirring for 1.5 hours at room temperature. Forty (40) ml of 1 M hydrochloric acid was added to the reaction mixture, and the residue was stirred for 3 hours under reflux. After the reaction mixture was cooled to room temperature, extraction was performed using ethyl acetate. The organic layer was washed with saturated saline, dried over magnesium sulfate, and concentrated under reduced pressure. The residues were subjected to silica gel column chromatography, thereby obtaining 2.69 g of 2-fluoro-5-trifluoroacetylbenzaldehyde.

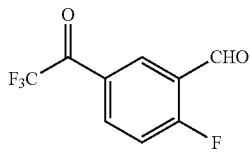 [SMILES: O=Cc1cc(C(=O)C(F)(F)F)ccc1F]

Step 2

A mixture of 1.00 g of 2-fluoro-5-(trifluoroacetyl)benzaldehyde, 391 mg of methyl thioglycolate, 763 mg of potassium carbonate, and 10 ml of N,N-dimethylformamide was stirred for 1 hour at 80° C. Water was added to the reaction mixture, and extraction was performed using ethyl acetate. The organic layer was washed with water and saturated saline, dried over magnesium sulfate, and then concentrated under reduced pressure. The residues were subjected to silica gel column chromatography, thereby obtaining 462 mg of methyl 5-trifluoroacetylbenzo[b]thiophene-2-carboxylate (hereinafter, described as a "compound 55 of the present invention").

Compound 55 of the Present Invention

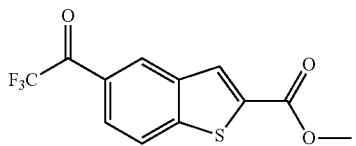 [SMILES: COC(=O)c1cc2cc(C(=O)C(F)(F)F)ccc2s1]

$^1$H-NMR (CDCl$_3$) δ: 8.60 (s, 1H), 8.19-8.20 (m, 1H), 8.14-8.11 (m, 1H), 8.04-8.01 (m, 1H), 3.99 (s, 3H).

Production Example 33

Step 1

Five point one (5.1) ml of n-butyllithium (1.6 M hexane solution) was added dropwise to a mixture of 2.00 g of 2-(5-bromo-2-fluorophenyl)-1,3-dioxolane and 10 ml of tetrahydrofuran at −70° C., followed by stirring for 30 minutes. A mixture of 919 mg of benzonitrile and 5 ml of tetrahydrofuran was added dropwise to the reaction mixture at −70° C., followed by stirring for 1 hour. Thereafter, the reaction mixture was stirred for 1.5 hours at room temperature, and then 30 ml of 1 M hydrochloric acid was added thereto, followed by stirring for 3 hours at 65° C. After the reaction mixture was cooled to room temperature, extraction was performed using ethyl acetate. The organic layer was washed with saturated saline, dried over magnesium sulfate, and concentrated under reduced pressure. The residues were subjected to silica gel column chromatography, thereby obtaining 414 mg of 5-benzoyl-2-fluorobenzaldehyde.

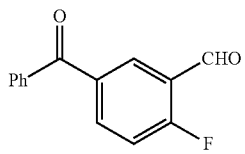

Step 2

A mixture of 414 mg of 5-benzoyl-2-fluorobenzaldehyde, 250 mg of methyl thioglycolate, 501 mg of potassium carbonate, and 3 ml of N,N-dimethylformamide was stirred for 1 hour at 80° C. Water was added to the reaction mixture, and extraction was performed using ethyl acetate. The organic layer was washed with saturated saline, dried over magnesium sulfate, and then concentrated under reduced pressure. The residues were subjected to silica gel column chromatography, thereby obtaining 271 mg of methyl 5-benzoylbenzo[b]thiophene-2-carboxylate (hereinafter, described as a "compound 56 of the present invention").

Compound 56 of the Present Invention

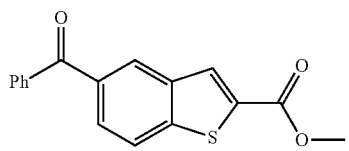 [SMILES: COC(=O)c1cc2cc(C(=O)c3ccccc3)ccc2s1]

$^1$H-NMR (CDCl$_3$, δ: 8.30 (s, 1H), 8.13 (s, 1H), 7.98-7.94 (m, 2H), 7.84-7.82 (m, 2H), 7.64-7.62 (m, 1H), 7.54-7.50 (m, 2H), 3.97 (s, 3H:

Production Example 34

Step 1

A mixture of 250 mg of methyl 4-cyanobenzo[b]thiophene-2-carboxylate, 608 mg of sodium hydroxide, 2 ml of water, and 3 ml of methanol was stirred for 14 hours under reflux. After the reaction mixture was cooled to room temperature, 5 ml of water and 2 ml of concentrated hydrochloric acid were added thereto, and the precipitated solids were collected by filtration and dried under reduced pressure, thereby obtaining 331 mg of benzo[b]thiophene-2,4-dicarboxylic acid.

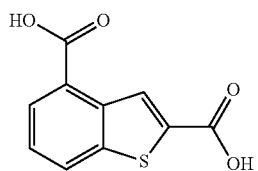 [SMILES: O=C(O)c1cc2c(C(=O)O)cccc2s1]

Step 2

A mixture of 200 mg of benzo[b]thiophene-2,4-dicarboxylic acid, 100 mg of sulfuric acid, and 5 ml of methanol was stirred for 23 hours under reflux. Water was added to the reaction mixture, and extraction was performed using ethyl acetate. The organic layer was washed with saturated saline, dried over magnesium sulfate, and then concentrated under reduced pressure, thereby obtaining 220 mg of dimethyl benzo[b]thiophene-2,4-dicarboxylate—(hereinafter, described as a "compound 57 of the present invention").

Compound 57 of the Present Invention

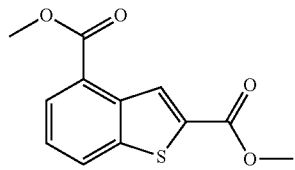

$^1$H-NMR (CDCl$_3$) δ: 8.89 (s, 1H), 8.18-8.16 (m, 1H), 8.07-8.05 (m, 1H), 7.53-7.51 (m, 1H), 4.02 (s, 3H), 3.97 (s, 3H).

Production Example 35

A mixture of 1.00 g of methyl 3-formyl-4-nitrobenzoate, 609 mg of methyl thioglycolate, 761 mg of potassium carbonate, and 15 ml of N,N-dimethylformamide was stirred for 3 hours at 60° C. The reaction mixture was cooled to room temperature, water was added to the reaction mixture, and extraction was performed three times with ethyl acetate. The collected organic layer was washed with water and saturated saline, dried over magnesium sulfate, and then concentrated under reduced pressure. The residues were subjected to silica gel column chromatography, thereby obtaining 323 mg of dimethyl benzo[b]thiophene-2,5-dicarboxylate (hereinafter, described as a "compound 58 of the present invention").

Compound 58 of the Present Invention

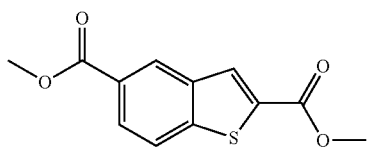

$^1$H-NMR (CDCl$_3$) δ: 8.60-8.56 (m, 1H), 8.13-8.10 (m, 2H), 7.93-7.91 (m, 1H), 3.97 (s, 3H), 3.97 (s, 3H).

Production Example 36

Step 1

A mixture of 1.87 g of 2,3-dihydro-1-benzothiophene-2,3-dione, 1.5 g of sodium carbonate, and 13.5 ml of water was stirred for 1 hour at room temperature. An aqueous solution composed of 1.16 g of chloroacetic acid, 0.6 g of sodium carbonate, and 5.4 ml of water was added dropwise to the mixture, followed by stirring for 1 hour at 80° C. After the reaction mixture was cooled to room temperature, insoluble matter was separated by filtration. Fifteen (15) g of sodium hydroxide was added to the filtrate under ice cooling, followed by stirring for 2 hours at room temperature. Concentrated hydrochloric acid was added to the aqueous solution under ice cooling, and the precipitated solids were collected by filtration and dried under reduced pressure, thereby obtaining 440 mg of benzo[b]thiophene-2,3-dicarboxylic acid.

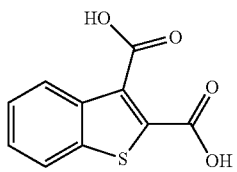 [SMILES: O=C(O)c1sc2ccccc2c1C(=O)O]

Step 2

A mixture of 280 mg of benzo[b]thiophene-2,3-dicarboxylic acid, 200 mg of concentrated sulfuric acid, and 6 ml of methanol was stirred for 4 hours at 80° C. After being cooled to room temperature, the reaction mixture was concentrated under reduced pressure. Ethyl acetate was added to the residues, and the residue was washed with an aqueous saturated sodium hydrogen carbonate solution and saturated saline, dried over magnesium sulfate, and then concentrated under reduced pressure. The residues were subjected to silica gel column chromatography, thereby obtaining 220 mg of dimethyl benzo[b]thiophene-2,3-dicarboxylate (hereinafter, described as a "compound 60 of the present invention").

Compound 60 of the Present Invention

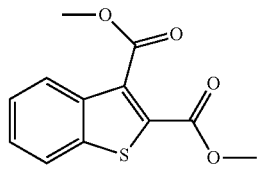 [SMILES: COC(=O)c1sc2ccccc2c1C(=O)OC]

$^1$H-NMR (CDCl$_3$) δ: 7.95-7.93 (m, 1H), 7.87-7.85 (m, 1H), 7.50-7.47 (m, 2H), 4.03 (s, 3H), 3.95 (s, 3H).

Production Example 37

Step 1

Two point zero zero (2.00) g of molecular sieves (4 Å), 341 mg of copper (II) chloride dehydrate, and 200 ml of water were stirred for 7 hours at room temperature, and the residue was collected by filtration. The substance collected by filtration was washed with 20 ml of water and 20 ml of acetone and then vacuum-dried for 1 hour at 150° C., thereby obtaining 2.00 g of light green solids.

Step 2

A mixture of 500 mg of light green solids obtained in Step 1, 1.00 g of methyl 5-cyanobenzo[b]thiophene-2-carboxylate, 2.8 ml of acetaldoxime, and 20 ml of methanol was stirred for 24 hours at 65° C. The reaction mixture was filtered, and the filtrate was concentrated under reduced pressure. Acetone was added to the residues, and insoluble matter was collected by filtration and dried under reduced pressure, thereby obtaining 696 mg of methyl 5-aminocarbonylbenzo[b]thiophene-2-carboxylate (hereinafter, described as a "compound 61 of the present invention").

Compound 61 of the Present Invention

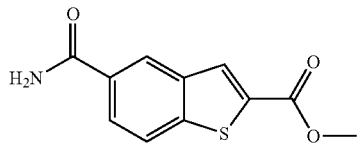

$^1$H-NMR (CDCl$_3$) δ: 8.37-8.36 (m, 1H), 8.12 (s, 1H), 7.95-7.92 (m, 1H), 7.89-7.89 (m, 1H), 6.10 (br s, 1H), 5.64 (br s, 1H), 3.97 (s, 3H).

Production Example 38

A mixture of 1.20 g of methyl 4-aminobenzo[b]thiophene-2-carboxylate, 2.7 g of methyl iodide, 1.76 g of potassium carbonate, and 4 ml of acetonitrile was stirred for 7 hours at 60° C. After the reaction mixture was cooled to room temperature, 60 ml of water and 60 ml of ethyl acetate were added thereto, insoluble matter was separated by filtration, and extraction was performed on the filtrate by using ethyl acetate. The collected organic layer was washed with saturated saline, dried over magnesium sulfate, and then concentrated under reduced pressure, thereby obtaining 255 mg of 4-(dimethylamino)benzo[b]thiophene-2-carboxylic acid (hereinafter, described as a "compound 66 of the present invention").

Compound 66 of the Present Invention

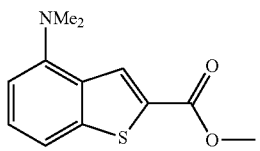

$^1$H-NMR (CDCl$_3$) δ: 8.25 (s, 1H), 7.42-7.41 (m, 1H), 7.35-7.33 (m, 1H), 6.82-6.80 (m, 1H), 3.94 (s, 3H), 2.97 (s, 6H).

Production Example 39

A mixture of 500 mg of methyl 5-aminobenzo[b]thiophene-2-carboxylate, 323 mg of acetic anhydride, 623 mg of diisopropylethylamine, and 10 ml of dichloromethane was stirred for 4 hours at room temperature. The reaction mixture was washed with an aqueous saturated sodium hydrogen carbonate solution and saturated saline, dried over magnesium sulfate, and concentrated under reduced pressure. The residues were subjected to silica gel column chromatography, thereby obtaining 449 mg of methyl 5-(acetylamino)benzo[b]thiophene-2-carboxylate (hereinafter, described as a "compound 67 of the present invention").

Compound 67 of the Present Invention

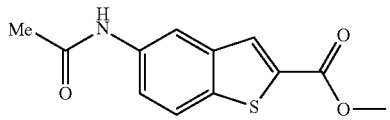 [SMILES: COC(=O)c1cc2cc(NC(C)=O)ccc2s1]

$^1$H-NMR (CDCl$_3$) δ: 8.22-8.21 (m, 1H), 7.99 (s, 1H), 7.78-7.76 (m, 1H), 7.44-7.40 (m, 2H), 3.94 (s, 3H), 2.22 (s, 3H).

Production Example 40

A mixture of 300 mg of methyl 5-aminobenzo[b]thiophene-2-carboxylate, 310 g of 1-ethyl-3-(3-dimethylaminopropyl)carbodiimide hydrochloride, 294 mg of benzoic acid, 18.4 mg of N,N-dimethyl-4-aminopyridine, and 20 ml of tetrahydrofuran was stirred for 24 hours at room temperature. The reaction mixture was concentrated under reduced pressure, and tert-butyl methyl ether was added to the residues. The organic layer was washed with a 1 M aqueous hydrochloric acid solution, a 1 M aqueous sodium hydrogen carbonate solution, and saturated saline, dried over magnesium sulfate, and concentrated under reduced pressure, thereby obtaining 318 mg of methyl 5-benzoylaminobenzo[b]thiophene-2-carboxylate (hereinafter, described as a "compound 68 of the present invention").

Compound 68 of the Present Invention

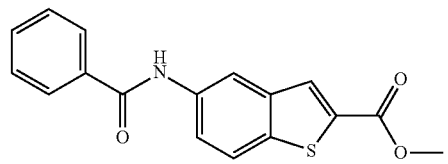 [SMILES: COC(=O)c1cc2cc(NC(=O)c3ccccc3)ccc2s1]

$^1$H-NMR (CDCl$_3$) δ: 8.40 (br s, 1H), 8.05 (s, 1H), 7.91-7.90 (m, 3H), 7.86-7.84 (m, 1H), 7.58-7.53 (m, 4H), 3.96 (s, 3H).

Production Example 41

A mixture of 5.60 g of acetic anhydride and 3.11 g of formic acid was stirred for 2 hours at 60° C. After the reaction mixture was cooled to room temperature, 10 ml of tetrahydrofuran was added thereto. A mixture of 4.37 g of methyl 3-amino-benzo[b]thiophene-2-carboxylate and 50 ml of tetrahydrofuran was added dropwise to the above mixture under ice cooling. The reaction mixture was stirred for 2 hours at room temperature. The reaction mixture was concentrated under reduced pressure, and the residues was recrystallized from tetrahydrofuran, thereby obtaining 4.06 g of methyl 3-formylaminobenzo[b]thiophene-2-carboxylate (hereinafter, described as a "compound 69 the present invention").

Compound 69 of the Present Invention

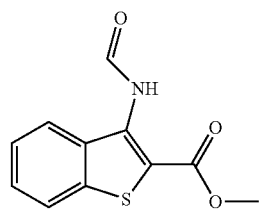 [SMILES: COC(=O)c1sc2ccccc2c1NC=O]

$^1$H-NMR (DMSO-D$_6$) δ: 10.45 (br s, 1H), 8.45-8.43 (m, 1H), 8.05-8.03 (m, 1H), 7.90 (br s, 1H), 7.60-7.58 (m, 1H), 7.51-7.49 (m, 1H), 3.84 (s, 3H).

Production Example 42

A mixture of 10 of methyl 3-amino-benzo[b]thiophene-2-carboxylate and 2 ml of tetrahydrofuran was stirred under ice cooling, and then 24 mg of 60% sodium hydride was added thereto. Forty and five (45) mg of acetyl chloride was added dropwise to the reaction mixture under ice cooling, followed by stirring for 46 hours at room temperature. Water was added to the mixture, and the precipitated solids were collected by filtration, washed with hexane, and then dried under reduced pressure, thereby obtaining 82 mg of methyl 3-acetylaminobenzo[b]thiophene-2-carboxylate (hereinafter, described as a "compound 70 of the present invention").

Compound 70 of the Present Invention

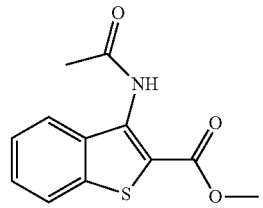 [SMILES: COC(=O)c1sc2ccccc2c1NC(C)=O]

$^1$H-NMR (CDCl$_3$) δ: 9.47 (br s, 1H), 8.10-8.08 (m, 1H), 7.77-7.75 (m, 1H), 7.50-7.46 (m, 1H), 7.42-7.38 (m, 1H), 3.94 (s, 3H), 2.33 (s, 3H).

Production Example 43

A mixture of 200 mg of methyl 5-aminobenzo[b]thiophene-2-carboxylate, 456 mg of trifluoroacetic anhydride, 205 mg of triethylamine, and 10 ml of tetrahydrofuran was stirred for 24 hours at room temperature. Tert-butyl methyl ether was added to the reaction mixture, and the residue was washed with water, 1 M hydrochloric acid, an aqueous saturated sodium hydrogen carbonate solution, and saturated saline, dried over magnesium sulfate, and concentrated under reduced pressure. The residues were subjected to silica gel column chromatography, thereby obtaining 260 mg of methyl 5-trifluoroacetylaminobenzo[b]thiophene-2-carboxylate (hereinafter, described as a "compound 71 of the present invention").

Compound 71 of the Present Invention

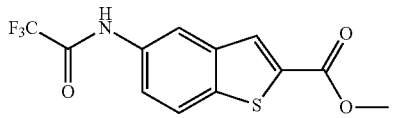 [SMILES: COC(=O)c1cc2cc(NC(=O)C(F)(F)F)ccc2s1]

$^1$H-NMR (DMSO-D$_6$) δ: 11.48 (br s, 1H), 8.40 (d, 1H, J=2.0 Hz), 8.27 (s, 1H), 8.11 (d, 1H, J=8.8 Hz), 7.75 (dd, 1H, J=8.8, 2.0 Hz), 3.92 (s, 3H).

Production Example 44

A mixture of 150 mg of methyl 5-aminobenzo[b]thiophene-2-carboxylate, 170 mg of chloroacetyl chloride, 304 mg of triethylamine, and 10 ml of tetrahydrofuran was stirred for 24 hours at room temperature. Tert-butyl methyl ether was added to the reaction mixture, and the residue was washed with water, 1 M hydrochloric acid, an aqueous saturated sodium hydrogen carbonate solution, and saturated saline, dried over magnesium sulfate, and concentrated under reduced pressure. The residues were subjected to silica gel column chromatography, thereby obtaining 160 mg of methyl 5-chloroacetylaminobenzo[b]thiophene-2-carboxylate (hereinafter, described as a "compound 72 of the present invention").

Compound 72 of the Present Invention

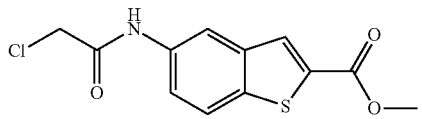 [SMILES: COC(=O)c1cc2cc(NC(=O)CCl)ccc2s1]

$^1$H-NMR (CDCl$_3$) δ: 8.36 (br s, 1H), 8.27 (s, 1H), 8.03 (s, 1H), 7.85-7.83 (m, 1H), 7.52-7.50 (m, 1H), 4.24 (s, 2H), 3.95 (s, 3H).

Production Example 45

Step 1

A mixture of 500 mg of methyl 5-aminobenzo[b]thiophene-2-carboxylate, 552 mg of methanesulfonyl chloride, 623 mg of diisopropylethylamine, and 10 ml of dichloromethane was stirred for 4 hours at room temperature. After the reaction mixture was concentrated under reduced pressure, water was added to the residues, and the precipitated solids were collected by filtration. The obtained solids were washed with water and hexane and dried under reduced pressure, thereby obtaining 449 mg of methyl 5-[bis(methylsulfonyl)amino]benzo[b]thiophene-2-carboxylate.

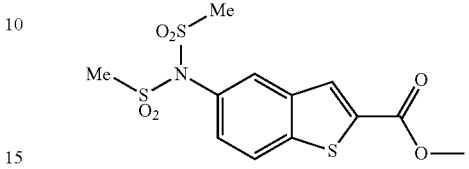

Step 2

A mixture of 760 mg of methyl 5-[bis(methylsulfonyl)amino]benzo[b]thiophene-2-carboxylate, 228 mg of lithium hydroxide monohydrate, 3 ml of water, and 6 ml of methanol was stirred for 2 hours at 80° C. The reaction mixture was concentrated under reduced pressure, water was added to the residues, and the residue was washed with tert-butyl methyl ether. Concentrated hydrochloric acid was added to the aqueous layer, and extraction was performed by using tert-butyl methyl ether. The collected organic layer was washed with saturated saline, dried over magnesium sulfate, and then concentrated under reduced pressure, thereby obtaining 568 mg of 5-methylsulfonylaminobenzo[b]thiophene-2-carboxylic acid.

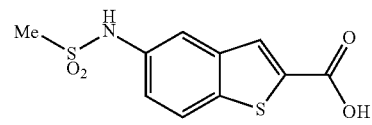

Step 3

A mixture of 406 mg of 5-(methylsulfonyl)aminobenzo[b]thiophene-2-carboxylic acid, 200 mg of sulfuric acid, and 6 ml of methanol was stirred for 6 hours at 90° C. Water was added to the reaction mixture, and extraction was performed using ethyl acetate. The collected organic layer was washed with saturated saline, dried over magnesium sulfate, and then concentrated under reduced pressure. The residues were subjected to silica gel column chromatography, thereby obtaining 315 mg of methyl 5-methylsulfonylaminobenzo[b]thiophene-2-carboxylate (hereinafter, described as a "compound 81 of the present invention").

Compound 81 of the Present Invention

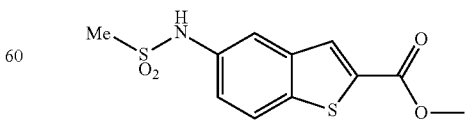

$^1$H-NMR (CDCl$_3$) δ: 8.02 (s, 1H), 7.85 (d, 1H, J=8.8 Hz), 7.79 (d, 1H, J=2.3 Hz), 7.33 (dd, 1H, J=8.8, 2.3 Hz), 6.70 (s, 1H), 3.96 (s, 3H), 3.04 (s, 3H).

Production Example 46

Step 1

A mixture of 500 mg of methyl 5-aminobenzo[b]thiophene-2-carboxylate, 1.37 g of trifluoromethanesulfonic anhydride, 623 mg of diisopropylethylamine, and 10 ml of dichloromethane was stirred for 4 hours at room temperature. An aqueous saturated sodium hydrogen carbonate solution was added to the reaction mixture, and extraction was performed using chloroform. The collected organic layer was washed with saturated saline, dried over magnesium sulfate, and then concentrated under reduced pressure. The residues were subjected to silica gel column chromatography, thereby obtaining 500 mg of methyl 5-[bis(trifluoromethylsulfonyl)amino]benzo[b]thiophene-carboxylate.

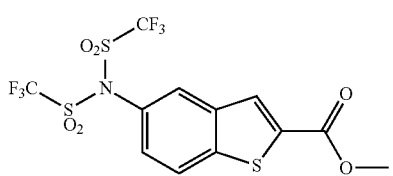

Step 2

A mixture of 493 mg of methyl 5-[bis(trifluoromethylsulfonyl)amino]benzo[b]thiophene-2-carboxylate, 152 mg of lithium hydroxide monohydrate, 3 ml of water, and 6 ml of methanol was stirred for 2 hours at 80° C. The reaction mixture was concentrated under reduced pressure, water was added to the residues, and the residue was washed with tert-butyl methyl ether. Concentrated hydrochloric acid was added to the aqueous layer, and extraction was performed using tert-butyl methyl ether. The collected organic layer was washed with saturated saline, dried over magnesium sulfate, and then concentrated under reduced pressure, thereby obtaining 308 mg of 5-(trifluoromethylsulfonylamino)benzo[b]thiophene-2-carboxylic acid.

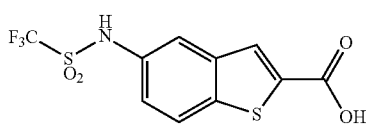 [SMILES: CS(=O)(=O)Nc1ccc2sc(C(=O)O)cc2c1]

Step 3

A mixture of 182 mg of 5-(trifluoromethylsulfonylamino)benzo[b]thiophene-2-carboxylic acid, 100 mg of sulfuric acid, and 6 ml of methanol was stirred for 6 hours at 80° C. Water was added to the reaction mixture, and extraction was performed using ethyl acetate. The collected organic layer was washed with saturated saline, dried over magnesium sulfate, and then concentrated under reduced pressure. The residues were subjected to silica gel column chromatography, thereby obtaining 169 mg of methyl 5-(trifluoromethylsulfonylamino)benzo[b]thiophene-2-carboxylate (hereinafter, described as a "compound 83 of the present invention").

Compound 83 of the Present Invention

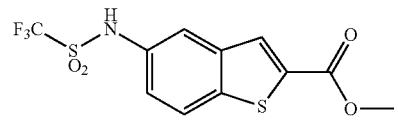 [SMILES: COC(=O)c1cc2cc(NS(C)(=O)=O)ccc2s1]

$^1$H-NMR (CDCl$_3$) δ: 8.04 (s, 1H), 7.88 (d, 1H, J=8.7 Hz), 7.83 (d, 1H, J=2.1 Hz), 7.38 (dd, 1H, J=8.7, 2.1 Hz), 3.97 (s, 3H).

Production Example 47

A mixture of 600 mg of methyl 3-hydroxybenzo[b]thiophene-2-carboxylate, 819 mg of methyl iodide, 797 mg of potassium carbonate, and 10 ml of N,N-dimethylformamide was stirred for 4 hours at 70° C. After the reaction mixture was cooled to room temperature, tert-butyl methyl ether was added thereto. The residue was washed with water, an aqueous 1 M sodium hydrogen carbonate solution, and saturated saline, dried over magnesium sulfate, and then dried under reduced pressure. The residues were subjected to silica gel column chromatography, thereby obtaining 195 mg of methyl 3-methoxybenzo[b]thiophene-2-carboxylate. Hereinafter, the compound is described as a "compound 94 of the present invention".

Compound 94 of the Present Invention

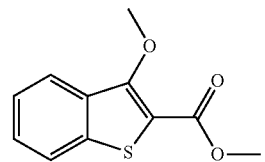

$^1$H-NMR (CDCl$_3$) δ: 7.90-7.88 (m, 1H), 7.76-774 (m, 1H), 7.52-7.46 (m, 1H), 7.42-7.38 (m, 1H), 4.17 (s, 3H), 3.93 (s, 3H).

Production Example 48

A mixture of 600 mg of methyl 3-hydroxybenzo[b]thiophene-2-carboxylate, 800 mg of ethyl iodide, 797 mg of potassium carbonate, and 10 ml of N,N-dimethylformamide was stirred for 12 hours at room temperature. Tert-butyl methyl ether was added thereto, and the residue was washed with water, a 1 M aqueous sodium hydroxide solution, and saturated saline, dried over magnesium sulfate, and then concentrated under reduced pressure. The residues were subjected to silica gel column chromatography, thereby obtaining 540 mg of methyl 3-ethoxybenzo[b]thiophene-2-carboxylate (hereinafter, described as a "compound 95 of the present invention").

Compound 95 of the Present Invention

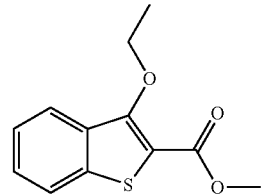 [SMILES: CCOc1c(C(=O)OC)sc2ccccc12]

$^1$H-NMR (CDCl$_3$) δ: 7.89-7.87 (m, 1H), 7.76-7.74 (m, 1H), 7.50-7.46 (m, 1H), 7.42-7.38 (m, 1H), 4.40 (q, 2H, J=7.0 Hz), 3.92 (s, 3H), 1.48 (t, 3H, J=7.0 Hz).

Production Example 49

A mixture of 300 mg of methyl 3-hydroxybenzo[b]thiophene-2-carboxylate, 450 mg of isopropyl iodide, 400 mg of potassium carbonate, and 10 ml of N,N-dimethylformamide was stirred for 12 hours at 70° C. After the reaction mixture was cooled to room temperature, tert-butyl methyl ether was added thereto. The residue was washed with water, a 1 M aqueous sodium hydroxide solution, and saturated saline, dried over magnesium sulfate, and then concentrated under reduced pressure. The residues were subjected to silica gel column chromatography, thereby obtaining 321 mg of methyl 3-isopropoxybenzo[b]thiophene-2-carboxylate (hereinafter, described as a "compound 96 of the present invention").

Compound 96 of the Present Invention

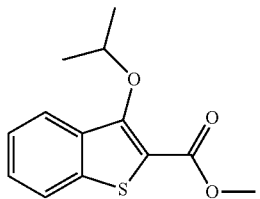 [SMILES: COC(=O)c1sc2ccccc2c1OC(C)C]

$^1$H-NMR (CDCl$_3$) δ: 7.87 (d, 1H, J=8.0 Hz), 7.74 (d, 1H, J=8.0 Hz), 7.49-7.45 (m, 1H), 7.41-7.37 (m, 1H), 4.87-4.81 (m, 1H), 3.92 (s, 3H), 1.41-1.40 (m, 6H).

Production Example 50

A mixture of 600 mg of methyl 3-hydroxybenzo[b]thiophene-2-carboxylate, 933 mg of benzyl bromide, 797 mg of potassium carbonate, and 10 ml of N,N-dimethylformamide was stirred for 12 hours at room temperature. Tert-butyl methyl ether was added to the reaction mixture, and the residue was washed with water, a 1 M aqueous sodium hydroxide solution, and saturated saline, dried over magnesium sulfate, and concentrated under reduced pressure. The residues were subjected to silica gel column chromatography, thereby obtaining 560 mg of methyl 3-benzyloxybenzo[b]thiophene-2-carboxylate (hereinafter, described as a "compound 97 of the present invention").

Compound 97 of the Present Invention

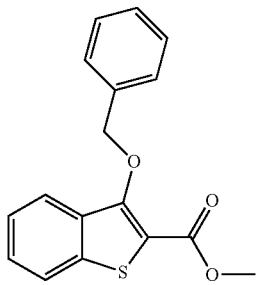 [SMILES: COC(=O)c1sc2ccccc2c1OCc1ccccc1]

$^1$H-NMR (CDCl$_3$) δ: 7.81-7.79 (m, 1H), 7.76-7.74 (m, 1H), 7.54-7.45 (m, 3H), 7.42-7.34 (m, 4H), 5.36 (s, 2H), 3.93 (s, 3H).

Production Example 51

A mixture of 3.00 g of 2-fluoro-3-trifluoromethoxybenzaldehyde, 1.33 g of methyl thioglycolate, 2.66 g of potassium carbonate, and 10 ml of N,N-dimethylformamide was stirred for 2 hours at 80° C. After the reaction mixture was cooled to room temperature, water was added thereto, and extraction was performed three times by using ethyl acetate. The collected organic layer was washed with water and saturated saline, dried over magnesium sulfate, and then concentrated under reduced pressure, thereby obtaining 1.38 g of methyl 5-trifluoromethoxybenzo[b]thiophene-2-carboxylate (hereinafter, described as a "compound 98 of the present invention").

Compound 98 of the Present Invention

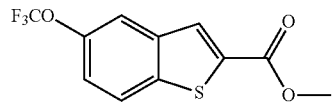

$^1$H-NMR (CDCl$_3$) δ: 8.05 (s, 1H), 7.87 (d, 1H, J=8.8 Hz), 7.73 (d, 1H, J=1.0 Hz), 7.34 (dq, 1H, J=8.8, 1.0 Hz), 3.96 (s, 3H).

Production Example 52

A mixture of 300 mg of methyl 6-hydroxybenzo[b]thiophene-2-carboxylate, 206 mg of propargyl bromide, 260 mg of potassium carbonate, and 5 ml of acetonitrile was stirred for 4 hours at 60° C. Ethyl acetate was added to the reaction mixture, and the residue was washed with water and saturated saline, dried over magnesium sulfate, and then concentrated under reduced pressure. The residues were subjected to silica gel column chromatography, thereby obtaining 327 mg of methyl 6-prepargyloxybenzo[b]thiophene-2-carboxylate (hereinafter, described as a "compound 99 of the present invention").

Compound 99 of the Present Invention

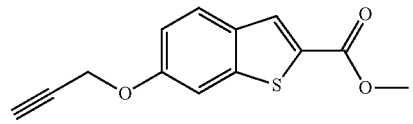 [SMILES: C#CCOc1ccc2cc(C(=O)OC)sc2c1]

$^1$H-NMR (CDCl$_3$) δ: 7.98 (s, 1H), 7.77 (d, 1H, J=8.8 Hz), 7.40 (s, 1H), 7.09 (d, 1H, J=8.8 Hz), 4.78 (s, 2H), 3.93 (s, 3H), 2.57 (s, 1H).

Production Example 53

A mixture of 300 mg of methyl 6-hydroxybenzo[b]thiophene-2-carboxylate, 414 mg of 4-(trifluoromethyl)benzyl bromide, 260 mg of potassium carbonate, and 5 ml of acetonitrile was stirred for 4 hours at 60° C. Chloroform was added to the reaction mixture, and the residue was washed with water and saturated saline, dried over magnesium sulfate, and then concentrated under reduced pressure. The residues were washed with a mixture of 6 ml of hexane and 18 ml of ethyl acetate and then dried under reduced pressure, thereby obtaining 486 mg of methyl 6-(4-trifluoromethylbenzyloxy)benzo[b]thiophene-2-carboxylate (hereinafter, described as a "compound 100 of the present invention").

Compound 100 of the Present Invention

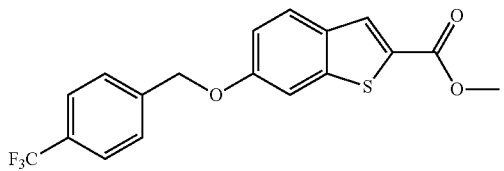 [SMILES: COC(=O)c1cc2ccc(OCc3ccc(C(F)(F)F)cc3)cc2s1]

¹H-NMR (CDCl₃) δ: 7.98 (s, 1H), 7.79-7.76 (m, 1H), 7.67 (d, 2H, J=8.1 Hz), 7.58 (d, 2H, J=8.1 Hz), 7.35 (s, 1H), 7.12-7.10 (m, 1H), 5.21 (s, 2H), 3.93 (s, 3H).

Production Example 54

A mixture of 300 mg of methyl 6-hydroxybenzo[b]thiophene-2-carboxylate, 348 mg of 3-methoxybenzyl bromide, 260 mg of potassium carbonate, and 5 ml of acetonitrile was stirred for 4 hours at 60° C. Ethyl acetate was added to the reaction mixture, and the residue was washed with water and saturated saline, dried over magnesium sulfate, and then concentrated under reduced pressure. The residues were subjected to silica gel column chromatography, thereby obtaining 442 mg of methyl 6-(3-methoxybenzyloxy)benzo[b]thiophene-2-carboxylate (hereinafter, described as a "compound 101 of the present invention").

Compound 101 of the Present Invention

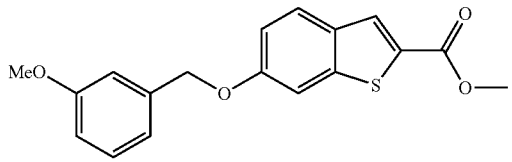 [SMILES: COC(=O)c1cc2ccc(OCc3cccc(OC)c3)cc2s1]

¹H-NMR (CDCl₃) δ: 7.97 (s, 1H), 7.75 (d, 1H, J=8.8 Hz), 7.35 (d, 1H, J=2.3 Hz), 7.33-7.31 (m, 1H), 7.10 (dd, 1H, J=8.8, 2.3 Hz), 7.04-7.01 (m, 2H), 6.90-6.87 (m, 1H), 5.12 (s, 2H), 3.92 (s, 3H), 3.83 (s, 3H).

Production Example 55

A mixture of 450 mg of methyl 7-hydroxybenzo[b]thiophene-2-carboxylate, 565 mg of 2-iodo toluene, 41.1 mg of copper iodide, 1.41 g of cesium carbonate, 90.4 mg of N,N-dimethylglycine hydrochloride, and 5 ml of 1,4-dioxane was stirred for 23 hours under reflux. After the reaction mixture was cooled to room temperature, water was added thereto, and extraction was performed by using ethyl acetate. The organic layer was washed with water and saturated saline, dried over magnesium sulfate, and then concentrated under reduced pressure. The residues were subjected to silica gel column chromatography, thereby obtaining 91 mg of methyl 7-(2-methylphenoxy)benzo[b]thiophene-2-carboxylate (hereinafter, described as a "compound 102 of the present invention").

Compound 102 of the Present Invention

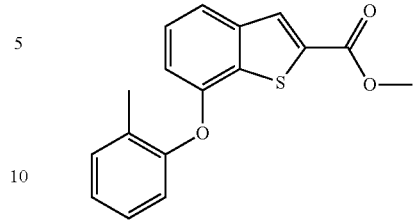

¹H-NMR (CDCl₃) δ: 8.10 (s, 1H), 7.59-7.57 (m, 1H), 7.31-7.28 (m, 2H), 7.22-7.18 (m, 1H), 7.14-7.12 (m, 1H), 7.01-6.99 (m, 1H), 6.71-6.69 (m, 1H), 3.95 (s, 3H), 2.26 (s, 3H).

Production Example 56

A mixture of 450 mg of methyl 7-hydroxybenzo[b]thiophene-2-carboxylate, 705 mg of 4-iodobenzotrifluoride, 41.1 mg of copper iodide, 1.41 g of cesium carbonate, 90.4 mg of N,N-dimethylglycine hydrochloride, and 5 ml of 1,4-dioxane was stirred for 23 hours under reflux. After the reaction mixture was cooled to room temperature, water was added thereto, and extraction was performed by using ethyl acetate. The organic layer was washed with water and saturated saline, dried over magnesium sulfate, and concentrated under reduced pressure. The residues were subjected to silica gel column chromatography, thereby obtaining 333 mg of methyl 7-(4-trifluoromethylphenoxy)benzo[b]thiophene-2-carboxylate (hereinafter, described as a "compound 103 of the present invention").

Compound 103 of the Present Invention

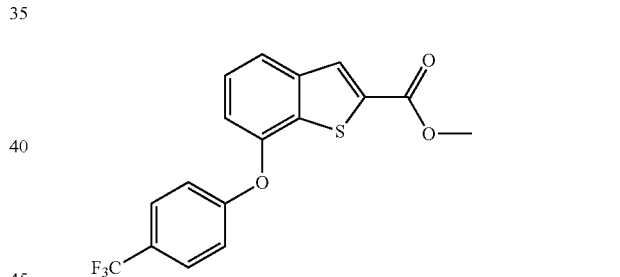

¹H-NMR (CDCl₃) δ: 8.11 (s, 1H), 7.74-7.72 (m, 1H), 7.61 (d, 2H, J=8.6 Hz), 7.42-0.40 (m, 1H), 7.12 (d, 2H, J=8.6 Hz), 7.07-7.05 (m, 1H), 3.94 (s, 3H).

Production Example 57

A mixture of 450 mg of methyl 7-hydroxybenzo[b]thiophene-2-carboxylate, 746 mg of 1-iodo-4-(trifluoromethoxy)benzene, 41.1 mg of copper iodide, 1.41 g of cesium carbonate, 90.4 mg of N,N-dimethylglycine hydrochloride, and 5 ml of 1,4-dioxane was stirred for 23 hours under reflux. After the reaction mixture was cooled to room temperature, water was added thereto, and extraction was performed by using ethyl acetate. The organic layer was washed with water and saturated saline, dried over magnesium sulfate, and concentrated under reduced pressure. The residues were subjected to silica gel column chromatography, thereby obtaining 241 mg of methyl 7-[4-(trifluoromethoxy)phenoxy)]benzo[b]thiophene-2-carboxylate (hereinafter, described as a "compound 104 of the present invention").

Compound 104 of the Present Invention

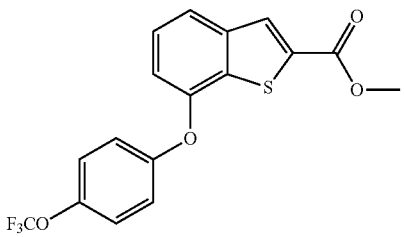 [SMILES: COC(=O)c1cc2cccc(Oc3ccc(OC(F)(F)F)cc3)c2s1]

¹H-NMR (CDCl₃) δ: 8.10 (s, 1H), 7.68-7.66 (m, 1H), 7.38-7.36 (m, 1H), 7.22 (d, 2H, J=9.1 Hz), 7.09 (d, 2H, J=9.1 Hz), 6.97-6.95 (m, 1H), 3.94 (s, 3H).

Production Example 58

A mixture of 300 mg of methyl 3-hydroxybenzo[b]thiophene-2-carboxylate, 294 mg of acetyl chloride, 291 mg of triethylamine, and 10 ml of tetrahydrofuran was stirred for 12 hours at room temperature. After being cooled to room temperature, the reaction mixture was concentrated under reduced pressure. Tert-butyl methyl ether was added to the residues, and the residue was washed with water and 1 M hydrochloric acid, a 1 M aqueous sodium hydroxide solution, and saturated saline, dried over magnesium sulfate, and concentrated under reduced pressure, thereby obtaining 343 mg of methyl 3-acetyloxybenzo[b]thiophene-2-carboxylate (hereinafter, described as a "compound 105 of the present invention").

Compound 105 of the Present Invention

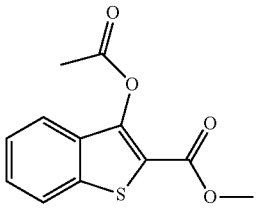 [SMILES: COC(=O)c1sc2ccccc2c1OC(C)=O]

¹H-NMR (CDCl₃) δ: 7.82-7.80 (m, 1H), 7.73-7.71 (m, 1H), 7.53-7.49 (m, 1H), 7.45-7.41 (m, 1H), 3.91 (s, 3H), 2.48 (s, 3H).

Production Example 59

Step 1

Six point zero (6.0) ml of n-butyllithium (1.6 M hexane solution) was added dropwise to a mixture of 2.27 g of 2-(5-bromo-2-fluorophenyl)-1,3-dioxolane and 10 ml of tetrahydrofuran at −70° C., followed by stirring for 30 minutes. A mixture of 1.04 g of dimethyl disulfide and 10 ml of tetrahydrofuran was added dropwise to the reaction mixture at −70° C., followed by stirring for 1 hour. Thereafter, the reaction mixture was stirred for 1.5 hours at room temperature, and 30 ml of 1 M hydrochloric acid was added thereto, followed by stirring for 3 hours at 65° C. After the reaction mixture was cooled to room temperature, extraction was performed by using ethyl acetate. The organic layer was washed with saturated saline, dried over magnesium sulfate, and then concentrated under reduced pressure. The residues were subjected to silica gel column chromatography, thereby obtaining 1.00 g of 2-fluoro-5-methylthiobenzaldehyde.

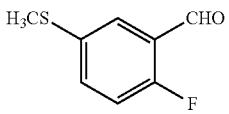

Step 2

A mixture of 1.00 g of 2-fluoro-5-methylthiobenzaldehyde, 811 mg of methyl thioglycolate, 1.62 g of potassium carbonate, and 10 ml of N,N-dimethylformamide was stirred for 1 hour at 80° C. After the reaction mixture was cooled to room temperature, water was added thereto, and extraction was performed three times by using ethyl acetate. The collected organic layer was washed with water and saturated saline, dried over magnesium sulfate, and then concentrated under reduced pressure. The residues were subjected to silica gel column chromatography, thereby obtaining 385 mg of methyl 5-methylthiobenzo[b]thiophene-2-carboxylate (hereinafter, described as a "compound 108 of the present invention").

Compound 108 of the Present Invention

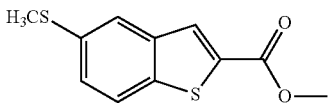

¹H-NMR (CDCl₃) δ: 7.98 (s, 1H), 7.76 (d, 1H, J=8.6 Hz), 7.72 (d, 1H, J=2.0 Hz), 7.39 (dd, 1H, J=8.6, 2.0 Hz), 3.95 (s, 3H), 2.55 (s, 3H).

Production Example 60

Step 1

A mixture of 7.0 g of 2-(5-bromo-2-fluorophenyl)-1,3-dioxolane and 10 ml of tetrahydrofuran was added dropwise to a mixture of 895 mg of magnesium and 20 ml of tetrahydrofuran at 50° C., followed by stirring for 30 minutes. Thereafter, 1.36 g of sulfur was added to the reaction mixture at 0° C., followed by stirring for 1.5 hours at room temperature. Fifty (50) ml of an aqueous saturated ammonium chloride solution and 50 ml of ethyl acetate was added to the reaction mixture, and insoluble matter was separated by filtration. Extraction was performed on the filtrate by using ethyl acetate. The organic layer was washed with saturated saline, dried over magnesium sulfate, and then concentrated under reduced pressure. The residues were subjected to silica gel column chromatography, thereby obtaining 3.78 g of bis[3-(1,3-dioxolan-2-yl)-4-fluorophenyl]disulfide.

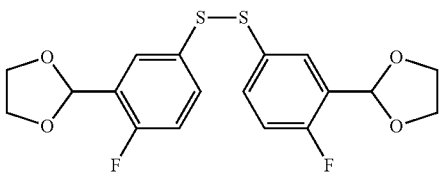 [SMILES: Fc1ccc(SSc2ccc(F)c(C3OCCO3)c2)cc1C1OCCO1]

Step 2

A mixture of 804 mg of [3-(1,3-dioxolan-2-yl)-4-fluorophenyl]disulfide, 267 mg of sodium borohydride, and 10 ml of tetrahydrofuran was stirred for 10 hours at room temperature. Fifty (50) ml of an aqueous saturated ammonium chloride solution was added to the reaction mixture, and extraction was performed using ethyl acetate. The organic layer was washed with saturated saline, dried over magnesium sulfate, and then concentrated under reduced pressure. A mixture of 734 mg of 1-trifluoromethyl-3,3-dimethyl-1,2-benziodoxole and 5 ml of dichloromethane was added to a mixture of the obtained residues and 10 ml of dichloromethane at −78° C., followed by stirring for 3 hours. Thereafter, the reaction mixture was stirred for 20 hours at room temperature, and then the residue was subjected to silica gel column chromatography, thereby obtaining 785 mg of 3-(1,3-dioxolan-2-yl)-4-fluoro-1-(trifluoromethylthio)benzene.

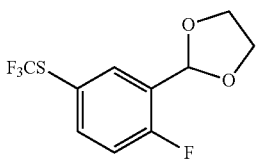

Step 3

Six (6) ml of 1 M hydrochloric acid was added to a mixture of 785 mg of 3-(1,3-dioxolan-2-yl)-4-fluoro-1-(trifluoromethylthio)benzene and 10 ml of tetrahydrofuran, followed by stirring for 10 hours under reflux. After the reaction mixture was cooled to room temperature, 40 ml of water was added thereto, and extraction was performed using ethyl acetate. The organic layer was washed with saturated saline, dried over magnesium sulfate, and then concentrated under reduced pressure. The residues were subjected to silica gel column chromatography, thereby obtaining 604 mg of 2-fluoro-5-trifluoromethylthiobenzaldehyde.

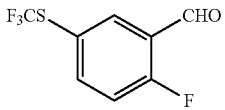

Step 4

A mixture of 600 mg of 2-fluoro-5-(trifluoromethylthio)benzaldehyde, 369 mg of methyl thioglycolate, 556 mg of potassium carbonate, and 6 ml of N,N-dimethylformamide was stirred for 1 hour at 80° C. After the reaction mixture was cooled to room temperature, water was added thereto, and extraction was performed three times by using ethyl acetate. The collected organic layer was washed with water and saturated saline, dried over magnesium sulfate, and then concentrated under reduced pressure. The residues were subjected to silica gel column chromatography, thereby obtaining 489 mg of methyl 5-trifluoromethylthiobenzo[b]thiophene-2-carboxylate (hereinafter, described as a "compound 109 of the present invention").

Compound 109 of the Present Invention

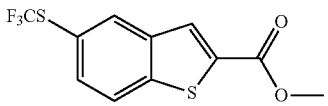

$^1$H-NMR (CDCl$_3$) δ: 8.20 (s, 1H), 8.08 (s, 1H), 7.92 (d, 1H, J=8.6 Hz), 7.69 (d, 1H, J=8.6 Hz), 3.97 (3H, s).

Production Example 61

Step 1

M-chloroperbenzoic acid (ca. 70%) 588 mg was added to a mixture of 609 mg of 3-(1,3-dioxolan-2-yl)-4-fluoro-1-(trifluoromethylthio)benzene and 10 ml of chloroform at 0° C. The temperature of the reaction mixture was returned to room temperature, followed by stirring for 19 hours. An aqueous saturated sodium hydrogen carbonate solution was added to the mixture, and extraction was performed using chloroform. The organic layer was washed with saturated saline, dried over magnesium sulfate, and then concentrated under reduced pressure. The residues were subjected to silica gel column chromatography, thereby obtaining 506 mg of 3-(1,3-dioxolan-2-yl)-4-fluoro-1-trifluoromethylsulfinylbenzene.

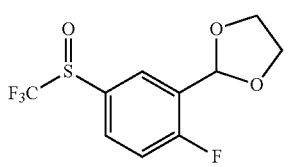 [SMILES: O=S(c1ccc(F)c(C2OCCO2)c1)C(F)(F)F]

Step 2

Five (5) ml of 1 M hydrochloric acid was added to a mixture of 504 ml of 3-(1,3-dioxolan-2-yl)-4-fluoro-1-trifluoromethylsulfinylbenzene and 5 ml of tetrahydrofuran, followed by stirring for 15 hours under reflux. After the reaction mixture was cooled to room temperature, 20 ml of water was added thereto, and extraction was performed using ethyl acetate. The organic layer was washed with saturated saline, dried over magnesium sulfate, and then concentrated under reduced pressure. A mixture of 432 g of the obtained residues, 210 mg of methyl thioglycolate, 323 mg of potassium carbonate, and 5 ml of N,N-dimethylformamide was stirred for 2 hours at 80° C. After the reaction mixture was cooled to room temperature, water was added thereto, and extraction was performed using ethyl acetate. The organic layer was washed with water and saturated saline, dried over magnesium sulfate, and then concentrated under reduced pressure. The residues were subjected to silica gel column chromatography, thereby obtaining 409 mg of methyl 5-(trifluoromethylsulfinyl)benzo[b]thiophene-2-carboxylate (hereinafter, described as a "compound 110 of the present invention").

Compound 110 of the Present Invention

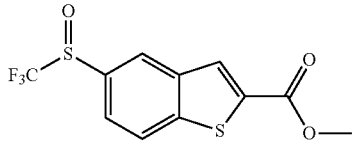

$^1$H-NMR (CDCl$_3$) δ: 6.36 (s, 1H), 8.16 (d, 1H, J=0.8 Hz), 8.10 (d, 1H, J=8.6 Hz), 7.80 (dd, 1H, J=8.6, 0.8 Hz), 3.99 (s, 3H).

Production Example 62

One point zero three (1.03) g (ca. 70%) of m-chloroperbenzoic acid was added to a mixture of 450 mg of 3-(1,3- dioxolan-2-yl)-4-fluoro-1-(trifluoromethylthio)benzene and 10 ml of chloroform at 0° C. The temperature of the reaction mixture was returned to room temperature, followed by stirring for 28 hours. An aqueous saturated sodium hydrogen carbonate solution was added to the mixture, and extraction was performed using chloroform. The organic layer was washed with saturated saline and dried over magnesium sulfate. Five (5) ml of 1 M hydrochloric acid was added to the mixture of the obtained residues and 5 ml of tetrahydrofuran, followed by stirring for 15 hours under reflux. After the reaction mixture was cooled to room temperature, 20 ml of water was added thereto, and extraction was performed using ethyl acetate. The organic layer was washed with saturated saline, dried over magnesium sulfate, and then concentrated under reduced pressure. A mixture of 432 mg of the obtained residues, 196 mg of methyl thioglycolate, 302 mg of potassium carbonate, and 5 ml of N,N-dimethylformamide was stirred for 2 hours at 80° C. After the reaction mixture was cooled to room temperature, water was added thereto, and extraction was performed using ethyl acetate. The organic layer was washed with water and saturated saline, dried over magnesium sulfate, and then concentrated under reduced pressure. The residues were subjected to silica gel column chromatography, thereby obtaining 178 mg of methyl 5-trifluoromethylsulfonylbenzo[b]thiophene-2-carboxylate (hereinafter, described as a "compound 111 of the present invention").

Compound 111

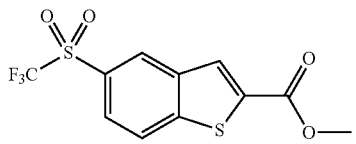 [SMILES: COC(=O)c1cc2cc(S(=O)(=O)C(F)(F)F)ccc2s1]

$^1$H-NMR (CDCl$_3$) δ: 8.60 (s, 1H), 8.22-8.21 (m, 1H), 8.16-8.14 (m, 1H), 8.03-8.01 (m, 1H), 4.00 (s, 3H).

Production Example 63

A mixture of 1.20 g of 2-fluoro-5-pentafluorosulfuranylbenzaldehyde, 520 mg of methyl thioglycolate, 607 mg of potassium carbonate, and 15 ml of N,N-dimethylformamide was stirred for 2 hours at 60° C., and the reaction mixture was cooled to room temperature. Water was added to the reaction mixture, and extraction was performed three times by using tert-butyl methyl ether. The collected organic layer was washed with water and saturated saline, dried over magnesium sulfate, and then concentrated under reduced pressure, thereby obtaining 1.40 g of methyl 5-pentafluorosulfuranylbenzo[b]thiophene-2-carboxylate (hereinafter, described as a "compound 117 of the present invention").

Compound 117 of the Present Invention

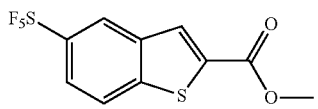

$^1$H-NMR (CDCl$_3$) δ: 8.29 (d, 1H, J=2.2 Hz), 8.13 (s, 1H), 7.94 (d, 1H, J=90 Hz), 7.83 (dd, 1H, J=9.0, 2.2 Hz), 3.99 (s, 3H).

Production Example 64

A mixture of 2.0 g of 2,3-dichloro-6-fluorobenzaldehyde, 1.16 g of methyl thioglycolate, 1.87 g of potassium carbonate, and 20 ml of N,N-dimethylformamide was stirred for 12 hours at room temperature. The reaction mixture was cooled to room temperature. Water was added to the reaction mixture, and extraction was performed three times by using tert-butyl methyl ether. The collected organic layer was washed with water and saturated saline, dried over magnesium sulfate, and then concentrated under reduced pressure. The residues were recrystallized from methanol, thereby obtaining 2.03 g of methyl 4,5-dichlorobenzo[b]thiophene-2-carboxylate (hereinafter, described as a "compound 118 of the present invention").

Compound 118 of the Present Invention

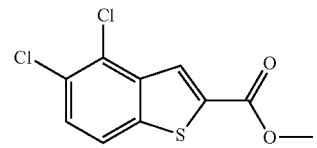

$^1$H-NMR (CDCl$_3$) δ: 8.18 (s, 1H), 7.68 (d, 1H, J=8.7 Hz), 7.51 (d, 1H, J=8.7 Hz), 3.98 (s, 3H).

Production Example 65

A mixture of 2.0 g of 3-chloro-5-trifluoromethyl-2-fluorobenzaldehyde, 985 mg of methyl thioglycolate, 1.16 g of potassium carbonate, and 15 ml of N,N-dimethylformamide was stirred for 4 hours at 60° C. The reaction mixture was cooled to room temperature. Water was added to the reaction mixture, and extraction was performed three times by using tert-butyl methyl ether. The collected organic layer was washed with water and saturated saline, dried over magnesium sulfate, and then concentrated under reduced pressure. The residues were recrystallized from methanol, thereby obtaining 2.07 g of methyl 7-chloro-5-trifluoromethylbenzo[b]thiophene-2-carboxylate (hereinafter, described as a "compound 122 of the present invention").

Compound 122 of the Present Invention

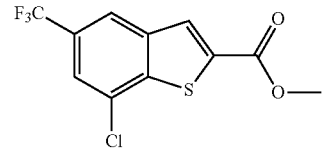 [SMILES: COC(=O)c1cc2cc(C(F)(F)F)cc(Cl)c2s1]

$^1$H-NMR (CDCl$_3$) δ: 8.15 (s, 1H), 8.07 (s, 1H), 7.68 (s, 1H), 4.00 (s, 3H).

Production Example 66

A mixture of 5.42 g of 3-trifluoromethyl cinnamic acid, 1.25 ml of N,N-dimethylformamide, and 0.5 ml of pyridine was stirred under ice cooling, and then 8.92 g of thionyl chloride was added dropwise thereto. After being stirred for 1 hour at 140° C., the mixture was cooled to room temperature. Twenty (20) ml of methanol was added to the mixture, followed by stirring for 1 hour at 140° C. After the reaction mixture was cooled to room temperature, water was added thereto, and extraction was performed using ethyl acetate.

The collected organic layer was washed with aqueous saturate sodium hydrogen carbonate solution and saturated saline, dried over magnesium sulfate, and then concentrated under reduced pressure. The residues were subjected to silica gel column chromatography and concentrated under reduced pressure. The residues were washed with hexane and dried under reduced pressure, thereby obtaining 234 mg of methyl 3-chloro-5-trifluoromethylbenzo[b]thiophene-2-carboxylate (hereinafter, described as a "compound 123 of the present invention").

Compound 123 of the Present Invention

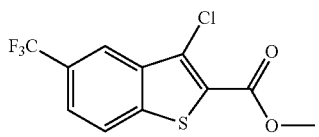

$^1$H-NMR (CDCl$_3$) δ: 8.26 (s, 1H), 7.96 (d, 1H, J=8.6 Hz), 7.76 (d, 1H, J=8.6 Hz), 4.00 (s, 3H).

Production Example 67

A mixture of 1.00 g of 2-fluoro-5-trifluoromethylacetophenone, 2.01 g of potassium carbonate, 669 mg of methyl thioglycolate, and 5 ml of N,N-dimethylformamide was stirred for 7 hours at 80° C. After the reaction mixture was cooled to room temperature, water was added thereto, and extraction was performed using ethyl acetate. The collected organic layer was washed with water and saturated saline, dried over magnesium sulfate, and then concentrated under reduced pressure. Hexane was added to the residues, and the precipitated solids were collected by filtration and dried under reduced pressure, thereby obtaining 474 mg of methyl 5-trifluoromethyl-3-methylbenzo[b]thiophene-2-carboxylate (hereinafter, described as a "compound 124 of the present invention").

Compound 124 of the Present Invention

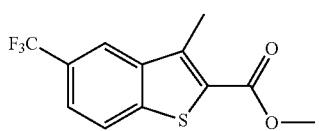 [SMILES: COC(=O)c1sc2ccc(C(F)(F)F)cc2c1C]

$^1$H-NMR (CDCl$_3$), δ: 8.10 (s, 1H), 7.94 (d, 1H, J=8.6 Hz), 7.68 (d, 1H, J=8.6 Hz), 3.95 (s, 3H), 2.82 (s, 3H).

Production Example 68

Step 1

Three point eight (3.8) ml of n-butyllithium (2.6 M hexane solution) was added dropwise to a mixture of 3.00 g of 1-chloro-2-iodo-4-(trifluoromethyl)benzene and 15 ml of tetrahydrofuran at −70° C., followed by stirring for 30 minutes. Thereafter, a mixture of 1.69 g of N-methoxy-N-methyltrifluoroacetamide and 5 ml of tetrahydrofuran was added dropwise thereto at −70° C. Subsequently, after the reaction mixture was stirred for 1 hour at room temperature, water was added thereto, and extraction was performed using ethyl acetate. The organic layer was washed with saturated saline, dried over magnesium sulfate, and then concentrated under reduced pressure. The residues were subjected to silica gel column chromatography, thereby obtaining 1.66 g of 2,2,2-trifluoro-1-[2-chloro-5-(trifluoromethyl)phenyl]ethanone.

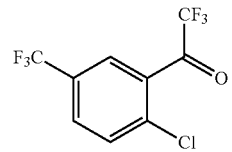

Step 2

A mixture of 1.66 g of 2,2,2-trifluoro-1-[2-chloro-5-(trifluoromethyl)phenyl]ethanone, 422 mg of methyl thioglycolate, 650 mg of potassium carbonate, and 5 ml of N,N-dimethylformamide was stirred for 2 hours at 80° C. After the reaction mixture was cooled to room temperature, water was added thereto, and extraction was performed three times by using ethyl acetate. The collected organic layer was washed with water and saturated saline, dried over magnesium sulfate, and then concentrated under reduced pressure. The residues were subjected to silica gel column chromatography, thereby obtaining 685 mg of methyl 3,5-bis(trifluoromethyl)benzo[b]thiophene-2-carboxylate (hereinafter, described as a "compound 125 of the present invention").

Compound 125 of the Present Invention

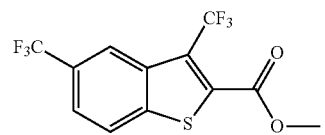 [SMILES: COC(=O)c1sc2ccc(C(F)(F)F)cc2c1C(F)(F)F]

$^1$H-NMR (CDCl$_3$) δ: 8.41 (s, 1H), 8.01 (d, 1H, J=8.6 Hz), 7.75 (d, 1H, J=8.6 Hz), 4.01 (s, 3H).

Production Example 69

A mixture of 15.0 g of 2-fluoro-5-trifluoromethylbenzoic acid, 0.1 ml of concentrated sulfuric acid, and 50 ml of methanol was stirred for 12 hours at 70° C. After being cooled to room temperature, the reaction mixture was concentrated under reduced pressure. Tert-butyl methyl ether was added to the residues, and the residue was washed with an aqueous saturated sodium hydrogen carbonate solution and saturated saline, dried over magnesium sulfate, and concentrated under reduced pressure. Methyl thioglycolate 7.24 g, potassium carbonate 8.6 g, and 100 ml of N,N-dimethylformamide were added to the residues, and this mixture was stirred for 4 hours at 60° C. After the reaction mixture was cooled to room temperature, water was added thereto, and the residue was washed three times with tert-butyl methyl ether. Concentrated hydrochloric acid was added to the aqueous layer, and extraction was performed three times using tert-butyl methyl ether. The collected organic layer was washed with water and saturated saline, dried over magnesium sulfate, and then concentrated under reduced pressure. The residues were recrystallized from ethyl acetate, thereby obtaining 14.2 g of methyl 3-hydroxy-5-trifluoromethylbenzo[b]thiophene-2-carboxylate (hereinafter, described as a "compound 126 of the present invention").

Compound 126 of the Present Invention

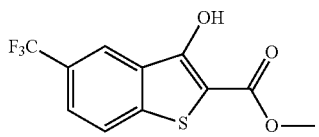 [SMILES: COC(=O)c1sc2ccc(C(F)(F)F)cc2c1O]

¹H-NMR (CDCl₃) δ: 10.10 (br s, 1H), 8.23 (s, 1H), 7.86 (d, 1H, J=8.6 Hz), 7.71 (d, 1H, J=8.6 Hz), 3.98 (s, 3H).

Production Example 70

A mixture of 1.20 g of methyl 3-hydroxy-5-trifluoromethylbenzo[b]thiophene-2-carboxylate, 1.2 g of methyl iodide, 1.2 g of potassium carbonate, and 15 ml of N,N-dimethylformamide was stirred for 12 hours at room temperature. Tert-butyl methyl ether was added to the reaction mixture, and the residue was washed with water, a 1 M aqueous sodium hydrogen carbonate solution, and saturated saline, dried over magnesium sulfate, and then concentrated under reduced pressure. The residues were subjected to silica gel column chromatography to obtain a roughly-purified product. The roughly-purified product was recrystallized from methanol, thereby obtaining 574 mg of methyl 3-methoxy-5-trifluoromethylbenzo[b]thiophene-2-carboxylate (hereinafter, described as a "compound 127 of the present invention").

Compound 127 of the Present Invention

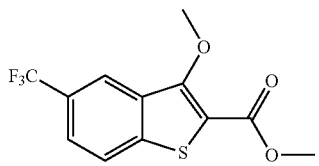 [SMILES: COC(=O)c1sc2ccc(C(F)(F)F)cc2c1OC]

¹H-NMR (CDCl₃) δ: 8.15 (s, 1H), 7.86 (d, 1H, J=8.5 Hz), 7.69 (d, 1H, J=8.5 Hz), 4.21 (s, 3H), 3.95 (s, 3H).

Production Example 71

A mixture of 800 mg of methyl 3-hydroxy-5-trifluoromethylbenzo[b]thiophene-2-carboxylate, 631 mg of ethyl iodide, 801 mg of potassium carbonate, and 20 ml of N,N-dimethylformamide was stirred for 12 hours at room temperature. After the reaction mixture was cooled to room temperature, tert-butyl methyl ether was added thereto. The residue was washed with a 1 M aqueous sodium hydroxide solution, water, and saturated saline, dried over magnesium sulfate, and concentrated under reduced pressure, thereby obtaining 480 mg of methyl 3-ethoxy-5-trifluoromethylbenzo[b]thiophene-2-carboxylate (hereinafter, described as a "compound 128 of the present invention").

Compound 128 of the Present Invention

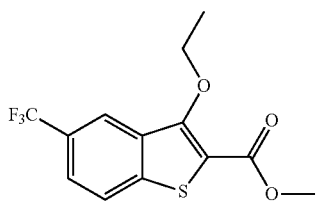 [SMILES: CCOc1c(C(=O)OC)sc2ccc(C(F)(F)F)cc12]

¹H-NMR (CDCl₃) δ: 8.13 (s, 1H), 7.87-7.85 (m, 1H), 7.69-7.67 (m, 1H), 4.45 (q, 2H, J=7.0 Hz), 3.93 (s, 3H), 1.50 (d, 3H, J=7.0 Hz).

Production Example 72

A mixture of 812 mg of methyl 3-hydroxy-5-trifluoromethylbenzo[b]thiophene-2-carboxylate, 985 mg of isopropyl iodide, 802 mg of potassium carbonate, and 20 ml of N,N-dimethylformamide was stirred for 12 hours at room temperature. Tert-butyl methyl ether was added to the reaction mixture, and the residue was washed with water, a 1 M aqueous sodium hydroxide solution, and saturated saline, dried over magnesium sulfate, and concentrated under reduced pressure, thereby obtaining 766 mg of methyl 3-isopropoxy-5-trifluoromethylbenzo[b]thiophene-2-carboxylate (hereinafter, described as a "compound 129 of the present invention").

Compound 129 of the Present Invention

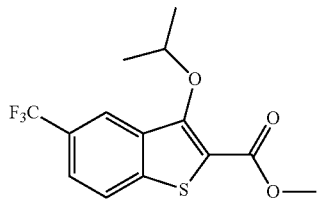 [SMILES: COC(=O)c1sc2ccc(C(F)(F)F)cc2c1OC(C)C]

¹H-NMR (CDCl₃) δ: 8.12 (s, 1H), 7.87-7.84 (m, 1H), 7.69-7.66 (m, 1H), 4.92-4.88 (m, 1H), 3.94 (s, 3H), 1.42-1.40 (m, 6H).

Production Example 73

A mixture of 900 mg of methyl 3-hydroxy-5-trifluoromethylbenzo[b]thiophene-2-carboxylate, 790 mg of allyl bromide, 900 mg of potassium carbonate, and 10 ml of N,N-dimethylformamide was stirred for 12 hours at room temperature. Tert-butyl methyl ether was added to the reaction mixture, and the residue was washed with water and saturated saline, dried over magnesium sulfate, and then concentrated under reduced pressure. The residues were subjected to silica gel column chromatography to obtain a roughly purified product. The roughly-purified product was recrystallized from methanol, thereby obtaining 673 mg of methyl 3-allyloxy-5-trifluoromethylbenzo[b]thiophene-2-carboxylate (hereinafter, described as a "compound 130 of the present invention").

Compound 130 of the Present Invention

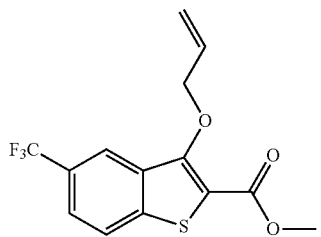 [SMILES: C=CCOc1c(C(=O)OC)sc2ccc(C(F)(F)F)cc12]

¹H-NMR (CDCl₃) δ: 8.15-8.14 (m, 1H), 7.86 (d, 1H, J=8.5 Hz), 7.69 (d, 1H, J=8.5 Hz), 6.19-6.09 (m, 1H), 5.46-5.41 (m, 1H), 5.33-5.29 (m, 1H), 4.91-4.89 (m, 2H), 3.94 (s, 3H).

Production Example 74

A mixture of 500 mg of methyl 3-hydroxy-5-trifluoromethylbenzo[b]thiophene-2-carboxylate, 378 mg of acetyl chloride, 377 mg of triethylamine, and 20 ml of tetrahydrofuran was stirred for 12 hours at room temperature. After being cooled to room temperature, the reaction mixture was concentrated under reduced pressure. Tert-butyl methyl ether was added to the residues, and the residue was washed with water, 1 M hydrochloric acid, a 1 N aqueous saturated sodium hydrogen carbonate solution, and saturated saline, dried over magnesium sulfate, and concentrated under reduced pressure, thereby obtaining 550 mg of methyl 3-acetyloxy-5-trifluoromethylbenzo[b]thiophene-2-carboxylate (hereinafter, described as a "compound 131 of the present invention")

Compound 131 of the Present Invention

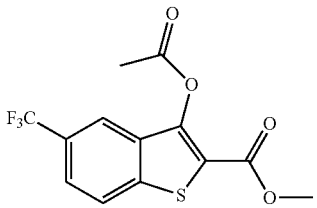 [SMILES: COC(=O)c1sc2ccc(C(F)(F)F)cc2c1OC(C)=O]

$^1$H-NMR (CDCl$_3$) δ: 7.99 (s, 1H), 7.93 (d, 1H, J=8.5 Hz), 7.72 (d, 1H, J=8.5 Hz), 3.93 (s, 3H), 2.50 (s, 3H).

Production Example 75

A mixture of 1.51 g of methyl 3-hydroxy-5-trifluoromethylbenzo[b]thiophene-2-carboxylate, 1.86 g of benzyl bromide, 1.50 g of potassium carbonate, and 10 ml of N,N-dimethylformamide was stirred for 12 hours at room temperature. Tert-butyl methyl ether was added to the reaction mixture, and the residue was washed with water, a 1 M aqueous sodium hydroxide solution, and saturated saline, dried over magnesium sulfate, and then concentrated under reduced pressure. The residues were subjected to silica gel column chromatography, thereby obtaining 1.18 g of methyl 3-benzyloxy-5-trifluoromethylbenzo[b]thiophene-2-carboxylate (hereinafter, described as a "compound 132 of the present invention").

Compound 132 of the Present Invention

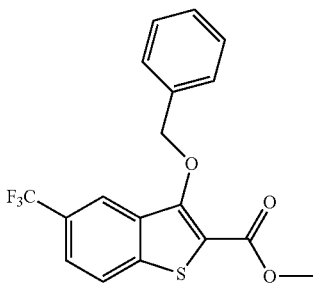 [SMILES: COC(=O)c1sc2ccc(C(F)(F)F)cc2c1OCc1ccccc1]

$^1$H-NMR (CDCl$_3$) δ: 7.96 (s, 1H), 7.86-7.84 (m, 1H), 7.66-7.64 (m, 1H), 7.49-7.47 (m, 2H), 7.40-7.35 (m, 3H), 5.39 (s, 2H), 3.95 (s, 3H).

Production Example 76

A mixture of 15.0 g of 2-chloro-5-trifluoromethylbenzonitrile, 7.10 g of methyl thioglycolate, 9.70 g of potassium carbonate, and 100 ml of N,N-dimethylformamide was stirred for 8 hours at 60° C. After the reaction mixture was cooled to room temperature, water was added thereto, and extraction was performed three times by using tert-butyl methyl ether. The collected organic layer was washed with water and saturated saline, dried over magnesium sulfate, and then concentrated under reduced pressure. The residues were subjected to silica gel column chromatography, thereby obtaining 9.57 g of methyl 3-amino-5-trifluoromethylbenzo[b]thiophene-2-carboxylate (hereinafter, described as a "compound 133 of the present invention").

Compound 133 of the Present Invention

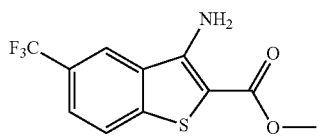 [SMILES: COC(=O)c1sc2ccc(C(F)(F)F)cc2c1N]

$^1$H-NMR (CDCl$_3$) δ: 7.91 (s, —H), 7.86-7.84 (m, 1H), 7.69-7.67 (m, 1H), 5.96 (br s, 2H), 3.91 (s, 3H).

Production Example 77

A mixture of 1.50 g of methyl 3-amino-5-trifluoromethylbenzo[b]thiophene-2-carboxylate, 6.00 g of methyl iodide, 6.0 g of potassium carbonate, and 15 ml of N,N-dimethylformamide was stirred for 12 hours at 40° C. Tert-butyl methyl ether was added to the reaction mixture, and the residue was washed with water and saturated saline and dried over magnesium sulfate, followed by concentration under reduced pressure. The residues were subjected to silica gel column chromatography, thereby obtaining 250 mg of methyl 3-(N-methylamino)-5-trifluoromethylbenzo[b]thiophene-2-carboxylate (hereinafter, described as a "compound 134 of the present invention").

Compound 134 of the Present Invention

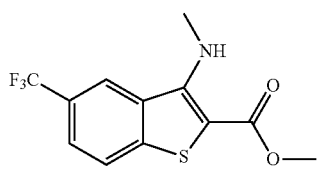 [SMILES: CNc1c(C(=O)OC)sc2ccc(C(F)(F)F)cc12]

$^1$H-NMR (CDCl$_3$) δ: 9.44 (s, 1H), 7.83-7.81 (m, 1H), 7.64-7.62 (m, 1H), 3.68 (s, 3H), 3.49 (d, 1H, J=5.6 Hz), 3.46 (d, 3H, J=5.6 Hz).

Production Example 78

A mixture of 1.50 g of methyl 3-amino-5-trifluoromethylbenzo[b]thiophene-2-carboxylate, 6.00 g of methyl iodide, 6.0 g of potassium carbonate, and 15 ml of N,N-dimethylformamide was stirred for 12 hours at 40° C. Tert-butyl methyl ether was added to the reaction mixture, and the residue was washed with water and saturated saline, dried over magnesium sulfate, and concentrated under reduced pressure. The residues were subjected to silica gel column chromatography, thereby obtaining 141 mg of methyl 3-(N,N-dimethylamino)-5-trifluoromethylbenzo[b]thiophene-2-carboxylate (hereinafter, described as a "compound 135 of the present invention").

Compound 135 of the Present Invention

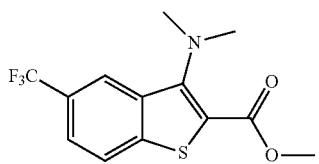 [SMILES: COC(=O)c1sc2ccc(C(F)(F)F)cc2c1N(C)C]

¹H-NMR (CDCl₃) δ: 8.19 (s, 1H), 7.84-7.82 (m, 1H), 7.64-7.63 (m, 1H), 3.91 (s, 3H), 3.14 (s, 6H).

Production Example 79

A mixture of 961 mg of acetyl anhydride and 533 mg of formic acid was stirred for 2 hours at 60° C. The reaction mixture was cooled to room temperature, and then 10 ml of tetrahydrofuran was added thereto. A mixture of 1.00 g of methyl 3-amino-5-(trifluoromethyl)benzo[b]thiophene-2-carboxylate and 10 ml of tetrahydrofuran was added dropwise to the reaction mixture under ice cooling. The reaction mixture was stirred for 6 hours under reflux. After being cooled to room temperature, the reaction mixture was concentrated under reduced pressure. The residues were recrystallized from ethyl acetate, thereby obtaining 940 mg of methyl 3-formylamino-5-(trifluoromethyl)benzo[b]thiophene-2-carboxylate (hereinafter, described as a "compound 136 of the present invention").

Compound 136 of the Present Invention

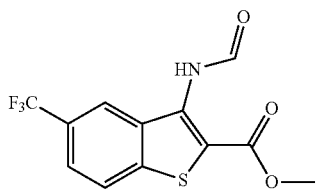 [SMILES: COC(=O)c1sc2ccc(C(F)(F)F)cc2c1NC=O]

¹H-NMR (DMSO-D₆) δ: 10.60 (br s, 1H), 8.45 (s, 1H), 8.32-8.30 (m, 2H), 7.90-7.88 (m, 1H), 3.87 (s, 3H).

Production Example 80

A mixture of 435 mg of methyl 3-amino-5-(trifluoromethyl)-benzo[b]thiophene-2-carboxylate, 371 mg of acetyl chloride, 460 mg of triethylamine, and 30 ml of tetrahydrofuran was stirred for 12 hours under reflux. After being cooled to room temperature, the reaction mixture was concentrated under reduced pressure. Tert-butyl methyl ether was added to the residues, and the residue was washed with 1 M hydrochloric acid, a 1 N aqueous saturated sodium hydrogen carbonate solution, and saturated saline, dried over magnesium sulfate, and then concentrated under reduced pressure. The residues were subjected to silica gel column chromatography, thereby obtaining 105 mg of methyl 3-(acetylamino)-5-(trifluoromethyl)benzo[b]thiophene-2-carboxylate (hereinafter, described as a "compound 137 of the present invention")

Compound 137 of the Present Invention

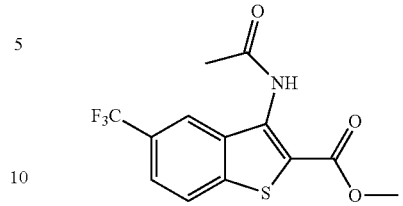

¹H-NMR (CDCl₃) δ: 9.56 (br s, 1H), 8.44 (s, 1H), 7.87 (d, 1H, J=8.3 Hz), 7.68 (d, 1H, J=8.3 Hz), 3.97 (s, 3H), 2.36 (s, 3H).

Production Example 81

A mixture of 500 mg of methyl 3-amino-5-(trifluoromethyl)-benzo[b]thiophene-2-carboxylate, 763 mg of trifluoroacetic anhydride, 377 mg of potassium carbonate, and 20 ml of N,N-dimethylformamide was stirred for 24 hours at room temperature. Tert-butyl methyl ether was added to the reaction mixture, and the residue was washed with water, 1 M hydrochloric acid, an aqueous saturated sodium hydrogen carbonate solution, and saturated saline, dried over magnesium sulfate, and then concentrated under reduced pressure. The residues were subjected to silica gel column chromatography, thereby obtaining 201 mg of methyl 3-(trifluoroacetylamino)-5-(trifluoromethyl)benzo[b]thiophene-2-carboxylate (hereinafter, described as a "compound 138 of the present invention").

Compound 138 of the Present Invention

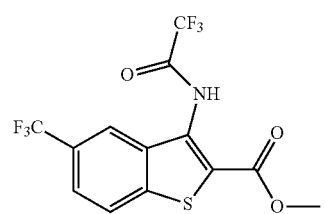 [SMILES: COC(=O)c1sc2ccc(C(F)(F)F)cc2c1NC(=O)C(F)(F)F]

¹H-NMR (CDCl₃) δ: 10.72 (br s, 1H), 8.50-8.48 (m, 1H), 7.95-7.93 (m, 1H), 7.76-7.74 (m, 1H), 4.02 (s, 3H).

Production Example 82

A mixture of 200 mg of methyl 5-iodobenzo[b]thiophene-2-carboxylate, 2.79 g of 1-iodoheptafluoropropane, 600 mg of copper (0), and 20 ml of N,N-dimethylformamide was stirred for 8 hours at 150° C. under a nitrogen atmosphere. After the reaction mixture was cooled to room temperature, tert-butyl methyl ether and an aqueous saturated ammonia solution were added thereto, and filtration was performed using Celite™. The filtrate was washed with water and saturated saline, dried over magnesium sulfate, and then concentrated under reduced pressure. The residues were subjected to silica gel column chromatography, thereby obtaining 140 mg of methyl 3,5-(bisheptafluoropropyl) benzo[b]thiophene-2-carboxylate (hereinafter, described as a "compound 139 of the present invention").

Compound 139 of the Present Invention

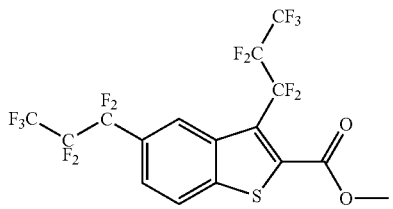 [SMILES: COC(=O)c1sc2ccc(C(F)(F)C(F)(F)C(F)(F)F)cc2c1C(F)(F)C(F)(F)C(F)(F)F]

¹H-NMR (CDCl₃) δ: 8.25 (s, 1H), 8.03 (d, 1H, J=8.5 Hz), 7.71 (d, 1H, J=8.5 Hz), 3.99 (s, 3H).

Production Example 84

Step 1

One point one five (1.15) ml of oxalyl chloride and 47.2 μl of N,N-dimethylformamide were added to a mixture of 3.00 g of 5-trifluoromethylbenzo[b]thiophene-2-carboxylic acid and 15 ml of dichloromethane at room temperature, followed by stirring for 2 hours under a nitrogen atmosphere. The reaction mixture was concentrated under reduced pressure, thereby obtaining 3.18 g of 5-trifluoromethylbenzo[b]thiophene-2-carbonyl chloride.

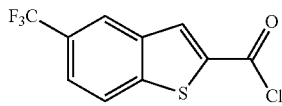

Step 2

5-Trifluoromethylbenzo[b]thiophene-2-carbonyl chloride 325 mg was added to 2 ml of 1-propanol at room temperature, followed by stirring for 1 hour. The mixture was concentrated under reduced pressure, and the obtained residues were subjected to silica gel column chromatography, thereby obtaining 336 mg of 5-trifluoromethylbenzo[b]thiophene-2-carboxylic acid-1-propyl ester (hereinafter, described as a "compound 144 of the present invention").

Compound 144 of the Present Invention

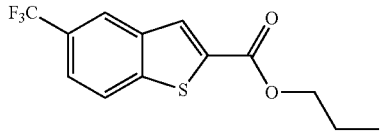 [SMILES: CCCOC(=O)c1cc2cc(C(F)(F)F)ccc2s1]

¹H-NMR (CDCl₃) δ: 8.16 (s, 1H), 8.12 (s, 1H), 7.98 (d, 1H, J=8.3 Hz), 7.67 (d, 1H, J=8.3 Hz), 4.34-4.33 (m, 2H), 1.83-1.82 (m, 2H), 1.06-1.04 (m, 3H).

Production Example 85

Oxalyl chloride 254 mg was added to a mixture of 400 mg of 5-trifluoromethylbenzo[b]thiophene-2-carboxylic acid and 20 ml of 2-propanol under ice cooling. The mixture was stirred for 24 hours under reflux. After being cooled to room temperature, the reaction mixture was concentrated under reduced pressure. Chloroform was added to the residues, and the organic layer was washed with a 1 M aqueous sodium hydroxide solution and saturated saline, dried over magnesium sulfate, and then concentrated under reduced pressure, thereby obtaining 217 mg of isopropyl 5-trifluoromethylbenzo[b]thiophene-2-carboxylate (hereinafter, described as a "compound 145 of the present invention").

Compound 145 of the Present Invention

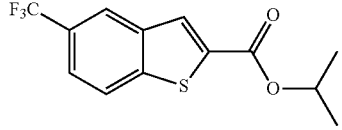 [SMILES: CC(C)OC(=O)c1cc2cc(C(F)(F)F)ccc2s1]

¹H-NMR (CDCl₃) δ: 8.14 (s, 1H), 8.12 (s, 1H), 7.98 (d, 1H, J=8.5 Hz), 7.67 (d, 1H, J=8.5 Hz), 5.28 (m, 1H), 1.41 (m, 6H).

Production Example 86

5-Trifluoromethylbenzo[b]thiophene-2-carbonyl chloride 325 mg was added to 2 ml of 1-butanol at room temperature, followed by stirring for 1.5 hours. The mixture was concentrated under reduced pressure, and the obtained residues were subjected to silica gel column chromatography, thereby obtaining 349 mg of butyl 5-trifluoromethylbenzo[b]thiophene-2-carboxylate (hereinafter, described as a "compound 146 of the present invention").

Compound 146 of the Present Invention

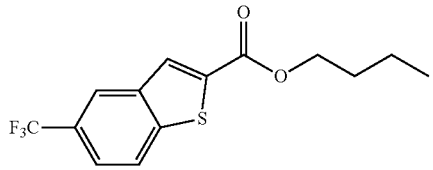 [SMILES: CCCCOC(=O)c1cc2cc(C(F)(F)F)ccc2s1]

¹H-NMR (CDCl₃, δ: 8.16 (s, 1H), 8.11 (s, 1H), 7.97 (d, 1H, J=8.6 Hz), 7.66 (d, 1H, J=8.6 Hz), 4.39-4.37 (m, 2H), 1.79-1.75 (m, 2H), 1.52-1.48 (m, 2H), 1.01-0.99 (m, 3H).

Production Example 87

5-Trifluoromethylbenzo[b]thiophene-2-carbonyl chloride 325 mg was added to 2 ml of n-amyl alcohol at room temperature, followed by stirring for 67 hours. The mixture was concentrated under reduced pressure, and the obtained residues were subjected to silica gel column chromatography, thereby obtaining 380 mg of pentyl 5-trifluoromethylbenzo[b]thiophene-2-carboxylate (hereinafter, described as a "compound 147 of the present invention").

Compound 147 of the Present Invention

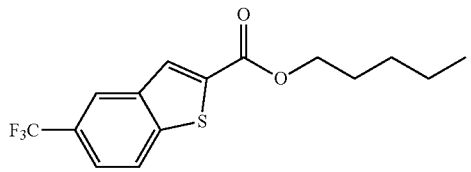 [SMILES: CCCCCOC(=O)c1cc2cc(C(F)(F)F)ccc2s1]

¹H-NMR (CDCl₃) δ: 8.16 (s, 1H), 8.11 (s, 1H), 7.98 (d, 1H, J=8.6 Hz), 7.67 (d, 1H, J=8.6 Hz), 4.37-4.36 (m, 2H), 1.81-1.77 (m, 2H), 1.45-1.41 (m, 4H), 0.96-0.93 (m, 3H).

Production Example 88

5-Trifluoromethylbenzo[b]thiophene-2-carbonyl chloride 325 mg was added to 2 ml of propargyl alcohol at room temperature, followed by stirring for 67 hours. The mixture was concentrated under reduced pressure, and the obtained residues were subjected to silica gel column chromatography, thereby obtaining 173 mg of propargyl 5-trifluoromethylbenzo[b]thiophene-2-carboxylate (hereinafter, described as a "compound 148 of the present invention").

Compound 148 of the Present Invention

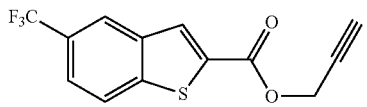 [SMILES: C#CCOC(=O)c1cc2cc(C(F)(F)F)ccc2s1]

$^1$H-NMR (CDCl$_3$) δ: 8.18-8.17 (m, 2H), 7.99 (d, 1H, J=8.6 Hz), 7.69 (d, 1H, J=8.6 Hz), 4.97 (d, 2H, J=2.5 Hz), 2.57 (t, 1H, J=2.5 Hz).

Production Example 89

A mixture of 325 mg of 5-trifluoromethylbenzo[b]thiophene-2-carbonyl chloride and 0.5 ml of dichloromethane was added dropwise to a mixture of 0.5 ml of ethylene glycol, 369 μl of triethylamine, and 0.5 ml of dichloromethane at 0° C. The reaction mixture was stirred for 6.5 hours at room temperature. Ethyl acetate was added to the mixture, and insoluble matter was separated by filtration. The filtrate was concentrated under reduced pressure, and the obtained residues were subjected to silica gel column chromatography, thereby obtaining 279 mg of (2-hydroxyethyl) 5-trifluoromethylbenzo[b]thiophene-2-carboxylate (hereinafter, described as a "compound 149 of the present invention").

Compound 149 of the Present Invention

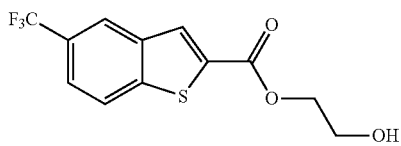 [SMILES: O=C(OCCO)c1cc2cc(C(F)(F)F)ccc2s1]

$^1$H-NMR (CDCl$_3$) δ: 8.18-8.15 (m, 2H), 7.99 (d, 1H, J=8.6 Hz), 7.69 (d, 1H, J=8.6 Hz), 4.53-4.51 (m, 2H), 4.02-3.98 (m, 2H), 1.94-1.92 (m, 1H).

Production Example 90

A mixture of 5.02 g of 2-fluoro-5-(trifluoromethyl)benzaldehyde, 5.00 g of benzyl mercaptoacetate, 4.69 g of potassium carbonate, and 20 ml of N,N-dimethylformamide was stirred for 2 hours at 60° C. The reaction mixture was cooled to room temperature, water was added thereto, and extraction was performed three times by using tert-butyl methyl ether. The collected organic layer was washed with water and saturated saline, dried over magnesium sulfate, and then concentrated under reduced pressure. The residues were subjected to silica gel column chromatography, thereby obtaining 6.54 g of benzyl 5-trifluoromethylbenzo[b]thiophene-2-carboxylate (hereinafter, described as a "compound 150 of the present invention").

Compound 150 of the Present Invention

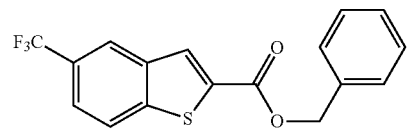 [SMILES: O=C(OCc1ccccc1)c1cc2cc(C(F)(F)F)ccc2s1]

$^1$H-NMR (CDCl$_3$) δ: 8.16-8.15 (m, 2H), 7.99-7.96 (m, 1H), 7.68-7.66 (m, 1H), 7.48-7.46 (m, 2H), 7.44-7.35 (m, 3H), 5.41 (s, 2H).

Production Example 91

A mixture of 300 mg of 5-trifluoromethylbenzo[b]thiophene-2-carboxylic acid, 257 mg of 1-ethyl-3-(3-dimethylaminopropyl)carbodimide hydrochloride, 14.9 mg of N,N-dimethyl-4-aminopyridine, 156 mg of 4-chlorobenzyl alcohol, and 20 ml of tetrahydrofuran was stirred for 12 hours under reflux. The reaction mixture was concentrated under reduced pressure, and ethyl acetate was added to the residues. The collected organic layer was washed with 1 M hydrochloric acid and saturated saline, dried over magnesium sulfate, and then concentrated under reduced pressure. The residues were subjected to silica gel column chromatography, thereby obtaining 291 mg of (4-chlorobenzyl) 5-trifluoromethylbenzo[b]thiophene-2-carboxylate (hereinafter, described as a "compound 151 of the present invention").

Compound 151 of the Present Invention

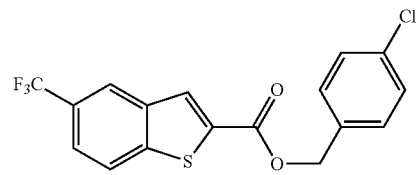 [SMILES: O=C(OCc1ccc(Cl)cc1)c1cc2cc(C(F)(F)F)ccc2s1]

$^1$H-NMR (DMSO-D$_6$) δ: 8.49 (s, 1H), 8.41 (s, 1H), 8.35 (d, 1H, J=8.5 Hz), 7.84 (d, 1H, J=8.5 Hz), 7.51 (m, 4H), 5.41 (s, 2H).

Production Example 92

A mixture of 325 mg of 5-trifluoromethylbenzo[b]thiophene-2-carbonyl chloride, 131 mg of methyl glycolate, 369 μl of triethylamine, and 2 ml of tetrahydrofuran was stirred for 6.5 hours at room temperature. The mixture was concentrated under reduced pressure, hexane was added to the obtained residues, and insoluble matter was collected by filtration and then washed with water and hexane. The collected substance was dried under reduced pressure, thereby obtaining 229 mg of methoxycarbonylmethyl 5-trifluoromethylbenzo[b]thiophene-2-carboxylate (hereinafter, described as a "compound 152 of the present invention").

Compound 152 of the Present Invention

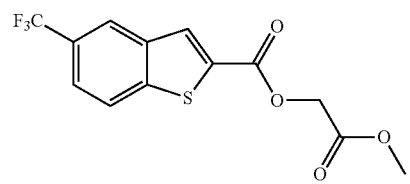 [SMILES: COC(=O)COC(=O)c1cc2cc(C(F)(F)F)ccc2s1]

$^1$H-NMR (CDCl$_3$) δ: 8.22 (s, 1H), 8.18 (s, 1H), 8.00 (d, 1H, J=8.6 Hz), 7.69 (d, 1H, J=8.6 Hz), 4.90 (s, 2H), 3.82 (s, 3H).

Production Example 93

A mixture of 325 mg of 5-trifluoromethylbenzo[b]thiophene-2-carbonyl chloride and 1.5 ml of dichloromethane was added dropwise to a mixture of 106 mg of acetoxime, 369 µl of triethylamine, and 2 ml of dichloromethane at 0° C. The reaction mixture was stirred for 6.5 hours at room temperature. The mixture was concentrated under reduced pressure, ethyl acetate was added to the residues, and insoluble matter was separated by filtration. The filtrate was concentrated under reduced pressure, hexane was added to the obtained residues, and insoluble matter was collected by filtration. The collected substance was washed with water and hexane and then dried under reduced pressure, thereby obtaining 325 mg of O-[(5-trifluoromethylbenzo[b]thiophen-2-yl)carbonyl]acetoxime (hereinafter, described as a "compound 153 of the present invention").

Compound 153 of the Present Invention

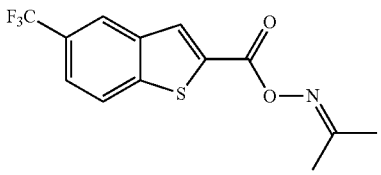 [SMILES: CC(C)=NOC(=O)c1cc2cc(C(F)(F)F)ccc2s1]

$^1$H-NMR (CDCl$_3$) δ: 8.22 (s, 1H), 8.18 (s, 1H), 7.99 (d, 1H, J=6.6 Hz), 7.69 (d, 1H, J=8.6 Hz), 2.17 (s, 3H), 2.15 (s, 3H).

Production Example 94

Oxalyl chloride 515 mg was added to a mixture of 500 mg of 5-trifluoromethylbenzo[b]thiophene-2-carboxylic acid and 10 ml of tetrahydrofuran under ice cooling. The mixture was stirred for 3 hours under reflux. After being cooled to room temperature, the mixture was concentrated under reduced pressure. Ten (10) ml of tetrahydrofuran was added to the residues, and then 1 ml of saturated aqueous ammonia was added thereto, followed by stirring for 1 hour at room temperature. The reaction mixture was concentrated under reduced pressure, water was added to the residues, and extraction was performed using ethyl acetate. The collected organic layer was washed with a 1 M aqueous sodium hydroxide solution and saturated saline, dried over magnesium sulfate, and then concentrated under reduced pressure, thereby obtaining 235 mg of 5-trifluoromethylbenzo[b]thiophene-2-carboxamide (hereinafter, described as a "compound 154 of the present invention").

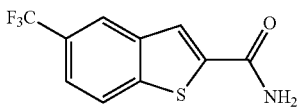

Compound 154 of the Present Invention
$^1$H-NMR (DMSO-D$_6$) δ: 8.64-8.61 (m, 1H), 8.25-8.23 (m, 1H), 8.17-8.13 (m, 1H), 8.03-7.99 (m, 1H).

Production Example 95

A mixture of 150 mg of 5-trifluoromethylbenzo[b]thiophene-2-carboxylic acid, 117 mg of i-ethyl-3-(3-dimethylaminopropyl)carbodiimide hydrochloride, 2.8 ml of methylamine (2 M tetrahydrofuran solution), 7.5 mg of N,N-dimethyl-4-aminopyridine, and 10 ml of tetrahydrofuran was stirred for 5 hours at room temperature. The reaction mixture was concentrated under reduced pressure, and chloroform and water were added to the residues. The organic layer was washed with an aqueous saturated sodium hydrogen carbonate solution, 1 M hydrochloric acid, and saturated saline, dried over magnesium sulfate, and then concentrated under reduced pressure. The residues were subjected to silica gel column chromatography, thereby obtaining 100 mg of N-methyl-5-trifluoromethylbenzo[b]thiophene-2-carboxamide (hereinafter, described as a "compound 155 of the present invention").

Compound 155 of the Present Invention

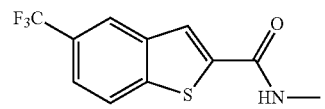 [SMILES: CNC(=O)c1cc2cc(C(F)(F)F)ccc2s1]

$^1$H-NMR (CDCl$_3$) δ: 8.10 (s, 1H), 7.97 (d, J=8.3 Hz, 1H), 7.80 (s, 1H), 7.64 (d, J=8.3 Hz, 1H), 3.06 (m, 3H).

Production Example 96

A mixture of 325 mg of 5-trifluoromethylbenzo[b]thiophene-2-carbonyl chloride and 1 ml of dichloromethane was added dropwise to a mixture of 61 mg of cyanamide, 369 µl of triethylamine, and 1 ml of dichloromethane at 0° C. The reaction mixture was stirred for 6 hours at room temperature. The mixture was concentrated under reduced pressure, ethyl acetate was added to the obtained residues, and insoluble matter was separated by filtration. The filtrate was concentrated under reduced pressure, and the obtained residues were subjected to silica gel column chromatography to obtain a roughly-purified product. Ethyl acetate was added to the obtained roughly-purified product, and the residue was washed with an aqueous saturated ammonium chloride solution and saturated saline, dried over magnesium sulfate, and concentrated under reduced pressure. The residues were washed with chloroform and hexane and then dried under reduced pressure, thereby obtaining 172 mg of N-cyano-5-trifluoromethylbenzo[b]thiophene-2-carboxamide (hereinafter, described as a "compound 156 of the present invention").

Compound 156 of the Present Invention

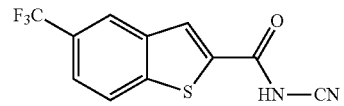

$^1$H-NMR (Methanol-D$_4$) δ: 8.19 (s, 1H), 6.04 (d, 1H, J=8.6 Hz), 7.99 (s, 1H), 7.62 (d, 1H, J=8.6 Hz).

Production Example 97

A mixture of 300 mg of 5-trifluoromethylbenzo[b]thiophene-2-carboxylic acid, 257 mg of 1-ethyl-3-(3-dimethylaminopropyl)carbodiimide hydrochloride, 14.9 mg of N,N- dimethyl-4-aminopyridine, 170 mg of aniline, and 20 ml of tetrahydrofuran was stirred for 18 hours at room temperature. The reaction mixture was concentrated under reduced pressure, and ethyl acetate was added to the residues. The organic layer was washed with a M aqueous sodium hydroxide solution, 1 M hydrochloric acid, and saturated saline, dried over magnesium sulfate, and then concentrated under reduced pressure. The residues were recrystallized from tert-butyl methyl ether, thereby obtaining 317 mg of N-phenyl-5-trifluoromethylbenzo[b]thiophene-2-carboxamide (hereinafter, described as a "compound 157 of the present invention").

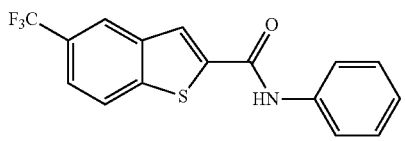 [SMILES: O=C(Nc1ccccc1)c1cc2cc(C(F)(F)F)ccc2s1]

Compound 157 of the Present Invention
$^1$H-NMR (DMSO-D$_6$) δ: 10.70 (br s, 1H), 8.48 (s, 1H), 8.46 (s, 1H), 8.33 (m, 1H), 7.79 (m, 2H), 7.77 (m, 1H), 7.40 (m, 2H), 7.15 (m, 1H).

Production Example 98

A mixture of 300 mg of 5-trifluoromethylbenzo[b]thiophene-2-carboxylic acid, 257 mg of 1-ethyl-3-(3-dimethylaminopropyl)carbodiimide hydrochloride, 14.9 mg of N,N-dimethyl-4-aminopyridine, 259 me of 4-amino-2-chlorotoluene, and 20 ml of tetrahydrofuran was stirred for 18 hours at room temperature. The reaction mixture was concentrated under reduced pressure, and ethyl acetate was added to the residues. The organic layer was washed with a 1 M aqueous sodium hydroxide solution, 1 M hydrochloric acid, and saturated saline, dried over magnesium sulfate, and then concentrated under reduced pressure. The residues were recrystallized from tert-butyl methyl ether, thereby obtaining 270 mg of N-(3-chloro-4-methylphenyl)-5-trifluoromethylbenzo[b]thiophene-2-carboxamide (hereinafter, described as a "compound 158 of the present invention").

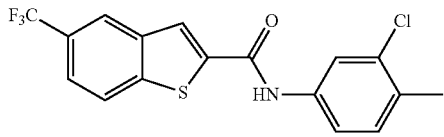 [SMILES: Cc1ccc(NC(=O)c2cc3cc(C(F)(F)F)ccc3s2)cc1Cl]

Compound 158 of the Present Invention
$^1$H-NMR (DMSO-D$_6$) δ: 10.77 (br s, 1H), 8.47 (s, 1H), 8.46 (s, 1H), 8.34 (d, 1H, J=8.5 Hz), 7.93 (m, 1H), 7.80 (d, 1H, J=8.5 Hz), 7.61 (m, 1H), 7.36 (m, 1H), 2.32 (s, 3H).

Production Example 99

A mixture of 300 mg of 5-trifluoromethylbenzo[b]thiophene-2-carboxylic acid, 257 mg of 1-ethyl-3-(3-dimethylaminopropyl)carbodiimide hydrochloride, 14.9 mg of N,N-dimethyl-4-aminopyridine, 280 mg of 2,4-dimethoxyaniline, and 20 ml of tetrahydrofuran was stirred for 24 hours at room temperature. The reaction mixture was concentrated under reduced pressure, and ethyl acetate was added to the residues. The organic layer was washed with a 1 M aqueous sodium hydroxide solution, 1 M hydrochloric acid, and saturated saline, dried over magnesium sulfate, and then concentrated under reduced pressure. The residues were subjected to silica gel column chromatography, thereby obtaining 125 mg of N-(2,4-dimethoxyphenyl)-5-trifluoromethylbenzo[b]thiophene-2-carboxamide (hereinafter, described as a "compound 159 of the present invention").

Compound 159 of the Present Invention

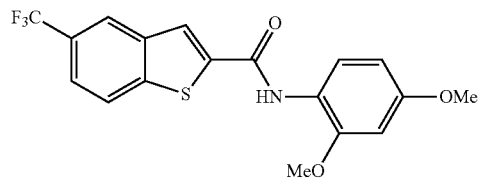 [SMILES: COc1ccc(NC(=O)c2cc3cc(C(F)(F)F)ccc3s2)c(OC)c1]

$^1$H-NMR (DMSO-D$_6$) δ: 9.92 (br, 1H), 8.42 (m, 2H), 8.31 (d, 1H, J=8.7 Hz), 7.78 (d, 1H, J=8.7 Hz), 7.44 (m, 1H), 6.68 (s, 1H), 6.56 (m, 1H), 3.82 (s, 3H), 3.79 (s, 3H).

Production Example 100

A mixture of 1.00 g of methyl 5-trifluoromethylbenzo[b]thiophene-2-carboxylate, 803 mg of hydroxylamine hydrochloride, 276 mg of triethylamine, and 15 ml of methanol was stirred for 12 hours under reflux. The reaction mixture was concentrated under reduced pressure, and tert-butyl methyl ether was added to the residues. The organic layer was washed with 1 M hydrochloric acid and saturated saline, dried over magnesium sulfate, and then concentrated under reduced pressure. The residues were subjected to silica gel column chromatography, thereby obtaining 217 mg of N-hydroxy-5-trifluoromethylbenzo[b]thiophene-2-carboxamide (hereinafter, described as a "compound 160 of the present invention").

Compound 160 of the Present Invention

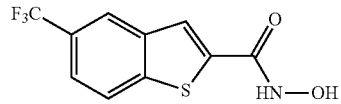 [SMILES: O=C(NO)c1cc2cc(C(F)(F)F)ccc2s1]

$^1$H-NMR (DMSO-D$_6$) δ: 11.66 (br s, 1H), 9.37 (br s, 1H), 8.39 (s, 1H), 8.29 (d, 1H, J=8.5 Hz), 8.06 (s, 1H), 7.75 (d, 1H, J=8.5 Hz).

Production Example 101

A mixture of 1.00 g of methyl 5-trifluoromethylbenzo[b]thiophene-2-carboxylate, 772 mg of hydrazine monohydrate, and 15 ml of ethanol was stirred for 12 hours under reflux. The reaction mixture was concentrated under reduced pressure, and tert-butyl methyl ether was added to the residues. The organic layer was washed with 1 M hydrochloric acid and saturated saline, dried over magnesium sulfate, and then concentrated under reduced pressure. The residues were recrystallized from tert-butyl methyl ether and ethanol, thereby obtaining 595 mg of N-amino-5-trifluoromethylbenzo[b]thiophene-2-carboxamide (hereinafter, described as a "compound 161 of the present invention").

Compound 161 of the Present Invention

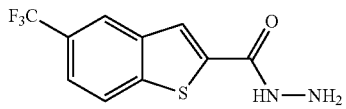

¹H-NMR (DMSO-D₆) δ: 10.21 (br s, 1H), 8.37 (s, 1H), 8.33-8.28 (m, 1H), 9.14 (s, 1H), 7.76-7.73 (m, 1H), 4.62 (br s, 2H).

Production Example 102

A mixture of 325 mg of 5-trifluoromethylbenzo[b]thiophene-2-carbonyl chloride and 2 ml of dichloromethane was added dropwise to a mixture of 106 mg of sodium methyl mercaptan and 1 ml of dichloromethane at 0° C. The reaction mixture was stirred for 3.5 hours at 0° C. The mixture was concentrated under reduced pressure, ethyl acetate was added to the obtained residues, and insoluble matter was separated by filtration. The filtrate was concentrated, and the residues were subjected to silica gel column chromatography, thereby obtaining 242 mg of S-methyl 5-trifluoromethylbenzo[b]thiophene-2-carbothioate (hereinafter, described as a "compound 162 of the present invention").

Compound 162 of the Present Invention

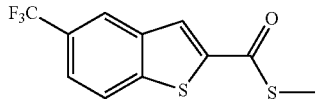

¹H-NMR (CDCl₃), δ: 8.17 (s, 1H), 8.11 (s, 1H), 7.99 (d, 1H, J=8.6 Hz), 7.68 (d, 1H, J=8.6 Hz), 2.55 (s, 3H).

Production Example 103

A mixture of 325 mg 5-trifluoromethylbenzo[b]thiophene-2-carbonyl chloride, 154 mg of methyl thioglycolate, 369 μl of triethylamine, and 2 ml of tetrahydrofuran was stirred for 4.5 hours at room temperature. The reaction mixture was filtered, and the filtrate was concentrated under reduced pressure. The obtained residues were washed with hexane, thereby obtaining 389 mg of S-methoxycarbonylmethyl 5-trifluoromethylbenzo[b]thiophene-2-carbothioate (hereinafter, described as a "compound 163 of the present invention").

Compound 163 of the Present Invention

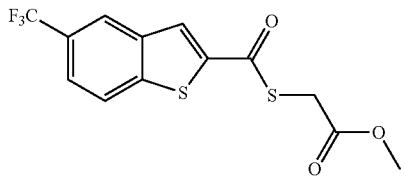

¹H-NMR (CDCl₃) δ: 8.19 (s, 1H), 8.16 (s, 1H), 8.00 (d, 1H, J=8.3 Hz), 7.70 (d, 1H, J=8.3 Hz), 3.95 (s, 2H), 3.80 (s, 3H).

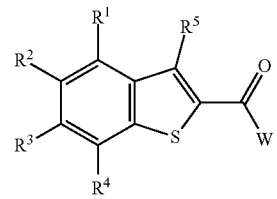

(1)

Specific examples of the compounds of the present invention include the compounds (compounds 1 to 163 of the present invention) represented by Formula (1) wherein $R^1$, $R^2$, $R^3$, $R^4$, and $R^5$ form a combination of groups shown in Tables 1 to 7.

In the following tables, Me represents a methyl group, Et represents a ethyl group, nPr represents a propyl group, iPr represents an isopropyl group, nBu represents a butyl group, tBu represents a tert-butyl group, Ph represents a phenyl group, and Bn represents a benzyl group.

TABLE 1

| Compound of the present invention | $R^1$ | $R^2$ | $R^3$ | $R^4$ | $R^5$ | W | Melting point |
|---|---|---|---|---|---|---|---|
| 1 | H | H | H | H | H | MeO— | 68.1° C. |
| 2 | F | H | H | H | H | MeO— | 95.6° C. |
| 3 | H | F | H | H | H | MeO— | * |
| 4 | H | H | F | H | H | MeO— | 91.5° C. |
| 5 | H | H | H | B | H | MeO— | 84.0° C. |
| 6 | Cl | H | H | H | B | MeO— | 89.4° C. |
| 7 | H | Cl | H | H | H | MeO— | — |
| 8 | H | H | Cl | H | H | MeO— | 100.8° C. |
| 9 | H | H | H | Cl | H | MeO— | 82.1° C. |
| 10 | H | H | H | H | Cl | MeO— | * |
| 11 | Br | H | H | H | H | MeO— | * |
| 12 | H | Br | H | H | H | MeO— | * |
| 13 | H | H | Br | H | H | MeO— | * |
| 14 | H | H | H | Br | H | MeO— | * |
| 15 | I | H | H | H | H | MeO— | * |
| 16 | H | I | H | H | H | MeO— | * |
| 17 | H | CN | H | H | H | MeO— | * |
| 18 | NO₂ | H | H | H | H | MeO— | * |
| 19 | H | NO₂ | H | H | H | MeO— | * |
| 20 | H | H | NO₂ | H | H | MeO— | * |
| 21 | H | H | H | H | NO₂ | MeO— | 104.8° C. |
| 22 | Me | H | H | H | H | MeO— | — |
| 23 | H | Me | H | H | H | MeO— | — |
| 24 | H | H | Me | H | H | MeO— | * |
| 25 | H | H | H | Me | H | MeO— | — |

TABLE 2

| Compound of the present invention | R¹ | R² | R³ | R⁴ | R⁵ | W | Melting point |
|---|---|---|---|---|---|---|---|
| 26 | H | H | H | H | Me | MeO— | 103.1° C. |
| 27 | H | t Bu | H | H | H | MeO— | — |
| 28 | H | H | H | H | CF₃ | MeO— | — |
| 29 | C₂F₅ | H | H | H | H | MeO— | — |
| 30 | H | C₂F₅ | H | H | H | MeO— | — |
| 31 | H | C₃F₇ | H | H | H | MeO— | — |
| 32 | H | H | H₂C=CH— | H | H | MeO— | — |
| 33 | H | H | HC≡C— | H | H | MeO— | — |
| 34 | Ph | H | H | H | H | MeO— | — |
| 35 | H | Ph | H | H | H | MeO— | — |
| 36 | H | H | Ph | H | H | MeO— | — |
| 37 | H | H | H | Ph | H | MeO— | — |
| 38 | H | H | H | H | Ph | MeO— | — |
| 39 | H | (2-Cl)Ph— | H | H | H | MeO— | — |
| 40 | H | (3-Cl)Ph— | H | H | H | MeO— | — |
| 41 | H | (4-Cl)Ph— | H | H | H | MeO— | — |
| 42 | H | H | H | (3-Me)Ph— | H | MeO— | — |
| 43 | H | (4-CF₃)Ph— | H | H | H | MeO— | — |
| 44 | H | H | H | (2-MeO)Ph— | H | MeO— | — |
| 45 | H | H | (4-CF₃O)Ph— | H | H | MeO— | — |
| 46 | H | 2-pyridyl | H | H | H | MeO— | — |
| 47 | H | 3-pyridyl | H | H | H | MeO— | — |
| 48 | H | 4-pyridyl | H | H | H | MeO— | — |
| 49 | H | H | 6-(trifluoromethyl)-3-pyridyl- | H | H | MeO— | — |
| 50 | H | 2-pyrimidinyl- | H | H | H | MeO— | — |

TABLE 3

| Compound of the present invention | R¹ | R² | R³ | R⁴ | R⁵ | W | Melting point |
|---|---|---|---|---|---|---|---|
| 51 | H | H | H | H | 1-pyrrolyl- | MeO— | 114.4° C. |
| 52 | 2-thienyl- | H | H | H | H | MeO— | — |
| 53 | H | 2-thienyl- | H | H | H | MeO— | — |
| 54 | H | MeC(O)— | H | H | H | MeO— | — |
| 55 | H | CF₃C(O)— | H | H | H | MeO— | — |
| 56 | H | PhC(O)— | H | H | H | MeO— | — |
| 57 | MeOC(O)— | H | H | H | H | MeO— | — |
| 58 | H | MeOC(O)— | H | H | H | MeO— | — |
| 59 | H | H | MeOC(O)— | H | H | MeO— | * |
| 60 | H | H | H | H | MeOC(O)— | MeO— | — |
| 61 | H | NH₂C(O)— | H | H | H | MeO— | — |
| 62 | NH₂ | H | H | H | H | MeO— | * |
| 63 | H | NH₂ | H | H | H | MeO— | * |
| 64 | H | H | NH₂ | H | H | MeO— | * |
| 65 | H | H | H | H | NH₂ | MeO— | * |
| 66 | Me₂N— | H | H | H | H | MeO— | — |
| 67 | H | MeC(O)NH— | H | H | H | MeO— | — |
| 66 | H | PhC(O)NH— | H | H | H | MeO— | — |
| 69 | H | H | H | H | HC(O)NH— | MeO— | — |
| 70 | H | H | H | H | MeC(O)NH— | MeO— | — |
| 71 | H | CF₃C(O)NH— | H | H | H | MeO— | — |
| 72 | H | ClCH₂C(O)NH₂— | H | H | H | MeO— | — |
| 73 | H | H | H | H | PhC(O)NH— | MeO— | 146.1° C. |
| 74 | H | H | H | H | [(3-methyl-5-isoxazolyl)carbonyl]amino- | MeO— | 208.0° C. (decomp.) |
| 75 | H | H | H | H | [(1-methyl-1H-pyrazol-3yl)carbonyl]amino- | MeO— | 191.6° C. |

TABLE 4

| Compound of the present invention | R¹ | R² | R³ | R⁴ | R⁵ | W | Melting point |
|---|---|---|---|---|---|---|---|
| 76 | H | H | H | H | [(1,4-dimethyl-1H-pyrazol-5-yl)carbonyl]amino- | MeO— | 201.9° C. (decomp.) |
| 77 | H | H | H | H | [(1,5-dimethyl-1H-pyrazol-3-yl)carbonyl]amino- | MeO— | 157.7° C. |
| 78 | H | (2-thienyl)C(O)NH— | H | H | H | MeO— | 217.6° C. |
| 79 | H | H | H | H | [3-(2.5-dichlorothienyl)]C(O)NH— | MeO— | 169.9° C. |
| 80 | H | H | H | H | [2-(5-Bromothienyl)]C(O)NH— | MeO— | 136.3° C. |
| 81 | H | MeSO₂NH— | H | H | H | MeO— | — |
| 82 | H | BnSO₂NH— | H | H | H | MeO— | 156.1° C. |
| 83 | H | CF₃SO₂NH— | H | H | H | MeO— | — |
| 84 | H | (4-Cl—Ph)SO₂NH— | H | H | H | MeO— | * |
| 85 | H | (4-Me—Ph)SO₂NH— | H | H | H | MeO— | * |
| 86 | H | OH | H | H | H | MeO— | * |
| 87 | H | H | OH | H | H | MeO— | * |
| 88 | H | H | H | OH | H | MeO— | * |
| 89 | H | H | H | H | OH | MeO— | * |
| 90 | MeO— | H | H | H | H | MeO— | * |
| 91 | H | MeO— | H | H | H | MeO— | * |
| 92 | H | H | MeO— | H | H | MeO— | * |
| 93 | H | H | H | MeO— | H | MeO— | * |
| 94 | H | H | H | H | MeO— | MeO— | — |
| 95 | H | H | H | H | EtO— | MeO— | — |
| 96 | H | H | H | H | iPrO— | MeO— | — |
| 97 | H | H | H | H | BnO— | MeO— | — |
| 98 | H | CF₃O— | H | H | H | MeO— | — |
| 99 | H | H | HC≡CCH₂O— | H | H | MeO— | — |
| 100 | H | H | (4-CF₃Bn)O— | H | H | MeO— | — |

TABLE 5

| Compound of the present invention | R¹ | R² | R³ | R⁴ | R⁵ | W | Melting point |
|---|---|---|---|---|---|---|---|
| 101 | H | H | (3-MeOBn)O— | H | H | MeO— | — |
| 102 | H | H | H | (2-Me)PhO— | H | MeO— | — |
| 103 | H | H | H | (4-CF₃)PhO— | H | MeO— | — |
| 104 | H | H | H | (4-CF₃O)PhO— | H | MeO— | — |
| 105 | H | H | H | H | MeC(O)O— | MeO— | — |
| 106 | H | H | H | H | (2-ClPh)C(O)O— | MeO— | 150.6° C. |
| 107 | H | H | H | H | (4-MePh)S(O)₂O— | MeO— | 154.9° C. |
| 108 | H | MeS— | H | H | H | MeO— | — |
| 109 | H | CF₃S— | H | H | H | MeO— | — |
| 110 | H | CF₃S(O)— | H | H | H | MeO— | — |
| 111 | H | CF₃S(O)₂— | H | H | H | MeO— | — |
| 112 | H | H | H | H | MeNHS(O)₂— | MeO— | 186.5° C. (decomp.) |
| 113 | H | H | H | H | (4-MePh)CH₂NHS(O)₂— | MeO— | 109.5° C. (decomp.) |
| 114 | H | H | H | H | (3-ClPH)CH₂NHS(O)₂— | MeO— | * |
| 115 | H | H | H | H | [(2-pyridinylmethyl)amino]sulfonyl- | MeO— | 146.2° C. (decomp.) |
| 116 | H | H | H | H | (4-MePh)NHS(O)₂— | MeO— | 161.2° C. (decomp.) |
| 117 | H | SF₅ | H | H | H | MeO— | — |
| 118 | Cl | Cl | H | H | H | MeO— | — |
| 119 | Cl | H | H | H | NH₂ | MeO— | * |
| 120 | H | H | [{1-(difluoromethyl)-1H-pyrazol-3-yl-}carbonyl]amino- | H | Cl | MeO— | 227.4° C. (decomp.) |
| 121 | H | NO₂ | H | H | OH | MeO— | * |
| 122 | H | CF₃ | H | Cl | H | MeO— | — |
| 123 | H | CF₃ | H | H | Cl | MeO— | — |

TABLE 6

| Compound of the present invention | $R^1$ | $R^2$ | $R^3$ | $R^4$ | $R^5$ | W | Melting point |
|---|---|---|---|---|---|---|---|
| 124 | H | $CF_3$ | H | H | Me | MeO— | — |
| 125 | H | $CF_3$ | H | H | $CF_3$ | MeO— | — |
| 126 | H | $CF_3$ | H | H | OH | MeO— | — |
| 127 | H | $CF_3$ | H | H | MeO— | MeO— | — |
| 128 | H | $CF_3$ | H | H | EtO— | MeO— | — |
| 129 | H | $CF_3$ | H | H | iPrO— | MeO— | — |
| 130 | H | $CF_3$ | H | H | $H_2C$=$CHCH_2O$— | MeO— | — |
| 131 | H | $CF_3$ | H | H | MeC(O)O— | MeO— | — |
| 132 | H | $CF_3$ | H | H | BnO— | MeO— | — |
| 133 | H | $CF_3$ | H | H | $NH_2$ | MeO— | — |
| 134 | H | $CF_3$ | H | H | MeNH— | MeO— | — |
| 135 | H | $CF_3$ | H | H | $Me_2N$— | MeO— | — |
| 136 | H | $CF_3$ | H | H | HC(O)NH— | MeO— | — |
| 137 | H | $CF_3$ | H | H | MeC(O)NH— | MeO— | — |
| 138 | H | $CF_3$ | H | H | $CF_3C$(O)NH— | MeO— | — |
| 139 | H | $C_3F_7$ | H | H | $C_3F_7$ | MeO— | — |
| 140 | H | H | $CF_3$ | H | $NH_2$ | MeO— | 125.3° C. |
| 141 | H | (2-ClPh)NHC(O)NH— | H | H | MeO— | MeO— | 235.3° C. (decomp.) |
| 142 | $CF_3$ | H | H | H | H | EtO— | 50.8° C. |
| 144 | H | $CF_3$ | H | H | H | nPrO— | — |
| 145 | H | $CF_3$ | H | H | H | iPrO— | — |
| 146 | H | $CF_3$ | H | H | H | nBuO— | — |
| 147 | H | $CF_3$ | H | H | H | $nC_5H_{11}O$— | — |
| 148 | H | $CF_3$ | H | H | H | HC≡$CCH_2O$— | — |
| 149 | H | $CF_3$ | H | H | H | $HOCH_2CH_2O$— | — |
| 150 | H | $CF_3$ | H | H | H | BnO— | — |

TABLE 7

| Compound of the present invention | $R^1$ | $R^2$ | $R^3$ | $R^4$ | $R^5$ | W |
|---|---|---|---|---|---|---|
| 151 | H | $CF_3$ | H | H | H | (4-ClBn)O— |
| 152 | H | $CF_3$ | H | H | H | $MeOC(O)CH_2O$— |
| 153 | H | $CF_3$ | H | H | H | $Me_2C$=NO— |
| 154 | H | $CF_3$ | H | H | H | $NH_2$ |
| 155 | H | $CF_3$ | H | H | H | MeNH— |
| 156 | H | $CF_3$ | H | H | H | (NC)NH— |
| 157 | H | $CF_3$ | H | H | H | PhNH— |
| 158 | H | $CF_3$ | H | H | H | (3-Cl-4-MePh)NH— |
| 159 | H | $CF_3$ | H | H | H | (2,4-diMeOPh)NH— |
| 160 | H | $CF_3$ | H | H | H | HCNH— |
| 161 | H | $CF_3$ | H | H | H | $NH_2NH$— |
| 162 | H | $CF_3$ | H | H | H | MeS— |
| 163 | H | $CF_3$ | H | H | H | $MeOC(O)CH_2S$— |

Regarding compounds marked with * in the column of a melting point in Tables 1 to 7, $^1$H-NMR data thereof are shown below.

Compound 3 of the Present Invention

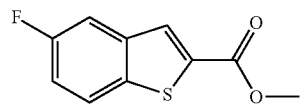

$^1$H-NMR (CDCl$_3$) δ: 8.01 (s, 1H), 7.81-7.79 (m, 1H), 7.54-7.52 (m, 1H), 7.24-7.22 (m, 1H), 3.95 (s, 3H)

Compound 10 of the Present Invention

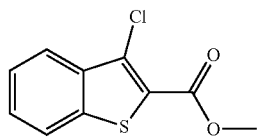

$^1$H-NMR (CDCl$_3$) δ: 8.00-7.97 (m, 1H), 7.84-7.82 (m, 1H), 7.56-7.48 (m, 2H), 3.97 (s, 3H)

Compound 11 of the Present Invention

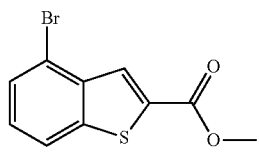

$^1$H-NMR (CDCl$_3$) δ: 8.19 (s, 1H), 7.80-7.78 (m, 1H), 7.59-7.57 (m, 1H), 7.31-7.29 (m, 1H), 3.97 (s, 3H)

Compound 12 of the Present Invention

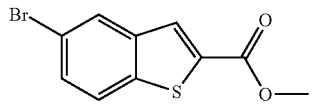

$^1$H-NMR (CDCl$_3$) δ: 8.03 (s, 1H), 7.98 (s, 1H), 7.73 (d, 1H, J=8.7 Hz), 7.55 (d, 1H, J=8.7 Hz), 3.96 (s, 3H)

Compound 13 of the Present Invention

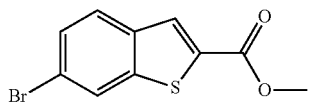

¹H-NMR (CDCl₃) δ: 8.02-8.01 (m, 2H), 7.74-7.72 (m, 1H), 7.52-7.50 (m, 1H), 3.95 (s, 3H)

Compound 14 of the Present Invention

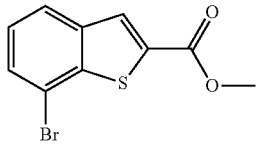

¹H-NMR (CDCl₃) δ: 8.15 (s, 1H), 7.85-7.83 (m, 1H), 7.62-7.60 (m, 1H), 7.31-7.29 (m, 1H), 3.96 (s, 3H)

Compound 15 of the Present Invention

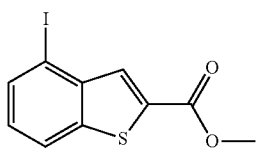

¹H-NMR (CDCl₃) δ: 8.12-8.11 (m, 1H), 7.83-7.81 (m, 2H), 7.16-7.14 (m, 1H), 3.96 (s, 3H)

Compound 16 of the Present Invention

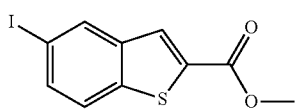

¹H-NMR (CDCl₃) δ: 8.23 (d, 1H, J=_0.5 Hz), 7.96 (s, 1H), 7.71 (dd, 1H, J=8.6, 1.5 Hz), 7.61 (d, 1H, J=8.6 Hz), 3.95 (s, 3H)

Compound 17 of the Present Invention

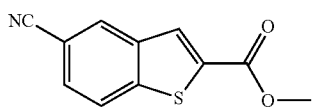

¹H-NMR (CDCl₃) δ: 8.22 (s, 1H), 8.10 (s, 1H), 7.98 (d, 1H, J=8.3 Hz), 7.66 (d, 1H, J=8.3 Hz), 3.98 (s, 3H)

Compound 18 of the Present Invention

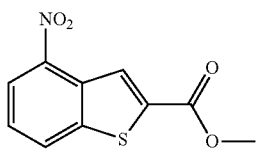

¹H-NMR (CDCl₃) δ: 8.88 (s, 1H), 8.39 (d, 1H, J=8.1 Hz), 8.19 (d, 1H, J=8.1 Hz), 7.61 (t, 1H, J=8.1 Hz), 4.01 (s, 3H)

Compound 19 of the Present Invention

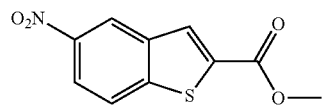 [SMILES: COC(=O)c1cc2cc([N+](=O)[O-])ccc2s1]

¹H-NMR (DMSO-D₆) δ: 9.01-9.00 (m, 1H), 8.46 (s, 1H), 8.37-8.32 (m, 2H), 3.93 (s, 3H)

Compound 20 of the Present Invention

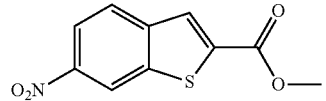 [SMILES: COC(=O)c1cc2ccc([N+](=O)[O-])cc2s1]

¹H-NMR (CDCl₃) δ: 8.82-8.80 (m, 1H), 8.28-8.25 (m, 1H), 8.14 (s, 1H), 8.02-7.99 (m, 1H), 3.99 (s, 3H)

Compound 24 of the Present Invention

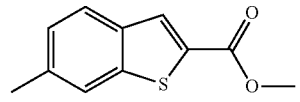

¹H-NMR (CDCl₃) δ: 8.01 (s, 1H), 7.76 (d, 1H, J=8.3 Hz), 7.66 (s, 1H), 7.23 (d, 1H, J=8.3 Hz), 3.94 (s, 3H), 2.49 (s, 3H)

Compound 59 of the Present Invention

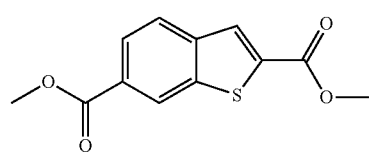

¹H-NMR (CDCl₃) δ: 8.60-8.58 (m, 1H), 8.10-8.08 (m, 1H), 8.07-8.05 (m, 1H), 7.93-7.91 (m, 1H), 3.98 (s, 3H), 3.97 (s, 3H)

Compound 62 of the Present Invention

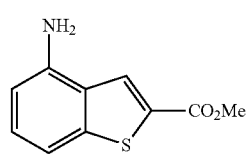 [SMILES: COC(=O)c1cc2c(N)cccc2s1]

¹H-NMR (CDCl₃) δ: 8.05 (s, 1H), 7.26-7.25 (m, 2H), 6.63-6.62 (m, 1H), 4.17 (br s, 2H), 3.94 (s, 3H)

Compound 63 of the Present Invention

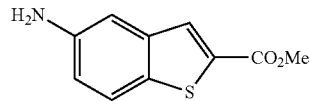 [SMILES: COC(=O)c1cc2cc(N)ccc2s1]

¹H-NMR (DMSO-D₆) δ: 7.92 (s, 1H), 7.65 (d, 1H, J=8.8 Hz), 7.05 (d, 1H, J=2.2 Hz), 6.89 (dd, 1H, J=8.8, 2.2 Hz), 5.28 (br s, 2H), 3.85 (s, 3H)

Compound 64 of the Present Invention

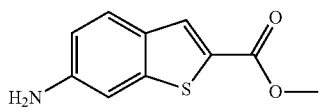

¹H-NMR (CDCl₃) δ: 7.91 (s, 1H), 7.63 (d, 1H, J=8.6 Hz), 7.06 (d, 1H, J=2.3 Hz), 6.77 (dd, 1H, J=8.6, 2.3 Hz), 3.94 (br s, 2H), 3.90 (s, 3H)

Compound 65 of the Present Invention

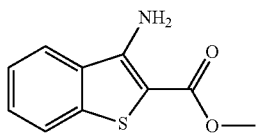

¹H-NMR (CDCl₃), δ: 7.74-7.72 (m, 1H), 7.65-7.63 (m, 1H), 7.49-7.46 (m, 1H), 7.38-7.36 (m, 1H), 5.91 (s, 2H), 3.89 (s, 3H)

Compound 84 of the Present Invention

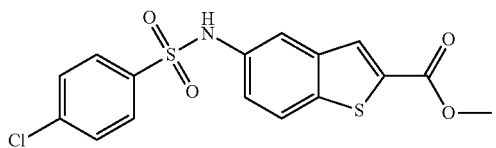 [SMILES: COC(=O)c1cc2cc(NS(=O)(=O)c3ccc(Cl)cc3)ccc2s1]

¹H-NMR (DMSO-D₆) δ: 10.54 (br s, 1H), 8.17 (s, 1H), 7.96-7.93 (m, 1H), 7.77-7.74 (m, 3H), 7.62-7.60 (m, 2H), 7.25-7.23 (m, 1H), 3.87 (s, 3H)

Compound 85 of the Present Invention

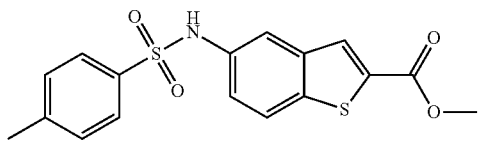

¹H-NMR (DMSO-D₆) δ: 10.40 (br s, 1H), 8.15 (s, 1H), 7.91 (d, 1H, J=8.8 Hz), 7.74 (d, 1H, J=2.3 Hz), 7.66 (d, 2H, J=8.3 Hz), 7.32 (d, 2H, J=8.3 Hz), 7.25 (dd, 1H, J=8.8, 2.3 Hz), 3.87 (s, 3H), 2.30 (s, 3H)

Compound 86 of the Present Invention

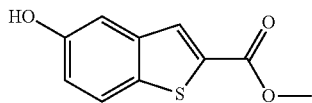

¹H-NMR (CDCl₃) δ: 7.94 (s, 1H), 7.71 (d, 1H, J=8.8 Hz), 7.28 (d, 1H, J=2.5 Hz), 7.05 (dd, 1H, J=8.8, 2.5 Hz), 5.02 (br s, 1H), 3.94 (s, 3H)

Compound 87 of the Present Invention

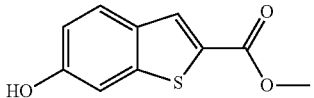

¹H-NMR (CDCl₃) δ: 7.97 (s, 1H), 7.75-7.73 (m, 1H), 7.28-7.27 (m, 1H), 6.97-6.95 (m, 1H), 5.33 (s, 1H), 3.93 (s, 3H)

Compound 88 of the Present Invention

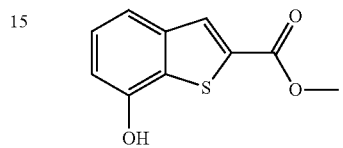

¹H-NMR (CDCl₃) δ: 8.06 (s, 1H), 7.50 (d, 1H, J=7.8 Hz), 7.30 (t, 1H, J=7.8 Hz), 6.85 (d, 1H, J=7.8 Hz), 5.54 (s, 1H), 3.96 (s, 3H)

Compound 89 of the Present Invention

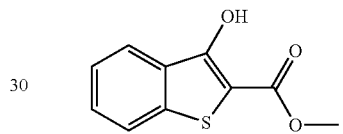

¹H-NMR (CDCl₃) δ: 10.13 (br s, 1H), 7.96-7.94 (m, 1H), 7.75-7.74 (m, 1H), 7.53-7.49 (m, 1H), 7.42-7.40 (m, 1H), 3.96 (s, 3H)

Compound 90 of the Present Invention

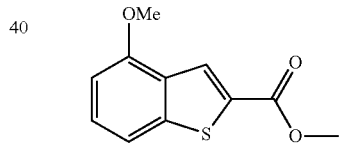

¹H-NMR (CDCl₃) δ: 8.24-8.23 (m, 1H), 7.41-7.38 (m, 2H), 6.76-6.74 (m, 1H), 3.96 (s, 3H), 3.93 (s, 3H)

Compound 91 of the Present Invention

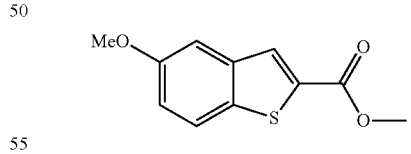

¹H-NMR (CDCl₃) δ: 7.99 (s, 1H), 7.73-7.71 (m, 1H), 7.29-7.28 (m, 1H), 7.13-7.11 (m, 1H), 3.94 (s, 3H), 3.88 (s, 3H)

Compound 92 of the Present Invention

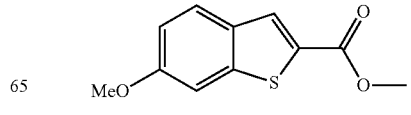

$^1$H-NMR (CDCl$_3$) δ: 7.97 (s, 1H), 7.74 (d, 1H, J=6.8 Hz), 7.29 (d, 1H, J=2.3 Hz), 7.02 (dd, 1H, J=8.8, 2.3 Hz), 3.93 (s, 3H), 3.89 (s, 3H)

Compound 93 of the Present Invention

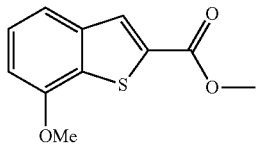

$^1$H-NMR (CDCl$_3$) δ: 8.05 (s, 1H), 7.48 (d, 1H, J=7.8 Hz), 7.35 (t, 1H, J=7.8 Hz), 6.86 (d, 1H, J=7.8 Hz), 4.01 (s, 3H), 3.94 (s, 3H)

Compound 114 of the Present Invention

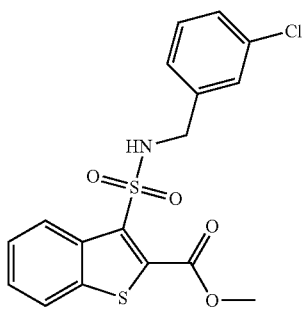 [SMILES: COC(=O)c1sc2ccccc2c1S(=O)(=O)NCc1cccc(Cl)c1]

$^1$H-NMR (CDCl$_3$) δ: 8.77-8.76 (m, 1H), 7.84-7.82 (m, 1H), 7.55-7.53 (m, 2H), 7.06-6.94 (m, 4H), 4.27-4.24 (m, 2H), 3.98 (s, 3H)

Compound 119 of the Present Invention

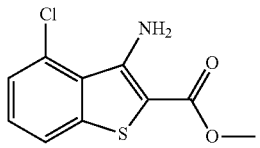

$^1$H-NMR (CDCl$_3$) δ: 7.61-7.59 (m, 1H), 7.32-7.28 (m, 2H), 6.84 (br s, 2H), 3.88 (s, 3H)

Compound 121 of the Present Invention

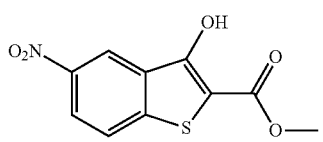 [SMILES: COC(=O)c1sc2ccc([N+](=O)[O-])cc2c1O]

$^1$H-NMR (CDCl$_3$) δ: 10.10 (s, 1H), 8.84 (s, 1H), 8.34 (d, 1H, J=8.8 Hz), 7.87 (d, 1H, J=8.8 Hz), 4.00 (s, 3H)

Formulation Example 1

One of the compounds 1 to 163 of the present invention is dissolved in an amount of 10 parts in a mixture of 35 parts of xylene and 35 parts of N,N-dimethylformamide, and 14 parts of polyoxyethylene styryl phenyl ether and 6 parts of calcium dodecylbenzene sulfonate were added thereto. The residue is mixed well by stirring, thereby obtaining 10% emulsion of each compound.

Formulation Example 2

One of the compounds 1 to 163 of the present invention is added in an amount of 20 parts to a mixture of 4 parts of sodium laurylsulfate, 2 parts of calcium lignin sulfonate, 20 parts of fine powder of synthetic hydrous silicon oxide, and 54 parts of diatomaceous earth. The residue is mixed well by stirring, thereby obtaining a 20% wettable powder of each compound.

Formulation Example 3

1 part of fine powder of synthetic hydrous silicon oxide, 2 parts of calcium lignin sulfonate, 30 parts of bentonite, and 65 parts of kaolin clay are added to 2 parts of one of the compounds 1 to 163 of the present invention, and the residue is sufficiently mixed by stirring. Subsequently, water is added in an appropriate amount to the mixture, and the residue is stirred, granulated by a granulator, and dried with air, thereby obtaining 2% granules of each compound.

Formulation Example 4

One of the compounds 1 to 163 of the present invention is dissolved in an amount of 1 part in acetone in an appropriate amount, and 5 parts of fine powder of synthetic hydrous silicon oxide, 0.3 parts of PAP, and 93.7 parts of Fubasami clay are added thereto. The residue is sufficiently mixed by stirring, and acetone is removed by evaporation, thereby obtaining 1% powder of the each compound.

Formulation Example 5

Ten (10) parts of one of the compounds 1 to 163 of the present invention, 17.5 parts of a polyoxyethylene alkyl ether sulfate ammonium salt, 17.5 parts of white carbon, and 55 parts of water are mixed with each other, and the mixture is finely pulverized by a wet pulverization method, thereby obtaining a 10% flowable agent of the each compound.

Formulation Example 6

One of the compounds 1 to 163 of the present invention is dissolved in an amount of 0.1 parts in 5 parts of xylene and 5 parts of trichloroethane, and the residue is mixed with 89.9 parts of deodorized kerosene, thereby obtaining 0.1% oil of each compound.

Next, application examples of the composition of the present invention to plant seeds are described.

Application Example 1

One hundred (100) kg of dried corn seeds are smeared with 200 ml of the respective flowable agents prepared in Formulation example 5 by using a rotary seed treatment machine (seed dresser, manufactured by Hans-Ulrich Hege GmbH), thereby obtaining the respective seeds treated.

Application Example 2

Ten (10) kg of dried wheat seeds are smeared with 40 ml the respective flowable agents prepared in Formulation example 5 by using a rotary seed treatment machine (seed dresser, manufactured by Hans-Ulrich Hege GmbH), thereby obtaining the respective seeds treated.

Application Example 3

One hundred (100) kg of dried rice seeds are smeared with 200 ml the respective flowable agents prepared in Formulation example 5 by using a rotary seed treatment machine (seed dresser, manufactured by Hans-Ulrich Hege GmbH), thereby obtaining the respective seeds treated.

Test Example 1. Test for Evaluating Promotion of Root Growth by Hydroponics of Rice (Test Plant)
Rice (variety: Nipponbare)
(Cultivation and Compound Treatment)

A DMSO solution, which contained one of the compounds 3, 9, 11, 14, 15, 20, 22, 23, 26, 27, 29 to 31, 34, 35, 37, 38, 40 to 43, 45, 47, 49, 50, 52, 54 to 56, 58, 60, 61, 63 to 69, 71, 74, 77, 79, 80, 82, 87, 88, 95 to 97, 100, 102 to 104, 106, 108, 109, 114, 120 to 124, 126 to 129, 131, 133, 136, 139 to 142, 144, 145, 147, 148, 150, 153, 157, 159, and 162 of the present invention at a concentration of 100,000 ppm, was added to Hoagland hydroponic solution (Hoagland and Arnon, California Agricultural Experiment Station 1950 Circular 347 pp. 34) of ¼-fold concentration at a volume ratio of 1/10,000. In this manner, hydroponic solutions containing one of the compounds 3, 9, 11, 14, 15, 20, 22, 23, 26, 27, 29 to 31, 34, 35, 37, 38, 40 to 43, 45, 47, 49, 50, 52, 54 to 56, 58, 60, 61, 63 to 69, 71, 74, 77, 79, 80, 82, 87, 88, 95 to 97, 100, 102 to 104, 106, 108, 109, 114, 120 to 124, 126 to 129, 131, 133, 136, 139 to 142, 144, 145, 147, 148, 150, 153, 157, 159, and 162 of the present invention at 10 ppm were prepared respectively. As an untreated control plot, a hydroponic solution obtained by adding DMSO to Hoagland hydroponic solution of ¼-fold concentration at a volume ratio of 1/10,000 was used.

Rice seeds were soaked in a 1% aqueous sodium hypochlorite solution for 10 minutes, then soaked in a 70% ethanol solution for surface sterilization, and then washed with distilled water. The sterilized seeds were soaked in a hydroponic solution containing the test compound described above at 10 ppm and incubated in a dark place for 3 days at 28° C. to perform treatment for hastening germination.

Thereafter, 30 ml of hydroponic solution containing the test compound at 10 ppm was dispensed in a plastic tube (diameter of 20 mm×height of 113 mm) of which the side was covered with cardboard to block light. A float prepared using a styrene board and vinyl mesh was floated, and the rice seeds that had undergone the treatment for hastening germination were placed on the float on the surface of the hydroponic solution. The seeds were cultured for 3 days at 26° C., under the conditions of an illuminance of 4,000 lux of the top surface of the tube, a humidity of 50%, and a day length of 16 hours.

(Evaluation Method)

The nursery plants of rice obtained after culturing were measured in terms of the length of seminal root by using WinRHIZO system (manufactured by Regent Instruments Inc.). For each test plot, an average of the measured values of the seminal root of 4 or 5 individuals were determined. As a result, as shown in Table 8, the seminal root was obviously longer in the test plot treated with one of the compounds 3, 9, 11, 14, 15, 20, 22, 23, 26, 27, 29 to 31, 34, 35, 37, 38, 40 to 43, 45, 47, 49, 50, 52, 54 to 56, 58, 60, 61, 63 to 69, 71, 74, 77, 79, 80, 82, 87, 88, 95 to 97, 100, 102 to 104, 106, 108, 109, 114, 120 to 124, 126 to 129, 131, 133, 136, 139 to 142, 144, 145, 147, 148, 150, 153, 157, 159, and 162 of the present invention than in the untreated control plot.

TABLE 8

| Test compound | Relative value of length of seminal root (%-untreated control plot) |
|---|---|
| Present Compound 3 | >5 |
| Present Compound 9 | >5 |
| Present Compound 11 | >5 |
| Present Compound 14 | >5 |
| Present Compound 15 | >5 |
| Present Compound 20 | >5 |
| Present Compound 22 | >5 |
| Present Compound 23 | >5 |
| Present Compound 26 | >5 |
| Present Compound 27 | >5 |
| Present Compound 29 | >5 |
| Present Compound 30 | >5 |
| Present Compound 31 | >5 |
| Present Compound 34 | >5 |
| Present Compound 35 | >5 |
| Present Compound 37 | >5 |
| Present Compound 38 | >5 |
| Present Compound 40 | >5 |
| Present Compound 41 | >5 |
| Present Compound 42 | >5 |
| Present Compound 43 | >5 |
| Present Compound 45 | >5 |
| Present Compound 47 | >5 |
| Present Compound 49 | >5 |
| Present Compound 50 | >5 |
| Present Compound 52 | >5 |
| Present Comoound 54 | >5 |
| Present Compound 55 | >5 |
| Present Compound 56 | >5 |
| Present Compound 58 | >5 |
| Present Compound 60 | >5 |
| Present Compound 61 | >5 |
| Present Compound 63 | >5 |
| Present Compound 64 | >5 |
| Present Compound 65 | >5 |

TABLE 9

| Test compound | Relative value of length of seminal root (%-untreated control plot) |
|---|---|
| Present Compound 66 | >5 |
| Present Compound 67 | >5 |
| Present Compound 68 | >5 |
| Present Compound 69 | >5 |
| Present Compound 71 | >5 |
| Present Compound 74 | >5 |
| Present Compound 77 | >5 |
| Present Compound 79 | >5 |
| Present Compound 80 | >5 |
| Present Compound 82 | >5 |
| Present Compound 87 | >5 |
| Present Compound 88 | >5 |
| Present Compound 95 | >5 |
| Present Compound 96 | >5 |
| Present Compound 97 | >5 |
| Present Compound 100 | >5 |
| Present Compound 102 | >5 |
| Present Compound 103 | >5 |
| Present Compound 104 | >5 |
| Present Compound 106 | >5 |
| Present Compound 108 | >5 |
| Present Compound 109 | >5 |

TABLE 10

| Test compound | Relative value of length of seminal root (%-untreated control plot) |
|---|---|
| Present Compound 114 | >5 |
| Present Compound 120 | >5 |
| Present Compound 121 | >5 |
| Present Compound 122 | >5 |
| Present Compound 123 | >5 |
| Present Compound 124 | >5 |
| Present Compound 126 | >5 |
| Present Compound 127 | >5 |
| Present Compound 128 | >5 |
| Present Compound 129 | >5 |
| Present Compound 131 | >5 |
| Present Compound 133 | >5 |
| Present Compound 136 | >5 |
| Present Compound 139 | >5 |
| Present Compound 140 | >5 |
| Present Compound 141 | >5 |
| Present Compound 142 | >5 |
| Present Compound 144 | >5 |
| Present Compound 145 | >5 |
| Present Compound 147 | >5 |
| Present Compound 148 | >5 |
| Present Compound 150 | >5 |
| Present Compound 153 | >5 |
| Present Compound 157 | >5 |
| Present Compound 159 | >5 |
| Present Compound 162 | >5 |

Test Example 2. Test for Evaluating Promotion of Root Growth by Hydroponics of Rice (Test Plant)
Rice (Variety: Nipponbare)
(Cultivation and Compound Treatment)

A DMSO solution, which contained one of the compounds 1, 4, 5, 7, 8, 10, 13, 16 to 18, 24, 25, 28, 32, 33, 36, 44, 46, 48, 53, 75, 76, 78, 90, 91, 94, 98, 99, 101, 105, 111, 112, 130, 132, 134, 135, 138, 146, 151, 152, 154, 155, 160, 161, and 163 of the present invention at a concentration of 100,000 ppm, was added to Hoagland hydroponic solution (Hoagland and Arnon, California Agricultural Experiment Station 1950 Circular 347 pp. 34) of ¼-fold concentration at a volume ratio of 1/10,000. In this manner, hydroponic solutions containing one of the compounds 1, 4, 5, 7, 8, 13, 16 to 18, 24, 25, 28, 32, 33, 36, 44, 46, 48, 53, 75, 76, 78, 90, 91, 94, 98, 99, 101, 105, 111, 112, 130, 132, 134, 135, 138, 146, 151, 152, 154, 155, 160, 161, and 163 of the present invention at 1 ppm were prepared respectively. As an untreated control plot, a hydroponic solution obtained by adding DMSO to Hoagland hydroponic solution of ¼-fold concentration at a volume ratio of 1/10,000 was used. Rice seeds were soaked in a 1% aqueous sodium hypochlorite solution for 10 minutes, then soaked in a 70% ethanol solution for surface sterilization, and then washed with distilled water. The sterilized seeds were soaked in a hydroponic solution containing the zest compound described above at 1 ppm and incubated in a dark place for 3 days at 28° C. to perform treatment for hastening germination.

Thereafter, 30 ml of hydroponic solution containing the test compound at 1 ppm was dispensed in a plastic tube (diameter of 20 mm×height of 113 mm) of which the side was covered with cardboard to block light. A float prepared using a styrene board and vinyl mesh was floated, and the rice seeds that had undergone the treatment for hastening germination were placed on the float on the surface of the hydroponic solution. The seeds were cultured for 3 days at 26° C., under the conditions of an illuminance of 4,000 lux of the top surface of the tube, a humidity of 50%, and a day length of 16 hours.

(Evaluation Method)

The nursery plants of rice obtained after cultivation were measured in terms of the length of seminal root by using WinRHIZO system (manufactured by Regent Instruments Inc.). For each test plot, an average of the measured values of the seminal root of 4 or 5 individuals were determined. As a result, as shown in Tables 11 and 12, the seminal root was obviously longer in the test plot treated with one of the compounds 1, 4, 5, 7, 8, 10, 13, 16 to 18, 24, 25, 28, 32, 33, 36, 44, 46, 48, 53, 75, 76, 78, 90, 91, 94, 98, 99, 101, 105, 111, 112, 130, 132, 134, 135, 138, 143, 146, 151, 152, 154, 155, 160, 161, and 163 of the present invention than in the untreated control plot.

TABLE 11

| Test compound | Relative value of length of seminal root (%-untreated control plot) |
|---|---|
| Present Compound 1 | >5 |
| Present Compound 4 | >5 |
| Present Compound 5 | >5 |
| Present Compound 7 | >5 |
| Present Compound 8 | >5 |
| Present Compound 10 | >5 |
| Present Compound 13 | >5 |
| Present Compound 16 | >5 |
| Present Compound 17 | >5 |
| Present Compound 18 | >5 |
| Present Compound 24 | >5 |
| Present Compound 25 | >5 |
| Present Compound 28 | >5 |
| Present Compound 32 | >5 |
| Present Compound 33 | >5 |

TABLE 12

| Test compound | Relative value of length of seminal root (%-untreated control plot) |
|---|---|
| Present Compound 36 | >5 |
| Present Compound 44 | >5 |
| Present Compound 46 | >5 |
| Present Compound 48 | >5 |
| Present Compound 53 | >5 |
| Present Compound 75 | >5 |
| Present Compound 76 | >5 |
| Present Compound 78 | >5 |
| Present Compound 90 | >5 |
| Present Compound 91 | >5 |
| Present Compound 94 | >5 |
| Present Compound 98 | >5 |
| Present Compound 99 | >5 |
| Present Compound 101 | >5 |
| Present Compound 105 | >5 |
| Present Compound 111 | >5 |
| Present Compound 112 | >5 |
| Present Compound 130 | >5 |
| Present Compound 132 | >5 |
| Present Compound 134 | >5 |
| Present Compound 135 | >5 |
| Present Compound 138 | >5 |
| Present Compound 143 | >5 |
| Present Compound 146 | >5 |
| Present Compound 151 | >5 |
| Present Compound 152 | >5 |
| Present Compound 154 | >5 |
| Present Compound 155 | >5 |
| Present Compound 160 | >5 |
| Present Compound 161 | >5 |
| Present Compound 163 | >5 |

Test Example 3. Test for Evaluating Promotion of Root Growth by Hydroponics of Rice (Test Plant)
Rice (Variety: Nipponbare)
(Cultivation and Compound Treatment)

A DMSO solution, which contained one of the compounds 6, 12, 39, 51, 57, 59, 62, 73, 86, 89, 92, 107, 110, 113, 123, 137, 149, and 156 of the present invention at a concentration of 1,000 ppm, was added to Hoagland hydroponic solution (Hoagland and Arnon, California Agricultural Experiment Station 1953 Circular 347 pp. 34) of ¼-fold concentration at a volume ratio of 1/10,000. In this manner, hydroponic solutions containing one of the compounds 6, 12, 39, 51, 57, 59, 62, 73, 86, 89, 92, 107, 110, 113, 125, 137, 149, and 156 of the present invention at 0.1 ppm were prepared respectively. As an untreated control plot, a hydroponic solution obtained by adding DMSO to Hoagland hydroponic solution of ¼-fold concentration at a volume ratio of 1/10,000 was used. Rice seeds were soaked in a 1% aqueous sodium hypochlorite solution for 10 minutes, then soaked in a 70% ethanol solution for surface sterilization, and then washed with distilled water. The sterilized seeds were soaked in a hydroponic solution containing the test compound described above at 0.1 ppm and incubated in a dark place for 3 days at 28° C. to perform treatment for hastening germination.

Thereafter, 30 ml of hydroponic solution containing the test compound at 0.1 ppm was dispensed in a plastic tube (diameter of 20 mm×height of 113 mm) of which the side was covered with cardboard to block light. A float prepared using a styrene board and vinyl mesh was floated, and the rice seeds that had undergone the treatment for hastening germination were placed on the float on the surface of the hydroponic solution. The seeds were cultured for 3 days at 26° C., under the conditions of an illuminance of 4,000 lux of the top surface of the tube, a humidity of 50%, and a day length of 16 hours.

(Evaluation Method)

The nursery plants of rice obtained after culturing were measured in terms of the length of seminal root by using WinRHIZO system (manufactured by Regent Instruments Inc.). For each test plot, an average of the measured values of the seminal root of 4 or 5 individuals were determined. As a result, as shown in Table 10, the seminal root was obviously longer in the test plot treated with one of the compounds 6, 12, 39, 51, 57, 59, 62, 73, 86, 89, 92, 107, 110, 113, 125, 137, 149, and 156 of the present invention than in the untreated control plot.

TABLE 13

| Test compound | Relative value of length of seminal root (%-untreated control plot) |
| --- | --- |
| Present Compound 6 | >5 |
| Present Compound 12 | >5 |
| Present Compound 39 | >5 |
| Present Compound 51 | >5 |
| Present Compound 57 | >5 |
| Present Compound 59 | >5 |
| Present Compound 62 | >5 |
| Present Compound 73 | >5 |
| Present Compound 86 | >5 |
| Present Compound 89 | >5 |
| Present Compound 92 | >5 |
| Present Compound 107 | >5 |
| Present Compound 110 | >5 |
| Present Compound 113 | >5 |
| Present Compound 125 | >5 |
| Present Compound 137 | >5 |
| Present Compound 149 | >5 |
| Present Compound 156 | >5 |

TABLE 13-continued

Test Example 4. Test for Evaluating Growth Promotion Under Low-Temperature Stress by Hydroponics of *Nicotiana benthamiana*

(Test Plant)
*Nicotiana benthamiana*
(Cultivation and Compound Treatment)

A DMSO solution, which contained one of the compounds 3, 4, 10, 12, 14, 22, 26, 28, 31, 39, 40, 42, 45, 54, 57, 58, 60, 65, 66, 68, 69, 71, 73, 76, 82, 89, 90, 97, 98, 101, 102, 104, 106, 108 to 111, 116, 118, 123, 133, 139, 141, 142, 150, 155, and 161 of the present invention a: a concentration of 10,000 ppm, was prepared. The DMSO solution of the compound of the present invention was added at a volume ratio of 1/1,000 to the Murashige•Scoog medium of a ½-fold concentration (a medium containing 2.3 g of mixed salts (manufactured by Wako Pure Chemical Industries, Ltd.), 200 mg of Myo-inositol (manufactured by Sigme-Aldrich Co. LLC.), 2 mg of niconitic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wako Pure Chemical Industries, Ltd.), 20 g of sucrose (manufactured by Wako Pure Chemical Industries, Ltd.), and 1 g of MES (manufactured by DOJINDO LABORATORIES) respectively per 1 L of water and having pH adjusted to 5.8), thereby preparing a medium containing the compound of the present invention at a concentration of 10 ppm.

Seeds of *Nicotiana benthamiana* were seeded in the 5 μL of the medium and cultured overnight at 22° C. Thereafter, 45 μL of the medium containing the compound of the present invention at a concentration of 10 ppm was added thereto, and the seeds are cultured for 7 days at 22° C., under the conditions of an illuminance of 4,000 lux, and a day length of 16 hours, and the nursery plants raised from the *Nicotiana benthamiana* were treated with the compound. Moreover, instead of the above medium a test plot, which was obtained by performing the same treatment by using a medium prepared by adding DMSO to the Murashige•Scoog medium of ½-fold concentration at a volume ratio of 1/1,000, was used as a control plot not treated with the compound.

(Low-Temperature Stress Treatment)

The nursery plants of the *Nicotiana benthamiana* treated with the compound were subjected to low-temperature treatment by being cultured for 7 days at 1.5±1.0° C., under the conditions of an illuminance of 2,000 lux, and a day length of 16 hours.

(Evaluation)

The nursery plants of the *Nicotiana benthamiana* having undergone the low-temperature stress treatment were cultured for 3 days at 22° C., under the conditions of an illuminance of 4,000 lux, and a day length of 16 hours. Thereafter, the area of green leaf was quantified by Scanalyzer HTS (manufactured by LemnaTec GmbH). Moreover, the value of the control plot not treated with the compound that had not yet been subjected to the low-temperature stress treatment was measured in the same manner. A value of a relative leaf area was calculated based on the following equation (1), and if the relative value of leafed area was 5 or greater, the compound was evaluated to have a growth promotion effect. As a result of the evaluation, it was confirmed that when the plant was treated with one of the compounds 3, 4, 10, 12, 14, 22, 26, 28, 31, 39, 40, 42, 45, 54, 57, 58, 60, 65, 66, 68, 69, 71, 73, 76, 82, 89, 90, 97, 98, 101, 102, 104, 106, 108 to 111, 116, 118, 123, 133, 139, 141, 142, 150, 155, and 161 of the present invention at 10 ppm, the value of a relative leaf area was 5 or greater, compared to the area of green leaf of the control plot not treated with compound. Accordingly, it was confirmed that the treatment using the compound of the present invention improve a growth promotion effect.

Relative leaf area=100*(a green area of a plot treated with the compound of the present invention minus (−) a green area of a plot not treated with the compound of the present invention)/(a green area of a control plot not treated with the compound of the present invention that had not yet been subjected to low-temperature stress treatment minus (−) a green area of a control plot not treated with the compound of the present invention)         Equation (1):

Test Example 5. Test for Evaluating Growth Promotion Under Low-Temperature Stress by Hydroponics of *Nicotiana benthamiana*

(Test Plant)
*Nicotiana benthamiana*
(Cultivation and Compound Treatment)

A DMSO solution, which contained one of the compounds 5, 6, 8, 9, 11, 13, 18, 21, 24, 30, 33 to 38, 43, 44, 46, 48, 49, 56, 61, 72, 74, 77, 79, 80, 86, 93, 96, 100, 103, 107, 115, 117, 122, 125, 126, 128, 130, 132, 134 to 137, 140, 151, and 157 to 160 of the present invention at a concentration of 1,000 ppm, was prepared. The DMSO solution of the compound of the present invention was added at a volume ratio of 1/1,000 to the Murashige•Scoog medium of a ½-fold concentration (a medium containing 2.3 g of mixed salts (manufactured by Wako Pure Chemical Industries, Ltd.), 200 mg of Myo-inositol (manufactured by Sigme-Aldrich Co. LLC.), 2 mg of niconitic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wacko Pure Chemical Industries, Ltd.), 20 g of sucrose (manufactured by Wako Pure Chemical Industries, Ltd.), and 1 g of MES (manufactured by DOJINDO LABORATORIES) respectively per 1 L of water and having pH adjusted to 5.8), thereby preparing a medium containing the compound of the present invention at a concentration of 1 ppm.

Seeds of *Nicotiana benthamiana* were seeded in the 5 μL of the medium and cultured overnight at 22° C. Thereafter, 45 μL of the medium containing the compound of the present invention at a concentration of 1 ppm was added thereto, and the seeds are cultured for 7 days at 22° C., under the conditions of an illuminance of 4,000 lux, and a day length of 16 hours, and the nursery plants raised from the *Nicotiana benthamiana* were treated with the compound. Moreover, instead of the above medium a test plot, which was obtained by performing the same treatment by using a medium prepared by adding DMSO to the Murashige•Scoog medium of ½-fold concentration at a volume ratio of 1/1, 000, was used as a control plot not treated with the compound.

(Low-Temperature Stress Treatment)
The nursery plants of the *Nicotiana benthamiana* treated with the compound were subjected to low-temperature treatment by being cultured for 7 days at 1.5±1.0° C., under the conditions of an illuminance of 2,000 lux, and a day length of 16 hours.

(Evaluation)
The nursery plants of the *Nicotiana benthamiana* having undergone the low-temperature stress treatment were cultured for 3 days at 22° C., under the conditions of an illuminance of 4,000 lux, and a day length of 16 hours. Thereafter, the area of green leaf was quantified by Scanalyzer HTS (manufactured by LemnaTec GmbH). Moreover, the value of the control plot not treated with the compound that had not yet been subjected to the low-temperature stress treatment was measured in the same manner. A value of a relative leaf area was calculated based on the following equation (1), and if the relative value of leaf area was 5 or greater, the compound was evaluated to have a growth promotion effect. As a result of the evaluation, it was confirmed that when the plan: was treated with one of the compounds 5, 6, 8, 9, 11, 13, 18, 21, 24, 30, 33 to 38, 43, 44, 46, 48, 49, 56, 61, 72, 74, 77, 79, 80, 86, 93, 96, 100, 103, 107, 115, 117, 122, 125, 126, 128, 130, 132, 134 to 137, 140, 151, and 157 to 160 of the present invention at 1 ppm, the value of a relative leaf area was 5 or greater, compared to the area of green leaf of the control plot not treated with compound. Accordingly, it was confirmed that the treatment using the compound of the present invention improve a growth promotion effect.

Relative leaf area=100*(a green area of a plot treated with the compound of the present invention minus (−) a green area of a plot not treated with the compound of the present invention)/(a green area of a control plot not treated with the compound of the present invention that had not yet been subjected to low-temperature stress treatment minus (−) a green area of a control plot not treated with the compound of the present invention)         Equation (1):

Test Example 6. Test for Evaluating Growth Promotion Under Low-Temperature Stress by Hydroponics of *Nicotiana benthamiana*

(Test Plant)
*Nicotiana benthamiana*
(Cultivation and Compound Treatment)

A DMSO solution, which contained one of the compounds 1, 2, 7, 16, 17, 25, 29, 41, 47, 50 to 52, 55, 59, 64, 75, 78, 85, 87, 88, 95, 99, 112 to 114, and 127, 154 of the present invention at a concentration of 100 ppm, was prepared. The DMSO solution of the compound of the present invention was added at a volume ratio of 1/1,000 to the Murashige•Scoog medium of a ½-fold concentration (a medium containing 2.3 g of mixed salts (manufactured by Wako Pure Chemical Industries, Ltd.), 200 mg of Myo-inositol (manufactured by Sigme-Aldrich Co. LLC.), 2 mg of niconitic acid (manufactured by Wako Pure Chemical Industries, Ltd.), 2 mg of pyridoxine hydrochloride (manufactured by Wako Pure Chemical Industries, Ltd.), 20 mg of thiamine hydrochloride (manufactured by Wako Pure Chemical Industries, Ltd.), 20 g of sucrose (manufactured by Wako Pure Chemical Industries, Ltd.), and 1 g of MES (manufactured by DOJINDO LABORATORIES) respectively per 1 L of water and having pH adjusted to 5.8), thereby preparing a medium containing the compound of the present invention at a concentration of 0.1 ppm.

Seeds of *Nicotiana benthamiana* were seeded in the 5 μL of the medium and cultured overnight at 22° C. Thereafter, 45 μL of the medium containing the compound of the present invention at a concentration of 0.1 ppm was added thereto, and the seeds are cultured for 7 days at 22° C., under the conditions of an illuminance of 4,000 lux, and a day length of 16 hours, and the nursery plants raised from the *Nicotiana benthamiana* were treated with the compound. Moreover, instead of the above medium a test plot, which was obtained by performing the same treatment by using a medium prepared by adding DMSO to the Murashige•Scoog medium of ½-fold concentration at a volume ratio of 1/1, 000, was used as a control plot not treated with the compound.

(Low-Temperature Stress Treatment)

The nursery plants of the *Nicotiana benthamiana* treated with the compound were subjected to low-temperature treatment by being cultured for 7 days at 1.5±1.0° C., under the conditions of an illuminance of 2,000 lux, and a day length of 16 hours.

(Evaluation)

The nursery plants of the *Nicotiana benthamiana* having undergone the low-temperature stress treatment were cultured for 3 days a: 22° C., under the conditions of an illuminance of 4,000 lux, and a day length of 16 hours. Thereafter, the area of green leaf was quantified by Scanalyzer HTS (manufactured by LemnaTec GmbH). Moreover, the value of the control plot not treated with the compound that had not yet been subjected to the low-temperature stress treatment was measured in the same manner. A value of a relative leaf area was calculated based on the following equation (1), and if the relative value of leaf area was 5 or greater, the compound was evaluated to have a growth promotion effect. As a result of the evaluation, it was confirmed that when the plant was treated with one of the compounds 1, 2, 7, 16, 17, 25, 29, 41, 47, 50 to 52, 55, 59, 64, 75, 78, 85, 87, 88, 95, 99, 112 to 114, 127, and 154 of the present invention at 0.1 ppm, the value of a relative leaf area was 5 or greater, compared to the area of green leaf of the control plot not treated with compound. Accordingly, it was confirmed that the treatment using the compound of the present invention improves a growth promotion effect.

Relative leaf area=100*(a green area of a plot treated with the compound of the present invention minus (−) a green area of a plot not treated with the compound of the present invention)/(a green area of a control plot not treated with the compound of the present invention that had not yet been subjected to low-temperature stress treatment minus (−) green area of a control plot not treated with the compound of the present invention)    Equation (1):

Test Example 7. Test for Evaluating Growth Promotion by Corn Seed Treatment (Test Plant)

Corn (Variety: Pioneer 31P41 (Manufactured by Pioneer Hi-Bred Japan))

(Seed Treatment)

A blank slurry solution containing 10% (V/V) color coat red (Becker Underwood, Inc.), 10% (V/V) CF-Clear (Becker Underwood, Inc.), and 1.66% Maxim4FS (Syngenta) is prepared. One of the compounds 1 to 163 of the present invention is dissolved in the blank slurry such that a predetermined amount of the compound is used for treatment per 100 kg corn seeds, thereby preparing a slurry solution. 0.35 ml of the slurry solution per 14.4 g of the seeds is put into a 50 ml centrifugal settling tube (manufactured by Becton, Dickinson and Company, Japan), and the slurry solution is stirred until it dries, thereby coating the seeds. Moreover, the seeds coated with the blank slurry are used as seeds for an untreated control plot.

(Cultivation)

Each of the seeds having undergone the seed treatment is seeded one by one in a culture soil (Aisai) in a pot (φ55 mm×height of 58 mm), and cultured for 18 days at 27° C., under the conditions of an illuminance of 5,000 lux, and a day length of 16 hours.

(Evaluation Method)

After cultivation, a fresh weight of the aerial part of each individual of the grown plant is measured, and an average weight of each individual is determined.

As a result, the fresh weight of the aerial part is expected to be larger in the plot having undergone seed treatment by using one of the compounds 1 to 163 of the present invention than in the untreated control plot.

Test Example 8. Test for Evaluating Growth Promotion Under Low-Temperature Stress by Corn Seed Treatment (Test Plant)

Corn (Variety: Pioneer 31P41 (Manufactured by Pioneer Hi-Bred Japan)

(Seed Treatment)

A blank slurry solution containing 10% (V/V) color coat red (Becker Underwood, Inc.), 10% (V/V) CF-Clear (Becker Underwood, Inc.), and 1.66% Maxim4FS (Syngenta) was prepared. One of the compounds 1 and 30 of the present invention was dissolved in the blank slurry such that 0.5 g, 5 g or 50 g of the compound was used for treatment per 100 kg corn seeds, thereby preparing a slurry solution. Zero point three five (0.35) ml of the slurry solution per 14.4 g of the seeds was put into a 50 ml centrifugal settling tube (manufactured by Becton, Dickinson and Company, Japan), and the slurry solution was stirred until it dries, thereby coating the seeds. Moreover, the seeds coated with the blank slurry were used as seeds for an untreated control plot.

(Cultivation)

Each of the seeds having undergone the seed treatment was seeded one by one in a culture soil (Aisai) in a pot (φ55 mm×height of 58 mm), and cultured for 19 days at 27° C., under the conditions of an illuminance of 5,000 lux, and a day length of 16 hours. The grown nursery plants were used for a test.

(Low-Temperature Stress Treatment Method)

A pot in which the seeds were seeded 10 days ago was put in a phytotron set to the following temperature condition, followed by cultivation for 4 days under the following conditions.

"Conditions; a temperature of 2.5±1° C., a day length of 16 hours, and an illuminance of 5,000 lux"

(Evaluation)

After low-temperature stress treatment was performed, the seeds were cultured for 4 days at 27° C., under the conditions of an illuminance of 5,000 lux, and a day length of 16 hours. Thereafter, a fresh weight of the overground portion of each individual of the plant having grown was weighed, and an average weight of each individual was determined.

As a result, the fresh weight of the aerial part was expected to be larger in the plot having undergone seed treatment by using one of the compounds 1 and 30 of the present invention at an amount of 0.5 g, 5 g or 50 g per 100 kg of the corn seeds than in the untreated control plot.

Test Example 9. Test for Evaluating Growth Promotion Under Low-Temperature Stress by Soaking Treatment of Rice (Test Plant)
Rice (Variety: Nipponbare)
(Cultivation)

Rice seeds in a required amount are soaked in an aqueous benlate solution at 1,000 ppm, and cultured overnight at 30° C. in a dark place. The aqueous benlate solution is then replaced with distilled water, and the seeds are cultured overnight again at 30° C. in a dark place to perform treatment for hastening germination.

Filter paper is placed in holes of a 406-hole plug tray, and rice seeds having undergone the germination hastening treatment are seeded on the filter paper. The Kimura B hydroponic solution (refer to Plant Science 119:39-47 (1996)) of ½-fold concentration is added thereto, and the seeds are cultured for 5 days in a phytotron under the following conditions.

"Conditions; a temperature 28° C. for day/23° C. for night, a humidity of 70%, an illuminance of 8,500 lux, a day length of 12 hours"

(Compound Treatment)

A DMSO solution containing one of the compounds 1 to 163 of the present invention at a predetermined concentration is prepared and diluted with the Kimura B hydroponic solution of ½-fold concentration. The hydroponic solution containing the compound is dispensed by 2 ml to each well of a 24-well plate, and each of nursery plants having grown is transferred to each well and cultured for 2 days on an illuminated culture shelf under the following conditions.

"Conditions; a temperature of 25° C., an illuminance of 5,000 lux, a day length of 12 hours"

Moreover, the nursery plants of rice cultured in the same manner by using a hydroponic solution containing 0.1% DMSO are used as an untreated control plot.

(Low-Temperature Stress Treatment)

The nursery plants of rice in a state of being in the 24-well plate are transferred to a cooling box and cultured for 5 days under the following conditions by using cold-cathode fluorescent lamps.

"Conditions; a temperature of 4° C., an illuminance of 3,500 lux, a day length of 12 hours"

(Evaluation)

After the low-temperature stress treatment, the nursery plants of rice having undergone the low-temperature stress treatment are transferred to an illuminated culture shelf and cultured for 4 more days under the following conditions.

"Conditions; a temperature of 25° C., an illuminance of 5,000 lux, a day length of 12 hours"

After 4 days, an image of the aerial part of the individual nursery plant of rice in each treated plot is taken, and an area of a green portion of the obtained image data is quantified by image analysis software Win Roof (manufactured by MITANI CORPORATION) to determine a green area of each individual of the aerial part of the plant. For each of the treated plots, an average of the green areas of the aerial part of individual nursery plant of rice is determined. As a result, the green area is expected to be larger in the plot treated with one of the compounds 1 to 163 of the present invention than in an untreated control plot.

Test Example 10. Test for Evaluating Growth Promotion Under Low-Temperature Stress by Rice Seed Treatment (Test Plant)
Rice (Variety: Nipponbare)
(Seed Treatment)

A blank slurry solution containing 5% (V/V) color coat red (Becker Underwood, Inc.), 5% (V/V) CF-Clear (Becker Underwood, Inc.), and 1% Maxim XL (Syngenta) is prepared. One of the compounds 1 to 163 of the present invention is dissolved in the blank slurry such that a predetermined amount of the compound is used for treatment per 100 kg rice seeds, thereby preparing a slurry solution. Zero point one (0.1) ml of the slurry solution per 3 g of the rice seeds is put into a 15 ml centrifugal settling tube (manufactured by AGC Techno Glass, Co., Ltd.), and the slurry solution is stirred until it dries, thereby coating the seeds. Moreover, the seeds coated with the blank slurry are used as seeds for an untreated control plot.

(Cultivation Method)

Filter paper is placed in holes of a 406-hole plug tray, and rice seeds having undergone the seed treatment are seeded. The Kimura B hydroponic solution (refer to Plant Science 119:39-47 (1996)) of ½-fold concentration is added thereto, and the seeds are cultured for 10 days in a phytotron under the following conditions.

"Conditions; a temperature 28° C. for day/23° C. for night, a humidity of 70%, an illuminance of 8,500 lux, a day length of 12 hours"

(Low-Temperature Stress Treatment)

Nursery plants of rice having grown after 10 days of cultivation that are in state of being in the plug tray are transferred to a cooling box, and cultivated for 5 days under cold-cathode fluorescent lamps under the following conditions.

"Conditions: a temperature of 4° C., an illuminance of 3,500 lux, a day length of -2 hours"

(Evaluation)

Four individuals of the nursery plant of rice in the same treated plot having undergone low-temperature stress treatment are transferred to a cup (C-AP square cup 88, manufactured by SHINGI CORPORATION) containing 60 ml of Hoagland hydroponic solution (Hoagland and Arnon, California Agricultural Experiment Station 1950 Circular 347 pp. 34) and cultured for 12 days on an illuminated culture shelf under the following conditions.

"Conditions: a temperature of 25° C., an illuminance of 5,000 lux, a day length of 12 hours"

After 12 days, a fresh weight of the aerial part of each individual of the plant is measured for each treated plot, and an average of the fresh weight of the aerial part of each individual of the plant is determined.

As a result, the fresh weight of the aerial part is expected to be larger in the plot having undergone treatment by using one of the compounds 1 to 163 of the present invention than in the untreated control plot.

Test Example 11. Test for Evaluating Growth Promotion Under Drought Stress by Soaking Treatment of Rice (Test Plant)
Rice (variety: Nipponbare)
(Cultivation)
Rice seeds are soaked in an aqueous benlate solution at 1,000 ppm and cultured overnight at 30° C. in a dark place. The aqueous Benlate solution is discarded and replaced with distilled water, and the seeds are further cultured overnight at 30° C. in a dark place.

Filter paper is placed in holes of a 406-hole plug tray, and rice seeds having undergone the germination hastening treatment are seeded on the filter paper. A DMSO solution containing one of the compounds 1 to 163 of the present invention at a predetermined concentration is added to the Kimura B hydroponic solution (refer to Plant Science 119: 39-47 (1996)) of ½-fold concentration at a volume ratio of 1/10,000, and the seeds are cultivated for 14 days under the conditions of a temperature of 28° C. for day/23° C. for night, a humidity of 60%, an illuminance of 8,500 lux, and a day length of 12 days.

(Drought Stress Treatment)
The grown nursery plants of rice are put into an empty flat-bottomed test tube (Assist/Sarstedt) by five individuals and left to standstill for 2 days without putting a lid under the conditions of a temperature of 28° C. for day/23° C. for night, a humidity of 60%, an illuminance of 8,500 lux, and a day length of 12 hours.

(Evaluation)
The plants having undergone drought stress treatment are put in a centrifugal settling tube (manufactured by AGC Techno Glass, Co., Ltd.) containing 100 ml of Hoagland hydroponic solution (Hoagland and Arnon, California Agricultural Experiment Station 1950 Circular 347 pp. 34) and cultivated for 14 days under the conditions of a temperature of 28° C. for day/23° C. for night, a humidity of 60%, an illuminance of 8,500 lux, and a day length of 12 hours.

After 14 days, a fresh weight of the overground portion of the test plant in each test plot is weighed, and an average is determined. As a result, the fresh weight of the aerial part of the rice treated with one of the compounds 1 to 163 of the present invention is expected to be larger than that of the rice in the untreated control plot.

Test Example 12. Test for Evaluating Growth Promotion Under High-Temperature Stress by Drench Treatment of Wheat (Test Plant)
Wheat (Variety: Apogee)
(Spraying Treatment)
Wheat seeds are seeded by five seeds in a culture soil (Aisai) in a plastic pot and cultivated for 10 days in a phytotron under the conditions of a temperature of 18° C. for day/15° C. for night, an illuminance of 7,000 lux, and a day length of 16 hours. Before the stress test, thinning is performed to leave three individuals per pot.

One of the compounds 1 to 163 of the present invention in a predetermined amount is dissolved in DMSO to conduct 1,000-fold dilution. Fifteen (15) ml of an aqueous solution containing the compound of the present invention at a predetermined concentration is used to perform soil drench treatment on the pot in which nursery plants of wheat have grown. Moreover, a 0.1% DMSO solution not containing the compound of the present invention is used as an untreated control plot.

(High-Temperature Stress Treatment)
The test plants obtained on the 13$^{th}$ days after seeding are left to standstill for 2.5 hours in a phytotron under the conditions of a temperature of 49° C., a humidity of 50%, and an illuminance of 7,000 lux.

(Evaluation)
After the high-temperature stress treatment, the plants are cultivated for 14 days in a phytotron under the conditions of a temperature of 18° C. for day/15° C. for night and an illuminance of 7,000 lux. The wheat obtained on the 14$^{th}$ days after the high-temperature stress treatment is imaged using Scanalyzer 3D-VIS (manufactured by LemnaTec GmbH), and an area of the green portion of the leaves is calculated. As a result, the wheat treated with one of the compounds 1 to 163 of the present invention is expected to have an effect of increasing the green leaf area, compared to the wheat (untreated control plot) not treated with the compound of the present invention.

Test Example 13. Test for Evaluating Growth Promotion Under Drought Stress by Rice Seed Treatment (Test Plant)
Rice (variety: Nipponbare)
(Seed Treatment)
A blank slurry solution containing 5% (V/V) color coat red (Becker Underwood, Inc.), 5% (V/V) CF-Clear (Becker Underwood, Inc.), and 1% Maxim XL (Syngenta) is prepared.

One of the compounds 1 to 163 of the present invention is dissolved in the blank slurry such that a predetermined amount of the compound is used per 100 kg rice seeds, thereby preparing a slurry solution. Zero point three zero (0.30) ml of the slurry solution per 13 g of the rice seeds is put into a 50 ml centrifugal settling tube (manufactured by AGC Techno Glass, Co., Ltd.), and the slurry solution is stirred until it dries, thereby coating the seeds. Moreover, the seeds coated with the blank slurry solution are used as seeds for an untreated control plot.

(Cultivation)
Filter paper is placed in holes of a 406-hole plug tray, and rice seeds having undergone the seed treatment as above are seeded on the filter paper. The Kimura B hydroponic solution (refer to Plant Science 119:39-47 (1996)) of ½-fold concentration is added thereto, and the seeds are cultured for 17 days under the conditions of t a temperature of 28° C. for day/23° C. for night, a humidity of 60%, an illuminance of 8,500 lux, and a day length of 12 hours.

(Drying Stress Treatment)
The grown nursery plants of rice are put into a 35 ml empty flat-bottomed test tube (Assist/Sarstedt) by five individuals and left to standstill for 2 days without putting a lid under the conditions of a temperature of 28° C. for day/23° C. for night, a humidity of 60%, an illuminance of 8,500 lux, and a day length of 12 hours.

(Evaluation)
The plants having undergone drought stress treatment a put in a centrifugal settling tube (manufactured by AGC Techno Glass, Co., Ltd.) containing 100 ml of Hoagland hydroponic solution (Hoagland and Arnon, California Agricultural Experiment Station 1950 Circular 347 pp. 34) and cultivated for 14 days under the conditions of a temperature of 28° C. for day/23° C. for night, a humidity of 60%, an illuminance of 8,500 lux, and a day length of 12 hours.

After 14 days, a fresh weight of the aerial part of the five individuals of the test plant in each test plot is weighed, and an average of each test plot is determined. As a result, the plot treated with one of the compounds 1 to 163 of the present invention is expected to have an effect of increasing the fresh weight of the aerial part, compared to the untreated control plot.

Test Example 14. Test for Evaluating Growth Promotion Under Low-Temperature Stress by Corn Soil Drench Treatment Corn seeds (variety: Pioneer 31P41) was seeded in a culture soil (Aisai) in a plastic pot (φ55 mm×height of 58 mm), and cultured for 7 days under the conditions of a temperature of 20-25° C., an illuminance of about 5,000 lux, and a day length of 16 hours.

A DMSO solution which contained one of the compounds 1, 3, 7, 10, 12, 13, 19, 26, 27, 30, 32, 38 to 43, 48, 49, 52, 55 to 58, 60, 62, 63, 65, 67, 69, 70, 73, 83, 85, 88, 93, 97, 100, 110, 111, 119, 125, 129 to 133, 135, 141, 145, 147, 152, 153, 156, 157, 159, 160 and 161 of the present invention was prepared at a 1,000-fold concentration as opposed to each test concentration, and was diluted with distilled water to prepare a test solution.

The 20 ml of obtained test solutions were soil drenched into plant foot and the plants were cultured for 2 days under the conditions of a temperature of 27° C., a humidity of 40-80%, an illuminance of about 5,000 lux, and a day length of 16 hours, to make it a treated plot with the present compound. A plot was treated by the soil drench treatment with a 20 ml of 0.1% DMSO solution in place of the DMSO solution of the compound to make it an untreated control plot.

The soil drenched plant was cultivated for 5 days in a phytotron under the conditions of a temperature of 2.5° C., a humidity of 40-80%, an illuminance of about 5,000 lux, and a day length of 16 hours, whereby the plants were exposed to low-temperature stress. After being exposed to the low-temperature stress, the plants were cultivated for 4 days in a phytotron under the conditions of a temperature of 27° C., a humidity of 40-80%, an illuminance of about 5,000 lux, and a day length of 16 hours.

After the cultivation, a degree of healthy of each plant individuals was scored according to the following performance index.

5: the number of the leave, of which ⅔ or greater of the area is healthy, is four or more;
4: the number of the leave, of which ⅔ or greater of the area is healthy, is three;
3: the number of the leave, of which ⅔ or greater of the area is healthy, is two;
2: the number of the leave, of which ⅔ or greater of the area is healthy, is one;
1: the number of the leave, of which ⅔ or greater of the area is healthy, is zero (0);
0: the number of the withered and died leaves.

The average values of the above healthy scores of four plant individuals were calculated. As a result of the evaluation, as shown in Tables 14, 15 and 16, it was evident that the treated plot of the plants, wherein the plants were treated with one of the compounds 1, 3, 7, 10, 12, 13, 19, 26, 27, 30, 32, 38 to 43, 48, 49, 52, 55 to 58, 60, 62, 63, 65, 67, 69, 70, 73, 83, 85, 88, 93, 97, 100, 110, 111, 119, 125, 129 to 133, 135, 141, 145, 147, 152, 153, 156, 157, 159, 160 and 161 of the present invention, had much higher scores than those of the non-treated plot.

TABLE 14

| Test compound | Test concentration (ppm) | Relative value of scores (%-untreated control plot) |
|---|---|---|
| Present compound 1 | 10 | >5 |
| Present compound 3 | 0.3 | >5 |
| Present compound 7 | 10 | >5 |
| Present compound 10 | 10 | >5 |
| Present compound 12 | 10 | >5 |
| Present compound 13 | 10 | >5 |
| Present compound 19 | 0.3 | >5 |
| Present compound 26 | 1 | >5 |
| Present compound 27 | 10 | >5 |
| Present compound 30 | 10 | >5 |
| Present compound 32 | 3 | >5 |
| Present compound 38 | 3 | >5 |
| Present compound 39 | 1 | >5 |
| Present compound 40 | 10 | >5 |
| Present compound 41 | 0.3 | >5 |
| Present compound 42 | 0.3 | >5 |
| Present compound 43 | 3 | >5 |
| Present compound 48 | 10 | >5 |
| Present compound 49 | 10 | >5 |
| Present compound 52 | 1 | >5 |

TABLE 15

| Test compound | Test concentration (ppm) | Relative value of scores (%-untreated control plot) |
|---|---|---|
| Present compound 55 | 10 | >5 |
| Present compound 56 | 10 | >5 |
| Present compound 57 | 10 | >5 |
| Present compound 58 | 10 | >5 |
| Present compound 60 | 10 | >5 |
| Present compound 62 | 0.3 | >5 |
| Present compound 63 | 3 | >5 |
| Present compound 65 | 0.3 | >5 |
| Present compound 67 | 3 | >5 |
| Present compound 69 | 1 | >5 |
| Present compound 70 | 10 | >5 |
| Present compound 73 | 1 | >5 |
| Present compound 83 | 0.3 | >5 |
| Present compound 85 | 10 | >5 |
| Present compound 88 | 3 | >5 |
| Present compound 93 | 10 | >5 |
| Present compound 97 | 0.3 | >5 |
| Present compound 100 | 3 | >5 |
| Present compound 110 | 1 | >5 |
| Present compound 111 | 10 | >5 |

TABLE 16

| Test compound | Test concentration (ppm) | Relative value of scores (%-untreated control plot) |
|---|---|---|
| Present compound 119 | 1 | >5 |
| Present compound 125 | 0.3 | >5 |
| Present compound 129 | 10 | >5 |
| Present compound 130 | 1 | >5 |
| Present compound 131 | 3 | >5 |
| Present compound 132 | 0.3 | >5 |
| Present compound 133 | 3 | >5 |
| Present compound 135 | 3 | >5 |
| Present compound 141 | 0.3 | >5 |
| Present compound 145 | 0.3 | >5 |
| Present compound 147 | 0.3 | >5 |
| Present compound 152 | 1 | >5 |

TABLE 16-continued

| Test compound | Test concentration (ppm) | Relative value of scores (%-untreated control plot) |
|---|---|---|
| Present compound 153 | 1 | >5 |
| Present compound 156 | 1 | >5 |
| Present compound 157 | 0.3 | >5 |
| Present compound 159 | 0.3 | >5 |
| Present compound 160 | 10 | >5 |
| Present compound 161 | 3 | >5 |

INDUSTRIAL APPLICABILITY

The use of the method of the present invention makes it possible to effectively promote the plant growth.

The invention claimed is:

1. A method for promoting plant growth, which comprises treating a plant with a compound represented by the following Formula (1):

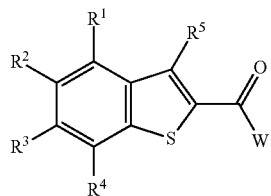

(1)

wherein,

W represents —$OR^6$, —$ON=CR^7R^8$, or —$SR^9$, $R^1$ represents a hydrogen atom, a halogen atom, a nitro group, a C1-C6 alkyl group optionally having one or more groups selected from a group X, a phenyl group optionally having one or more groups selected from a group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^{11}R^{12}$, —$S(O)_2NR^7R^{11}$, —$OR^{11}$, —$S(O)_mR^{11}$, or —$SF_5$, $R^2$ represents a hydrogen atom, a halogen atom, a cyano group, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^{12}R^{13}$, —$S(O)_2NR^7R^{11}$, —$OR^{13}$, —$S(O)_mR^{13}$, or —$SF_5$, $R^3$ and $R^4$ are the same or different and each represents a hydrogen atom, a halogen atom, a cyano group, a nitro group, a C1-C6 alkyl group optionally having one or more groups selected from the group X, a phenyl group optionally having one or more groups selected from the group Y, a 6-membered aromatic heterocyclic group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —$NR^{11}R^{12}$, —$S(O)_2NR^7R^{11}$, —$OR^{11}$, —$S(O)_mR^{11}$, or —$SF_5$, $R^5$ represents a hydrogen atom, a halogen atom, a cyano group, a nitro group, a C1-C6 alkyl group optionally having one or more groups selected from the group X, a carboxy group, a C2-C6 alkoxycarbonyl group, —$NR^{11}R^{12}$, —$S(O)_2NR^7R^{11}$, —$OR^{14}$, a phenyl group optionally having one or more groups selected from the group Y, a 6-membered aromatic heterocyclic group optionally having one or more groups selected from the group Y, or a 5-membered aromatic heterocyclic group optionally having one or more groups selected from the group Y, $R^6$ represents a C3-C6 alkyl group optionally having one or more groups selected from a group Z, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a phenyl group optionally having one or more groups selected from the group Y, or a C7-C9 phenylalkyl group wherein a benzene ring portion may have optionally one or more groups selected from the group Y, $R^7$ and $R^8$ are the same or different and each represents a C1-C6 alkyl group optionally having one or more halogen atoms, a phenyl group optionally having one or more groups selected from the group Y, or a hydrogen atom, $R^9$ represents a hydrogen atom, a C1-C6 alkyl group optionally having one or more groups selected from the group Z, a C3-C6 alkenyl group optionally having one or more groups selected from the group X, a C3-C6 alkynyl group optionally having one or more groups selected from the group X, a phenyl group optionally having one or more groups selected from the group Y, or a C7-C9 phenylalkyl group wherein a benzene ring portion may have optionally one or more groups selected from the group Y, $R^{11}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C7-C9 phenylalkyl group wherein a benzene ring portion may have optionally one or more groups selected from the group Y, a 6-membered aromatic heterocyclic-C1-C3 alkyl group wherein a 6-membered aromatic heterocyclic portion may have optionally one or more groups selected from the group Y, a phenyl group optionally having one or more groups selected from the group Y, a C3-C6 cycloalkyl group optionally having one or more halogen atoms, or a hydrogen atom (provided that when m in —$S(O)_mR^{11}$ is 1 or 2, $R^{11}$ is not a hydrogen atom), R$^{12}$ represents a hydrogen atom, a C1-C4 alkyl group optionally having one or more halogen atoms, a C1-C4 alkylsulfonyl group optionally having one or more halogen atoms, a phenylsulfonyl group optionally having one or more groups selected from the group Y, a C7-C9 phenylalkylsulfonyl group wherein a benzene ring portion may have optionally one or more groups selected from the group Y, a C2-C6 alkoxycarbonyl group, —C(O)R$^{15}$, or —C(O)NR$^7$R$^8$, R$^{13}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a C7-C9 phenylalkyl group wherein a benzene ring portion may have optionally one or more groups selected from the group Y, or a hydrogen atom (provided that when m in —S(O)$_m$R$^{13}$ is 1 or 2, R$^{13}$ is not a hydrogen atom), R$^{14}$ represents a C1-C6 alkyl group optionally having one or more groups selected from the group X, a C3-C6 alkenyl group optionally having one or more groups selected from the group X, a C3-C6 alkynyl group optionally having one or more groups selected from the group X, a C4-C7 cycloalkylalkyl group optionally having one or more halogen atoms, a C3-C6 cycloalkyl group optionally having one or more halogen atoms, a C7-C9 phenylalkyl group wherein a benzene ring portion may have optionally one or more groups selected from the group Y, a phenyl group optionally having one or more groups selected from the group Y, a C2-C6 alkylcarbonyl group optionally having one or more halogen atoms, a benzoyl group optionally having one or more groups selected from the group Y, a C1-C6 alkylsulfonyl group optionally having one or more halogen atoms, a phenylsulfonyl group optionally having one or more groups selected from the group Y, or a hydrogen atom, R$^{15}$ represents a hydrogen atom, a C1-C6 alkyl group optionally having one or more halogen atoms, a phenyl group optionally having one or more groups selected from the group Y, a 5-membered aromatic heterocyclic group optionally having one or more groups selected from the group Y, or a 6-membered aromatic heterocyclic group optionally having one or more groups selected from the group Y, and m represents 0, 1, or 2, the group X represents a group consisting of a halogen atom, a cyano group, and a C1-C6 alkoxy group optionally having one or more halogen atoms, the group Y represents a group consisting of a halogen atom, a cyano group, a nitro group, a C1-C6 alkyl group optionally having one or more halogen atoms, and a C1-C6 alkoxy group optionally having one or more halogen atoms, and the group Z represents a group consisting of a halogen atom, a hydroxy group, a C1-C6 alkoxy group optionally having one or more halogen atoms, and a C2-C6 alkoxycarbonyl group, provided that a method for promoting plant growth which comprises treating plants with a compound corresponding to any one of the following (1) to (8) is excluded, (1) Methyl 4-(trifluoromethyl)benzo[b]thiophene-2-carboxylate, (2) Methyl 5-(trifluoromethyl)benzo[b]thiophene-2-carboxylate, (3) Methyl 6-(trifluoromethyl)benzo[b]thiophene-2-carboxylate, (4) Methyl 7-(trifluoromethyl)benzo[b]thiophene-2-carboxylate, (5) Ethyl 4-(trifluoromethyl)benzo[b]thiophene-2-carboxylate, (6) Ethyl 5-(trifluoromethyl)benzo[b]thiophene-2-carboxylate, (7) Ethyl 6-(trifluoromethyl)benzo[b]thiophene-2-carboxylate, and (8) Ethyl 7-(trifluoromethyl)benzo[b]thiophene-2-carboxylate; and wherein the plant is a plant that has been or will be exposed to an abiotic stress, and the abiotic stress is a high-temperature stress, a low-temperature stress or a drought stress.

2. The method according to claim 1, in which the compound represented by Formula (1) is a compound wherein R$^1$ represents a hydrogen atom, a halogen atom, a nitro group, a C1-C6 alkyl group optionally having one or more groups selected from the group X, a phenyl group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —NR$^{11}$R$^{12}$, —S(O)$_2$NR$^7$R$^{11}$, —OR$^{11}$, —S(O)$_m$R$^{11}$, or —SF$_5$, and R$^4$ represents a hydrogen atom, a halogen atom, a cyano group, a nitro group, a C1-C6 alkyl group optionally having one or more groups selected from the group X, a phenyl group optionally having one or more groups selected from the group Y, a 5-membered aromatic heterocyclic group optionally having one or more groups selected from the group Y, a carboxy group, a C2-C6 alkylcarbonyl group optionally having one or more halogen atoms, a benzoyl group optionally having one or more groups selected from the group Y, a C2-C6 alkoxycarbonyl group, an aminocarbonyl group, —NR$^{11}$R$^{12}$, —S(O)$_2$NR$^7$R$^{11}$, —OR$^{11}$, —S(O)$_m$R$^{11}$, or —SF$_5$.

3. The method according to claim 1, in which the compound represented by Formula (1) is a compound wherein R$^1$ represents a hydrogen atom, a halogen atom, a nitro group, a C1-C4 alkyl group optionally having one or more halogen atoms, a phenyl group optionally having one or more groups selected from the group Y, a pyridyl group optionally having one or more groups selected from the group Y, a pyrimidinyl group optionally having one or more groups selected from the group Y, a thienyl group optionally having one or more groups selected from the group Y, a pyrrolyl group optionally having one or more groups selected from the group Y, a C2-C5 alkylcarbonyl group optionally having one or more halogen atoms, a benzoyl group optionally having one or more groups selected from the group Y, a C2-C4 alkoxycarbonyl group, an aminocarbonyl group, —NR$^{11}$R$^{12}$, —OR$^{11}$, —S(O)$_m$R$^{11}$, or —SF$_5$, R$^2$ represents a hydrogen atom, a halogen atom, a cyano group, a nitro group, a C1-C4 alkyl group optionally having one or more halogen atoms, a phenyl group optionally having one or more groups selected from the group Y, a pyridyl group optionally having one or more groups selected from the group Y, a pyrimidinyl group optionally having one or more groups selected from the group Y, a thienyl group optionally having one or more groups selected from the group Y, a pyrrolyl group optionally having one or more groups selected from the group Y, a C2-C5 alkylcarbonyl group optionally having one or more halogen atoms, a benzoyl group optionally having one or more groups selected from the group Y, a C2-C4 alkoxycarbonyl group, an aminocarbonyl group, —NR$^{12}$R$^{13}$, —OR$^{13}$, —S(O)$_m$R$^{13}$, or —SF$_5$, R$^3$ and R$^4$ are the same or different and each represents a hydrogen atom, a halogen atom, a cyano group, a nitro group, a C1-C4 alkyl group optionally having one or more halogen atoms, a phenyl group optionally having one or more groups selected from the group Y, a pyridyl group optionally having one or more groups selected from the group Y, a pyrimidinyl group optionally having one or more groups selected from the group Y, a thienyl group optionally having one or more groups selected from the group Y, a pyrrolyl group optionally having one or more groups selected from the group Y, a C2-C5 alkylcarbonyl group optionally having one or more halogen atoms, a benzoyl group optionally having one or more groups selected from the group Y, a C2-C4 alkoxycarbonyl group, an aminocarbonyl group, —NR$^{11}$R$^{12}$, —OR$^{11}$, —S(O)$_m$R$^{11}$, or —SF$_5$, R$^5$ represents a hydrogen atom, a halogen atom, a cyano group, a nitro group, a C1-C4 alkyl group optionally having one or more halogen atoms, a C2-C5 alkoxycarbonyl group, —NR$^{11}$R$^{12}$, —S(O)$_2$NR$^7$R$^{11}$, —OR$^{14}$, or a phenyl group optionally having one or more groups selected from the group Y, R$^6$ represents a C3-C6 alkyl group optionally having one or more groups selected from the group Z, a C3-C6 alkenyl group optionally having one or more halogen atoms, a C3-C6 alkynyl group optionally having one or more halogen atoms, a phenyl group optionally having one or more groups selected from the group Y, or a C7-C9 phenylalkyl group wherein a benzene ring portion may have optionally one or more groups selected from the group Y, R$^7$ and R$^8$ are the same or different and each represents a C1-C4 alkyl group optionally having one or more halogen atoms, a phenyl group optionally having one or more groups selected from the group Y, or a hydrogen atom, R$^9$ represents a hydrogen atom, a C1-C6 alkyl group optionally having one or more groups selected from the group Z, a C3-C6 alkenyl group optionally having one or more halogen atoms, a C3-C6 alkynyl group optionally having one or more halogen atoms, a phenyl group optionally having one or more groups selected from the group Y, or a C7-C9 phenylalkyl group wherein a benzene ring portion may have optionally one or more groups selected from the group Y, R$^{11}$ represents a C1-C3 alkyl group optionally having one or more halogen atoms, a C3-C4 alkynyl group optionally having one or more groups selected from the group X, a C7-C9 phenylalkyl group wherein a benzene ring portion may have optionally one or more groups selected from the group Y, a pyridyl-C1-C3 alkyl group wherein a pyridine ring portion may have optionally one or more groups selected from the group Y, a phenyl group optionally having one or more groups selected from the group Y, or a hydrogen atom (provided that when m in —S(O)$_m$R$^{11}$ is 1 or 2, R$^{11}$ is not a hydrogen atom), R$^{12}$ represents a hydrogen atom, a C1-C4 alkyl group optionally having one or more halogen atoms, a C1-C4 alkylsulfonyl group optionally having one or more halogen atoms, a phenylsulfonyl optionally having one or more groups selected from the group Y, a benzylsulfonyl group wherein a benzene ring portion may have optionally one or more groups selected from the group Y, —C(O)R$^{15}$, or —C(O)NR$^7$R$^8$, R$^{13}$ represents a C1-C3 alkyl group optionally having one or more halogen atoms or a hydrogen atom (provided that when m in —S(O)$_m$R$^{13}$ is 1 or 2, R$^{13}$ is not a hydrogen atom), R$^{14}$ represents a C1-C4 alkyl group optionally having one or more groups selected from the group X, a C3-C6 alkenyl group optionally having one or more halogen atoms, a benzyl group wherein a benzene ring portion may have optionally one or more groups selected from the group Y, a phenyl group optionally having one or more groups selected from the group Y, a C2-C5 alkylcarbonyl group optionally having one or more halogen atoms, a benzoyl group optionally having one or more groups selected from the group Y, a phenylsulfonyl group optionally having one or more groups selected from the group Y, or a hydrogen atom, and R$^{15}$ represents a hydrogen atom, a C1-C4 alkyl group optionally having one or more halogen atoms, a phenyl group optionally having one or more groups selected from the group Y, a thienyl group optionally having one or more groups selected from the group Y, a pyrazolyl group optionally having one or more groups selected from the group Y, or an isoxazolyl group optionally having one or more groups selected from the group Y.

4. The method according to claim 1, in which the treatment of the plant is a spraying treatment, a soil treatment, a seed treatment, or a hydroponic treatment.

5. The method according to claim 4, in which the treatment of the plant is the seed treatment.

6. The method according to claim 1, in which the plant is rice, corn, or wheat.

7. The method according to claim 1, in which the plant is a transgenic plant.

8. The method according to claim 1, in which the abiotic stress is the high-temperature stress.

9. The method according to claim 1, in which the abiotic stress is the low-temperature stress.

10. The method according to claim 1, in which the abiotic stress is the drought stress.

11. The method according to claim 1, in which the plant is soybean.

12. The method according to claim 1, in which the plant is cotton.

* * * * *